United States Patent
Otsu

(10) Patent No.: US 9,216,968 B2
(45) Date of Patent: Dec. 22, 2015

(54) HETEROCYCLIC DERIVATIVE AND PHARMACEUTICAL DRUG

(75) Inventor: Hironori Otsu, Matsubara (JP)

(73) Assignee: NIPPON SHINYAKU CO., LTD., Kyoto (JP)

( * ) Notice: Subject to any disclaimer, the term of this patent is extended or adjusted under 35 U.S.C. 154(b) by 0 days.

(21) Appl. No.: 14/238,749

(22) PCT Filed: Aug. 17, 2012

(86) PCT No.: PCT/JP2012/070902
§ 371 (c)(1),
(2), (4) Date: Feb. 13, 2014

(87) PCT Pub. No.: WO2013/024898
PCT Pub. Date: Feb. 21, 2013

(65) Prior Publication Data
US 2014/0221339 A1      Aug. 7, 2014

(30) Foreign Application Priority Data
Aug. 18, 2011   (JP) .................. 2011-179134

(51) Int. Cl.
| | |
|---|---|
| *C07D 235/30* | (2006.01) |
| *C07D 235/08* | (2006.01) |
| *C07D 235/12* | (2006.01) |
| *C07D 405/04* | (2006.01) |
| *C07D 263/56* | (2006.01) |
| *C07D 403/12* | (2006.01) |
| *A61K 31/343* | (2006.01) |
| *A61K 31/416* | (2006.01) |
| *A61K 31/4184* | (2006.01) |
| *A61K 31/423* | (2006.01) |
| *A61K 31/428* | (2006.01) |
| *A61K 31/433* | (2006.01) |
| *A61K 31/4439* | (2006.01) |
| *A61K 31/454* | (2006.01) |
| *A61K 31/496* | (2006.01) |
| *A61K 31/5377* | (2006.01) |
| *C07D 231/56* | (2006.01) |
| *C07D 235/06* | (2006.01) |
| *C07D 235/10* | (2006.01) |
| *C07D 235/14* | (2006.01) |
| *C07D 401/12* | (2006.01) |
| *C07D 235/26* | (2006.01) |

(Continued)

(52) U.S. Cl.
CPC ........... *C07D 405/04* (2013.01); *A61K 31/343* (2013.01); *A61K 31/416* (2013.01); *A61K 31/4184* (2013.01); *A61K 31/423* (2013.01); *A61K 31/428* (2013.01); *A61K 31/433* (2013.01); *A61K 31/4439* (2013.01); *A61K 31/454* (2013.01); *A61K 31/496* (2013.01); *A61K 31/5377* (2013.01); *C07D 231/56* (2013.01); *C07D 235/06* (2013.01); *C07D 235/08* (2013.01); *C07D 235/10* (2013.01); *C07D 235/12* (2013.01); *C07D 235/14* (2013.01); *C07D 235/26* (2013.01); *C07D 235/30* (2013.01); *C07D 263/56* (2013.01); *C07D 307/79* (2013.01); *C07D 401/12* (2013.01); *C07D 403/04* (2013.01); *C07D 403/12* (2013.01); *C07D 405/12* (2013.01); *C07D 409/12* (2013.01); *C07D 413/12* (2013.01); *C07D 417/12* (2013.01)

(58) Field of Classification Search
USPC ........................................ 548/307.4, 310.1
See application file for complete search history.

(56) References Cited

U.S. PATENT DOCUMENTS

| | | |
|---|---|---|
| 2009/0186922 A1 | 7/2009 | Alisi et al. |
| 2010/0324086 A1 | 12/2010 | Wannberg et al. |

FOREIGN PATENT DOCUMENTS

| | | |
|---|---|---|
| CN | 101490000 A | 7/2009 |
| WO | 2006/099379 A2 | 9/2006 |

(Continued)

OTHER PUBLICATIONS

Golub et al., Science, vol. 286, Oct. 15, 1999, pp. 531-537.*

(Continued)

*Primary Examiner* — Laura L. Stockton

(57) ABSTRACT

The present invention provides a novel heterocyclic derivative or a pharmaceutically acceptable salt thereof. For example, the present invention provides a heterocyclic derivative of the general formula [1] or its tautomer, or a pharmaceutically acceptable salt thereof:

[1]

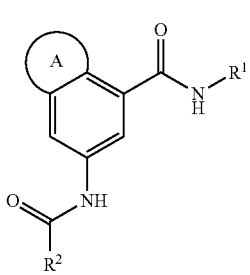

wherein $R^1$ and $R^2$ are the same or different aromatic rings, etc., and ring A is a heterocyclic ring. The compound of the invention or a pharmaceutically acceptable salt thereof has potent mPGES-1 inhibiting activity and is useful as an agent for the treatment or prevention of a disease, such as rheumatoid arthritis, osteoarthritis, temporomandibular joint disorders, low back pain, endometriosis, dysmenorrhea, overactive bladder, malignant tumors or neurodegenerative disease.

24 Claims, No Drawings

(51) Int. Cl.

| | | |
|---|---|---|
| *C07D 403/04* | (2006.01) | |
| *C07D 405/12* | (2006.01) | |
| *C07D 409/12* | (2006.01) | |
| *C07D 413/12* | (2006.01) | |
| *C07D 417/12* | (2006.01) | |
| *C07D 307/79* | (2006.01) | |

(56) References Cited

FOREIGN PATENT DOCUMENTS

| | | |
|---|---|---|
| WO | 2008/071944 A1 | 6/2008 |
| WO | 2009/103778 A1 | 8/2009 |
| WO | 2011/048004 A1 | 4/2011 |

OTHER PUBLICATIONS

Tohru Araki, Teryhiko Yokoyama, Motoo Araki, and Seiji Furuya, "A Clinical Investigation of the Mechanism of Loxoprofen, a Non-steroidal Anti-inflammatory Drug, for Patients with Nocturia," Acta Medica Okayama, vol. 62, No. 6, pp. 373-378 (2008), Okayama University Medical School.

Christine A. Martey et al., "Cigarette Smoke Induces Cyclooxygenase-2 and Microsomal Prostaglandin E2 Synthase in Human Lung Fibroblasts: Implications for Lung Inflammation and Cancer," American Journal of Physiology Lung Cellular and Molecular Physiology, vol. 287, L981-991 (2004), The American Physiological Society.

Katherine M. A. O'Reilly, et al., "Crystalline and Amorphous Silica Differentially Regulate the Cyclooxygenase-Prostaglandin Pathway in Pulmonary Fibroblasts: Implications for Pulmonary Fibrosis," American Journal of Physiology Lung Cellular and Molecular Physiology, vol. 288, L1010-1016 (2005), The American Physiological Society.

Matthew R. McCann, et al., "mPGES-1 Null Mice are Resistant to Bleomycin-Induced Skin Fibrosis," Arthritis Research & Therapy, vol. 13, R6 (2011), BioMed Central Ltd.

Naomi Tanikawa et al., "Identification and Characterization of a Novel Type of Membrane-Associated Prostaglandin E Synthase," Biochemical and Biophysical Research Communications, vol. 291, pp. 884-889 (2002), Elsevier Science.

Akiko Numao et al., "The Inducible Prostaglandin E Synthase mPGES-1 Regulates Growth of Endometrial Tissues and Angiogenesis in a Mouse Implantation Model," Biomedicine & Phamacotherapy, vol. 65, No. 1, pp. 77-84 (2011), Elsevier Masson SAS (advance online publication).

Masako Nakanishi, David C. Montrose, Patsy Clark, et al., "Genetic Deletion of mPGES-1 Suppresses Intestinal Tumorigenesis," Cancer Research, vol. 68, No. 9, pp. 3251-3259 (2008), American Association of Cancer Research.

N. Foudi, L. Louedec, T. Cachina, C. Brink, and X. Norel, "Selective Cyclooxygenase-2 Inhibition Directly Increases Human Vascular Reactivity to Norepinephrine During Acute Inflammation," Cardiovascular Research, vol. 81, pp. 269-277 (2009), European Society of Cardiology.

Shunji Kunori et al., "A Novel Role of Prostaglandin E2 in Neurophathic Pain: Blockade of Microglial Migration in the Spinal Cord," GLIA, vol. 59, pp. 208-218 (2011), Wiley-Liss Inc.

T. Tanioka, Y. Nakatani, N. Semmyo, M. Murakami, and I. Kudo, "Molecular Identification of Cytosolic Prostaglandin E2 Synthase That is Functionally Coupled with Cyclooxygenase-1 in Immediate Prostaglandin E2 Biosynthesis," The Journal of Biological Chemistry, vol. 275, No. 42, pp. 32775-32782 (2000), The American Society for Biochemistry and Molecular Biology, Inc.

Makoto Murakami et al., "Regulation of Prostaglandin E2 Biosynthesis by Inducible Membrane-Associated Prostaglandin E2 Synthase That Acts in Concert with Cyclooxygenase-2," The Journal of Biological Chemistry, vol. 275, No. 42, pp. 32783-32792 (2000), The American Society for Biochemistry and Molecular Biology, Inc.

Daisuke Kamei et al., "Potential Role of Microsomal Prostaglandin E Synthase-1 in Tumorigenesis," The Journal of Biological Chemistry, vol. 278, No. 21, pp. 19396-19405 (2003), The American Society for Biochemistry and Molecular Biology, Inc.

Kotha Subbaramaiah et al., "Microsomal Prostaglandin E Synthase-1 is Overexpressed in Inflammatory Bowel Disease: Evidence for Involvement of the Transcription Factor Egr-1," The Journal of Biological Chemistry, vol. 279, No. 13, pp. 12647-12658 (2004), The American Society for Biochemistry and Molecular Biology, Inc.

Daisuke Kamei et al., "Reduced Pain Hypersensitivity and Inflammation in Mice Lacking Microsomal Prostaglandin E Synthase-1," The Journal of Biological Chemistry, vol. 279, No. 32, pp. 33684-33695 (2004), The American Society for Biochemistry and Molecular Biology, Inc.

J. T. Promes, K. Safcsak, L. Pavliv, B. Voss, and A. Rock, "A Prospective, Multicenter, Randomized, Double-Blind Trial of IV Ibuprofen for Treatment of Fever and Pain in Burn Patients," Journal of Burn Care & Research, vol. 32, No. 1, pp. 79-90 (2011).

Yan Cheng et al., "Cyclooxygenases, Microsomal Prostaglandin E Synthase-1, and Cardiovascular Function," The Journal of Clinical Investigation, vol. 116, No. 5, pp. 1391-1399 (2006), American Society of Clinical Investigation.

Fumiaki Kojima et al., "Defective Generation of a Humoral Immune Response Is Associated with a Reduced Incidence and Severity of Collagen-Induced Arthritis in Microsomal Prostaglandin E Synthase-1 Null Mice," The Journal of Immunology, vol. 180, pp. 8361-8368 (2008), The American Association of Immunologists, Inc.

Rachel J. Church, Leigh A. Jania, and Bevely H. Koller, "Prostaglandin E2 Produced by the Lung Augments the Effector Phase of Allergic Inflammation," The Journal of Immunology, vol. 188, pp. 4093-4102 (2012), The American Association of Immunologists, Inc.

Daigen Xu, et al., " MF63 [2-(6-Chloro-1H-phenanthro[9, 10-d]imidazol-2yl)-isophthalonitrile], a Selective Microsomal Prostaglandin E Synthase-1 Inhibitor, Relieves Pyresis and Pain in Preclinical Models of Inflammation," The Journal of Pharmacology and Experimental Therapeutics, vol. 326, No. 3, pp. 754-763 (2008), The American Society of Pharmacology and Experimental Therapeutics.

Xinfang Li, et al., "Expression and Regulation of Microsomal Prostaglandin E Synthase-1 in Human Osteoarthritic Cartilage and Chondrocytes," The Journal of Rheumatology, vol. 32, No. 5, pp. 887-895 (2005), The Journal of Rheumatology.

David Engblom et al., "Microsomal Prostaglandin E Synthase-1 is the Central Switch During Immune-Induced Pyresis," Nature Neuroscience, vol. 6, No. 11, pp. 1137-1138 (2003), Nature Publishing Group.

Y. Sasaki, et al., "Microsomal Prostaglandin E Synthase-1 is Involved in Multiple Steps of Colon Carcinogenesis," Oncogene, vol. 31, pp. 2943-2952 (2012), Macmillan Publishers Ltd.

P. Jakobsson, S. Thoren, R. Morgenstern, and B. Samuelsson, "Identification of Human Prostaglandin E Synthase: A Microsomal, Glutathione-Dependent, Inducible Enzyme, Constituting a Potential Novel Drug Target," Proceedings of the National Academy of Sciences of the United States of America, vol. 96, pp. 7220-7225 (1999).

Yuri Ikeda-Matsuo et al, "Microsomal Prostaglandin E Synthase-1 is a Critical Factor of Stroke-Reperfusion Injury," Proceedings of the National Academy of Sciences of the United States of America, vol. 103, No. 31, pp. 11790-11795 (2006).

Miao Wang et al., "Deletion of Microsomal Prostaglandin E Synthase-1 Augments Prostacyclin and Retards Atherogenesis," Proceedings of the National Academy of Sciences of the United States of America, vol. 103, No. 39, pp. 14507-14512 (2006).

Yasuyuki Kihara et al., "Targeted Lipidomics Reveals mPGES-1-PGE2 as a Therapeutic Target for Multiple Sclerosis," Proceedings of the National Academy of Sciences of the United States of America, vol. 106, No. 51, pp. 21807-21812 (2009).

Zhanjun Jia et al., "Amelioration of Cisplatin Nephrotoxicity by Generic or Pharmacologic Blockade of Prostaglandin Synthesis," Kidney International, vol. 79(1), pp. 77-88 (2011) (advance online publication of Sep. 15, 2010).

Hiromi Hanaka et al., "Microsomal prostaglandin E synthase 1 determines tumor growth in vivo of prostate and lung cancer cells", PNAS, vol. 106, No. 44, pp. 18757-18762 (Nov. 3, 2009).

English translation of: The State Intellectual Property Office of the People's Republic of China, Notice on the First Office Action, issued in Chinese Patent Application No. 201280049365.2, which is a Chinese counterpart of U.S. Appl. No. 14/238,749, mailed on Oct. 20, 2014, 8 pages.

\* cited by examiner

HETEROCYCLIC DERIVATIVE AND PHARMACEUTICAL DRUG

CROSS REFERENCE TO RELATED APPLICATIONS

This patent application is a U.S. national stage entry under 35 U.S.C. §371 of International Patent Application No. PCT/JP2012/070902 filed on Aug. 17, 2012, which claims the benefit of foreign priority to Japanese Patent Application No. JP 2011-179134 filed on Aug. 18, 2011, the disclosures of all of which are hereby incorporated by reference in their entireties. The International Application was published in Japanese on Feb. 21, 2013, as International Publication No. WO 2013/024898 A1 under PCT Article 21(2).

FIELD OF THE INVENTION

The present invention relates to novel heterocyclic derivatives.

BACKGROUND OF THE INVENTION

Prostaglandins (PG) are produced abundantly in the site of inflammation and involved in progress of inflammation. Prostaglandin production is initiated with the release of arachidonic acid from membrane glycerophospholipid by phospholipase A2, and the arachidonic acid is then converted into prostaglandin H2 (PGH2) by cyclooxygenase (COX). PGH2 is converted into prostaglandins including prostaglandin E2 (PGE2), prostaglandin F2α (PGF2α), prostaglandin D2 (PGD2), prostaglandin I2 (PGI2), and thromboxane A2 (TXA2). These prostaglandins are known to have various physiological or pathophysiological activities, including inflammation-inducing effect. Especially, PGE2 is known as an inflammatory inducer in acute and chronic inflammations and further known to induce pyrexia and hyperpathia. Non-steroidal anti-inflammatory drugs (NSAIDs) and selective COX-2 inhibitors have anti-inflammatory effect via reduced production of PGE2 based on their COX-1 and/or COX-2 inhibitory effect. PGE2 synthase (PGES) catalyzes the final step of the synthetic pathway of PGE2, which is an inflammatory mediator. To date, three subtypes of PGES, microsomal prostaglandin E synthase-1 (mPGES-1) (for example, Jakobsson et al., Proc. Natl. Acad. Sci. USA, 1999, 96, 7220-7225), mPGES-2 (for example, Tanikawa et al., Biochem. Biophys. Res. Commun., 2002, 291, 884-889) and cytosolic prostaglandin synthase (cPGES) (for example, Tanioka et al., J. Biol. Chem., 2000, 275, 32775-32782) are known. Among these, mPGES-1, in the same manner as COX-2, is primarily induced during inflammation and plays a major part in PGE2 production in inflammatory lesion. On the other hand, cPGES is constitutively expressed PGES and coupled to COX-1 to play a part in basal PGE2 production (for example, Murakami et al., J. Biol. Chem., 2000, 275, 32783-32792). As to mPGES-2, it is a subject of controversy as there is a report that it can be coupled to both COX isoforms. The studies in mPGES-1-deficient mouse suggest that mPGES-1 contributes to pathological progress in various inflammation models, such as acetic acid writhing model (e.g., Kamei et al., J. Biol. Chem., 2004, 279, 33684-33695), arthritis model (e.g., Kamei et al., J. Biol. Chem., 2004, 279, 33684-33695 and Kojima et al., J. Immunol., 2008, 108, 3861-3868), multiple sclerosis model (e.g., Kimura et al., Proc. Natl. Acad. Sci. USA, 2000, 106, 21807-21812), and fever model (e.g., Engblom et al., Nat. Neurosci., 2003, 6, 1137-1138). Also, mPGES-1 inhibitors specifically inhibit COX-2-dependent PGE2 production, and therefore, they are expected to reduce various side effects, compared with NSAIDs or COX-2 inhibitors. It is believed that elevated risk of cardiovascular events by COX-2 inhibitors is attributed to enhanced coagulation system and vasoconstriction via inhibited COX-2-dependent PGI2 production (e.g., Foudi et al., Cardiovasc. Res., 2009, 81, 269-277). In contrast, mPGES-1 inhibitors are believed not to increase the risk of cardiovascular events, which is a problem with COX-2 inhibitors, since they do not inhibit PGI2 production (e.g., Cheng et al., J. Clin. Invest., 2006, 116, 1391-1399), mPGES-1 inhibitors are expected to serve as a safe anti-inflammatory agent by inhibiting only PGE2 production, which participates in inflammation. Thus, a pharmaceutical agent which is able to inhibit mPGES-1, and reduce PGE2 production is useful in the treatment or prevention of a disease, such as an inflammatory disease in which mPGES-1 participates. mPGES-1 inhibitors have been disclosed in the patent applications by NovaSAID AB (WO2009/103778 and US2010/0324086) and Boehringer Ingelheim International GmbH (WO2011/048004).

BRIEF SUMMARY OF THE INVENTION

The present invention provides a novel heterocycle derivative or a pharmaceutically acceptable salt thereof. Also, the invention provides a pharmaceutical composition containing such heterocycle derivative or a pharmaceutically acceptable salt thereof as an active ingredient.

The present invention is based on the inventors' discovery that the novel heterocycle derivative or a pharmaceutically acceptable salt thereof, as described below, has an excellent mPGES-1 inhibiting activity.

The present invention provides a heterocycle derivative represented by the general formula [1] or its tautomer (hereinafter referred to as "compound of the invention"), or a pharmaceutically acceptable salt thereof.

[Chemical Formula 1]

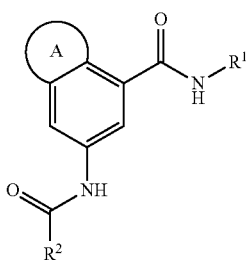

[1]

wherein ring A is a group represented by the general formula [2], [3] or [4]:

[Chemical Formula 2]

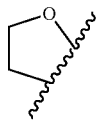

[2]

-continued

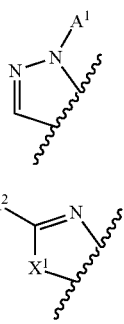

[3]

[4]

wherein
X¹ is NH, N-alkyl, or O;
A¹ is hydrogen or alkyl;
A² is
  i) hydrogen;
  ii) halogen;
  iii) alkyl optionally substituted with one to three groups selected from the group consisting of halogen, amino, monoalkylamino, dialkylamino, carbamoyl, monoalkylaminocarbonyl, dialkylaminocarbonyl, a saturated cyclic aminocarbonyl, alkoxy, alkoxyalkoxy and alkylcarbonyloxy;
  iv) cycloalkyl optionally substituted with alkyl optionally substituted with one to three halogens;
  v) alkoxy;
  vi) a saturated heterocycle group optionally substituted with alkyl, alkyloxycarbonyl, alkylcarbonyl or oxo;
  vii) alkylthio;
  viii) alkylsulfonyl;
  ix) alkylsulfinyl;
  x) a group represented by the general formula [5]:

[Chemical Formula 3]

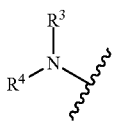

[5]

wherein R³ and R⁴ are the same or different group selected from
    a) hydrogen,
    b) alkyl optionally substituted with a group selected from the group consisting of monoalkylamino, dialkylamino, a saturated cyclic amino optionally substituted with alkyl, a saturated heterocycle group optionally substituted with alkyl, alkoxy, hydroxycarbonyl, hydroxyl, alkyloxycarbonyl and alkylthio, or
    c) cycloalkyl; or
  xi) a saturated cyclic amino optionally substituted with alkyl, amino, monoalkylamino, dialkylamino, alkoxy or hydroxyl;
R¹ is phenyl, benzyl, naphthyl, cycloalkyl, cycloalkylmethyl, heteroaryl, heteroarylmethyl, 1,2,3,4-tetrahydronaphthalen-5-yl, 1,2,3,4-tetrahydronaphthalen-6-yl, 2,3-dihydro-1H-inden-4-yl, 2,3-dihydro-1H-inden-5-yl, 1,2-dihydrocyclobutabenzen-3-yl, 1,2-dihydrocyclobutabenzen-4-yl or alkyl, wherein said phenyl, benzyl, cycloalkyl, cycloalkylmethyl, heteroaryl and heteroarylmethyl is optionally substituted with one to three groups selected from the group consisting of
  i) halogen,
  ii) alkyl optionally substituted with one to three groups selected from the group consisting of halogen, hydroxy and phenyl,
  iii) alkoxy,
  iv) hydroxy, and
  v) cyano; and
R² is phenyl or pyridyl,
  wherein said phenyl and pyridyl is optionally substituted with one to three groups selected from the group consisting of
  i) halogen,
  ii) alkylsulfonyl,
  iii) alkoxy optionally substituted with one to three halogens or alkoxy;
  iv) alkynyl optionally substituted with alkoxyalkyl or cycloalkyl, and
  v) alkyl optionally substituted with one to three groups selected from the group consisting of alkoxy, alkoxyalkoxy, cycloalkyl, phenyl and halogen.

A preferred embodiment of the invention is any one of the following (A) to (C), or a pharmaceutically acceptable salt thereof:
  (A) a compound of the invention or a pharmaceutically acceptable salt thereof, wherein the ring A is a group of formula [4] and X¹ is NH;
  (B) a compound of the invention or a pharmaceutically acceptable salt thereof, wherein R¹ is phenyl, 1,2,3,4-tetrahydronaphthalen-5-yl, 1,2,3,4-tetrahydronaphthalen-6-yl, 2,3-dihydro-1H-inden-4-yl, 2,3-dihydro-1H-inden-5-yl, 1,2-dihydrocyclobutabenzen-3-yl, or 1,2-dihydrocyclobutabenzen-4-yl, and said phenyl is optionally substituted with one to three groups selected from the group consisting of
    i) halogen,
    ii) alkyl optionally substituted with one to three halogens,
    iii) alkoxy, and
    iv) cyano; or
  (C) a compound of the invention or a pharmaceutically acceptable salt thereof, wherein R² is phenyl and said phenyl is optionally substituted with one to three groups selected from the group consisting of
    i) halogen
    ii) alkylsulfonyl,
    iii) alkoxy optionally substituted with alkoxy,
    iv) alkynyl optionally substituted with alkoxyalkyl or cycloalkyl, and
    v) alkyl optionally substituted with one to three groups selected from the group consisting of halogen, alkoxy, alkoxyalkyl, cycloalkyl and phenyl.

A more preferred embodiment of the invention is a compound of the invention or a pharmaceutically acceptable salt thereof, wherein
the ring A is a group of formula [4],
X¹ is NH,
A² is
  i) hydrogen,
  ii) alkyl optionally substituted with a group selected from the group consisting of halogen, monoalkylamino, dialkylamino, monoalkylaminocarbonyl, dialkylaminocarbonyl, a saturated cyclic aminocarbonyl, alkoxy, alkoxyalkoxy and alkylcarbonyloxy, iii) cycloalkyl optionally substituted with alkyl optionally substituted with one to three halogens,
iv) alkoxy,
v) a saturated heterocyclic group optionally substituted with alkyl or alkyloxycarbonyl,
vi) alkylthio,
vii) alkylsulfonyl,
viii) alkylsulfinyl,
ix) amino substituted with alkyl wherein said alkyl is optionally substituted with a group selected from the group consisting of monoalkylamino, dialkylamino, a saturated cyclic amino optionally substituted with alkyl, tetrahydrofuryl, morpholino, alkoxy, hydroxycarbonyl, hydroxyl and alkylthio,
x) amino substituted with cycloalkyl or
xi) a saturated cyclic amino optionally substituted with alkyl, dialkylamino, alkoxy or hydroxyl, and $R^1$ is
i) phenyl optionally substituted with one to three groups selected from the group consisting of halogen, alkyl optionally substituted with one to three halogens, alkoxy and cyano,
ii) 1,2,3,4-tetrahydronaphthalen-5-yl,
iii) 2,3-dihydro-1H-inden-5-yl,
iv) benzyl optionally substituted with halogen or alkyl optionally substituted with one to three halogens,
v) cycloalkyl,
vi) cycloalkylmethyl,
vii) naphthyl,
viii) pyridylmethyl optionally substituted with alkyl optionally substituted one to three halogens,
ix) thienyl,
x) thienylmethyl,
xi) benzothiazolyl,
xii) benzothiadiazolyl,
xiii) indolyl or
xiv) alkyl, and $R^2$ is phenyl or pyridyl
wherein said phenyl is optionally substituted with one to three groups selected from the group consisting of
i) halogen,
ii) alkylsulfonyl,
iii) alkoxy optionally substituted with alkoxy,
iv) alkynyl optionally substituted with alkoxyalkyl or cycloalkyl, and
v) alkyl optionally substituted with one to three groups selected from the group consisting of halogen, alkoxy, alkoxyalkoxy, cycloalkyl and phenyl, and
said pyridyl is optionally substituted with halogen.

A further more preferred embodiment of the invention is a compound of the invention or a pharmaceutically acceptable salt thereof, wherein
the ring A is a group of formula [4],
$X^1$ is NH,
$A^2$ is alkyl substituted with alkoxy, dialkylamino, tetrahydrofuryl, tetrahydrofurylmethyl, alkoxyalkylamino, or cycloalkyl optionally substituted with alkyl optionally substituted with one to three halogens,
$R^1$ is phenyl substituted with one halogen and one methyl, and
$R^2$ is phenyl optionally substituted with one trifluoromethyl or two halogens.

A particularly preferred embodiment of the invention is any one of the following (1)-(239), or its tautomer or a pharmaceutically acceptable salt thereof:

(1) N-[2-(trifluoromethyl)benzyl]-6-({[2-(trifluoromethyl)phenyl]carbonyl}amino)-1H-benzimidazole-4-carboxamide,
(2) N-cyclohexyl-6-({[2-(trifluoromethyl)phenyl]carbonyl}amino)-1H-benzimidazole-4-carboxamide,
(3) N-(3-chloro-2-methylphenyl)-6-({[2-(trifluoromethyl)phenyl]carbonyl}amino)-1H-benzimidazole-4-carboxamide,
(4) N-[(1-hydroxycyclohexyl)methyl]-6-({[2-(trifluoromethyl)phenyl]carbonyl}amino)-1H-benzimidazole-4-carboxamide,
(5) N-[2-(trifluoromethyl)benzyl]-5-({[2-(trifluoromethyl)phenyl]carbonyl}amino)-2,3-dihydro-1-benzofuran-7-carboxamide,
(6) N-cyclohexyl-5-({[2-(trifluoromethyl)phenyl]carbonyl}amino)-2,3-dihydro-1-benzofuran-7-carboxamide,
(7) N-(3-chloro-2-methylphenyl)-5-({[2-(trifluoromethyl)phenyl]carbonyl}amino)-2,3-dihydro-1-benzofuran-7-carboxamide,
(8) N-cyclohexyl-5-({[2-(trifluoromethyl)phenyl]carbonyl}amino)-1H-indazole-7-carboxamide,
(9) N-[2-(trifluoromethyl)benzyl]-5-({[2-(trifluoromethyl)phenyl]carbonyl}amino)-1H-indazole-7-carboxamide,
(10) N-(3-chloro-2-methylphenyl)-2-(methoxymethyl)-6-({[2-(trifluoromethyl)phenyl]carbonyl}amino)-1H-benzimidazole-4-carboxamide,
(11) 2-methyl-N-[2-(trifluoromethyl)benzyl]-6-({[2-(trifluoromethyl)phenyl]carbonyl}amino)-1H-benzimidazole-4-carboxamide,
(12) N-cyclohexyl-2-methyl-6-({[2-(trifluoromethyl)phenyl]carbon yl}amino)-1H-benzimidazole-4-carboxamide,
(13) N-(3-chloro-2-methylphenyl)-2-methyl-6-({[2-(trifluoromethyl)phenyl]carbonyl}amino)-1H-benzimidazole-4-carboxamide,
(14) N-cyclopentyl-2-methyl-6-({[2-(trifluoromethyl)phenyl]carbonyl}amino)-1H-benzimidazole-4-carboxamide,
(15) N-cyclobutyl-2-methyl-6-({[2-(trifluoromethyl)phenyl]carbon yl}amino)-1H-benzimidazole-4-carboxamide,
(16) N-(3-chloro-2-methylphenyl)-2-ethyl-6-({[2-(trifluoromethyl)phenyl]carbonyl}amino)-1H-benzimidazole-4-carboxamide,
(17) N-cyclohexyl-2-ethyl-6-({[2-(trifluoromethyl)phenyl]carbonyl}amino)-1H-benzimidazole-4-carboxamide,
(18) 2-ethyl-N-[2-(trifluoromethyl)benzyl]-6-({[2-(trifluoromethyl)phenyl]carbonyl}amino)-1H-benzimidazole-4-carboxamide,
(19) N-cyclohexyl-2-(methoxymethyl)-6-({[2-(trifluoromethyl)phenyl]carbonyl}amino)-1H-benzimidazole-4-carboxamide,
(20) 2-(methoxymethyl)-N-[2-(trifluoromethyl)benzyl]-6-({[2-(tri fluoromethyl)phenyl]carbonyl}amino)-1H-benzimidazole-4-carboxamide,
(21) 2-(methoxymethyl)-N-(2-methylphenyl)-6-({[2-(trifluoromethyl)phenyl]carbonyl}amino)-1H-benzimidazole-4-carboxamide,
(22) 2-(methoxymethyl)-N-(4-methylphenyl)-6-({[2-(trifluoromethyl)phenyl]carbonyl}amino)-1H-benzimidazole-4-carboxamide,
(23) N-(2-chlorobenzyl)-2-(methoxymethyl)-6-({[2-(trifluoromethyl)phenyl]carbonyl}amino)-1H-benzimidazole-4-carboxamide,
(24) 2-(methoxymethyl)-N-(4-methylbenzyl)-6-({[2-(trifluoromethyl)phenyl]carbonyl}amino)-1H-benzimidazole-4-carboxamide,
(25) N-(4,4-difluorocyclohexyl)-2-(methoxymethyl)-6-({[2-(trifluoromethyl)phenyl]carbonyl}amino)-1H-benzimidazole-4-carboxamide,

(26) N-(4-tert-butylphenyl)-2-(methoxymethyl)-6-({[2-(trifluoromethyl)phenyl]carbonyl}amino)-1H-benzimidazole-4-carboxamide,
(27) 2-(methoxymethyl)-N-[4-(trifluoromethyl)phenyl]-6-({[2-(tri fluoromethyl)phenyl]carbonyl}amino)-1H-benzimidazole-4-carboxamide,
(28) N-(2,4-dimethylphenyl)-2-(methoxymethyl)-6-({[2-(trifluoromethyl)phenyl]carbonyl}amino)-1H-benzimidazole-4-carboxamide,
(29) N-(2-chloro-4-methylphenyl)-2-(methoxymethyl)-6-({[2-(trifluoromethyl)phenyl]carbonyl}amino)-1H-benzimidazole-4-carboxamide,
(30) N-(3,4-dimethylphenyl)-2-(methoxymethyl)-6-({[2-(trifluoromethyl)phenyl]carbonyl}amino)-1H-benzimidazole-4-carboxamide,
(31) N-(3-chloro-4-methylphenyl)-2-(methoxymethyl)-6-({[2-(trifluoromethyl)phenyl]carbonyl}amino)-1H-benzimidazole-4-carboxamide,
(32) N-(2,3-dihydro-1H-inden-5-yl)-2-(methoxymethyl)-6-({[2-(tri fluoromethyl)phenyl]carbonyl}amino)-1H-benzimidazole-4-carboxamide,
(33) 2-(methoxymethyl)-N-(5,6,7,8-tetrahydronaphthalen-1-yl)-6-({[2-(trifluoromethyl)phenyl]carbonyl}amino)-1H-benzimidazole-4-carboxamide,
(34) N-(2-fluorophenyl)-2-(methoxymethyl)-6-({[2-(trifluoromethyl)phenyl]carbonyl}amino)-1H-benzimidazole-4-carboxamide,
(35) 2-(methoxymethyl)-N-(2-methoxyphenyl)-6-({[2-(trifluoromethyl)phenyl]carbonyl}amino)-1H-benzimidazole-4-carboxamide,
(36) 2-(methoxymethyl)-N-(4-methoxyphenyl)-6-({[2-(trifluoromethyl)phenyl]carbonyl}amino)-1H-benzimidazole-4-carboxamide,
(37) N-(3-bromo-2-methylphenyl)-2-(methoxymethyl)-6-({[2-(trifluoromethyl)phenyl]carbonyl}amino)-1H-benzimidazole-4-carboxamide,
(38) N-(3-chloro-2-methylbenzyl)-2-(methoxymethyl)-6-({[2-(trifluoromethyl)phenyl]carbonyl}amino)-1H-benzimidazole-4-carboxamide,
(39) N-(2,6-difluorophenyl)-2-(methoxymethyl)-6-({[2-(trifluoromethyl)phenyl]carbonyl}amino)-1H-benzimidazole-4-carboxamide,
(40) N-(3-cyano-2-methylphenyl)-2-(methoxymethyl)-6-({[2-(trifluoromethyl)phenyl]carbonyl}amino)-1H-benzimidazole-4-carboxamide,
(41) 2-(methoxymethyl)-6-({[2-(trifluoromethyl)phenyl]carbonyl}amino)-N-{[3-(trifluoromethyl)pyridin-2-yl]methyl}-1H-benzimidazole-4-carboxamide,
(42) N-(2-chloro-6-methylphenyl)-2-(methoxymethyl)-6-({[2-(trifluoromethyl)phenyl]carbonyl}amino)-1H-benzimidazole-4-carboxamide,
(43) 2-(2-amino-2-oxoethyl)-N-(3-chloro-2-methylphenyl)-6-({[2-(trifluoromethyl)phenyl]carbonyl}amino)-1H-benzimidazole-4-carboxamide,
(44) 2-(2-amino-2-oxoethyl)-N-[2-(trifluoromethyl)benzyl]-6-({[2-(trifluoromethyl)phenyl]carbonyl}amino)-1H-benzimidazole-4-carboxamide,
(45) N-(3-chloro-2-methylphenyl)-1-methyl-6-({[2-(trifluoromethyl)phenyl]carbonyl}amino)-1H-benzimidazole-4-carboxamide,
(46) N-cyclohexyl-1-methyl-6-({[2-(trifluoromethyl)phenyl]carbon yl}amino)-1H-benzimidazole-4-carboxamide,
(47) 1-methyl-N-[2-(trifluoromethyl)benzyl]-6-({[2-(trifluoromethyl)phenyl]carbonyl}amino)-1H-benzimidazole-4-carboxamide,
(48) N-(3-chloro-2-methylphenyl)-1-ethyl-6-({[2-(trifluoromethyl)phenyl]carbonyl}amino)-1H-benzimidazole-4-carboxamide,
(49) N-cyclohexyl-1-ethyl-6-({[2-(trifluoromethyl)phenyl]carbonyl}amino)-1H-benzimidazole-4-carboxamide,
(50) 1-ethyl-N-[2-(trifluoromethyl)benzyl]-6-({[2-(trifluoromethyl)phenyl]carbonyl}amino)-1H-benzimidazole-4-carboxamide,
(51) N-(3-chloro-2-methylphenyl)-2-methyl-6-({[2-(trifluoromethyl)phenyl]carbonyl}amino)-1,3-benzoxazole-4-carboxamide,
(52) 2-methyl-N-[2-(trifluoromethyl)benzyl]-6-({[2-(trifluoromethyl)phenyl]carbonyl}amino)-1,3-benzoxazole-4-carboxamide,
(53) N-(3-chloro-2-methylphenyl)-2-ethyl-6-({[2-(trifluoromethyl)phenyl]carbonyl}amino)-1,3-benzoxazole-4-carboxamide,
(54) N-(3-chloro-2-methylphenyl)-2-ethoxy-6-({[2-(trifluoromethyl)phenyl]carbonyl}amino)-1H-benzimidazole-4-carboxamide,
(55) 2-ethoxy-N-[2-(trifluoromethyl)benzyl]-6-({[2-(trifluoromethyl)phenyl]carbonyl}amino)-1H-benzimidazole-4-carboxamide,
(56) N-(3-chloro-2-methylphenyl)-2-(1-chloro-2-methylpropan-2-yl)-6-({[2-(trifluoromethyl)phenyl]carbonyl}amino)-1H-benzimidazole-4-carboxamide,
(57) N-(3-chloro-2-methylphenyl)-2-[(dimethylamino)methyl]-6-({[2-(trifluoromethyl)phenyl]carbonyl}amino)-1H-benzimidazole-4-carboxamide,
(58) N-(3-chloro-2-methylphenyl)-2-(2-methylpropyl)-6-({[2-(trifluoromethyl)phenyl]carbonyl}amino)-1H-benzimidazole-4-carboxamide,
(59) 2-(2-methylpropyl)-N-[2-(trifluoromethyl)benzyl]-6-({[2-(trifluoromethyl)phenyl]carbonyl}amino)-1H-benzimidazole-4-carboxamide,
(60) tert-butyl 3-{4-[(3-chloro-2-methylphenyl)carbamoyl]-6-({[2-(trifluoro methyl)phenyl]carbonyl}amino)-1H-benzimidazol-2-yl}azetidine-1-carboxylate,
(61) N-(3-chloro-2-methylphenyl)-2-[(methylamino)methyl]-6-({[2-(trifluoromethyl)phenyl]carbonyl}amino)-1H-benzimidazole-4-carboxamide,
(62) {4-[(3-chloro-2-methylphenyl)carbamoyl]-6-({[2-(trifluoromethyl)phenyl]carbonyl}amino)-1H-benzimidazol-2-yl}methyl acetate,
(63) N-(3-chloro-2-methylphenyl)-2-[(2R)-tetrahydrofuran-2-yl]-6-({[2-(trifluoromethyl)phenyl]carbonyl}amino)-1H-benzimidazole-4-carboxamide,
(64) 2-[(2R)-tetrahydrofuran-2-yl]-N-[2-(trifluoromethyl)benzyl]-6-({[2-(trifluoromethyl)phenyl]carbonyl}amino)-1H-benzimidazole-4-carboxamide,
(65) N-(3-chloro-2-methylphenyl)-2-[(2S)-tetrahydrofuran-2-yl]-6-({[2-(trifluoromethyl)phenyl]carbonyl}amino)-1H-benzimidazole-4-carboxamide,
(66) 2-[(2S)-tetrahydrofuran-2-yl]-N-[2-(trifluoromethyl)benzyl]-6-({[2-(trifluoromethyl)phenyl]carbonyl}amino)-1H-benzimidazole-4-carboxamide,
(67) 2-(1-acetylazetidin-3-yl)-N-(3-chloro-2-methylphenyl)-6-({[2-(trifluoromethyl)phenyl]carbonyl}amino)-1H-benzimidazole-4-carboxamide,
(68) tert-butyl (2S)-2-{4-[(3-chloro-2-methylphenyl)carbamoyl]-6-({[2-(trifluoromethyl)phenyl]carbonyl}amino)-1H-benzimidazol-2-yl}pyrrolidine-1-carboxylate,
(69) tert-butyl (2R)-2-{4-[(3-chloro-2-methylphenyl)carbamoyl]-6-({[2-(trifluoromethyl)phenyl]carbonyl}amino)-1H-benzimidazol-2-yl}pyrrolidine-1-carboxylate,

(70) N-(3-chloro-2-methylphenyl)-2-[(2S)-pyrrolidin-2-yl]-6-({[2-(trifluoromethyl)phenyl]carbonyl}amino)-1H-benzimidazole-4-carboxamide,
(71) N-(3-chloro-2-methylphenyl)-2-[(2S)-1-methylpyrrolidin-2-yl]-6-({[2-(trifluoromethyl)phenyl]carbonyl}amino)-1H-benzimidazole-4-carboxamide,
(72) 2-[(2S)-1-acetylpyrrolidin-2-yl]-N-(3-chloro-2-methylphenyl)-6-({[2-(trifluoromethyl)phenyl]carbonyl}amino)-1H-benzimidazole-4-carboxamide,
(73) N-(3-chloro-2-methylphenyl)-2-[(2-methoxyethoxy)methyl]-6-({[2-(trifluoromethyl)phenyl]carbonyl}amino)-1H-benzimidazole-4-carboxamide,
(74) N-(3-chloro-2-methylphenyl)-2-(1-methoxy-2-methylpropan-2-yl)-6-({[2-(trifluoromethyl)phenyl]carbonyl}amino)-1H-benzimidazole-4-carboxamide,
(75) 2-tert-butyl-N-(3-chloro-2-methylphenyl)-6-({[2-(trifluoromethyl)phenyl]carbonyl}amino)-1H-benzimidazole-4-carboxamide,
(76) 2-tert-butyl-6-({[2-(trifluoromethyl)phenyl]carbonyl}amino)-N-{[3-(trifluoromethyl)pyridin-2-yl]methyl}-1H-benzimidazole-4-carboxamide,
(77) N-(3-chloro-2-methylphenyl)-2-(2-ethoxyethyl)-6-({[2-(trifluoromethyl)phenyl]carbonyl}amino)-1H-benzimidazole-4-carboxamide,
(78) N-(3-chloro-2-methylphenyl)-2-(ethoxymethyl)-6-({[2-(trifluoromethyl)phenyl]carbonyl}amino)-1H-benzimidazole-4-carboxamide,
(79) 2-(ethoxymethyl)-6-({[2-(trifluoromethyl)phenyl]carbonyl}amino)-N-{[3-(trifluoromethyl)pyridin-2-yl]methyl}-1H-benzimidazole-4-carboxamide,
(80) N-(3-chloro-2-methylphenyl)-2-(2-methoxyethyl)-6-({[2-(trifluoromethyl)phenyl]carbonyl}amino)-1H-benzimidazole-4-carboxamide,
(81) N-(3-chloro-2-methylphenyl)-2-(2,2-dimethylpropyl)-6-({[2-(trifluoromethyl)phenyl]carbonyl}amino)-1H-benzimidazole-4-carboxamide,
(82) N-(3-chloro-2-methylphenyl)-2-cyclopropyl-6-({[2-(trifluoro methyl)phenyl]carbonyl}amino)-1H-benzimidazole-4-carboxamide,
(83) N-(3-chloro-2-methylphenyl)-2-(2-methylpentan-2-yl)-6-({[2-(trifluoromethyl)phenyl]carbonyl}amino)-1H-benzimidazole-4-carboxamide,
(84) N-(3-chloro-2-methylphenyl)-2-(1-methylcyclopropyl)-6-({[2-(trifluoromethyl)phenyl]carbonyl}amino)-1H-benzimidazole-4-carboxamide,
(85) 2-tert-butyl-N-(3-chloro-4-methylphenyl)-6-({[2-(trifluoromethyl)phenyl]carbonyl}amino)-1H-benzimidazole-4-carboxamide,
(86) 2-tert-butyl-N-(3-chloro-2-methylphenyl)-6-{[(2,5-dichlorophenyl)carbonyl]amino}-1H-benzimidazole-4-carboxamide,
(87) 2-tert-butyl-N-(3-chloro-4-methylphenyl)-6-{[(2,5-dichlorophenyl)carbonyl]amino}-1H-benzimidazole-4-carboxamide,
(88) N-(3-chloro-2-methylphenyl)-2-[1-(trifluoromethyl)cyclopropyl]-6-({[2-(trifluoromethyl)phenyl]carbonyl}amino)-1H-benzimidazole-4-carboxamide,
(89) N-(3-chloro-2-methylphenyl)-2-(methoxymethyl)-1-methyl-6-({[2-(trifluoromethyl)phenyl]carbonyl}amino)-1H-benzimidazole-4-carboxamide,
(90) N-(2-chlorobenzyl)-2-(methoxymethyl)-1-methyl-6-({[2-(trifluoromethyl)phenyl]carbonyl}amino)-1H-benzimidazole-4-carboxamide,
(91) 6-{[(2-chloro-6-fluorophenyl)carbonyl]amino}-N-(3-chloro-2-methylphenyl)-2-(methoxymethyl)-1H-benzimidazole-4-carboxamide,
(92) 6-{[(2-chloro-4-fluorophenyl)carbonyl]amino}-N-(3-chloro-2-methylphenyl)-2-methoxymethyl-1H-benzimidazole-4-carboxamide,
(93) 6-{[(2-chloro-5-fluorophenyl)carbonyl]amino}-N-(3-chloro-2-methylphenyl)-2-(methoxymethyl)-1H-benzimidazole-4-carboxamide,
(94) N-(3-chloro-2-methylphenyl)-6-{[(2-chlorophenyl)carbonyl]amino}-2-(methoxymethyl)-1H-benzimidazole-4-carboxamide,
(95) N-(3-chloro-2-methylphenyl)-2-[(2-chloropyridin-3-yl)carbonyl]amino}-2-(methoxymethyl)-1H-benzimidazole-4-carboxamide,
(96) 6-{[(2-bromophenyl)carbonyl]amino}-N-(3-chloro-2-methylphenyl)-2-(methoxymethyl)-1H-benzimidazole-4-carboxamide,
(97) N-(3-chloro-2-methylphenyl)-6-{[(2,6-dichlorophenyl)carbonyl]amino}-2-(methoxymethyl)-1H-benzimidazole-4-carboxamide,
(98) N-(3-chloro-2-methylphenyl)-6-{[(2,5-dichlorophenyl)carbonyl]amino}-2-(methoxymethyl)-1H-benzimidazole-4-carboxamide,
(99) 6-{[(2-chloro-3-fluorophenyl)carbonyl]amino}-N-(3-chloro-2-methylphenyl)-2-(methoxymethyl)-1H-benzimidazole-4-carboxamide,
(100) 6-{[(2-chloro-3,6-difluorophenyl)carbonyl]amino}-N-(3-chloro-2-methylphenyl)-2-(methoxymethyl)-1H-benzimidazole-4-carboxamide,
(101) 6-{[(2-bromo-6-chlorophenyl)carbonyl]amino}-N-(3-chloro-2-m ethylphenyl)-2-(methoxymethyl)-1H-benzimidazole-4-carboxamide,
(102) 6-{[(2-bromo-6-fluorophenyl)carbonyl]amino}-N-(3-chloro-2-m ethylphenyl)-2-(methoxymethyl)-1H-benzimidazole-4-carboxamide,
(103) N-(3-chloro-2-methylphenyl)-6-{[(2-chloro-6-methylphenyl)carbonyl]amino}-2-(methoxymethyl)-1H-benzimidazole-4-carboxamide,
(104) N-(3-chloro-2-methylphenyl)-6-{[(2-chloro-4-methylphenyl)carbonyl]amino}-2-(methoxymethyl)-1H-benzimidazole-4-carboxamide,
(105) 6-{[(5-bromo-2-chlorophenyl)carbonyl]amino}-N-(3-chloro-2-m ethylphenyl)-2-(methoxymethyl)-1H-benzimidazole-4-carboxamide,
(106) 6-{[(2-bromo-5-chlorophenyl)carbonyl]amino}-N-(3-chloro-2-methylphenyl)-2-(methoxymethyl)-1H-benzimidazole-4-carboxamide,
(107) N-(3-chloro-2-methylphenyl)-6-{[(2-chloro-5-methylphenyl)carbonyl]amino}-2-(methoxymethyl)-1H-benzimidazole-4-carboxamide,
(108) N-(3-chloro-2-methylphenyl)-2-(methoxymethyl)-6-({[5-methyl-2-(trifluoromethyl)phenyl]carbonyl}amino)-1H-benzimidazole-4-carboxamide,
(109) 6-({[2,5-bis(trifluoromethyl)phenyl]carbonyl}amino)-N-(3-chloro-2-methylphenyl)-2-(methoxymethyl)-1H-benzimidazole-4-carboxamide,
(110) 6-({[2,4-bis(trifluoromethyl)phenyl]carbonyl}amino)-N-(3-chloro-2-methylphenyl)-2-(methoxymethyl)-1H-benzimidazole-4-carboxamide,
(111) N-(3-chloro-2-methylphenyl)-6-({[5-fluoro-2-(trifluoromethyl)phenyl]carbonyl}amino)-2-(methoxymethyl)-1H-benzimidazole-4-carboxamide,
(112) N-(3-chloro-2-methylphenyl)-6-({[2-chloro-6-(trifluoromethyl)phenyl]carbonyl}amino)-2-(methoxymethyl)-1H-benzimidazole-4-carboxamide,
(113) N-(3-chloro-2-methylphenyl)-6-[({2-chloro-5-[2-(propan-2-yl oxy)ethoxy]phenyl}carbonyl)amino]-2-(methoxymethyl)-1H-benz imidazole-4-carboxamide, (114) 6-({[2-chloro-5-(2-ethoxyethoxy)phenyl]carbonyl}amino)-N-(3-chloro-2-methylphenyl)-2-(methoxymethyl)-1H-benzimidazole-4-carboxamide,
(115) 6-({[2-chloro-5-(3-methoxypropyl)phenyl]carbonyl}amino)-N-(3-chloro-2-methylphenyl)-2-(methoxymethyl)-1H-benzimidazole-4-carboxamide,
(116) 6-({[5-(3-tert-butoxyprop-1-yn-1-yl)-2-chlorophenyl]carbonyl}amino)-N-(3-chloro-2-methylphenyl)-2-(methoxymethyl)-1H-benzimidazole-4-carboxamide,
(117) 6-({[5-(3-tert-butoxypropyl)-2-chlorophenyl]carbonyl}amino)-N-(3-chloro-2-methylphenyl)-2-(methoxymethyl)-1H-benzimidazole-4-carboxamide,
(118) 6-({[2-chloro-5-(3-hydroxy-3-methylbutyl)phenyl]carbonyl}amino)-N-(3-chloro-2-methylphenyl)-2-(methoxymethyl)-1H-benzimidazole-4-carboxamide,
(119) 6-({[2-chloro-5-(ethoxymethyl)phenyl]carbonyl}amino)-N-(3-chloro-2-methylphenyl)-2-(methoxymethyl)-1H-benzimidazole-4-carboxamide,
(120) 6-[({2-chloro-5-[(2-ethoxyethoxy)methyl]phenyl}carbonyl)amino]-N-(3-chloro-2-methylphenyl)-2-(methoxymethyl)-1H-benzimidazole-4-carboxamide,
(121) 6-({[2-chloro-5-(2-cyclopropylethyl)phenyl]carbonyl}amino)-N-(3-chloro-2-methylphenyl)-2-(methoxymethyl)-1H-benzimidazole-4-carboxamide,
(122) N-(3-chloro-2-methylphenyl)-6-({[2-chloro-5-(2-phenylethyl)phenyl]carbonyl}amino)-2-(methoxymethyl)-1H-benzimidazole-4-carboxamide,
(123) N-(3-chloro-2-methylphenyl)-2-cyclopentyl-6-({[2-(trifluoro methyl)phenyl]carbonyl}amino)-1H-benzimidazole-4-carboxamide,
(124) N-(3-chloro-2-methylphenyl)-2-cyclopentyl-6-{[(2,5-dichloro phenyl)carbonyl]amino}-1H-benzimidazole-4-carboxamide,
(125) 6-{[(2-chloro-6-fluorophenyl)carbonyl]amino}-N-(3-chloro-2-methylphenyl)-2-cyclopentyl-1H-benzimidazole-4-carboxamide,
(126) 6-{[(2-chloro-6-fluorophenyl)carbonyl]amino}-N-(3-chloro-2-methylphenyl)-2-[(2R)-tetrahydrofuran-2-yl]-1H-benzimidazole-4-carboxamide,
(127) N-(3-chloro-2-methylphenyl)-6-{[(2,6-dichlorophenyl)carbonyl]amino}-2-[(2R)-tetrahydrofuran-2-yl]-1H-benzimidazole-4-carboxamide,
(128) N-(3-chloro-2-methylphenyl)-6-{[(2,5-dichlorophenyl)carbonyl]amino}-2-[(2R)-tetrahydrofuran-2-yl]-1H-benzimidazole-4-carboxamide,
(129) N-(3-chloro-2-methylphenyl)-2-[(2S)-5-oxopyrrolidin-2-yl]-6-({[2-(trifluoromethyl)phenyl]carbonyl}amino)-1H-benzimidazole-4-carboxamide,
(130) N-(3-chloro-2-methylphenyl)-2-[(2R)-5-oxopyrrolidin-2-yl]-6-({[2-(trifluoromethyl)phenyl]carbonyl}amino)-1H-benzimidazole-4-carboxamide,
(131) N-(3-chloro-2-methylphenyl)-2-[2-oxo-2-(pyrrolizin-1-yl)ethyl]-6-({[2-(trifluoromethyl)phenyl]carbonyl}amino)-1H-benzimidazole-4-carboxamide,
(132) N-(3-chloro-2-methylphenyl)-2-[2-(dimethylamino)-2-oxoethyl]-6-({[2-(trifluoromethyl)phenyl]carbonyl}amino)-1H-benzimidazole-4-carboxamide,
(133) N-(3-chloro-2-methylphenyl)-2-[2-(methylamino)-2-oxoethyl]-6-({[2-(trifluoromethyl)phenyl]carbonyl}amino)-1H-benzimidazole-4-carboxamide,
(134) 2-chloro-N-(3-chloro-2-methylphenyl)-6-({[2-(trifluoromethyl)phenyl]carbonyl}amino)-1H-benzimidazole-4-carboxamide,
(135) N-(3-chloro-2-methylphenyl)-2-[(2-methoxyethyl)amino]-6-({[2-(trifluoromethyl)phenyl]carbonyl}amino)-1H-benzimidazole-4-carboxamide,
(136) N-(3-chloro-2-methylphenyl)-2-[(2-hydroxyethyl)amino]-6-({[2-(trifluoromethyl)phenyl]carbonyl}amino)-1H-benzimidazole-4-carboxamide,
(137) N-(3-chloro-2-methylphenyl)-2-(methylamino)-6-({[2-(trifluoromethyl)phenyl]carbonyl}amino)-1H-benzimidazole-4-carboxamide,
(138) N-(3-chloro-2-methylphenyl)-2-(ethylamino)-6-({[2-(trifluoromethyl)phenyl]carbonyl}amino)-1H-benzimidazole-4-carboxamide,
(139) N-(3-chloro-2-methylphenyl)-2-[(2,2-dimethylpropyl)amino]-6-({[2-(trifluoromethyl)phenyl]carbonyl}amino)-1H-benzimidazole-4-carboxamide,
(140) N-(3-chloro-2-methylphenyl)-2-(cyclopentylamino)-6-({[2-(trifluoromethyl)phenyl]carbonyl}amino)-1H-benzimidazole-4-carboxamide,
(141) N-(3-chloro-2-methylphenyl)-2-(piperidin-1-yl)-6-({[2-(trifluoromethyl)phenyl]carbonyl}amino)-1H-benzimidazole-4-carboxamide,
(142) N-(3-chloro-2-methylphenyl)-2-(4-methylpiperazin-1-yl)-6-({[2-(trifluoromethyl)phenyl]carbonyl}amino)-1H-benzimidazole-4-carboxamide,
(143) 2-[bis(2-hydroxyethyl)amino]-N-(3-chloro-2-methylphenyl)-6-({[2-(trifluoromethyl)phenyl]carbonyl}amino)-1H-benzimidazole-4-carboxamide,
(144) N-(3-chloro-2-methylphenyl)-2-(dimethylamino)-6-({[2-(trifluoromethyl)phenyl]carbonyl}amino)-1H-benzimidazole-4-carboxamide,
(145) N-(3-chloro-2-methylphenyl)-2-{[2-(morpholin-4-yl)ethyl]amino}-6-({[2-(trifluoromethyl)phenyl]carbonyl}amino)-1H-benzimidazole-4-carboxamide,
(146) N-(3-chloro-2-methylphenyl)-2-{[2-(dimethylamino)ethyl]amino}-6-({[2-(trifluoromethyl)phenyl]carbonyl}amino)-1H-benzimidazole-4-carboxamide,
(147) N-(3-chloro-2-methylphenyl)-2-(3-hydroxyazetidin-1-yl)-6-({[2-(trifluoromethyl)phenyl]carbonyl}amino)-1H-benzimidazole-4-carboxamide,
(148) N-(3-chloro-2-methylphenyl)-2-[(3S)-3-(dimethylamino)pyrrolizin-1-yl]-6-({[2-(trifluoromethyl)phenyl]carbonyl}amino)-1H-benzimidazole-4-carboxamide,
(149) N-(3-chloro-2-methylphenyl)-2-[(3S)-3-hydroxypyrrolizin-1-yl]-6-({[2-(trifluoromethyl)phenyl]carbonyl}amino)-1H-benzimidazole-4-carboxamide,
(150) N-(3-chloro-2-methylphenyl)-2-{[2-(diethylamino)ethyl]amino}-6-({[2-(trifluoromethyl)phenyl]carbonyl}amino)-1H-benzimidazole-4-carboxamide,
(151) N-(3-chloro-2-methylphenyl)-2-{[2-(pyrrolizin-1-yl)ethyl]amino}-6-({[2-(trifluoromethyl)phenyl]carbonyl}amino)-1H-benz imidazole-4-carboxamide,
(152) N-(3-chloro-2-methylphenyl)-2-{[3-(dimethylamino)propyl]amino}-6-({[2-(trifluoromethyl)phenyl]carbonyl}amino)-1H-benzimidazole-4-carboxamide,
(153) N-(3-chloro-2-methylphenyl)-2-{[3-(dimethylamino)-2,2-dimethylpropyl]amino}-6-({[2-(trifluoromethyl)phenyl]carbonyl}amino)-1H-benzimidazole-4-carboxamide,
(154) N-(3-chloro-2-methylphenyl)-2-{[2-(dipropan-2-ylamino)ethyl]amino}-6-({[2-(trifluoromethyl)phenyl]carbonyl}amino)-1H-benzimidazole-4-carboxamide,
(155) N-(3-chloro-2-methylphenyl)-2-(morpholin-4-yl)-6-({[2-(trifluoromethyl)phenyl]carbonyl}amino)-1H-benzimidazole-4-carboxamide,
(156) 2-amino-N-(3-chloro-2-methylphenyl)-6-({[2-(trifluoromethyl)phenyl]carbonyl}amino)-1H-benzimidazole-4-carboxamide,
(157) N-(3-chloro-2-methylphenyl)-2-[(3-hydroxy-2,2-dimethylpropyl)amino]-6-({[2-(trifluoromethyl)phenyl]carbonyl}amino)-1H-benzimidazole-4-carboxamide, (158) N-(3-chloro-2-methylphenyl)-2-{[(3-methyloxetan-3-yl)methyl]amino}-6-({[2-(trifluoromethyl)phenyl]carbonyl}amino)-1H-benzimidazole-4-carboxamide, (159) tert-butyl N-{4-[(3-chloro-2-methylphenyl)carbamoyl]-6-({[2-(trifluoro methyl)phenyl]carbonyl}amino)-1H-benzimidazol-2-yl}glycinate, (160) N-{4-[(3-chloro-2-methylphenyl)carbamoyl-6-({[2-(trifluoro methyl)phenyl]carbonyl}amino)-1H-benzimidazol-2-yl}glycine, (161) N-(3-chloro-2-methylphenyl)-2-[(3-hydroxy-2,2-dimethylpropyl)amino]-1-methyl-6-({[2-(trifluoromethyl)phenyl]carbonyl}amino)-1H-benzimidazole-4-carboxamide, (162) N-(3-chloro-2-methylphenyl)-2-[(3-methoxy-2,2-dimethylpropyl)amino]-6-({[2-(trifluoromethyl)phenyl]carbonyl}amino)-1H-benzimidazole-4-carboxamide, (163) N-(3-chloro-2-methylphenyl)-2-(pyrrolizin-1-yl)-6-({[2-(tri fluoromethyl)phenyl]carbonyl}amino)-1H-benzimidazole-4-carb oxamide, (164) 2-(azetidin-1-yl)-N-(3-chloro-2-methylphenyl)-6-({[2-(trifluoromethyl)phenyl]carbonyl}amino)-1H-benzimidazole-4-carboxamide, (165) N-(3-chloro-2-methylphenyl)-2-(3-methoxyazetidin-1-yl)-6-({[2-(trifluoromethyl)phenyl]carbonyl}amino)-1H-benzimidazole-4-carboxamide, (166) N-(3-chloro-2-methylphenyl)-2-[(2-hydroxy-2-methylpropyl)amino]-6-({[2-(trifluoromethyl)phenyl]carbonyl}amino)-1H-benzimidazole-4-carboxamide, (167) N-(3-chloro-2-methylphenyl)-2-{[(2S)-tetrahydrofuran-2-ylmethyl]amino}-6-({[2-(trifluoromethyl)phenyl]carbonyl}amino)-1H-benzimidazole-4-carboxamide, (168) N-(3-chloro-2-methylphenyl)-2-{[(2R)-tetrahydrofuran-2-ylmethyl]amino}-6-({[2-(trifluoromethyl)phenyl]carbonyl}amino)-1H-benzimidazole-4-carboxamide, (169) N-(3-chloro-2-methylphenyl)-2-{[(2S)-1-hydroxy-3-methylbutan-2-yl]amino}-6-({[2-(trifluoromethyl)phenyl]carbonyl}amino-1H-benzimidazole-4-carboxamide, (170) N-(3-chloro-2-methylphenyl)-2-{[(2R)-1-hydroxy-3-methylbutan-2-yl]amino}-6-({[2-(trifluoromethyl)phenyl]carbonyl}amino-1H-benzimidazole-4-carboxamide, (171) N-(3-chloro-2-methylphenyl)-2-{[(2S)-1-hydroxy-3,3-dimethyl butan-2-yl]amino}-6-({[2-(trifluoromethyl)phenyl]carbonyl}amino)-1H-benzimidazole-4-carboxamide, (172) N-(3-chloro-2-methylphenyl)-2-[(3-methoxy-2,2-dimethylpropyl)(methyl)amino]-6-({[2-(trifluoromethyl)phenyl]carbonyl}amino)-1H-benzimidazole-4-carboxamide, (173) N-(3-chloro-2-methylphenyl)-2-[(3-methoxypropyl)amino]-6-({[2-(trifluoromethyl)phenyl]carbonyl}amino)-1H-benzimidazole-4-carboxamide, (174) N-(3-chloro-2-methylphenyl)-2-{[2-(propan-2-yloxy)ethyl]amino}-6-({[2-(trifluoromethyl)phenyl]carbonyl}amino)-1H-benzimidazole-4-carboxamide, (175) 2-[(2-tert-butoxyethyl)amino]-N-(3-chloro-2-methylphenyl)-6-({[2-(trifluoromethyl)phenyl]carbonyl}amino)-1H-benzimidazole-4-carboxamide, (176) N-(3-chloro-2-methylphenyl)-2-[(2-methoxy-2-methylpropyl)amino]-6-({[2-(trifluoromethyl)phenyl]carbonyl}amino)-1H-benz imidazole-4-carboxamide, (177) N-(3-chloro-2-methylphenyl)-2-{[2-(methylsulfanyl)ethyl]amino}-6-({[2-(trifluoromethyl)phenyl]carbonyl}amino)-1H-benzimidazole-4-carboxamide, (178) N-(3-chloro-2-methylphenyl)-2-(methylsulfanyl)-6-({[2-(trifluoromethyl)phenyl]carbonyl}amino)-1H-benzimidazole-4-carboxamide, (179) N-(3-chloro-2-methylphenyl)-2-(methylsulfonyl)-6-({[2-(trifluoromethyl)phenyl]carbonyl}amino)-1H-benzimidazole-4-carboxamide, (180) N-(3-chloro-2-methylphenyl)-2-(methylsulfinyl)-6-({[2-(trifluoromethyl)phenyl]carbonyl}amino)-1H-benzimidazole-4-carboxamide, (181) 6-{[(2-chloro-6-fluorophenyl)carbonyl]amino}-N-(3-chloro-2-methylphenyl)-2-(dimethylamino)-1H-benzimidazole-4-carboxamide, (182) N-(3-chloro-2-methylphenyl)-6-{[(2,6-dichlorophenyl)carbonyl]amino}-2-(dimethylamino)-1H-benzimidazole-4-carboxamide, (183) N-(3-chloro-2-methylphenyl)-6-{[(2,4-dichlorophenyl)carbonyl]amino}-2-(dimethylamino)-1H-benzimidazole-4-carboxamide, (184) N-(3-chloro-2-methylphenyl)-6-{[(2,5-dichlorophenyl)carbonyl]amino}-2-(dimethylamino)-1H-benzimidazole-4-carboxamide, (185) 6-{[(2-bromo-6-fluorophenyl)carbonyl]amino}-N-(3-chloro-2-m ethylphenyl)-2-(dimethylamino)-1H-benzimidazole-4-carboxamide, (186) 6-{[(2-bromo-6-chlorophenyl)carbonyl]amino}-N-(3-chloro-2-m ethylphenyl)-2-(dimethylamino)-1H-benzimidazole-4-carboxamide, (187) 6-({[2-chloro-5-(cyclopropylethynyl)phenyl]carbonyl}amino)-N-(3-chloro-2-methylphenyl)-2-(dimethylamino)-1H-benzimidazole-4-carboxamide, (188) N-(3-chloro-2-methylphenyl)-6-{[(2,5-dichlorophenyl)carbonyl]amino}-2-[(3-hydroxy-2,2-dimethylpropyl)amino]-1H-benzimidazole-4-carboxamide, (189) N-(3-chloro-2-methylphenyl)-6-{[(2,5-dichlorophenyl)carbonyl]amino}-2-[(3-methoxy-2,2-dimethylpropyl)amino]-1H-benzimidazole-4-carboxamide, (190) N-(3-chloro-2-methylphenyl)-6-{[(2,5-dichlorophenyl)carbonyl]amino}-2-[(2-hydroxy-2-methylpropyl)amino]-1H-benzimidazole-4-carboxamide, (191) N-(3-chloro-2-methylphenyl)-6-{[(2,5-dichlorophenyl)carbonyl]amino}-2-[(2-methoxy-2-methylpropyl)amino]-1H-benzimidazole-4-carboxamide, (192) N-(3-chloro-2-methylphenyl)-6-{[(2,5-dichlorophenyl)carbonyl]amino}-2-{[2-(propan-2-yloxy)ethyl]amino}-1H-benzimidazole-4-carboxamide, (193) 6-{[(2-chloro-6-fluorophenyl)carbonyl]amino}-N-(3-chloro-2-methylphenyl)-2-{[2-(propan-2-yloxy)ethyl]amino}-1H-benzimidazole-4-carboxamide, (194) 2-[(2-tert-butoxyethyl)amino]-6-{[(2-chloro-6-fluorophenyl)carbonyl]amino}-N-(3-chloro-2-methylphenyl)-1H-benzimidazole-4-carboxamide, (195) 6-{[(2-chloro-6-fluorophenyl)carbonyl]amino}-N-(3-chloro-2-methylphenyl)-2-[(3-methoxy-2,2-dimethylpropyl)amino]-1H-benzimidazole-4-carboxamide, (196) 6-{[(2-chloro-6-fluorophenyl)carbonyl]amino}-N-(3-chloro-2-methylphenyl)-2-[(2-methoxy-2-methylpropyl)amino]-1H-benzimidazole-4-carboxamide, (197) 6-{[(2-chloro-6-fluorophenyl)carbonyl]amino}-N-(3-chloro-2-methylphenyl)-2-{[(2S)-tetrahydrofuran-2-ylmethyl]amino}-1H-benzimidazole-4-carboxamide, (198) 6-{[(2-chloro-6-fluorophenyl)carbonyl]amino}-N-(3-chloro-2-methylphenyl)-2-{[(2R)-tetrahydrofuran-2-ylmethyl]amino}-1H-benzimidazole-4-carboxamide, (199) 6-{[(2-chloro-6-fluorophenyl)carbonyl]amino}-N-(3-chloro-2-methylphenyl)-2-[(3-hydroxy-2,2-dimethylpropyl)amino]-1H-benzimidazole-4-carboxamide, (200) 6-{[(2-chloro-6-fluorophenyl)carbonyl]amino}-N-(3-chloro-2-methylphenyl)-2-{[(2S)-1-hydroxy-3-methylbutan-2-yl]amino}-1H-benzimidazole-4-carboxamide, (201) N-(3-chloro-4-methylphenyl)-2-(dimethylamino)-6-({[2-(trifluoromethyl)phenyl]carbonyl}amino)-1H-benzimidazole-4-carboxamide,
(202) N-(4-tert-butylphenyl)-2-(dimethylamino)-6-({[2-(trifluoromethyl)phenyl]carbonyl}amino)-1H-benzimidazole-4-carboxamide,
(203) N-(2,3-dihydro-1H-inden-5-yl)-2-(dimethylamino)-6-({[2-(tri fluoromethyl)phenyl]carbonyl}amino)-1H-benzimidazole-4-carboxamide,
(204) 6-{[(2-chloro-6-fluorophenyl)carbonyl]amino}-N-(3-chloro-4-methylphenyl)-2-(dimethylamino)-1H-benzimidazole-4-carboxamide,
(205) N-(3-chloro-4-methylphenyl)-6-{[(2,6-dichlorophenyl)carbonyl]amino}-2-(dimethylamino)-1H-benzimidazole-4-carboxamide,
(206) N-(3-chloro-4-methylphenyl)-6-{[(2,5-dichlorophenyl)carbonyl]amino}-2-(dimethylamino)-1H-benzimidazole-4-carboxamide,
(207) N-(3-chloro-2-methylphenyl)-2-cyclopropyl-6-{[(2,5-dichloro phenyl)carbonyl]amino}-1H-benzimidazole-4-carboxamide,
(208) N-(3-chloro-4-methylphenyl)-2-cyclopropyl-6-{[(2,5-dichloro phenyl)carbonyl]amino}-1H-benzimidazole-4-carboxamide,
(209) N-(3-chloro-2-methylphenyl)-6-{[(2,5-dichlorophenyl)carbonyl]amino}-2-(1-methylcyclopropyl)-1H-benzimidazole-4-carboxamide,
(210) N-(3-chloro-4-methylphenyl)-6-{[(2,5-dichlorophenyl)carbonyl]amino}-2-(1-methylcyclopropyl)-1H-benzimidazole-4-carboxamide,
(211) N-(3-chloro-2-methylphenyl)-2-(methoxymethyl)-6-({[2-(methylsulfonyl)phenyl]carbonyl}amino)-1H-benzimidazole-4-carboxamide,
(212) N-(3-chloro-4-methylphenyl)-6-{[(2,5-dichlorophenyl)carbonyl]amino}-2-(2-methoxyethyl)-1H-benzimidazole-4-carboxamide,
(213) 2-(methoxymethyl)-N-phenyl-6-({[2-(trifluoromethyl)phenyl]carbonyl}amino)-1H-benzimidazole-4-carboxamide,
(214) 2-(methoxymethyl)-N-propyl-6-({[2-(trifluoromethyl)phenyl]carbonyl}amino)-1H-benzimidazole-4-carboxamide,
(215) 2-(methoxymethyl)-N-(pyridin-3-yl)-6-({[2-(trifluoromethyl)phenyl]carbonyl}amino)-1H-benzimidazole-4-carboxamide,
(216) N-benzyl-2-(methoxymethyl)-6-({[2-(trifluoromethyl)phenyl]carbonyl}amino)-1H-benzimidazole-4-carboxamide,
(217) N-(cyclohexylmethyl)-2-(methoxymethyl)-6-({[2-(trifluoromethyl)phenyl]carbonyl}amino)-1H-benzimidazole-4-carboxamide,
(218) 2-(methoxymethyl)-N-(naphthalen-1-yl)-6-({[2-(trifluoromethyl)phenyl]carbonyl}amino)-1H-benzimidazole-4-carboxamide,
(219) 2-(methoxymethyl)-N-(thiophen-3-yl)-6-({[2-(trifluoromethyl)phenyl]carbonyl}amino)-1H-benzimidazole-4-carboxamide,
(220) N-(2,1,3-benzothiadiazol-4-yl)-2-(methoxymethyl)-6-({[2-(trifluoromethyl)phenyl]carbonyl}amino)-1H-benzimidazole-4-carboxamide,
(221) N-(1,1-dioxide-1-benzothiophen-6-yl)-2-(methoxymethyl)-6-({[2-(trifluoromethyl)phenyl]carbonyl}amino)-1H-benzimidazole-4-carboxamide,
(222) 2-(methoxymethyl)-N-(thiophen-2-ylmethyl)-6-({[2-(trifluoro methyl)phenyl]carbonyl}amino)-1H-benzimidazole-4-carboxamide,
(223) N-(1H-indol-5-yl)-2-(methoxymethyl)-6-({[2-(trifluoromethyl)phenyl]carbonyl}amino)-1H-benzimidazole-4-carboxamide,
(224) N-(1,3-benzothiazol-2-yl)-2-(methoxymethyl)-6-({[2-(trifluoromethyl)phenyl]carbonyl}amino)-1H-benzimidazole-4-carboxamide,
(225) N-(2,2-dimethylpropyl)-2-(methoxymethyl)-6-({[2-(trifluoromethyl)phenyl]carbonyl}amino)-1H-benzimidazole-4-carboxamide,
(226) 2-(methoxymethyl)-N-(thiophen-2-yl)-6-({[2-(trifluoromethyl)phenyl]carbonyl}amino)-1H-benzimidazole-4-carboxamide,
(227) N-(5-chloro-1,3-benzoxazol-2-yl)-2-(methoxymethyl)-6-({[2-(trifluoromethyl)phenyl]carbonyl}amino)-1H-benzimidazole-4-carboxamide,
(228) N-(2-benzylphenyl)-2-(methoxymethyl)-6-({[2-(trifluoromethyl)phenyl]carbonyl}amino)-1H-benzimidazole-4-carboxamide,
(229) 2-(methoxymethyl)-N-(quinolin-8-yl)-6-({[2-(trifluoromethyl)phenyl]carbonyl}amino)-1H-benzimidazole-4-carboxamide,
(230) N-(cycloheptylmethyl)-2-(methoxymethyl)-6-({[2-(trifluoromethyl)phenyl]carbonyl}amino)-1H-benzimidazole-4-carboxamide,
(231) N-(1,3-benzoxazol-2-yl)-2-(methoxymethyl)-6-({[2-(trifluoro methyl)phenyl]carbonyl}amino)-1H-benzimidazole-4-carboxamide,
(232) N-(6-chloro-1,3-benzoxazol-2-yl)-2-(methoxymethyl)-6-({[2-(trifluoromethyl)phenyl]carbonyl}amino)-1H-benzimidazole-4-carboxamide,
(233) N-[3-chloro-2-(hydroxymethyl)phenyl]-2-(methoxymethyl)-6-({[2-(trifluoromethyl)phenyl]carbonyl}amino)-1H-benzimidazole-4-carboxamide,
(234) N-(3-chloro-2-methylphenyl)-6-{[(3-fluoropyridin-2-yl)carbonyl]amino}-2-(methoxymethyl)-1H-benzimidazole-4-carboxamide,
(235) N-(3-chloro-2-methylphenyl)-6-{[(3-chloropyridin-4-yl)carbonyl]amino}-2-(methoxymethyl)-1H-benzimidazole-4-carboxamide,
(236) N-(3-chloro-2-methylphenyl)-6-{[(3,5-dichloropyridin-4-yl)carbonyl]amino}-2-(methoxymethyl)-1H-benzimidazole-4-carboxamide,
(237) 6-{[(5-butoxy-2-chlorophenyl)carbonyl]amino}-N-(3-chloro-2-methylphenyl)-2-(methoxymethyl)-1H-benzimidazole-4-carboxamide,
(238) 6-({[2-chloro-5-(2,2-difluoroethoxy)phenyl]carbonyl}amino)-N-(3-chloro-2-methylphenyl)-2-(methoxymethyl)-1H-benzimidazole-4-carboxamide,
(239) N-(3-chloro-2-methylphenyl)-6-({[2-chloro-5-(4,4,4-trifluorobutoxy)phenyl]carbonyl}amino)-2-(methoxymethyl)-1H-benzimidazole-4-carboxamide.

DETAILED DESCRIPTION OF THE INVENTION

Detailed description of the terms used in the present specification is provided as follows.

Examples of "halogen" include fluorine, chlorine, bromine and iodine.

Examples of "alkyl" include straight or branched alkyl having 1 to 8 carbon atoms, such as, for example, methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl. Among these, alkyl having 1 to 6 carbon atoms is preferred, and alkyl having 1 to 3 carbon atoms is more preferred.

The alkyl moiety of "monoalkylamino", "dialkylamino", "monoalkyl aminocarbonyl", "dialkylaminocarbonyl", "alkylcarbonyloxy", "alkyloxycarbonyl", "alkylcarbonyl", "alkylthio", "alkylsulfonyl", "alkylsulfinyl", "alkoxyalkyl", "monohaloalkyl", "dihaloalkyl", "trihaloalkyl" and "alkoxyalkylamino" is as defined above for "alkyl".

Examples of "alkoxy" include straight or branched alkoxy having 1 to 8 carbon atoms, such as, for example, methoxy, ethoxy, n-propoxy, isopropoxy, n-butoxy, isobutoxy, sec-butoxy, t-butoxy, n-pentyloxy, n-hexyloxy, n-heptyloxy, n-octyloxy.

The alkoxy moiety of "alkoxyalkoxy", "alkoxyalkyl" and "alkoxyalkylamino" is as defined above for "alkoxy".

Examples of "heteroaryl" include monocyclic or bicyclic aromatic rings having 1 to 3 hetero atoms selected from the group consisting of nitrogen atom, oxygen atom and sulfur atom. Specific examples include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazoryl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,3,4-oxadiazol-2-yl), thiazolyl (e.g., 2-thiazolyl, 4-thiazolyl, 5-thiazolyl), thiadiazolyl (e.g., 1,3,4-thiadiazolyl, 1,2,4-thiadiazolyl, 1,2,3-thiadiazolyl), isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl (e.g., 2-pyrazinyl), benzothiadiazolyl (e.g., 1,2,3-benzothiadiazol-4-yl, 1,2,3-benzothiadiazol-5-yl, 2,1,3-benzothiadiazol-4-yl, 2,1,3-benzothiadiazol-5-yl), benzothiazolyl (e.g., benzothiazol-2-yl, benzothiazol-4-yl, benzothiazol-5-yl, benzothiazol-6-yl, benzothiazol-7-yl), indolyl (e.g., indol-3-yl and indol-4-yl, indol-5-yl, indol-6-yl, indol-7-yl), benzothiophenyl (e.g., 1-benzothiophen-2-yl, 1-benzothiophen-3-yl, 1-benzothiophen-4-yl, 1-benzothiophen-5-yl, 1-benzothiophen-6-yl, 1-benzothiophen-7-yl), 1,1-dioxo-1-benzothiophenyl (e.g., 1,1-dioxo-1-benzothiophen-2-yl, 1,1-dioxo-1-benzothiophen-3-yl, 1,1-dioxo-1-benzothiophen-4-yl, 1,1-dioxo-1-benzothiophen-5-yl, 1,1-dioxo-1-benzothiophen-6-yl, 1,1-dioxo-1-benzothiophen-7-yl), quinolyl (quinolin-2-yl, quinolin-3-yl, quinolin-4-yl, quinolin-5-yl, quinolin-6-yl, quinolin-7-yl, quinolin-8-yl) and 1,3-benzoxazol-2-yl.

The heteroaryl moiety of "heteroarylmethyl" is as defined above for "heteroaryl".

Examples of "a saturated cyclic amino" include 4- to 7-membered saturated cyclic amino groups having one or two nitrogen atoms, said ring optionally having one oxygen or sulfur atom and optionally substituted with oxo. Specific examples include 1-azetidinyl, 1-pyrrolidinyl, 1-imidazolidinyl, piperidino, 1-piperazinyl, 1-tetrahydropyrimidinyl, 4-morpholino, 4-thiomorpholino, 1-homopiperazinyl, and 2-oxo-oxazolidin-3-yl.

The saturated cyclic amino moiety of "a saturated cyclic aminocarbonyl" is as defined above for "a saturated cyclic amino".

Examples of "a saturated heterocycle group" include 4- to 6-membered saturated heterocycle group having one nitrogen or oxygen atom in the ring. Specific examples include 2-pyrrolidinyl, 3-pyrrolidinyl, 2-piperidinyl, 3-piperidinyl, 4-piperidinyl, 2-oxetanyl, 3-oxetanyl, 2-tetrahydrofuranyl, and 3-tetrahydrofuranyl.

Examples of "cycloalkyl" include cycloalkyl having 3 to 8 carbon atoms. Specific examples include cyclopropyl, cyclobutyl, cyclopentyl, cyclohexyl, cycloheptyl and cyclooctyl.

The cycloalkyl moiety of "cycloalkyl methyl" is as defined above for "cycloalkyl".

Examples of "naphthyl" include 1-naphthyl and 2-naphthyl.

Examples of "pyridyl" include 2-pyridyl, 3-pyridyl and 4-pyridyl.

Examples of "alkynyl" include straight or branched alkynyl having 2 to 6 carbon atoms. Specific examples include ethynyl, 1-propynyl, 1-butynyl, 1-pentynyl, 2-propynyl, 2-butynyl, 3-butynyl, 1-methyl-2-propynyl, 2-pentynyl, 3-pentynyl and 4-pentynyl.

MODE FOR CARRYING OUT THE INVENTION

The compound of the invention can be prepared according to the following procedures, working examples or procedures known in the art. If the starting material has a substituent group that may interfere with a reaction during the process, it may be protected with an appropriate protecting group according to known method before subjecting to the reaction.

The following abbreviations can be used herein to simplify the description.

p-: para-, t-: tert-, s-: sec-, m-: meta-,

THF: tetrahydrofuran,

DMF: N,N-dimethylformamide,

DMA: N,N-dimethylacetamide,

HBTU: O-(benzotriazol-1-yl)-N,N,N',N'-tetramethyluronium hexafluorophosphate,

HATU: O-(7-azabenzotriazol-1-yl)-N,N,N',N'-tetramethyluronium hexafluorophosphate, TFA: trifluoroacetic acid, DME: ethylene glycol dimethyl ether, NMP: N-methyl-2-pyrrolidone, DMSO: dimethyl sulfoxide, MeOH: methanol, EtOH: ethanol.

Process 1

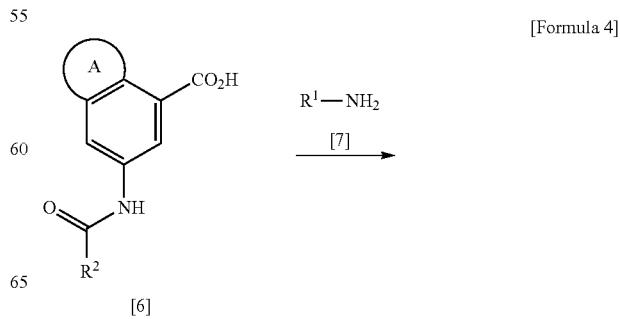

[Formula 4]

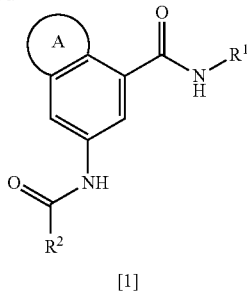

[1]

wherein ring A, $R^1$ and $R^2$ are as defined above.

This reaction is the condensation of Compound [6] with Compound [7] and can be performed according to a method for condensation reaction known per se. A compound of the invention can be synthesized by the reaction of a carboxylic acid Compound [6] or its reactive derivative with an amine derivative [7]. Examples of such reactive derivative of Compound [6] include those commonly used in an amide condensation formation, such as, for example, acid halides (e.g., acid chloride, acid bromide), mixed anhydrides, imidazolides, active amides. When using Compound [6], the reaction can be performed using a condensing agent at a temperature in the range from −20° C. to 100° C. in the presence or absence of a base. Examples of the condensing agent which may be used for this reaction include 1,1'-oxalyldiimidazole, 1-ethyl-3-(3-dimethylaminopropyl)carbodiimide, dicyclohexylcarbodiimide, diethyl cyanophosphonate, HBTU, HATU, 1H-benzotriazol-1-yl-oxy-tris-pyrrolidino-phosphonium hexafluorophosphate. Examples of the base which can be used for this reaction include organic bases such as triethylamine, N,N-diisopropylethylamine, N,N-dimethylaniline, pyridine, 1,8-diazabicyclo[5,4,0]-7-undecene. Any solvent may be used so long as it does not interfere with the reaction, and examples of such solvent include ethers such as THF, 1,4-dioxane and diethyl ether, amides such as DMF and DMA, nitriles such as acetonitrile and propionitrile, hydrocarbons such as benzene and toluene, halogenated hydrocarbons such as chloroform and methylene chloride, and mixed solvents thereof. Also, an additive agent can be used if necessary. Examples of such additive agent which can be used include 1-hydroxybenzotriazol and 1-hydroxy-7-aza-benzotriazol. Preferred reaction time is generally within the range from 10 minutes to 24 hours, but it should vary depending on the starting material, the reaction temperature, etc. Preferred amounts of Compound [7] and the condensing agent to be used are within the range from 1 to 3 moles for one mole of Compound [6]. Preferred amount of the base to be used is within the range from 1 Eq to 10 Eq, preferably from 1 Eq to 4 Eq, to Compound [6].

For example, Compound [6] can be prepared according to the process as described below.

[Formula 5]

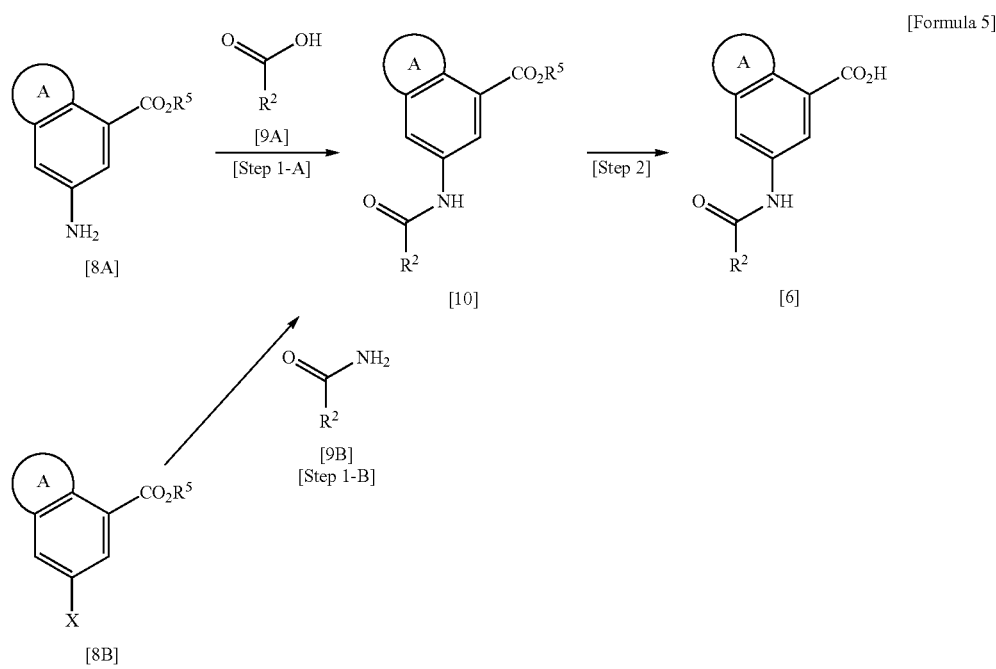

wherein ring A and $R^2$ are as defined above, X represents halogen and $R^5$ represents alkyl.

Step 1-A

This reaction is a condensation reaction of Compound [8A] with Compound [9A] to synthesize Compound [10] according to Process 1 as described above.

Step 1-B

The reaction is a coupling reaction of Compound [8B] with Compound [9B] using palladium catalyst, and the reaction is performed according to a method known per se. The solvent which can be used is not limited so long as it does not interfere with a reaction, and examples of such solvent include hydrocarbons such as toluene and xylene, ethers such as 1,4-dioxane and THF, amides such as DMF, DMA and NMP, and a mixed solvent thereof. The reaction is performed in the presence of a base at a temperature in the range from 20° C. to 200° C., optionally using microwave. Examples of the palladium catalyst which can be used include tris(dibenzylideneacetone) (chloroform)dipalladium (0), tris(dibenzylideneacetone)dipalladium (0) and palladium acetate (II). Suitable amount of such palladium catalyst is within the range from 0.001 mol to 0.3 mol, to 1 mol of aryl halide. Examples of the ligand for the palladium catalyst which can be used include 1,1'-bis(diphenylphosphino)ferrocene, 4,5-bis(diphenylphosphino)-9,9'-dimethylxanthene, 2-dicyclohexylphosphino-2',4',6'-triisopropylbiphenyl, (±)-2,2'-bis(diphenylphosphino)-1,1'-binaphthyl, 2-(di-t-butylphosphino) biphenyl, bis[2-(diphenylphosphino) phenyl]ether, tri-t-butylphosphine, etc. Examples of the base which can be used include sodium t-butoxide, tripotassium phosphate and cesium carbonate. The amount of the base to be used is within the range from 1 Eq to 10 Eq, preferably within the range from 1 Eq to 4 Eq, to Compound [8B]. Appropriate reaction time is generally within the range from 10 minutes to 24 hours, but it should vary depending on the starting material, the reaction temperature, etc.

Step 2

Compound [6] can be prepared by hydrolyzing Compound [10] according to a known method. The reaction is usually performed in the presence of acid or base in a suitable solvent. Examples of the acid used in the hydrolysis include inorganic acids such as hydrochloric acid and sulfuric acid, and examples of the base include inorganic bases such as sodium hydroxide and potassium hydroxide. Examples of reaction solvent include alcohols such as MeOH and EtOH, ethers such as THF and dioxane, water, and mixed solvents thereof. The reaction is performed at a temperature within the range from 0° C. to 100° C., and the reaction time is usually within the range from 30 minutes to 24 hours.

For example, Compound [8A] can be prepared by the following process.

[Formula 6]

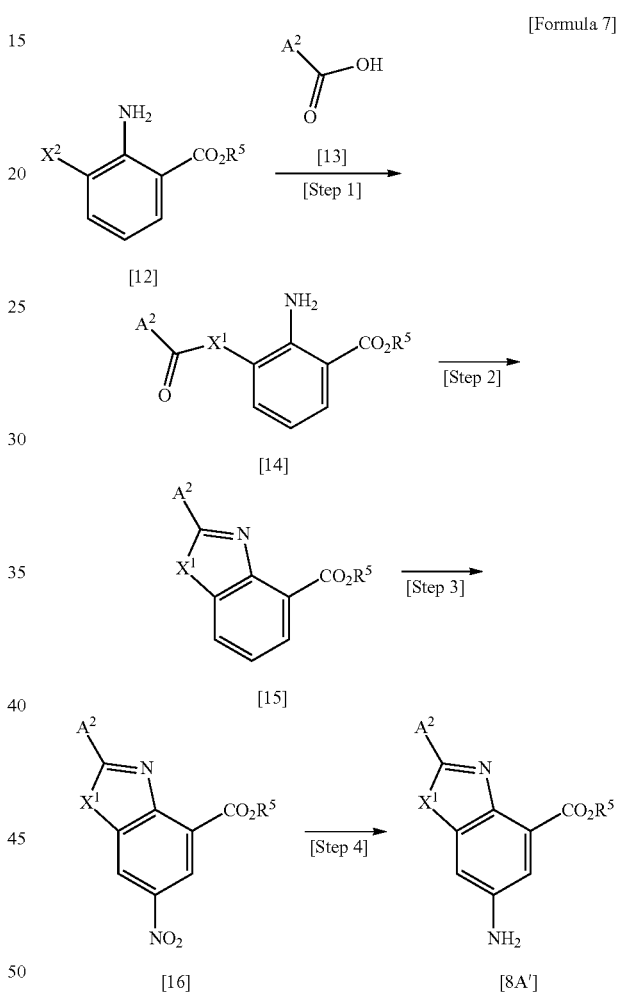

wherein ring A and $R^5$ are as defined above.

This reaction is a reduction reaction of Compound [11] to aromatic amine, and the reaction can be carried out with a conventional method. For example, the reaction is achieved by catalytic hydrogen reduction of Compound [11] using a catalyst such as Raney nickel, palladium, rhodium, platinum, etc., in a suitable solvent under hydrogen gas atmosphere, hydride reduction using lithium aluminum hydride, etc., iron reduction using reduced iron reagent and ammonium chloride etc., or zinc reduction using zinc dust and acetic acid, etc. In addition, there are also a method using sulfides such as hydrosulfite sodium and a reducing method by ammonium formate, hydrazine, etc. with a metal catalyst such as palladium on carbon. Selection of the solvent depends on the kind of compound or reagent to be used, and the solvent may be used alone or as a mixture thereof. Examples of such solvent include toluene, THF, 1,4-dioxane, 1,2-dimethoxyethane, ethyl acetate, acetone, acetonitrile, DMF, or alcohols such as MeOH, EtOH and tert-butanol, and water. Although the reaction temperature depends on the kind of compound and reagent to be used, it is usually within the range from 0° C. to 300° C., preferably within the range from 20° C. to 150° C.

When the ring A of Compound [8A] is a group represented by the general formula [2] or [3], the compound can be prepared according to the method described in WO2008/65508. When the ring A of Compound [8A] is a group represented by the general formula [4], the compound can be prepared according to a method described in literature (e.g., EP2226315, J. Org. Chem., 1960, 25, 942, etc.). Also, the compound may be prepared according to the following process.

[Formula 7]

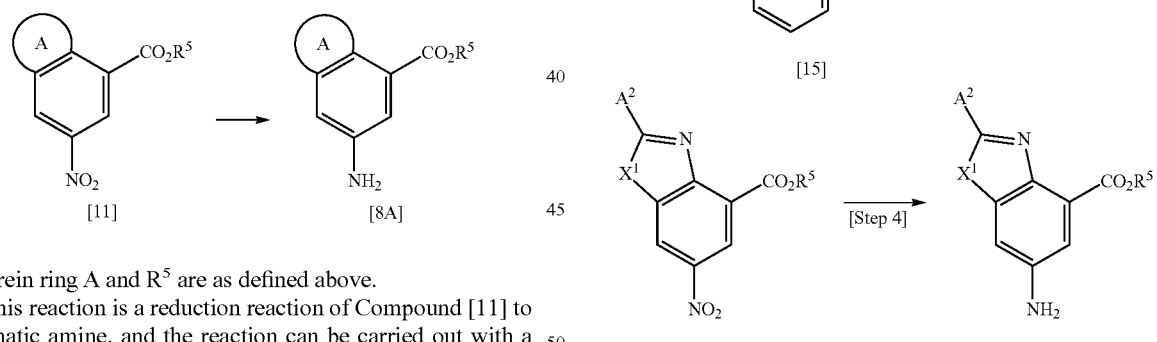

wherein $X^1$, $R^5$ and $A^2$ are as defined above, and $X^2$ represents $NH_2$ or OH.

Step 1

This reaction is an acylation reaction of Compound [12] with Compound [13] or its reactive derivative and can be performed according to a method known per se as acylation reaction. Examples of the reactive derivative of Compound [13] include those generally used for acylation reaction and include acid halides (e.g., acid chloride, acid bromide), mixed acid anhydrides, imidazolides, active amides, etc. When using Compound [13], the reaction can be conducted using a condensing agent in the presence or absence of a base at a temperature within a range from −20° C. to 100° C. Examples of the condensing agent which can be used for this reaction include 1,1'-oxalyldiimidazole, 1-ethyl-3-(3-dimethylaminopropyl) carbodiimide, dicyclohexylcarbodiimide, diethyl cyanophosphonate, HBTU, HATU and 1H-benzotriazol-1-yl-oxytripyrrolidinophosphonium hexafluorophosphate. Examples of the base which can be used for this reaction include organic bases such as triethylamine, N,N-diisopropylethylamine, N,N-dimethylaniline, pyridine, 1,8-diazabicyclo[5,4,0]-7-undecene. The solvent to be used is not limited so long as it does not interfere with a reaction, and examples of such solvent include ethers such as THF, 1,4-dioxane and diethyl ether, amides such as DMF and DMA, nitriles such as acetonitrile and propionitrile, hydrocarbons such as benzene and toluene, halogenated hydrocarbons such as chloroform and methylene chloride, and a mixed solvent thereof. Also, an additive agent can be used if necessary. Examples of such additive agent which can be used include 1-hydroxybenzotriazol and 1-hydroxy-7-aza-benzotriazol. Preferred amount of the base to be used is within the range from 1 Eq to 10 Eq, preferably 1 Eq to 4 Eq, to Compound [13]. Preferred reaction time is generally within the range from 10 minutes to 24 hours, but it should vary depending on the starting material, the reaction temperature, etc. Preferred amounts of Compound [13] and the condensing agent to be used are within the range from 1 to 3 moles for one mole of Compound [12].

Step 2

This reaction is intramolecular cyclization of Compound [14] using an acid catalyst and can be performed according to a method known per se. The reaction is performed in a suitable solvent or in the absence of a solvent, and examples of the acid which can be used include hydrochloric acid, p-toluenesulfonic acid, acetic acid, pyridinium p-toluenesulfonate, polyphosphoric acid, phosphoryl chloride, etc. The reaction can be carried out usually at a temperature within the range from 0° C. to 200° C.

The solvent which can be used is not limited so long as it does not interfere with a reaction, and examples of such solvent includes hydrocarbons such as toluene and xylene, alcohols such as MeOH and EtOH, ethers such as 1,4-dioxane and THF, amides such as DMF and DMA, halogenated hydrocarbon such as chloroform and dichloromethane, acetonitrile, or a mixed solvent thereof. The reaction time is generally within the range from 30 minutes to 48 hours although it should vary depending on the starting material and the reaction temperature.

Step 3

This reaction is a nitration reaction of Compound [15] and can be performed according to a known method. Generally, a nitrating agent, such as nitric acid, mixed acid, metal nitrate, acetyl nitrate, dinitrogen pentaoxide, nitronium salt (e.g., nitronium tetrafluoro borate, nitronium trifluoromethanesulfonate), etc., is used. The reaction solvent is not limited so long as it does not interfere with a reaction, and examples of such solvent include halogenated solvents such as dichloromethane and chloroform, pentane, TFA, sulfolane, acetonitrile, etc.

The reaction is carried out under neutral or acidic condition. When the reaction is carried out under acidic condition, examples of the acid to be used include sulfuric acid, nitric acid, acetic acid, and acetic anhydride. Also, only such acid may be used as a reaction solvent without using the reaction solvent as mentioned above. The reaction temperature is generally within the range from −20° C. to room temperature although it should vary depending on the compound and reagent to be used. Preferred reaction time is generally within the range from 30 minutes to 24 hours although it should vary depending on the starting material and the reaction temperature.

Step 4

This reaction is a reduction reaction of Compound [16] to an aromatic amine and can be carried out to prepare Compound [8A'] according to the similar process of the preparation of Compound [8A].

Compound [8B] can be prepared according to the method described in literature (e.g., J. Med. Chem., 1999, 42, 5020, WO2008/65508). When the ring A of Compound [8B] is a group represented by the general formula [4], the compound also can be prepared by the following process.

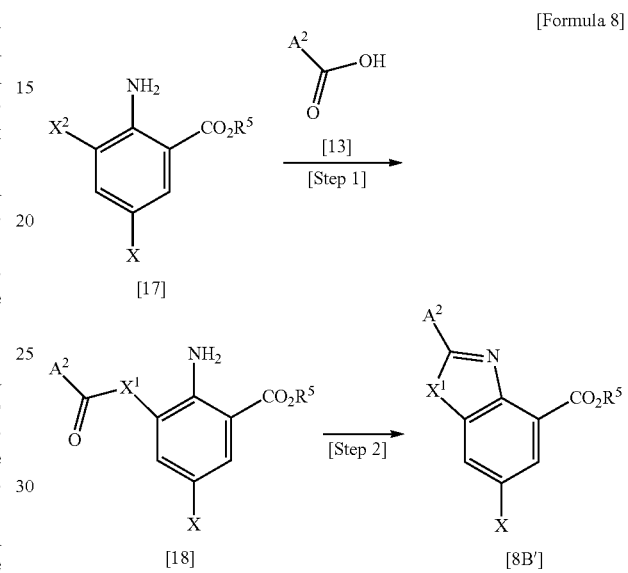

[Formula 8]

wherein $A^2$, X, $X^1$, $X^2$ and $R^5$ are as defined above.

Step 1

This reaction is a condensation reaction of Compound [17] with Compound [13] or its reactive derivative and can be carried out to prepare Compound [18] according to the similar procedure of Step 1 in the process for Compound [8A'].

Step 2

This reaction is an intramolecular cyclization reaction of acyl group and amino group using an acid catalyst and can be carried out to prepare Compound [8B'] according to the procedure of Step 2 in the above-mentioned process of the preparation of Compound [8A'].

For example, Compound [17] can be prepared according to the following process.

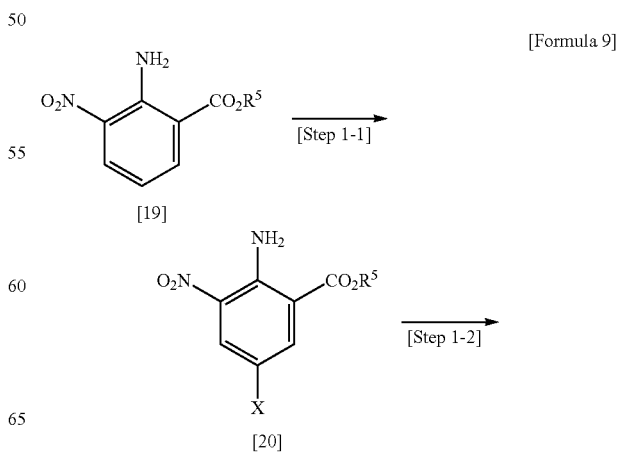

[Formula 9]

-continued

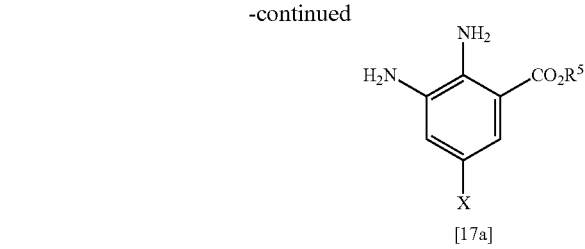

[17a]

$X^2 = -NH_2$

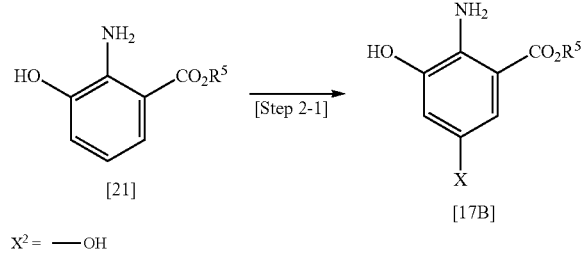

$X^2 = -OH$ wherein X and $R^5$ are as defined above.

Step 1-1

This reaction is a halogenation reaction of Compound [19] and can be carried out according to a method known per se as halogenation reaction. Examples of halogenating agent which can be used include N-bromosuccinimide, N-iodosuccinimide, bromine, iodine, etc., and generally, the reaction can be carried out at a temperature within the range from 0° C. to 200° C. The solvent which can be used is not limited so long as it does not interfere with a reaction, and examples of such solvent include hydrocarbons, such as toluene and xylene, ethers such as 1,4-dioxane and THF, amides such as DMF and DMA, halogenated hydrocarbons such as chloroform and dichloromethane, acetonitrile, and a mixed solvent thereof. Also a suitable base may be added if necessary, and examples of such base which can be used include pyridine, N,N-diisopropylethylamine, etc. The amount of the base to be used, for example, is within the range from 1 Eq to 10 Eq, preferably within the range from 1 Eq-4 Eq, to Compound [19]. Preferred reaction time is generally within the range from 30 minutes to 24 hours although it should vary depending on the starting material and the reaction temperature.

Step 1-2

This reaction is a reduction reaction of Compound [20] to an aromatic amine, and can be performed to prepare Compound [17A] according to the similar process of the above-mentioned Compound [8A].

Step 2-1

This reaction is a halogenation reaction of Compound [21] and can be performed to prepare Compound [17B] according to the similar procedure of Step 1-1 in the process of the preparation of Compound [17].

Process 2

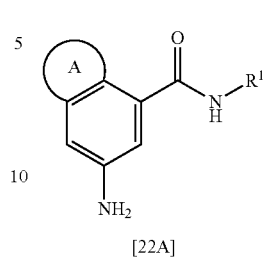 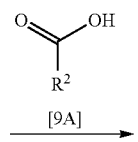

[22A] [9A]

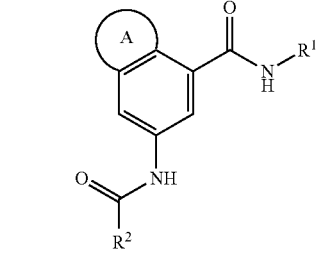

[1]

wherein ring A, $R^1$ and $R^2$ are as defined above.

This reaction is a condensation reaction of Compound [22A] with Compound [9A] and can be performed according to Process 1 to prepare a compound of the invention.

Also, a compound of the invention may be prepared by the following procedures.

[Formula 11]

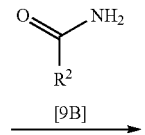

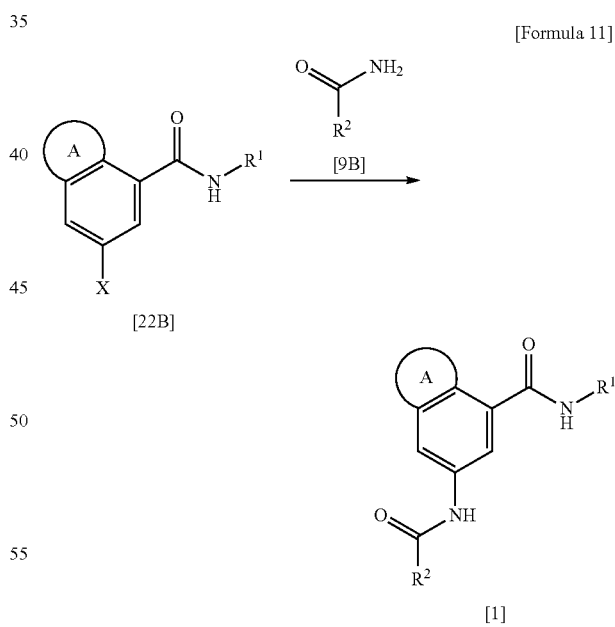

wherein ring A, $R^1$, $R^2$ and X are as defined above.

This reaction is a coupling reaction of Compound [22B] with Compound [9B], and can be performed to prepare a compound of the invention according to the similar procedure of Step 1-B in the process of Compound [6].

Compound [22A] can be prepared according to the following process, for example.

[Formula 12]

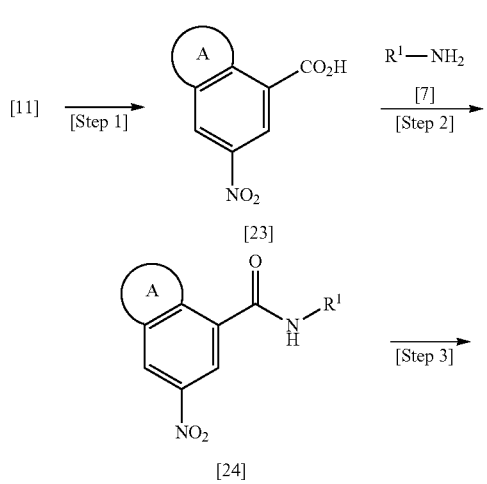

wherein ring A and $R^1$ are as defined above.

Step 1

This reaction is a hydrolysis reaction of Compound [11] as starting material and can be performed to prepare Compound [23] according to the similar procedure of Step 2 in the process of the preparation of Compound [6].

Step 2

This reaction is a condensation reaction of Compound [23] with Compound [7] and can be performed to prepare Compound [24] according to Process 1.

Step 3

This reaction is a reduction reaction of Compound [24] to an aromatic amine and can be performed to prepare Compound [22A] according to the process of the preparation of Compound [8A].

For example, Compound [22B] can also be prepared by the following process.

[Formula 13]

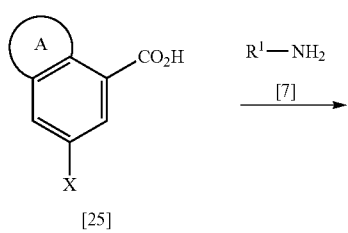

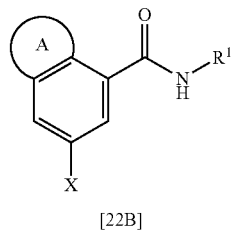

wherein ring A, $R^1$ and X are as defined above.

This reaction is a condensation reaction of Compound [25] with Compound [7], and can be performed to prepare Compound [22B] according to Process 1. Compound [25] can be prepared according to a method described in literature (e.g., EP234872B1; U.S. Pat. No. 6,387,938B1; Bioorg. Med. Chem., 1999, 7, 2271; J. Med. Chem., 1999, 42, 5020), and can also be prepared by hydrolyzing Compound [8B] according to the similar procedure of Step 2 in the process of the preparation of Compound [6].

Process 3

When the ring A is a group represented by the general formula [4] and $A^2$ is alkylthio, alkoxy or a group represented by the general formula [5], the compound can be prepared according to the following process.

[Formula 14]

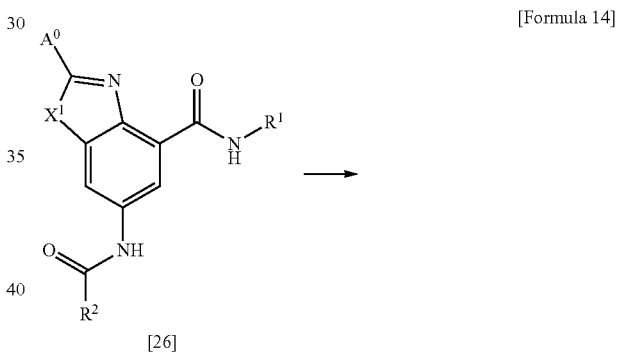

wherein $R^1$, $R^2$ and $X^1$ are as defined above, and $A^0$ represents halogen, mesylate, tosylate, etc., and $A^3$ represents alkylthio, alkoxy or a group represented by the general formula [5].

This reaction is a nucleophilic substitution reaction of Compound [26] by amines, metal alkoxy or substituted thiol and can be carried out according to known method. The reaction is carried out in a suitable solvent or in the absence of a solvent, using an excessive amount of reagents, or in the presence of a base. Examples of suitable base to be used include pyridine, triethylamine, N,N-diisopropylethylamine, potassium carbonate, sodium hydrogencarbonate, etc. The solvent to be used is not limited so long as it does not interfere with a reaction, and examples of such solvent include ethers such as THF and diethyl ether, amides such as DMF and DMA, nitriles such as acetonitrile and propionitrile, hydrocarbons such as benzene and toluene, alcohols such as MeOH and EtOH, water, or a mixed solvent thereof. Also, an excessive amount of the amine may be used in the reaction instead of the solvent. The reaction is generally carried out at a temperature within the range from 0° C. to 200° C. although it should depend on the compound and reagents to be used. The amount of the base is, for example, within the range from 1 Eq to 10 Eq, preferably within the range from 1 Eq to 4 Eq, to Compound [26]. Preferred reaction time is generally within the range from 30 minutes to 24 hours although it should vary depending on the starting material and the reaction temperature.

Compound [26] can be prepared, for example, according to the following process.

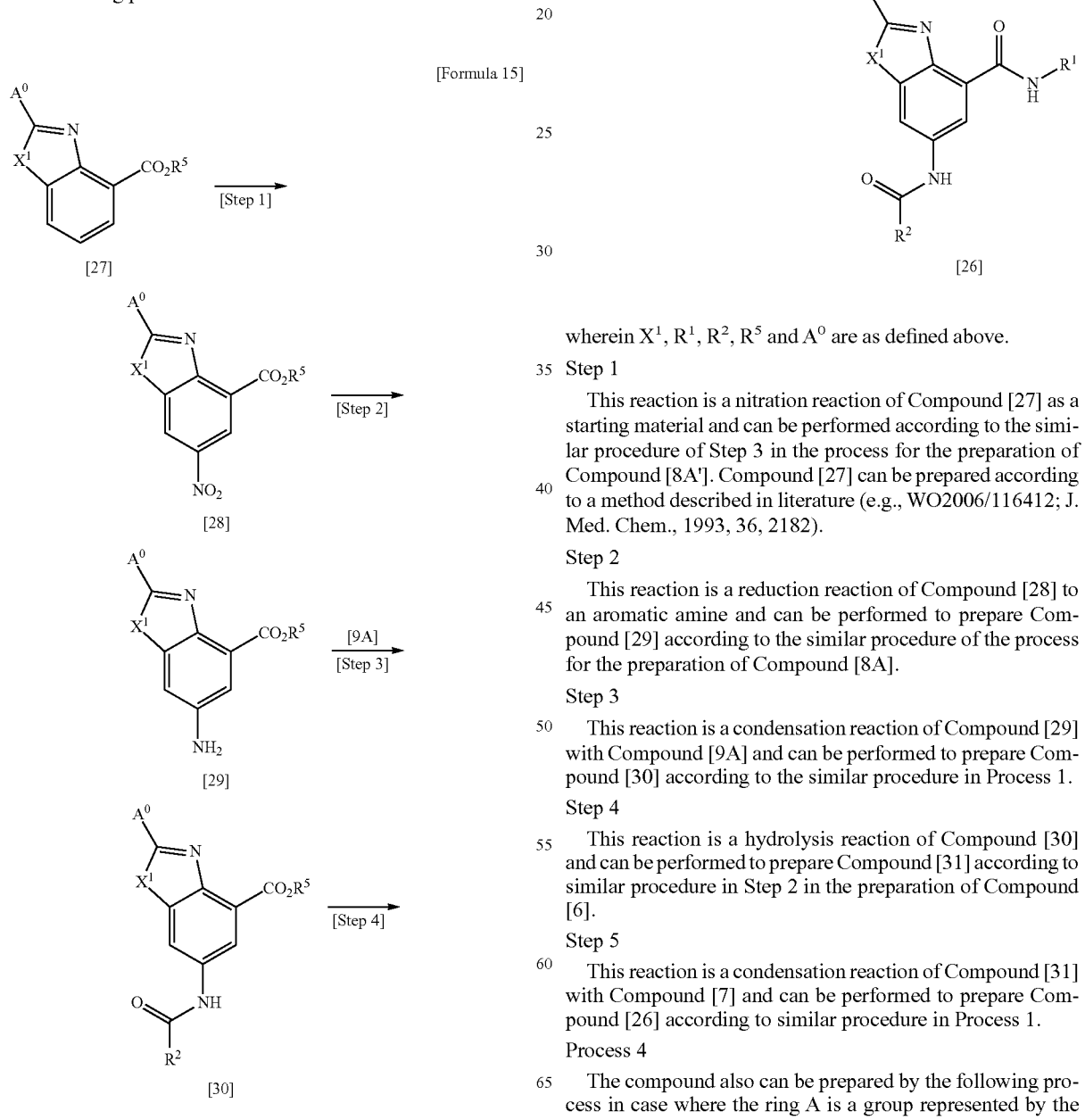

[Formula 15]

wherein $X^1$, $R^1$, $R^2$, $R^5$ and $A^0$ are as defined above.

Step 1

This reaction is a nitration reaction of Compound [27] as a starting material and can be performed according to the similar procedure of Step 3 in the process for the preparation of Compound [8A']. Compound [27] can be prepared according to a method described in literature (e.g., WO2006/116412; J. Med. Chem., 1993, 36, 2182).

Step 2

This reaction is a reduction reaction of Compound [28] to an aromatic amine and can be performed to prepare Compound [29] according to the similar procedure of the process for the preparation of Compound [8A].

Step 3

This reaction is a condensation reaction of Compound [29] with Compound [9A] and can be performed to prepare Compound [30] according to the similar procedure in Process 1.

Step 4

This reaction is a hydrolysis reaction of Compound [30] and can be performed to prepare Compound [31] according to similar procedure in Step 2 in the preparation of Compound [6].

Step 5

This reaction is a condensation reaction of Compound [31] with Compound [7] and can be performed to prepare Compound [26] according to similar procedure in Process 1.

Process 4

The compound also can be prepared by the following process in case where the ring A is a group represented by the general formula [4] and A is alkylsulfinyl or alkylsulfonyl.

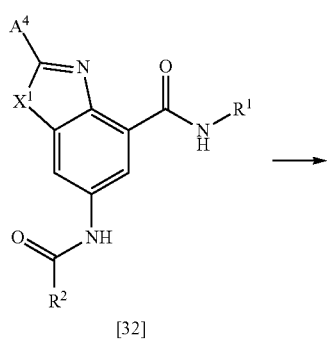

[Formula 16]

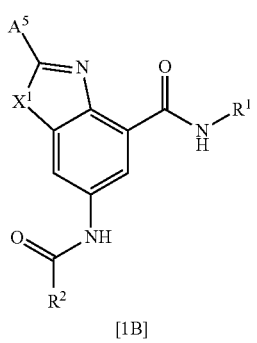

[1B]

wherein R¹, R², and X¹ are as defined above, A⁴ represents alkylthio and A⁵ represents alkylsulfinyl or alkylsulfonyl.

This reaction is an oxidation reaction of Compound [32] as a starting material and can be carried out according to a conventional method. For example, the reaction is achieved in a suitable solvent using a peroxide such as potassium permanganate, metachloro perbenzoic acid and oxone permonosulfate. The solvent should be selected according to the kind of starting material and not limited so long as it does not interfere with a reaction, and examples of such solvent include dichloromethane, chloroform, dichloroethane, THF, 1,4-dioxane, DME, toluene, MeOH, etc., and such solvent may be used alone or as a mixed solvent. The amount of the oxidizing agent is within the range from 0.5 Eq to 10 Eq, preferably within the range from 0.9 Eq to 3 Eq, to the starting material. The reaction temperature is usually within the range from −20° C. to 80° C., preferably within the range from 0° C. to 50° C. although it should depend on the kinds of the compound and reagent to be used. Preferred reaction temperature is usually within the range from 30 minutes to 24 hours although it depends on the kind of starting material to be used and the reaction temperature.

The compound of the invention may be used as a pharmaceutical as it is, and also a pharmaceutically acceptable salt thereof formed according to known method may be used. Examples of such salt include inorganic salt of acids such as hydrochloric acid, hydrobromic acid, sulfuric acid and phosphoric acid, and organic salt of acids such as acetic acid, citric acid, tartaric acid, maleic acid, succinic acid, fumaric acid, p-toluenesulfonic acid, benzenesulfonic acid, and methanesulfonic acid.

For example, a hydrochloride of a compound of the invention can be formed by dissolving the compound of the invention in a solution of hydrogen chloride in alcohol, ethyl acetate or diethyl ether.

The compound of the invention may have an asymmetrical carbon, and each of such optical isomers and a mixture thereof are within the scope of the present invention. Such optical isomer can be prepared by optical resolution from a racemic mixture as obtained in the following working examples, according to known method using an optically active acid such as tartaric acid, dibenzoyltartaric acid, mandelic acid, 10-camphor sulfonic acid, etc., or by the use of an optically active compound previously prepared as a starting material. Alternatively, such compound may be prepared by optical resolution using a chiral column or asymmetric synthesis.

Some of the compounds of the invention may exist as tautomers, and each of such tautomers and a mixture thereof are within the scope of the invention.

For example, the heterocycle derivative represented by the general formula [1] (i.e., heterocycle derivative represented by the following genera formula [1X]), wherein the ring A is a group represented by the general formula [4] and X¹ is NH, may form a heterocycle derivative represented by the following general formula [1×A].

[Formula 17]

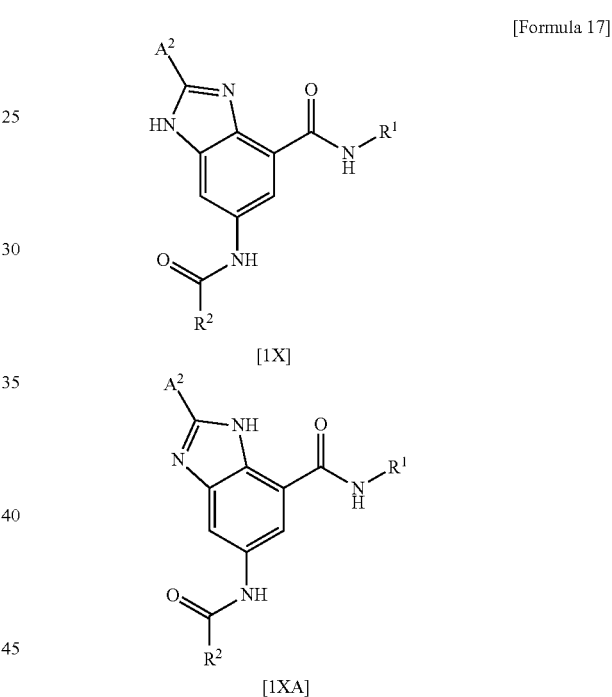

wherein R¹, R², and A² are as defined above.

As shown in the test examples as described below, the compound of the invention or a pharmaceutically acceptable salt thereof has mPGES-1 inhibiting activity. Also, since the compound of the invention or a pharmaceutically acceptable salt thereof has mPGES-1 inhibiting activity, it has PGE2 inhibitory effect, analgesic action and anti-inflammatory effect.

Therefore, the compound of the invention or a pharmaceutically acceptable salt thereof can be used as a preventing or treating agent for diseases that involve mPGES-1, diseases associated with PGE2, and diseases on which effectiveness is expected based on analgesic or anti-inflammatory action.

Examples of a disease to which a compound of the invention or a pharmaceutically acceptable salt thereof can be applied include inflammatory bowel disease (e.g., see J. Biol. Chem., 2004, 279(13), 12647-12658) irritable bowel syndrome, migraine, headache, low back pain, spinal stenosis, herniated disk, temporomandibular joint disorders, cervical syndrome, cervical spondylosis, endometriosis (e.g., see Biomed. Pharmacother., 2011, 65(1), 77-84), adenomyosis, preterm labour and delivery, threatened premature delivery, dysmenorrhea, overactive bladder, nocturia (e.g., see Acta. Med. Okayama, 2008, 62(6), 373-378), interstitial cystitis, neurodegenerative disease such as Alzheimer's disease, multiple sclerosis (e.g., see Proc. Natl. Acad. Sci. USA, 2009, 106, 21807-21812), psoriasis, rheumatoid arthritis (e.g., see J. Biol. Chem., 279(32), 33684-33695 and J. Immunol., 2008, 180, 8361-8368), rheumatic fever, fibromyalgia, neuralgia (e.g., see Glia, 2011, 59, 208-218), complex regional pain syndrome, fascial dysfunction, viral infections such as influenza, common cold, zoster and AIDS, bacterial infection, mycosis, burn (e.g., see J. Burn. Care. Res., 2011, 32(1), 79-90), inflammation and pain after operation, injury and dental extraction, malignant tumors such as colon cancer, breast cancer, lung cancer, prostatic cancer, etc. (e.g., see J. Biol. Chem., 2003, 278(21), 19396-19405, Oncogene, 2012, 31(24), 2943-2952, and Cancer Res., 2008, 68(9), 3251-3259), atherosclerosis (e.g., see Proc. Natl. Acad. Sci. USA, 2006, 103, 14507-14512), stroke (e.g., Proc. Natl. Acad. Sci. USA, 2006, 103(31), 11790-11795), gout, arthritis, osteoarthritis (e.g., see J. Rheumatol., 2005, 32(5), 887-895 and J. Pharmacol. Exp. Ther., 2008, 326, 754-763), juvenile arthritis, ankylosing spondylitis, tenosynovitis, ligament ossification, systemic lupus erythematosus, vasculitis, pancreatitis, nephritis (e.g., see Kidney Int., 2011, 79(1), 77-88), conjunctivitis, iritis, scleritis, uveitis, wound therapy, dermatitis, eczema, osteoporosis, asthma (e.g., see J. Immunol., 2012, 188, 4093-4102), chronic obstructive pulmonary disease (e.g., see Am. J. Physiol. Lung Cell Mol. Physiol., 2004, 287, L981-L991), pulmonary fibrosis (e.g., see Am. J. Physiol. Lung Cell Mol. Physiol., 2005, 288, L1010-L1016), allergic disease (e.g., see J. Immunol., 2012, 188, 4093-4102), familial adenomatous polyposis (e.g., see Oncogene, 2012, 31(24), 2943-2952), scleroderma (e.g., see Arthritis Res. Ther., 2011, 13, R6), bursitis, leiomyoma of uterus, prostatitis, and pain from cancer.

When administered as a pharmaceutical, a compound of the invention or a pharmaceutically acceptable salt thereof is administered as it is or as a pharmaceutical composition containing, for example, 0.001% to 99.5%, preferably 0.1% to 90%, in a pharmaceutically acceptable non-toxic and inactive carrier to a mammal including human.

In the pharmaceutical composition, a diluent in the form of a solid, a semi-solid or a liquid, a bulking agent, and one or more of other formulation additives can be used as a carrier. Preferably, the pharmaceutical composition of the invention is administered in a unit dosage form. The pharmaceutical composition may be administered by intra-tissue administration, oral administration, intravenous administration, local administration such as dermal administration, ocular instillation, intraperitoneal administration, intrathoracic administration, etc., or transrectal administration. Of course, the composition should be administered in a dosage form suitable for these administration routes.

The dosage as a medicament should be adjusted preferably in consideration of conditions of the patient such as age, body weight, nature and severity of the disease, route of administration, the compound of the invention to be administered, whether such compound is a salt or not, and the kind of such salt. For oral administration, a daily dosage of the compound of the invention or a pharmaceutically acceptable salt thereof as an active ingredient for adult is generally within the range from 0.01 mg to 5 g, preferably 1 mg to 500 mg for adult human. However, a lower dosage under said range may be sufficient in some cases, or a higher dosage over said range may be needed in other cases. Generally, a daily dosage is administered once in a day or may be administered in several divisions in a day. Alternatively, a daily dosage can be administered intravenously by prompt administration or continuous infusion over 24 hours.

EXAMPLES

Although the present invention is further described in detail in the following Reference Examples, Examples, Test Examples and Formulation Examples, the present invention is not limited thereto.

The measurement conditions for high-performance liquid chromatography mass spectrometer; LCMS are as follows.
Analytical instrument: ACUITY UPLC MS/PDA System (Waters)
Mass spectrometer: Waters 3100 MS detector
Photodiode array detector: ACUITY PDA detector (210-400 nm)
Column: Acuity BEH $C_{18}$, 1.7 μm, 2.1×50 mm
Flow rate: 0.5 mL/min
Column temperature: 40° C.
Solvent:
　A liquid: 0.1% formic acid/$H_2O$ (v/v)
　B liquid: 0.1% formic acid/acetonitrile (v/v)
Gradient Condition:
　Method A:
　0.0-2.5 min; % A liquid/% B liquid=90/10→10/90
　2.5-3.0 min; % A liquid/% B liquid=10/90
　3.0-3.5 min; % A liquid/% B liquid=0/100
　Method B:
　0.0-2.5 min; % A liquid/% B liquid=50/50→10/90
　2.5-3.0 min; % A liquid/% B liquid=10/90
　3.0-3.5 min; % A liquid/% B liquid=0/100

The values [MS (m/z)] (MS: mass spectrometry) observed in the mass spectrometry are expressed in m/z, and the retention times are expressed in Rt (minute).

Reference Example 1

2-Chloro-5-(ethoxymethyl)benzoic acid

The mixture of methyl 5-(bromomethyl)-2-chlorobenzoate (prepared as described in WO2010/132999) (0.2 g), potassium carbonate (0.21 g), EtOH (3 mL) and THF (3 mL) was stirred at 80° C. for 4 hours. The reaction mixture was cooled to room temperature, water was then added, and the mixture was extracted with ethyl acetate. The organic layer was separated and washed with brine, and dried over magnesium sulfate and concentrated in vacuo. The residue was purified on column chromatography to obtain ethyl 2-chloro-5-(ethoxymethyl)benzoate (0.15 g). This was dissolved in THF-MeOH—$H_2O$ (3:3:2, 8 mL), and lithium hydroxide hydrate (0.15 g) was added, and the mixture was stirred at room temperature for 14 hours. The reaction mixture was acidified with 1N hydrochloric acid and extracted with ethyl acetate. The organic layer was washed with brine, dried over magnesium sulfate, and concentrated in vacuo to obtain the titled compound (0.12 g) as pale yellow oil.

Reference Example 2

2-Chloro-5-[(2-ethoxyethoxy)methyl]benzoic acid

The titled compound was obtained according to the procedure as described in Reference Example 1, using 2-ethoxyethanol instead of EtOH.

Reference Example 3

2-Chloro-5-(cyclopropylethynyl)benzoic acid

To a solution of ethyl 5-bromo-2-chlorobenzoate (1.9 g) in DMF (12 mL), toluene (0.3 mL), cyclopropylacetylene (714 mg), copper iodide (275 mg), dichloro bis(triphenylphosphine)palladium (1.01 g) and triethylamine (20.1 mL) were added, and the mixture was degassed, stirred at 100° C. under argon atmosphere for 8 hours, and then the reaction mixture was cooled to room temperature and diluted with ethyl acetate. The insoluble material was filtered off on celite. The mother liquor was washed with brine, dried over magnesium sulfate and concentrated. By purification on column chromatography, ethyl 2-chloro-5-(cyclopropylethynyl)benzoate (1.86 g) was obtained as brown oil.

This was dissolved in MeOH-THF (1:1, 60 mL), 10% aqueous sodium hydroxide solution (20 mL) was added, and the solution was stirred at room temperature for 2 hours. The solvent was removed under reduced pressure, water was added to the residue, and the mixture was separated with diethyl ether.

The aqueous layer was separated, acidified with 1N hydrochloric acid and extracted with ethyl acetate. The organic layer was dried over magnesium sulfate and concentrated in vacuo. The residual solid was washed with n-hexane, and the titled compound (1.02 g) was obtained as beige powder.

Reference Example 4

2-Chloro-5-(2-cyclopropylethyl)benzoic acid

To a solution of 2-chloro-5-(cyclopropylethynyl)benzoic acid (200 mg) in ethyl acetate (20 mL) was added 10% palladium on carbon (40 mg), and the mixture was stirred under hydrogen atmosphere (0.2 MPa) for 14 hours, then was filtered off on celite, and the mother liquor was concentrated in vacuo. The residue was purified on silica gel column chromatography to obtain the titled compound (190 mg) as yellow oil.

Reference Example 5

2-Chloro-5-(2-phenylethyl)benzoic acid

Step 1

2-chloro-5-(phenylethynyl)benzoic acid

According to the procedure as described in Reference Example 3 using phenylacetylene instead of cyclopropylacetylene, 2-chloro-5-(phenylethynyl)benzoic acid was obtained as yellow powder.

Step 2

2-Chloro-5-(2-phenylethyl)benzoic acid

The titled compound was obtained as pale yellow powder, according to the procedure as described in Reference Example 4, using 2-chloro-5-(phenylethynyl)benzoic acid instead of 2-chloro-5-(cyclopropylethynyl)benzoic acid.

Reference Example 6

5-(3-tert-Butoxy-1-propynyl)-2-chlorobenzoic acid

The titled compound was obtained as white powder according to the procedure as described in Reference Example 3, using tert-butylpropargyl ether was used instead of cyclopropylacetylene.

Reference Example 7

5-(3-tert-Butoxypropyl)-2-chlorobenzoic acid

The titled compound was obtained as a pale yellow oil according to the procedure as described in Reference Example 4, using 5-(3-tert-butoxy-1-propynyl)-2-chlorobenzoic acid instead of 2-chloro-5-(cyclopropylethynyl)benzoic acid.

Reference Example 8

2-Chloro-5-(3-hydroxy-3-methylbutyl)benzoic acid

Step 1

2-Chloro-5-(3-hydroxy-3-methyl-1-butynyl)benzoic acid

The titled compound was obtained as white powder according to the procedure as described in Reference Example 3, using 2-methyl-3-butyn-2-ol instead of cyclopropylacetylene.

Step 2

2-Chloro-5-(3-hydroxy-3-methylbutyl)benzoic acid

The titled compound was obtained as a pale yellow oil according to the procedure as described in Reference Example 4, using 2-chloro-5-(3-hydroxy-3-methyl-1-butynyl)benzoic acid instead of 2-chloro-5-(cyclopropylethynyl)benzoic acid.

Reference Example 9

3-Methoxy-N,2,2-trimethylpropan-1-amine

Step 1 tert-Butyl (3-hydroxy-2,2-dimethylpropyl) carbamate

A solution of 3-amino-2,2-dimethyl-1-propanol (6.98 g) and sodium carbonate (7.18 g) in 1,4-dioxane-$H_2O$ (1:1, 240 mL) was stirred under ice-cooling, and di-tert-butyl dicarbonate (14.77 g) was added, and the mixture was stirred for 5 hours. Ethyl acetate was added, and the organic layer was separated, washed sequentially with water and brine, dried over magnesium sulfate and concentrated in vacuo to obtain the titled compound (12.7 g) as a colorless solid.

Step 2

3-Methoxy-N,2,2-trimethylpropan-1-amine

A solution of 60% sodium hydride (1.89 g) in DMF (60 mL) was stirred under ice-cooling, and a solution of tert-butyl (3-hydroxy-2,2-dimethylpropyl)carbamate (3.84 g) in DMF (45 mL) was dropped slowly over 5 minutes. Methyl iodide (10.73 g) was added and the mixture was stirred at room temperature for 3 hours. Diethyl ether was added to the reaction mixture. The organic layer was separated, washed sequentially with water and brine, dried over magnesium sulfate and concentrated in vacuo. The residue was purified on column chromatography to obtain tert-butyl (3-methoxy-2,2-dimethylpropyl)methyl carbamate (3.1 g) as a colorless oil. This was stirred under ice-cooling, TFA (8 mL) was added, and the mixture was stirred at room temperature for 1 hour. The mixture was stirred under ice-cooling, and the pH was raised to about pH 9 with 1N aqueous sodium hydroxide solution, and extracted with diethyl ether. The diethyl ether layer was dried and concentrated in vacuo with magnesium sulfate to obtain the titled compound (2.6 g) as pale yellow oil.

Reference Example 10

5-Butoxy-2-chlorobenzoic acid

To a solution of 2-chloro-5-fluorobenzoic acid (50 mg) and 1-butanol (263 µL) in THF (0.5 mL) and DMF (3 mL) was added potassium t-butoxide (329 mg) and the solution was reacted at 120° C. for 10 minutes in a microwave synthesizer (Biotage, Initiator). The reaction mixture was cooled and acidified by addition of water and 2M hydrochloric acid, extracted with diethyl ether, and dried over anhydrous sodium sulfate. The solvent was removed in vacuo, and the residue was purified on column chromatography to obtain the titled compound (17 mg) as white powder.

Reference Example 11

2-Chloro-5-(2,2-difluoroethoxy)benzoic acid

Step 1

Methyl 2-chloro-5-(2,2-difluoroethoxy)benzoate

To a suspension of methyl 2-chloro-5-hydroxybenzoate (50 mg) and potassium carbonate (111 mg) in acetone (1 mL) was added 2-iodo-1,1-difluoroethane (35 µL), and the suspension was reacted at 120° C. for 10 minutes in a microwave synthesizer (Biotage, Initiator). After reaction at 130° C. for additional 15 minutes, the reaction mixture was directly purified on silica gel column chromatography to obtain the titled compound (55 mg) as yellow oil.

Step 2

2-Chloro-5-(2,2-difluoroethoxy)benzoic acid

To a solution of methyl 2-chloro-5-(2,2-difluoroethoxy) benzoate (55 mg) in MeOH (1 mL) was added 1M aqueous lithium hydroxide (0.88 mL), and the solution was stirred at room temperature for 12 hours. The reaction mixture was stirred under ice-cooling, 2M hydrochloric acid was added slowly to acidify to pH 2-3, and the precipitated solid was filtered. The solid was washed sequentially with a small amount of water and diethyl ether, and dried under reduced pressure to obtain the titled compound (28 mg) as white powder.

Reference Example 12

2-Chloro-5-(4,4,4-trifluorobutoxy)benzoic acid

Step 1

Methyl 2-chloro-5-(4,4,4-trifluorobutoxy)benzoate

To a suspension of methyl 2-chloro-5-hydroxy benzoate (50 mg) and potassium carbonate (111 mg) in acetone (1 mL) was added 1-bromo-4,4,4-trifluorobutane (50 µl) and the suspension was reacted at 120° C. for 10 minutes in a microwave synthesizer (Biotage, Initiator). The reaction mixture was directly purified on silica gel column chromatography to obtain the titled compound (74 mg) as colorless oil.

Step 2

2-Chloro-5-(4,4,4-trifluorobutoxy)benzoic acid

To a solution of methyl 2-chloro-5-(4,4,4-trifluorobutoxy) benzoate (74 mg) in MeOH (1 mL) was added 1M aqueous lithium hydroxide solution (0.99 mL) and the reaction mixture was stirred at room temperature for 12 hours. The reaction mixture was stirred under ice-cooling, and 2M hydrochloric acid was added slowly to acidify to pH 2-3. The precipitated solid was filtered, washed with water, and dried under reduced pressure to obtain the titled compound (49 mg) as a colorless powder.

Example 1

N-[2-(Trifluoromethyl)benzyl]-6-({[2-(trifluoromethyl)phenyl]carbonyl}amino)-1H-benzimidazol-4-carboxamide Step 1

Methyl 1H-benzimidazole-4-carboxylate

To a suspension of methyl 2-amino-3-nitrobenzoate (1.0 g) in formic acid (>87%) was added 5% palladium on carbon (100 mg) and the suspension was heated with stirring at 100° C. for 23 hours. After the reaction mixture was cooled to room temperature, the catalyst was filtered off on celite, and the mother liquor was concentrated in vacuo. The residual solid was washed with diethyl ether under stirring, the solid was collected by filtration to obtain the titled compound (872 mg) as a colorless powder.

Step 2

Methyl 6-nitro-1H-benzimidazole-4-carboxylate

Methyl 1H-benzimidazole-4-carboxylate (315 mg) was dissolved in conc. sulfuric acid (3 mL), and the solution was stirred on ice bath. A small amount of potassium nitrate (199 mg) was added portion-wise, and the solution was stirred at room temperature for 4 hours. The reaction mixture was poured into ice, alkalified with 3N aqueous sodium hydroxide solution under stirring on ice bath, and extracted with ethyl acetate. The ethyl acetate layer was washed sequentially with water and brine, and dried over anhydrous magnesium sulfate. The titled compound (334 mg) was obtained as colorless powder after distilling off the solvent under reduced pressure.

Step 3

Methyl 6-amino-1H-benzimidazole-4-carboxylate

Methyl 6-nitro-1H-benzimidazole-4-carboxylate (304 mg) was suspended in MeOH (10 mL), the suspension was added with 5% palladium on carbon (30 mg), and stirred under hydrogen (1 atm) atmosphere. The catalyst was filtered off on celite and washed with MeOH, and the mother liquor was concentrated in vacuo to obtain the titled compound (269 mg) as pale yellow powder.
MS (ESI+) m/z 192 (M+H)$^+$

Step 4 methyl 6-({[2-(Trifluoromethyl)phenyl]carbonyl}amino)-1H-benzimidazole-4-carboxylate To a solution of methyl 6-amino-1H-benzimidazole-4-carboxylate (266 mg) in dehydrated THF (12 mL), N,N-diisopropylethylamine (284 μL) was added, and the solution was stirred under ice-cooling. To this solution, 2-(trifluoromethyl)benzoyl chloride (284 μL) in dehydrated THF (5 mL) was added slowly dropwise, and stirred at the same temperature for 3 hours. After ice water was added, THF was removed under reduced pressure, and aqueous saturated sodium bicarbonate was added, and the mixture was extracted with ethyl acetate. The organic layer was washed with brine, dried over anhydrous magnesium sulfate, and the solvent was removed under reduced pressure. The residue was purified on NH silica gel column chromatography (ethyl acetate→ethyl acetate/MeOH) to obtain the titled compound (309 mg) as pale yellow powder.

Step 5

6-({[2-(Trifluoromethyl)phenyl]carbonyl}amino)-1H-benzimidazole-4-carboxylic acid Methyl 6-({[2-(trifluoromethyl)phenyl]carbonyl}amino)-1H-benzimidazole-4-carboxylate (356 mg) was dissolved in MeOH (10 mL), and 1N aqueous sodium hydroxide solution (2 mL) was added, and the reaction mixture was stirred at room temperature overnight. After MeOH was removed under reduced pressure, water was added to the residue, and the solution was acidified with 1N hydrochloric acid to pH 5 under ice-cooling. The precipitate was collected by filtration to obtain the titled compound (276 mg) as slightly brown powder.

Step 6

N-[2-(Trifluoromethyl)benzyl]-6-({[2-(trifluoromethyl)phenyl]carbonyl}amino)-1H-benzimidazole-4-carboxamide To a solution of 6-({[2-(trifluoromethyl)phenyl]carbonyl}amino-1H-benzimidazole-4-carboxylic acid (50 mg) in DMF (2 mL) were added N'-(ethylcarbonimidoyl)-N,N-dimethyl-1,3-propanediamine hydrochloride (33 mg), 1-hydroxybenzotriazol (23 mg) and triethylamine (24 μL), and 2-(trifluoromethyl)benzylamine (24 μL) was added under ice-cooling, and the solution was stirred at room temperature overnight. The mixture was poured into ice water and extracted with ethyl acetate. The ethyl acetate layer was washed sequentially with water and brine, dried over anhydrous magnesium sulfate, and the solvent was removed under reduced pressure. The residue was washed with n-hexane/ethyl acetate (1:1), and collected by filtration to obtain the titled compound (61 mg) as colorless powder. MS (ESI+) m/z 507 (M+H)$^+$

Example 2

N-Cyclohexyl-6-({[2-(trifluoromethyl)phenyl]carbonyl}amino)-1H-benzimidazole-4-carboxamide The titled compound was obtained as colorless powder according to the procedure as described in Step 6 of Example 1 using cyclohexylamine instead of 2-(trifluoromethyl)benzylamine. MS (ESI+) m/z 431 (M+H)$^+$

Example 3

N-(3-Chloro-2-methylphenyl)-6-({[2-(trifluoromethyl)phenyl]carbonyl}mino)-1H-benzimidazole-4-carboxamide To a solution of 6-({[2-(trifluoromethyl)phenyl]carbonyl}amino)-1H-benzimidazole-4-carboxylic acid (Example 1, Step 5) (40 mg) in DMF (2 mL), HBTU (53 mg) and triethylamine (20 μL) were added. Under ice-cooling, 3-chloro-2-methylaniline (17 μL) was added and the solution was stirred at room temperature for 24 hours. The reaction mixture was poured into ice water, and extracted with ethyl acetate. The ethyl acetate layer was washed sequentially with water and brine, dried over anhydrous magnesium sulfate, and the solvent was removed under reduced pressure.
The residue was washed with n-hexane/ethyl acetate (1:1) and collected by filtration to obtain the titled compound (33 mg) as colorless powder. MS (ESI+) m/z 473 (M+H)$^+$

Example 5

N-[(1-Hydroxycyclohexyl)methyl]-6-({[2-(trifluoromethyl)phenyl]carbonyl}amino)-1H-benzimidazole-4-carboxamide The titled compound was obtained as colorless powder according to the procedure as described in Step 6 of Example 1, using 1-aminomethyl-1-cyclohexanol instead of 2-(trifluoromethyl)benzylamine. MS (ESI+) m/z 461 (M+H)$^+$

Example 6

N-[2-(Trifluoromethyl)benzyl]-5-({[2-(trifluoromethyl)phenyl]carbonyl}amino)-2,3-dihydro-1-benzofuran-7-carboxamide

Step 1

Ethyl 5-bromo-2,3-dihydro-1-benzofuran-7-carboxylate

To a solution of 5-bromo-2,3-dihydro-1-benzofuran-7-carboxylic acid (1.0 g) in EtOH (15 mL), sulfuric acid (0.5 mL) was added, and the solution was heated at reflux for 30 hours. The reaction mixture was cooled to room temperature, and EtOH was removed. To the residue was added water, and the solution was extracted with ethyl acetate. The ethyl acetate layer was washed sequentially with saturated aqueous sodium bicarbonate and brine, and dried over anhydrous magnesium sulfate. The solvent was removed under reduced pressure to obtain the titled compound (1.07 g) as pale yellow powder.

Step 2

Ethyl 5-({[2-(Trifluoromethyl)phenyl]carbonyl}amino)-2,3-dihydro-1-benzofuran-7-carboxylate 1,4-dioxane (20 ml) was added to ethyl 5-bromo-2,3-dihydro-1-benzofuran-7-carboxylate (600 mg), 2-(trifluoromethyl)benzamide (501 mg), 4,5-bis(diphenylphosphino)-9,9-dimethylxanthene (Xantphos) (96 mg), cesium carbonate (1.01 g) and tris(dibenzylideneacetone)dipalladium (114 mg). After degassing, the mixture was stirred at 100° C. under argon atmosphere for 24 hours. The reaction mixture was filtered off on celite, and the solvent was removed under reduced pressure. The resultant residue was purified on silica gel column chromatography to obtain the titled compound (220 mg) as slightly yellow powder.

Step 3

5-({[2-(Trifluoromethyl)phenyl]carbonyl}amino)-2,3-dihydro-1-benzofuran-7-carboxylic acid To a suspension of ethyl 5-({[2-(trifluoromethyl)phenyl]carbonyl}amino)-2,3-dihydro-1-benzofuran-7-carboxylate (220 mg) obtained in Step 2 in EtOH (5 mL), 1N aqueous sodium hydroxide solution (1 mL) was added and the mixture was stirred at 80° C. for 4 hours. The reaction mixture was cooled to room temperature, and EtOH was removed under reduced pressure. To the residue was added water, and the solution was acidified to pH 3 with 1N hydrochloric acid under ice-cooling and extracted with ethyl acetate. The organic layer was washed sequentially with water and brine, dried over anhydrous magnesium sulfate, and the solvent was removed under reduced pressure to obtain the titled compound (195 mg) as slightly yellow powder.

Step 4

N-[2-(Trifluoromethyl)benzyl]-5-({[2-(trifluoromethyl)phenyl]carbonyl}amino)-2,3-dihydro-1-benzofuran-7-carboxamide To a solution of 5-({[2-(trifluoromethyl)phenyl]carbonyl}amino)-2,3-dihydro-1-benzofuran-7-carboxylic acid (35 mg) in DMF (2 mL), N'-(ethylcarbonimidoyl)-N,N-dimethyl-1,3-propanediamine hydrochloride (23 mg), 1-hydroxybenzotriazol (23 mg) and triethylamine (17 µL) were added. Under ice-cooling, to the mixture was added 2-(trifluoromethyl)benzylamine (15 µL), and it was stirred at room temperature overnight. The reaction mixture was poured into ice water, and extracted with ethyl acetate. The ethyl acetate layer was washed sequentially with water and brine, dried over anhydrous magnesium sulfate, and the solvent was removed under reduced pressure. The residue was washed with n-hexane/ethyl acetate (1:1) and collected by filtration to obtain the titled compound (43 mg) as colorless powder. MS (ESI+) m/z 509 (M+H)$^+$, Rt=2.31 minutes (method A)

Example 7

N-Cyclohexyl-5-({[2-(trifluoromethyl)phenyl]carbonyl}amino)-2,3-dihydro-1-benzofuran-7-carboxamide The titled compound was obtained as colorless powder according to the procedure as described in Step 4 of Example 6 using cyclohexylamine instead of 2-(trifluoromethyl)benzylamine.
MS (ESI+) m/z 433 (M+H)$^+$, Rt=2.25 minutes (method A)

Example 8

N-(3-Chloro-2-methylphenyl)-5-({[2-(trifluoromethyl)phenyl]carbonyl}amino)-2,3-dihydro-1-benzofuran-7-carboxamide The titled compound was obtained as colorless powder according to the procedure as described in Example 3, using 5-({[2-(trifluoromethyl)phenyl]carbonyl}amino)-2,3-dihydro-1-benzofuran-7-carboxylic acid instead of 6-({[2-(trifluoromethyl)phenyl]carbonyl}amino)-1H-benzimidazole-4-carboxylic acid. MS (ESI+) m/z 475 (M+H)$^+$, Rt=2.47 minutes (method A)

Example 9

N-Cyclohexyl-5-({[2-(trifluoromethyl)phenyl]carbonyl}amino)-1H-indazole-7-carboxamide Step 1

Methyl 5-bromo-1-{[2-(trimethylsilyl)ethoxy]methyl}-1H-indazole-7-carboxylate

Under argon atmosphere, a solution of methyl 5-bromo-1H-indazole-7-carboxylate (as prepared according to WO2008/65508) (658 mg) in DMF (20 mL) was stirred under ice-cooling. 60% Sodium hydride (124 mg) was added slowly, and the mixture was stirred for 30 minutes at the same temperature. 2-(Trimethylsilyl)ethoxymethyl chloride (544 µL) was added dropwise slowly using a syringe, and the mixture was stirred at room temperature for 4 hours. The mixture was poured into ice water and extracted with ethyl acetate. The ethyl acetate layer was washed sequentially with water and brine, dried over anhydrous magnesium sulfate, and the solvent was removed under reduced pressure. The residue was purified on silica gel column chromatography to obtain the titled compound (696 mg) as slightly yellow oil.

Step 2

Methyl 5-{[(benzyloxy)carbonyl]amino}-1-{[2-(trimethylsilyl)ethoxy]methyl}-1H-indazole-7-carboxylate The titled compound was obtained as slightly yellow oil from methyl 5-bromo-1-{[2-(trimethylsilyl)ethoxy]methyl}-1H-indazole-7-carboxylate prepared in Step 1, according to the procedure as described in Step 2 of Example 6, using benzyl carbamate instead of 2-(trifluoromethyl)benzamide.

Step 3

Methyl 5-amino-1-{[2-(trimethylsilyl)ethoxy]methyl}-1H-indazole-7-carboxylate

To a solution of methyl 5-{[(benzyloxy)carbonyl]amino}-1-{[2-(trimethylsilyl)ethoxymethyl}-1H-indazole-7-carboxylate (364 mg) in MeOH (10 mL) was added 5% palladium on carbon (55 mg), and the reaction mixture was stirred overnight under hydrogen atmosphere at an ordinary pressure. The reaction mixture was filtered off on celite and washed with MeOH. The mother liquor was concentrated under reduced pressure to obtain the titled compound (234 mg) as green powder.

Step 4

Methyl 5-({[2-(trifluoromethyl)phenyl]carbonyl}amino)-1-{[2-(trimethylsilyl)ethoxy]methyl}-1H-indazole-7-carboxylate The titled compound (323 mg) was obtained as colorless powder according to the procedure as described in Step 4 of Example 1, using methyl 5-amino-1-{[2-(trimethylsilyl)ethoxy]methyl}-1H-indazole-7-carboxylate (231 mg).

Step 5

5-({[2-(Trifluoromethyl)phenyl]carbonyl}amino)-1-{[2-(trimethylsilyl)ethoxy]methyl}-1H-indazole-7-carboxylic acid The titled compound (291 mg) was obtained as colorless powder according to the procedure as described in Step 5 of Example 1, using methyl 5-({[2-(trifluoromethyl)phenyl]carbonyl}amino)-1-{[2-(trimethylsilyl)ethoxy]methyl}-1H-indazole-7-carboxylate (321 mg).

Step 6

N-Cyclohexyl-5-({[2-(trifluoromethyl)phenyl]carbonyl}amino)-1H-indazole-7-carboxamide To a solution of 5-({[2-(trifluoromethyl)phenyl]carbonyl}amino)-1-{[2-(trimethylsilyl)ethoxy]methyl}-1H-indazole-7-carboxylic acid (obtained in Step 5) (48 mg) in DMF (2 mL) were added HBTU (46 mg) and triethylamine (17 µL), and the mixture was stirred at room temperature, cyclohexylamine (12.5 µL) was added, and it was stirred at the same temperature overnight. The reaction mixture was poured into ice water, and extracted with ethyl acetate. The ethyl acetate layer was washed sequentially with saturated aqueous sodium bicarbonate and brine, dried over anhydrous magnesium sulfate, and the solvent was removed under reduced pressure. The residue was triturated in n-hexane/ethyl acetate (10:1), and collected by filtration to obtain 59 mg of N-cyclohexyl-5-({[2-(trifluoromethyl)phenyl]carbonyl}amino)-1-[2-(trimethylsilyl)ethoxymethyl]-indazole-7-carboxamide as colorless powder. This was dissolved in MeOH (2 mL), 6N hydrochloric acid (2 mL) was added, and the solution was stirred on oil bath at 60-80° C. for 10 hours. The solvent was removed, and ice water was added to the residue. The precipitate was collected by filtration and dried to obtain the titled compound (33 mg) as colorless powder.

MS (ESI+) m/z 431 (M+H)$^+$, Rt=1.91 minutes (method A)
Elemental Analysis for $C_{22}H_{21}F_3N_4O_2+0.1H_2O$
Calcd. (%) C, 61.13; H, 4.94; N, 12.96.
Found. (%) C, 60.93; H, 4.91; N, 12.71.

Example 10

N-[2-(Trifluoromethyl)benzyl]-5-({[2-(trifluoromethyl)phenyl]carbonyl}amino)-1H-indazole-7-carboxamide The titled compound was obtained as colorless powder according to the procedure as described in Step 6 of Example 9, using 2-(trifluoromethyl)benzylamine instead of cyclohexylamine.

MS (ESI+) m/z 507 (M+H)$^+$, Rt=2.05 minutes (method A)

Example 11

N-(3-Chloro-2-methylphenyl)-2-(methoxymethyl)-6-({[2-(trifluoromethyl)phenyl]carbonyl}amino)-1H-benzimidazole-4-carboxamide hydrochloride

Step 1

Methyl 2-amino-3-[(methoxyacetyl)amino]benzoate

To a solution of methyl 2,3-diaminobenzoate (3.0 g) in THF (50 mL) was added N,N-diisopropylethylamine (4.0 mL). The solution was stirred under ice-cooling, methoxyacetyl chloride (1.81 mL) in THF (10 mL) was added dropwise slowly, and it was stirred for 3 hours at the same temperature. To the reaction mixture was added saturated aqueous sodium bicarbonate, and THF was removed under reduced pressure. To the residue was added saturated aqueous sodium bicarbonate, and it was extracted with ethyl acetate, dried over anhydrous magnesium sulfate, and the solvent was removed under reduced pressure. The residue was purified on silica gel column chromatography to obtain the titled compound (3.60 g) as pale yellow powder.

Step 2

Methyl 2-(methoxymethyl)-1H-benzimidazole-4-carboxylate

Methyl 2-amino-3-[(methoxyacetyl)amino]benzoate (280 mg) was dissolved in acetic acid (6 mL), and the solution was heated at 100° C. for 0.5 hour with stirring. After cooling the reaction mixture to room temperature, acetic acid was removed. To the residue was added saturated aqueous sodium bicarbonate under ice-cooling, and it was extracted with ethyl acetate. The organic layer was washed sequentially with water and brine, dried over anhydrous magnesium sulfate, and the solvent was removed under reduced pressure to obtain the titled compound (241 mg) as pale yellow powder.

Step 3

Methyl 2-(methoxymethyl)-6-nitro-1H-benzimidazole-4-carboxylate

The titled compound (274 mg) was obtained as colorless powder according to the procedure as described in Step 2 of Example 1, using methyl 2-(methoxymethyl)-1H-benzimidazole-4-carboxylate (240 mg) instead of methyl 1H-benzimidazole-4-carboxylate.

Step 4

Methyl 6-amino-2-(methoxymethyl)-1H-benzimidazole-4-carboxylate

The titled compound (202 mg) was obtained as yellow powder according to the procedure as described in Step 3 of Example 1, using methyl 2-(methoxymethyl)-6-nitro-1H-benzimidazole-4-carboxylate (271 mg) instead of methyl 6-nitro-1H-benzimidazole-4-carboxylate.

Step 5

Methyl 2-(methoxymethyl)-6-({[2-(trifluoromethyl)phenyl]carbonyl}amino)-1H-benzimidazole-4-carboxylate The titled compound (281 mg) was obtained as colorless powder according to the procedure as described in Step 4 of Example 1, using methyl 6-amino-2-(methoxymethyl)-1H-benzimidazole-4-carboxylate (200 mg) instead of methyl 6-amino-1H-benzimidazole-4-carboxylate.

Step 6

2-(Methoxymethyl)-6-({[2-(trifluoromethyl)phenyl]carbonyl}amino)-1H-benzimidazole-4-carboxylic acid The titled compound (263 mg) was obtained as colorless powder according to the procedure as described in Step 5 of Example 1, using methyl 2-(methoxymethyl)-6-({[2-(trifluoromethyl)phenyl]carbonyl}amino)-1H-benzimidazole-4-carboxylate (278 mg) instead of methyl 6-({[2-(trifluoromethyl)phenyl]carbonyl}amino)-1H-benzimidazole-4-carboxylate.

Step 7

N-(3-Chloro-2-methylphenyl)-2-(methoxymethyl)-6-({[2-(trifluoromethyl)phenyl]carbonyl}amino)-1H-benzimidazole-4-carboxamide To a solution of 2-(methoxymethyl)-6-({[2-(trifluoromethyl)phenyl]carbonyl}amino)-1H-benzimidazole-4-carboxylic acid (153 mg) in DMF (5 mL), were added HBTU (178 mg) and triethylamine (65 μL). To the mixture was added 3-chloro-2-methylaniline (56 μL) under stirring at room temperature, and the mixture was stirred overnight. The reaction mixture was poured into saturated aqueous sodium bicarbonate, and extracted with ethyl acetate. The ethyl acetate layer was washed sequentially with water and brine, dried over anhydrous magnesium sulfate, and the solvent was removed under reduced pressure. The residue was purified on silica gel column chromatography to obtain N-(3-chloro-2-methylphenyl)-2-(methoxymethyl)-6-({[2-(trifluoromethyl)phenyl]carbonyl}amino)-1H-benzimidazole-4-carboxamide (165 mg) as colorless powder.

Step 8

N-(3-Chloro-2-methylphenyl)-2-(methoxymethyl)-6-({[2-(trifluoromethyl)phenyl]carbonyl}amino)-1H-benzimidazole-4-carboxamide hydrochloride N-(3-chloro-2-methylphenyl)-2-(methoxymethyl)-6-({[2-(trifluoromethyl)phenyl]carbonyl}amino)-1H-benzimidazole-4-carboxamide (165 mg) obtained in Step 7 was suspended in EtOH (3 mL). To the suspension was added 1M hydrochloric acid (0.32 mL), it was stirred to obtain a homogeneous solution, and the solvent was removed under reduced pressure. The residue was triturated in ethyl acetate, collected by filtration, and dried to obtain the titled compound (167 mg) as colorless powder.

MS (ESI+) m/z 517 (M+H)$^+$, Rt=2.41 minutes (method A)
Elemental Analysis for $C_{25}H_{20}ClF_3N_4O_3 \cdot HCl + 1.0H_2O$
Calcd. (%) C, 52.55; H, 4.06; N, 9.81.
Found. (%) C, 52.35; H, 3.96; N, 9.89.

Example 12

2-Methyl-N-[2-(trifluoromethyl)benzyl]-6-({[2-(trifluoromethyl)phenyl]carbonyl}amino)-1H-benzimidazole-4-carboxamide hydrochloride The titled compound was obtained as pale yellow powder according to the procedure as described in Example 11, using acetyl chloride instead of methoxyacetyl chloride, and 2-(trifluoromethyl)benzylamine instead of 3-chloro-2-methylaniline.

MS (ESI+) m/z 521 (M+H)$^+$,
Rt=1.74 minutes (method A)
Elemental Analysis for $C_{25}H_{18}F_6N_4O_2 \cdot HCl + 1.5H_2O$
Calcd. (%) C, 51.42; H, 3.80; N, 9.60.
Found. (%) C, 51.68; H, 3.81; N, 9.45.

Example 13

N-Cyclohexyl-2-methyl-6-({[2-(trifluoromethyl)phenyl]carbonyl}amino)-1H-benzimidazole-4-carboxamide hydrochloride The titled compound was obtained as pale yellow powder according to the procedure as described in Example 11, using acetyl chloride instead of methoxyacetyl chloride, and cyclohexylamine instead of 3-chloro-2-methylaniline.

MS (ESI+) m/z 445 (M+H)$^+$, Rt=1.52 minutes (method A)

Example 14

N-(3-Chloro-2-methylphenyl)-2-methyl-6-({[2-(trifluoromethyl)phenyl]carbonyl}amino)-1H-benzimidazole-4-carboxamide hydrochloride The titled compound was obtained as pale yellow powder according to the procedure as described in Example 11, using acetyl chloride instead of methoxyacetyl chloride.

MS (ESI+) m/z 487 (M+H)$^+$, Rt=2.10 minutes (method A)

Example 15

N-Cyclopentyl-2-methyl-6-({[2-(trifluoromethyl)phenyl]carbonyl}amino)-1H-benzimidazole-4-carboxamide The titled compound was obtained as colorless powder according to the procedure as described in Step 1 to Step 7 of Example 11, using acetyl chloride instead of methoxyacetyl chloride, and cyclopentylamine instead of 3-chloro-2-methylaniline.

MS (ESI+) m/z 431 (M+H)$^+$, Rt=1.39 minutes (method A)

Example 16

N-Cyclobutyl-2-methyl-6-({[2-(trifluoromethyl)phenyl]carbonyl}amino)-1H-benzimidazole-4-carboxamide The titled compound was obtained as colorless powder according to the procedure as described in Step 1 to Step 7 of Example 11, using acetyl chloride instead of methoxyacetyl chloride, and cyclobutylamine instead of 3-chloro-2-methylaniline.
MS (ESI+) m/z 417 (M+H)$^+$, Rt=1.29 minutes (method A)

Example 17

N-(3-Chloro-2-methylphenyl)-2-ethyl-6-({[2-(trifluoromethyl)phenyl]carbonyl}amino)-1H-benzimidazole-4-carboxamide The titled compound was obtained as white powder according to the procedure as described in Step 1 to Step 7 of Example 11, using propionyl chloride instead of methoxyacetyl chloride.
MS (ESI+) m/z 501 (M+H)$^+$, Rt=2.39 minutes (method A)

Example 18

N-Cyclohexyl-2-ethyl-6-({[2-(trifluoromethyl)phenyl]carbonyl}amino)-1H-benzimidazole-4-carboxamide The titled compound was obtained as colorless powder according to the procedure as described in Step 1 to Step 7 of Example 11, using propionyl chloride instead of methoxyacetyl chloride, and cyclohexylamine instead of 3-chloro-2-methylaniline.
MS (ESI+) m/z 459 (M+H)$^+$, Rt=1.75 minutes (method A)

Example 19

2-Ethyl-N-[2-(trifluoromethyl)benzyl]-6-({[2-(trifluoromethyl)phenyl]carbonyl}amino)-1H-benzimidazole-4-carboxamide The titled compound was obtained as colorless powder according to the procedure as described in Step 1 to Step 7 of Example 11, using propionyl chloride instead of methoxyacetyl chloride, and 2-(trifluoromethyl)benzylamine instead of 3-chloro-2-methylaniline.
MS (ESI+) m/z 535 (M+H)$^+$, Rt=1.96 minutes (method A)

Example 20

N-Cyclohexyl-2-(methoxymethyl)-6-({[2-(trifluoromethyl)phenyl]carbonyl}amino)-1H-benzimidazole-4-carboxamide The titled compound was obtained as colorless powder according to the procedure as described in Step 1 to Step 7 of Example 11, using cyclohexylamine instead of 3-chloro-2-methylaniline.
MS (ESI+) m/z 475 (M+H)$^+$, Rt=1.97 minutes (method A)

Example 21

2-(Methoxymethyl)-N-[2-(trifluoromethyl)benzyl]-6-({[2-(trifluoromethyl)phenyl]carbonyl}amino)-1H-benzimidazole-4-carboxamide The titled compound was obtained as colorless powder according to the procedure as described in Step 1 to Step 7 of Example 11, using 2-(trifluoromethyl)benzylamine instead of 3-chloro-2-methylaniline.
MS (ESI+) m/z 551 (M+H)$^+$, Rt=2.12 minutes (method A)

Example 22

2-(Methoxymethyl)-N-(2-methylphenyl)-6-({[2-(trifluoromethyl)phenyl]carbonyl}amino)-1H-benzimidazole-4-carboxamide hydrochloride The titled compound was obtained as colorless powder according to the procedure as described in Example 11, using ortho-toluidine instead of 3-chloro-2-methylaniline.
MS (ESI+) m/z 483 (M+H)$^+$, Rt=1.06 minutes (method B)

Example 23

2-(Methoxymethyl)-N-(4-methylphenyl)-6-({[2-(trifluoromethyl)phenyl]carbonyl}amino)-1H-benzimidazole-4-carboxamide hydrochloride The titled compound was obtained as colorless powder according to the procedure as described in Example 11, using para-toluidine instead of 3-chloro-2-methylaniline.
MS (ESI+) m/z 483 (M+H)$^+$, Rt=1.06 minutes (method B)

Example 24

N-(2-Chlorobenzyl)-2-(methoxymethyl)-6-({[2-(trifluoromethyl)phenyl]carbonyl}amino)-1H-benzimidazole-4-carboxamide hydrochloride The titled compound was obtained as pale yellow powder according to the procedure as described in Example 11, using 2-chlorobenzylamine instead of 3-chloro-2-methylaniline.
MS (ESI+) m/z 517 (M+H)$^+$, Rt=2.04 minutes (method A)

Example 25

2-(Methoxymethyl)-N-(4-methylbenzyl)-6-({[2-(trifluoromethyl)phenyl]carbonyl}amino)-1H-benzimidazole-4-carboxamide hydrochloride The titled compound was obtained as colorless powder according to the procedure as described in Example 11, using 4-methylbenzylamine instead of 3-chloro-2-methylaniline.
MS (ESI+) m/z 497 (M+H)$^+$, Rt=1.99 minutes (method A)

Example 26

N-(4,4-Difluorocyclohexyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 4,4-difluorocyclohexylamine instead of 3-chloro-2-methylaniline.
MS (ESI+) m/z 511 (M+H)$^+$, Rt=1.88 minutes (method A)

Example 27

N-(4-tert-Butylphenyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 4-tert-butylaniline instead of 3-chloro-2-methylaniline.
MS (ESI+) m/z 525 (M+H)$^+$, Rt=1.63 minutes (method B)

Example 28

2-(Methoxymethyl)-N-[4-(trifluoromethyl)phenyl]-6-({[2-(trifluoromethyl)phenyl]carbonyl}amino)-1H-benzimidazole-4-carboxamide hydrochloride The titled compound was obtained as colorless powder according to the procedure as described in Example 11, using 1-amino-4-(trifluoromethyl)benzene instead of 3-chloro-2-methylaniline.
MS (ESI+) m/z 537 (M+H)$^+$, Rt=1.39 minutes (method B)

Example 29

N-(2,4-Dimethylphenyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 2,4-dimethylaniline instead of 3-chloro-2-methylaniline.
MS (ESI+) m/z 497 (M+H)$^+$, Rt=1.24 minutes (method B)

Example 30

N-(2-Chloro-4-methylphenyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 2-chloro-4-methylaniline instead of 3-chloro-2-methylaniline.
MS (ESI+) m/z 517 (M+H)$^+$, Rt=1.42 minutes (method B)

Example 31

N-(3,4-Dimethylphenyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 3,4-dimethylaniline instead of 3-chloro-2-methylaniline.
MS (ESI+) m/z 497 (M+H)$^+$, Rt=1.22 minutes (method B)

Example 32

N-(3-Chloro-4-methylphenyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 3-chloro-4-methylaniline instead of 3-chloro-2-methylaniline.
MS (ESI+) m/z 517 (M+H)$^+$, Rt=1.46 minutes (method B)

Example 33

N-(2,3-Dihydro-1H-inden-5-yl)-2-(methoxymethyl)-6-({[2-(trifluoromethyl)phenyl]carbonyl}amino)-1H-benzimidazole-4-carboxamide hydrochloride The titled compound was obtained as gray powder according to the procedure as described in Example 11, using 5-aminoindan instead of 3-chloro-2-methylaniline.
MS (ESI+) m/z 509 (M+H)$^+$, Rt=2.36 minutes (method A)

Example 34

2-(Methoxymethyl)-N-(5,6,7,8-tetrahydronaphthalen-1-yl)-6-({[2-(trifluoromethyl)phenyl]carbonyl}amino)-1H-benzimidazole-4-carboxamide hydrochloride The titled compound was obtained as white powder according to the procedure as described in Example 11, using 5,6,7,8-tetrahydro-1-naphthylamine instead of 3-chloro-2-methylaniline.
MS (ESI+) m/z 523 (M+H)$^+$, Rt=2.44 minutes (method A)

Example 35

N-(2-Fluorophenyl)-2-(methoxymethyl)-6-({[2-(trifluoromethyl)phenyl]carbonyl}amino)-1H-benzimidazole-4-carboxamide A solution of 2-(methoxymethyl)-6-({[2-(trifluoromethyl)phenyl]carbonyl}amino)-1H-benzimidazole-4-carboxylic acid in THF (2 mL) was stirred under ice-cooling, a catalytic amount of DMF was added, and then oxalyl chloride (7.7 μL) was added. One hour later, to the reaction mixture was added additional oxalyl chloride (7.7 μL), it was stirred for additional one hour, and volatile elements were removed under reduced pressure. The residue was dissolved in THF (2 mL), 2-fluoroaniline (8.8 μL) and triethylamine (11 μL) were added sequentially, the mixture was stirred at room temperature for 1 hour, saturated aqueous sodium bicarbonate was added, and the solution was extracted with ethyl acetate.

The ethyl acetate layer was washed with brine, dried over anhydrous magnesium sulfate, and concentrated. The residue was triturated in n-hexane/diethyl ether to obtain the titled compound (21 mg) as colorless powder.
MS (ESI+) m/z 487 (M+H)$^+$, Rt=2.14 minutes (method A)

Example 36

2-(Methoxymethyl)-N-(2-methoxyphenyl)-6-({[2-(trifluoromethyl)phenyl]carbonyl}amino)-1H-benzimidazole-4-carboxamide The titled compound was obtained as colorless powder according to the procedure as described in Step 1 to Step 7 of Example 11, using ortho-anisidine instead of 3-chloro-2-methylaniline.
MS (ESI+) m/z 499 (M+H)$^+$, Rt=2.07 minutes (method A)

Example 37

2-(Methoxymethyl)-N-(4-methoxyphenyl)-6-({[2-(trifluoromethyl)phenyl]carbonyl}amino)-1H-benzimidazole-4-carboxamide The titled compound was obtained as colorless powder according to the procedure as described in Step 1 to Step 7 of Example 11, using para-anisidine instead of 3-chloro-2-methylaniline.
MS (ESI+) m/z 499 (M+H)$^+$, Rt=1.96 minutes (method A)

Example 38

N-(3-Bromo-2-methylphenyl)-2-(methoxymethyl)-6-({[2-(trifluoromethyl)phenyl]carbonyl}amino)-1H-benzimidazole-4-carboxamide The titled compound was obtained as colorless powder according to the procedure as described in Step 1 to Step 7 of Example 11, using 3-bromo-2-methylaniline instead of 3-chloro-2-methylaniline.
MS (ESI+) m/z 563 (M+H)$^+$, Rt=2.45 minutes (method A)

Example 39

N-(3-Chloro-2-methylbenzyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Step 1 to Step 7 of Example 11, using 3-chloro-2-methylbenzylamine instead of 3-chloro-2-methylaniline.
MS (ESI+) m/z 531 (M+H)$^+$, Rt=2.19 minutes (method A)

Example 40

N-(2,6-Difluorophenyl)-2-(methoxymethyl)-6-({[2-(trifluoromethyl)phenyl]carbonyl}amino)-1H-benzimidazole-4-carboxamide The titled compound was obtained as colorless powder according to the procedure as described in Example 35, using 2,6-difluoroaniline instead of 2-fluoroaniline.
MS (ESI+) m/z 505 (M+H)$^+$, Rt=1.94 minutes (method A)

Example 41

N-(3-Cyano-2-methylphenyl)-2-(methoxymethyl)-6-({[2-(trifluoromethyl)phenyl]carbonyl}amino)-1H-benzimidazole-4-carboxamide To a solution of N-(3-bromo-2-methylphenyl)-2-(methoxymethyl)-6-({[2-(trifluoromethyl)phenyl]carbonyl}amino)-1H-benzimidazole-4-carboxamide (Example 38) (85 mg) in DMF (0.5 mL), was added zinc cyanide (60% content, 60 mg). After degassing, to the mixture was added tetrakis(triphenylphosphine) palladium (88 mg), and it was stirred at 100° C. for 24 hours. To the reaction mixture was added ice water, and it was extracted with ethyl acetate. The ethyl acetate layer was washed sequentially with water and brine, dried over anhydrous magnesium sulfate, and the solvent was removed under reduced pressure. The residue was purified on preparative thin-layer chromatography to obtain the titled compound (14 mg) as colorless powder.
MS (ESI+) m/z 508 (M+H)$^+$, Rt=1.02 minutes (method B)

Example 42

2-(Methoxymethyl)-6-({[2-(trifluoromethyl)phenyl]carbonyl}amino)-N-{[3-(trifluoromethyl)pyridin-2-yl]methyl}-1H-benzimidazole-4-carboxamide dihydrochloride The titled compound was obtained as colorless powder according to the procedure as described in Example 11, using 2-(aminomethyl)-3-(trifluoromethyl)pyridine instead of 3-chloro-2-methylaniline.
MS (ESI+) m/z 552 (M+H)$^+$, Rt=1.86 minutes (method A)

Example 43

N-(2-Chloro-6-methylphenyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 2-chloro-6-methylaniline instead of 3-chloro-2-methylaniline.
MS (ESI+) m/z 517 (M+H)$^+$, Rt=2.35 minutes (method A)

Example 44

2-(2-Amino-2-oxoethyl)-N-(3-chloro-2-methylphenyl)-6-({[2-(trifluoromethyl)phenyl]carbonyl}amino)-1H-benzimidazole-4-carboxamide hydrochloride

Step 1

Methyl 2-(2-amino-2-oxoethyl)-6-nitro-1H-benzimidazole-4-carboxylate

Under ice-cooling, potassium nitrate (117 mg) was added slowly portion-wise to a stirring solution of methyl 2-(cyanomethyl)-1H-benzimidazole-4-carboxylate (prepared as described in EP1479681) (226 mg) in conc. sulfuric acid (5 mL), and the mixture was stirred at room temperature for 5 hours. The reaction mixture was poured into ice, and alkalified with 3N aqueous sodium hydroxide solution, and extracted with ethyl acetate. The ethyl acetate layer was washed sequentially with water and brine, dried over anhydrous magnesium sulfate, and the solvent was removed under reduced pressure. The residue was washed with MeOH, filtered and dried to obtain the titled compound (243 mg).

Step 2

Methyl 6-amino-2-(2-amino-2-oxoethyl)-1H-benzimidazole-4-carboxylate

The titled compound was obtained as yellow powder according to the procedure as described in Step 4 of Example 11, using methyl 2-(2-amino-2-oxoethyl)-6-nitro-1H-benzimidazole-4-carboxylate instead of methyl 2-(methoxymethyl)-6-nitro-1H-benzimidazole-4-carboxylate.

Step 3

Methyl 2-(2-amino-2-oxoethyl)-6-({[2-(trifluoromethyl)phenyl]carbonyl}amino)-1H-benzimidazole-4-carboxylate The titled compound was obtained as orange powder according to the procedure as described in Step 4 of Example 1, using methyl 6-amino-2-(2-amino-2-oxoethyl)-1H-benzimidazole-4-carboxylate instead of methyl 6-amino-1H-benzimidazole-4-carboxylate.

Step 4

2-(2-Amino-2-oxoethyl)-6-({[2-(trifluoromethyl) phenyl]carbonyl}amino)-1H-benzimidazole-4-carboxylic acid The titled compound was obtained as brown powder according to the procedure as described in Step 5 of Example 1, using methyl 2-(2-amino-2-oxoethyl)-6-({[2-(trifluoromethyl)phenyl]carbonyl}amino)-1H-benzimidazole-4-carboxylate instead of methyl 6-({[2-(trifluoromethyl)phenyl]carbonyl}amino)-1H-benzimidazole-4-carboxylate.

Step 5

2-(2-Amino-2-oxoethyl)-N-(3-chloro-2-methylphenyl)-6-({[2-(trifluoromethyl)phenyl] carbonyl}amino)-1H-benzimidazole-4-c arboxamide hydrochloride The titled compound was obtained as pale yellow powder according to the procedure as described in Step 7 of Example 11, using 2-(2-amino-2-oxoethyl)-6-({[2-(trifluoromethyl) phenyl]carbonyl}amino)-1H-benzimidazole-4-carboxylic acid instead of 2-(methoxymethyl)-6-({[2-(trifluoromethyl) phenyl]carbonyl}amino)-1H-benzimidazole-4-carboxylic acid.
MS (ESI+) m/z 530 (M+H)$^+$, Rt=1.86 minutes (method A)

Example 45

2-(2-Amino-2-oxoethyl)-N-[2-(trifluoromethyl)benzyl]-6-({[2-(trifluoromethyl)phenyl] carbonyl}amino)-1H-benzimidazole-4-carboxamide hydrochloride The titled compound was obtained as pale yellow powder according to the procedure as described in Step 7 of Example 11, using 2-(2-amino-2-oxoethyl)-6-({[2-(trifluoromethyl) phenyl]carbonyl}amino)-1H-benzimidazole-4-carboxylic acid instead of 2-(methoxymethyl)-6-({[2-(trifluoromethyl) phenyl]carbonyl}amino)-1H-benzimidazole-4-carboxylic acid, and 2-(trifluoromethyl)benzylamine instead of 3-chloro-2-methylaniline.
MS (ESI+) m/z 564 (M+H)$^+$, Rt=1.72 minutes (method A)

Example 46

N-(3-Chloro-2-methylphenyl)-1-methyl-6-({[2-(trifluoromethyl)phenyl]carbonyl}amino)-1H-benzimidazole-4-carboxamide Step 1

Methyl 1-methyl-6-({[2-(trifluoromethyl)phenyl] carbonyl}amino)-1H-benzimidazole-4-carboxylate To a solution of methyl 6-({[2-(trifluoromethyl)phenyl] carbonyl}amino)-1H-benzimidazole-4-carboxylate (Example 1, Step 4) (189 mg) in THF (5 mL), NaH (60%, 25 mg) was added slowly under ice-cooling, and the mixture was stirred at the same temperature for 30 minutes and additionally at room temperature for 1 hour. The reaction mixture was further stirred under ice-cooling, methyl iodide (81 µL) was added slowly, and it was stirred at room temperature overnight. To the reaction mixture was added saturated aqueous ammonium chloride, and it was extracted with ethyl acetate. The organic layer was washed sequentially with water and brine, dried over anhydrous magnesium sulfate, and the solvent was removed under reduced pressure. The residue was purified on column chromatography to obtain the titled compound (78 mg) as colorless powder.

Step 2

1-Methyl-6-({[2-(trifluoromethyl)phenyl] carbonyl}amino)-1H-benzimidazole-4-carboxylic acid The titled compound was obtained as colorless powder according to the procedure as described in Step 5 of Example 1, using methyl 1-methyl-6-({[2-(trifluoromethyl)phenyl] carbonyl}amino)-1H-benzimidazole-4-carboxylate instead of methyl 6-({[2-(trifluoromethyl)phenyl]carbonyl}amino)-1H-benzimidazole-4-carboxylate.

Step 3

N-(3-Chloro-2-methylphenyl)-1-methyl-6-({[2-(trifluoromethyl)phenyl]carbonyl}amino)-1H-benzimidazole-4-carboxamide The titled compound was obtained as colorless powder according to the procedure as described in Step 7 of Example 11, using 1-methyl-6-({[2-(trifluoromethyl)phenyl] carbonyl}amino)-1H-benzimidazole-4-carboxylic acid instead of 2-(methoxymethyl)-6-({[2-(trifluoromethyl)phenyl]carbonyl}amino)-1H-benzimidazole-4-carboxylic acid.
MS (ESI+) m/z 487 (M+H)$^+$, Rt=1.44 minutes (method B)

Example 47

N-Cyclohexyl-1-methyl-6-({[2-(trifluoromethyl) phenyl]carbonyl}amino)-1H-benzimidazole-4-carboxamide The titled compound was obtained as colorless powder according to the procedure as described in Example 46, using cyclohexylamine instead of 3-chloro-2-methylaniline.
MS (ESI+) m/z 445 (M+H)$^+$ Example 48

1-Methyl-N-[2-(trifluoromethyl)benzyl]-6-({[2-(trifluoromethyl)phenyl]carbonyl}amino)-1H-benzimidazole-4-carboxamide The titled compound was obtained as colorless powder according to the procedure as described in Example 46, using 2-(trifluoromethyl)benzylamine instead of 3-chloro-2-methylaniline.
MS (ESI+) m/z 521 (M+H)$^+$, Rt=1.06 minutes (method B)

Example 49

N-(3-Chloro-2-methylphenyl)-1-ethyl-6-({[2-(trifluoromethyl)phenyl]carbonyl}amino)-1H-benzimidazole-4-carboxamide The titled compound was obtained as white powder according to the procedure as described in Example 46, using ethyl iodide instead of methyl iodide.
MS (ESI+) m/z 501 (M+H)$^+$, Rt=2.53 minutes (method A)

Example 50

N-Cyclohexyl-1-ethyl-6-({[2-(trifluoromethyl)phenyl]carbonyl}amino)-1H-benzimidazole-4-carboxamide The titled compound was obtained as colorless powder according to the procedure as described in Example 46, using ethyl iodide instead of methyl iodide, and cyclohexylamine instead of 3-chloro-2-methylaniline.
MS (ESI+) m/z 459 (M+H)$^+$, Rt=2.14 minutes (method A)

Example 51

1-Ethyl-N-[2-(trifluoromethyl)benzyl]-6-({[2-(trifluoromethyl)phenyl]carbonyl}amino)-1H-benzimidazole-4-carboxamide The titled compound was obtained as colorless powder according to the procedure as described in Example 46, using ethyl iodide instead of methyl iodide, and 2-(trifluoromethyl)benzylamine instead of 3-chloro-2-methylaniline.
MS (ESI+) m/z 535 (M+H)$^+$, Rt=2.28 minutes (method A)

Example 52

N-(3-Chloro-2-methylphenyl)-2-methyl-6-({[2-(trifluoromethyl)phenyl]carbonyl}amino)-1,3-benzoxazole-4-carboxamide

Step 1

6-Bromo-2-methyl-1,3-benzoxazole-4-carboxylic acid

To a solution of 5-bromo-3-hydroxyanthranilic acid (prepared as described in Eur. J. Med. Chem., 1999, 34, 729) (400 mg) in xylene (30 mL), were added acetyl chloride (135 μL), triethylamine (265 μL) and pyridinium p-toluenesulfonate (130 mg), and the mixture was heated at reflux for 8 hours. The reaction mixture was cooled to room temperature, diluted with ethyl acetate, washed sequentially with water and brine, and dried over anhydrous magnesium sulfate, and the solvent was removed under reduced pressure. The residue was purified on silica gel column chromatography to obtain the titled compound (471 mg).

Step 2

6-Bromo-N-(3-chloro-2-methylphenyl)-2-methyl-1,3-benzoxazole-4-carboxamide

To a solution of 6-bromo-2-methyl-1,3-benzoxazole-4-carboxylic acid (136 mg) in DMF (2 mL), were added HBTU (242 mg) and triethylamine (110 μL). To the mixture was added 3-chloro-2-methylaniline (76 μL) and it was stirred at room temperature over night. The reaction mixture was poured into ice water and extracted with ethyl acetate. The ethyl acetate layer was washed sequentially with water and brine, dried over anhydrous magnesium sulfate, and the solvent was removed under reduced pressure. The residue was purified on silica gel column chromatography to obtain the titled compound (53 mg) as white powder.

Step 3

N-(3-Chloro-2-methylphenyl)-2-methyl-6-({[2-(trifluoromethyl)phenyl]carbonyl}amino)-1,3-benzoxazole-4-carboxamide The titled compound was obtained as white powder according to the procedure as described in Step 2 of Example 6, using 6-bromo-N-(3-chloro-2-methylphenyl)-2-methyl-1,3-benzoxazole-4-carboxamide instead of ethyl 5-bromo-2,3-dihydro-1-benzofuran-7-carboxylate.
MS (ESI) m/z 488 (M+H)$^+$, Rt=1.96 minutes (method B)

Example 53

2-Methyl-N-[2-(trifluoromethyl)benzyl]-6-({[2-(trifluoromethyl)phenyl]carbonyl}amino)-1,3-benzoxazole-4-carboxamide

Step 1

6-Bromo-2-methyl-N-[2-(trifluoromethyl)benzyl]-1,3-benzoxazole-4-carboxamide

The titled compound was obtained as white powder according to the procedure as described in Step 2 of Example 52, using 2-(trifluoromethyl)benzylamine instead of 3-chloro-2-methylaniline.

Step 2

2-Methyl-N-[2-(trifluoromethyl)benzyl]-6-({[2-(trifluoromethyl)phenyl]carbonyl}amino)-1,3-benzoxazole-4-carboxamide The titled compound was obtained as white powder according to the procedure as described in Step 2 of Example 6, using 6-bromo-2-methyl-N-[2-(trifluoromethyl)benzyl]-1,3-benzoxazole-4-carboxamide instead of ethyl 5-bromo-2,3-dihydro-1-benzofuran-7-carboxylate.
MS (ESI) m/z 522 (M+H)$^+$, Rt=2.49 minutes (method A)

Example 54

N-(3-Chloro-2-methylphenyl)-2-ethyl-6-({[2-(trifluoromethyl)phenyl]carbonyl}amino)-1,3-benzoxazole-4-carboxamide

Step 1

6-Bromo-2-ethyl-1,3-benzoxazole-4-carboxylic acid

The titled compound was obtained according to the procedure as described in Step 1 of Example 52, using propionyl chloride instead of acetyl chloride.

Step 2

6-Bromo-N-(3-chloro-2-methylphenyl)-2-ethyl-1,3-benzoxazole-4-carboxamide

The titled compound was obtained according to the procedure as described in Step 2 of Example 52, using 6-bromo-2-ethyl-1,3-benzoxazole-4-carboxylic acid instead of 6-bromo-2-methyl-1,3-benzoxazole-4-carboxylic acid.

Step 3

N-(3-Chloro-2-methylphenyl)-2-ethyl-6-({[2-(trifluoromethyl)phenyl]carbonyl}amino)-1,3-benzoxazole-4-carboxamide The titled compound was obtained as powder according to the procedure as described in Step 2 of Example 6, using 6-bromo-N-(3-chloro-2-methylphenyl)-2-ethyl-1,3-benzoxazole-4-carboxamide instead of ethyl 5-bromo-2,3-dihydro-1-benzofuran-7-carboxylate.

MS (ESI) m/z 502 (M+H)$^+$, Rt=2.29 minutes (method B)

Example 55

N-(3-Chloro-2-methylphenyl)-2-ethoxy-6-({[2-(trifluoromethyl)phenyl]carbonyl}amino)-1H-benzimidazole-4-carboxamide

Step 1

Methyl 2-ethoxy-6-nitro-1H-benzimidazole-4-carboxylate

To a stirring solution of methyl 2-ethoxy-1H-benzimidazole-4-carboxylate (prepared as described in J. Med. Chem., 1993, 36, 2182) (500 mg) in conc. sulfuric acid (5 mL), potassium nitrate (275 mg) was added portion-wise under ice-cooling, and the mixture was stirred at room temperature for 2.5 hours. The reaction mixture was poured into ice, alkalified with aqueous sodium hydroxide solution, and extracted with ethyl acetate. The ethyl acetate layer was washed sequentially with water and brine, dried over anhydrous magnesium sulfate, and the solvent was removed under reduced pressure to obtain the titled compound (595 mg) as white powder.

Step 2

Methyl 6-amino-2-ethoxy-1H-benzimidazole-4-carboxylate

The titled compound was obtained as pale yellow powder according to the procedure as described in Step 3 of Example 1, using methyl 2-ethoxy-6-nitro-1H-benzimidazole-4-carboxylate instead of methyl 6-nitro-1H-benzimidazole-4-carboxylate.

Step 3

Methyl 2-ethoxy-6-({[2-(trifluoromethyl)phenyl]carbonyl}amino)-1H-benzimidazole-4-carboxylate The titled compound was obtained as colorless powder according to the procedure as described in Step 4 of Example 1, using methyl 6-amino-2-ethoxy-1H-benzimidazole-4-carboxylate instead of methyl 6-amino-1H-benzimidazole-4-carboxylate.

Step 4

2-Ethoxy-6-({[2-(trifluoromethyl)phenyl]carbonyl}amino)-1H-benzimidazole-4-carboxylic acid The titled compound was obtained as colorless powder according to the procedure as described in Step 5 of Example 1, using methyl 2-ethoxy-6-({[2-(trifluoromethyl)phenyl]carbonyl}amino)-1H-benzimidazole-4-carboxylate instead of methyl 6-({[2-(trifluoromethyl)phenyl]carbonyl}amino)-1H-benzimidazole-4-carboxylate.

Step 5

N-(3-Chloro-2-methylphenyl)-2-ethoxy-6-({[2-(trifluoromethyl)phenyl]carbonyl}amino)-1H-benzimidazole-4-carboxamide The titled compound was obtained as white powder according to the procedure as described in Step 7 of Example 11, using 2-ethoxy-6-({[2-(trifluoromethyl)phenyl]carbonyl}amino)-1H-benzimidazole-4-carboxylic acid instead of 2-(methoxymethyl)-6-({[2-(trifluoromethyl)phenyl]carbonyl}amino)-1H-benzimidazole-4-carboxylic acid.

MS (ESI+) m/z 517 (M+H)$^+$, Rt=1.72 minutes (method B)

Example 56

2-Ethoxy-N-[2-(trifluoromethyl)benzyl]-6-({[2-(trifluoromethyl)phenyl]carbonyl}amino)-1H-benzimidazole-4-carboxamide The titled compound was obtained as white powder according to the procedure as described in Example 55, using 2-(trifluoromethyl)benzylamine instead of 3-chloro-2-methylaniline.

MS (ESI+) m/z 551 (M+H)$^+$, Rt=1.32 minutes (method B)

Example 57

N-(3-Chloro-2-methylphenyl)-2-(1-chloro-2-methylpropan-2-yl)-6-({[2-(trifluoromethyl)phenyl]carbonyl}amino)-1H-benzimidazole-4-carboxamide The titled compound was obtained as white powder according to the procedure as described in Example 11, using 3-chloro-2,2-dimethylpropionyl chloride instead of methoxyacetyl chloride.

MS (ESI+) m/z 563 (M+H)$^+$, Rt=2.75 minutes (method A)

Example 58

N-(3-Chloro-2-methylphenyl)-2-[(dimethylamino)methyl]-6-({[2-(trifluoromethyl)phenyl]carbonyl}amino)-1H-benzimidazole-4-carboxamide hydrochloride

Step 1

Methyl 2-(chloromethyl)-6-nitro-1H-benzimidazole-4-carboxylate

The titled compound was obtained as slightly yellow powder according to the procedure as described in Step 2 of Example 1, using methyl 2-(chloromethyl)-1H-benzimidazole-4-carboxylate (prepared as described in WO2003/106430) instead of methyl 1H-benzimidazole-4-carboxylate.

Step 2

Methyl 2-[(dimethylamino)methyl]-6-nitro-1H-benzimidazole-4-carboxylate

To a solution of methyl 2-(chloromethyl)-6-nitro-1H-benzimidazole-4-carboxylate (72 mg) in acetonitrile (3 mL), was added 2M dimethylamine/MeOH solution (1.3 mL), and the mixture was stirred at 80° C. overnight.
The solvent was removed under reduced pressure, and the residue was purified on silica gel chromatography to obtain the titled compound (68 mg) as slightly yellow solid.

Step 3

Methyl 6-amino-2-[(dimethylamino)methyl]-1H-benzimidazole-4-carboxylate

The titled compound was obtained as yellow amorphous according to the procedure as described in Step 3 of Example 1, using methyl 2-[(dimethylamino)methyl]-6-nitro-1H-benzimidazole-4-carboxylate instead of methyl 6-nitro-1H-benzimidazole-4-carboxylate.

Step 4

Methyl 2-[(dimethylamino)methyl]-6-({[2-(trifluoromethyl)phenyl]carbonyl}amino)-1H-benzimidazole-4-carboxylate The titled compound was obtained as colorless powder according to the procedure as described in Step 4 of Example 1, using methyl 6-amino-2-[(dimethylamino)methyl]-1H-benzimidazole-4-carboxylate instead of methyl 6-amino-1H-benzimidazole-4-carboxylate.

Step 5

2-[(Dimethylamino)methyl]-6-({[2-(trifluoromethyl)phenyl]carbonyl}amino)-1H-benzimidazole-4-carboxylic acid The titled compound was obtained as yellow amorphous according to the procedure as described in Step 5 of Example 1, using methyl 2-[(dimethylamino)methyl]-6-({[2-(trifluoromethyl)phenyl]carbonyl}amino)-1H-benzimidazole-4-carboxylate instead of methyl 6-({[2-(trifluoromethyl)phenyl]carbonyl}amino)-1H-benzimidazole-4-carboxylate.

Step 6

N-(3-Chloro-2-methylphenyl)-2-[(dimethylamino)methyl]-6-({[2-(trifluoromethyl)phenyl]carbonyl}amino)-1H-benzimidazole-4-carboxamide hydrochloride The titled compound was obtained as white powder according to the procedure as described in Step 7 of Example 11, using 2-[(dimethylamino)methyl]-6-({[2-(trifluoromethyl)phenyl]carbonyl}amino)-1H-benzimidazole-4-carboxylic acid instead of 2-(methoxymethyl)-6-({[2-(trifluoromethyl)phenyl]carbonyl}amino)-1H-benzimidazole-4-carboxylic acid.
MS (ESI+) m/z 530 (M+H)$^+$, Rt=1.54 minutes (method A)

Example 59

N-(3-Chloro-2-methylphenyl)-2-(2-methylpropyl)-6-({[2-(trifluoromethyl)phenyl]carbonyl}amino)-1H-benzimidazole-4-carboxamide hydrochloride The titled compound was obtained as white powder according to the procedure as described in Example 11, using isovaleryl chloride instead of methoxyacetyl chloride.
MS (ESI+) m/z 529 (M+H)$^+$, Rt=1.95 minutes (method B)

Example 60

2-(2-Methylpropyl)-N-[2-(trifluoromethyl)benzyl]-6-({[2-(trifluoromethyl)phenyl]carbonyl}amino)-1H-benzimidazole-4-carboxamide hydrochloride The titled compound was obtained as white powder according to the procedure as described in Example 11, using isovaleryl chloride instead of methoxyacetyl chloride, and 2-(trifluoromethyl)benzylamine instead of 3-chloro-2-methylaniline.
MS (ESI+) m/z 563 (M+H)$^+$, Rt=1.20 minutes (method B)

Example 61 tert-Butyl 3-{4-[(3-chloro-2-methylphenyl)carbamoyl]-6-({[2-(trifluoro methyl)phenyl]carbonyl}amino)-1H-benzimidazol-2-yl}azetidine-1-carboxylate The titled compound was obtained as pale yellow powder according to the procedures as described in Steps 1 to 7 of Example 11, using 1-(tert-butoxycarbonyl)azetidine-3-carbonyl chloride (prepared as described in U.S. Pat. No. 6,020,368) instead of methoxyacetyl chloride.
MS (ESI+) m/z 628 (M+H)$^+$, Rt=1.87 minutes (method B)

Example 62

N-(3-Chloro-2-methylphenyl)-2-[(methylamino)methyl]-6-({[2-(trifluoromethyl)phenyl]carbonyl}amino)-1H-benzimidazole-4-carboxamide dihydrochloride Step 1

Methyl 2-{[(tert-butoxycarbonyl)(methyl)amino]methyl}-6-nitro-1H-benzimidazole-4-carboxylate To a solution of methyl 2-(chloromethyl)-6-nitro-1H-benzimidazole-4-carboxylate (Example 58, Step 1) (72 mg) in acetonitrile (2 mL), was added 40% methylamine/MeOH solution (0.27 mL), and the mixture was stirred at 80° C. for 1 hour. The solvent was removed under reduced pressure. To the residue was added water, and it was extracted with ethyl acetate. The ethyl acetate layer was washed with brine, dried over anhydrous magnesium sulfate, and concentrated. The obtained residue (68 mg) was dissolved in anhydrous THF (2 mL), and triethylamine (93 µL) was added to the solution. Di-tert-butyl dicarbonate (141 µL) was added to the solution with stirring under ice-cooling for 3 hours. To the reaction mixture was added water, and it was extracted with ethyl acetate. The ethyl acetate layer was washed with brine, dried over anhydrous magnesium and concentrated under reduced pressure. The residue was purified on column chromatography to obtain the titled compound (54 mg) as slightly yellow amorphous.

Step 2

Methyl 6-amino-2-{[(tert-butoxycarbonyl)(methyl) amino]methyl}-1H-benzimidazole-4-carboxylate The titled compound was obtained as yellow amorphous according to the procedure as described in Step 3 of Example 1, using methyl 2-{[(tert-butoxycarbonyl)(methyl)amino] methyl}-6-nitro-1H-benzimidazole-4-carboxylate instead of methyl 6-nitro-1H-benzimidazole-4-carboxylate.

Step 3

Methyl 2-{[(tert-butoxycarbonyl)(methyl)amino] methyl}-6-({[2-(trifluoromethyl)phenyl] carbonyl}amino)-1H-benzimidazole-4-carboxylate The titled compound was obtained as slightly yellow amorphous according to the procedure as described in Step 4 of Example 1, using methyl 6-amino-2-{[(tert-butoxycarbonyl) (methyl)amino]methyl}-1H-benzimidazole-4-carboxylate instead of methyl 6-amino-1H-benzimidazole-4-carboxylate.

Step 4

2-{[(tert-Butoxycarbonyl)(methyl)amino]methyl}-6-({[2-(trifluoromethyl)phenyl]carbonyl}amino)-1H-benzimidazole-4-carboxylic acid The titled compound was obtained as yellow amorphous according to the procedure as described in Step 5 of Example 1, using methyl 2-{[(tert-butoxycarbonyl)(methyl)amino] methyl}-6-({[2-(trifluoromethyl)phenyl]carbonyl}amino)-1H-benzimidazole-4-carboxylate instead of methyl 6-({[2-(trifluoromethyl)phenyl]carbonyl}amino)-1H-benzimidazole-4-carboxylate.

Step 5

N-(3-Chloro-2-methylphenyl)-2-[(methylamino) methyl]-6-({[2-(trifluoromethyl)phenyl] carbonyl}amino)-1H-benzimidazole-4-carboxamide dihydrochloride 2-{[(tert-Butoxycarbonyl)(methyl)amino]methyl}-N-(3-chloro-2-methylphenyl)-6-({[2-(trifluoromethyl)phenyl] carbon yl}amino)-1H-benzimidazole-4-carboxamide (9 mg) was obtained according to the procedure as described in Step 7 of Example 11, using 2-{[(tert-butoxycarbonyl)(methyl) amino]methyl}-6-({[2-(trifluoromethyl)phenyl] carbonyl}amino)-1H-benzimidazole-4-carboxylic acid instead of 2-(methoxymethyl)-6-({[2-(trifluoromethyl)phenyl]carbonyl}amino)-1H-benzimidazole-4-carboxylic acid. This was dissolved in methylene chloride (1 mL). To the residue was added TFA (0.5 mL) under ice-cooling, and it was stirred for 0.5 hour. To the reaction mixture were added ice and then saturated aqueous sodium bicarbonate, and it was extracted with ethyl acetate. The organic layer was washed with brine, dried over anhydrous magnesium sulfate, and concentrated under reduced pressure. The residue was purified on column chromatography to obtain N-(3-chloro-2-methylphenyl)-2-[(methylamino)methyl]-6-({[2-(trifluoromethyl)phenyl]carbonyl}amino)-1H-benzimidazole-4-carboxamide (5 mg) as slightly yellow powder. This was dissolved in MeOH (0.5 mL), and treated with 1M hydrochloric acid (2 Eq), and concentrated to obtain the titled compound (5 mg) as slightly yellow powder.

MS (ESI+) m/z 516 (M+H)$^+$, Rt=1.55 minutes (method A)

Example 63

{4-[(3-Chloro-2-methylphenyl)carbamoyl]-6-({[2-(trifluoromethyl)phenyl]carbonyl}amino)-1H-benzimidazol-2-yl}methyl acetate Step 1

Methyl 2-[(acetyloxy)methyl]-6-nitro-1H-benzimidazole-4-carboxylate

To a solution of methyl 2-(chloromethyl)-6-nitro-1H-benzimidazole-4-carboxylate (Example 58, Step 1) (99 mg) in DMF (1 mL), was added sodium acetate (17 mg), and the mixture was stirred at 50° C. for 6 hours. To the reaction mixture was added ice water, and it was extracted with ethyl acetate. The ethyl acetate layer was washed with brine, dried over anhydrous magnesium sulfate and concentrated. The residue was purified on column chromatography to obtain the titled compound (65 mg) as colorless powder.

Step 2

Methyl 2-[(acetyloxy)methyl]-6-amino-1H-benzimidazole-4-carboxylate

The titled compound was obtained as pale yellow powder according to the procedure as described in Step 3 of Example 1, using methyl 2-[(acetyloxy)methyl]-6-nitro-1H-benzimidazole-4-carboxylate instead of methyl 6-nitro-1H-benzimidazole-4-carboxylate.

Step 3

Methyl 2-[(acetyloxy)methyl]-6-({[2-(trifluoromethyl)phenyl]carbonyl}amino)-1H-benzimidazole-4-carboxylate The titled compound was obtained as pale yellow amorphous according to the procedure as described in Step 4 of Example 1, using methyl 2-[(acetyloxy)methyl]-6-amino-1H-benzimidazole-4-carboxylate instead of methyl 6-amino-1H-benzimidazole-4-carboxylate.

Step 4

2-(Hydroxymethyl)-6-({[2-(trifluoromethyl)phenyl] carbonyl}amino)-1H-benzimidazole-4-carboxylic acid The titled compound was obtained as colorless powder according to the procedure as described in Step 5 of Example 1, using methyl 2-[(acetyloxy)methyl]-6-({[2-(trifluoromethyl)phenyl]carbon yl}amino)-1H-benzimidazole-4-car boxylate instead of methyl 6-({[2-(trifluoromethyl)phenyl] carbonyl}amino)-1H-benzimidazole-4-carboxylate.

Step 5

{4-[(3-Chloro-2-methylphenyl) carbamoyl]-6-({[2-(trifluoromethyl)phenyl]carbonyl}amino)-1H-benzimidazol-2-yl}methyl acetate A mixture of 2-(hydroxymethyl)-6-({[2-(trifluoromethyl) phenyl]carbonyl}amino)-1H-benzimidazole-4-carboxylic acid (50 mg) and N,N-diisopropylethylamine (49 µL) in methylene chloride-THF (1:1) (2 mL) was stirred under ice-cooling, acetyl chloride (19 µL) was added, and it was stirred at room temperature overnight. The reaction mixture was poured into a cold 10% aqueous citric acid solution, and extracted with ethyl acetate. The organic layer was separated, washed with brine, dried over anhydrous magnesium sulfate, and concentrated under reduced pressure. The residue was dissolved in DMF (3 mL), HBTU (65 mg) and triethylamine (24 µL) were added, and it was stirred at room temperature. To the mixture was added 3-chloro-2-methylaniline (16 µL) and it was stirred overnight. The reaction mixture was poured into ice water, and extracted with ethyl acetate. The organic layer was washed sequentially with water and brine, dried over anhydrous magnesium sulfate, and concentrated under reduced pressure.
The obtained residue was purified on column chromatography to obtain the titled compound (6 mg) as colorless powder.
MS (ESI+) m/z 545 (M+H)$^+$, Rt=2.41 minutes (method A)

Example 64

N-(3-Chloro-2-methylphenyl)-2-[(2R)-tetrahydrofuran-2-yl]-6-({[2-(trifluoromethyl)phenyl] carbonyl}amino)-1H-benzimidazole-4-carboxamide hydrochloride The titled compound was obtained as white powder according to the procedure as described in Example 11, using (2R)-tetrahydro-2-furancarbonyl chloride (prepared as described in WO2006/79642) instead of methoxyacetyl chloride.
MS (ESI+) m/z 543 (M+H)$^+$, Rt=2.56 minutes (method A)
Elemental Analysis for $C_{27}H_{22}ClF_3N_4O_3 \cdot HCl+1.5H_2O$
Calcd. (%) C, 53.48; H, 4.32; N, 9.24.
Found. (%) C, 53.26; H, 4.17; N, 9.19.

Example 65

2-[(2R)-Tetrahydrofuran-2-yl]-N-[2-(trifluoromethyl)benzyl]-6-({[2-(trifluoromethyl)phenyl] carbonyl}amino)-1H-benzimidazole-4-carboxamide The titled compound was obtained as white powder according to the procedure as described in Example 11, using (2R)-tetrahydro-2-furancarbonyl chloride (prepared as described in WO2006/79642) instead of methoxyacetyl chloride, and 2-(trifluoromethyl)benzylamine instead of 3-chloro-2-methylaniline.
MS (ESI+) m/z 577 (M+H)$^+$, Rt=2.25 minutes (method A)

Example 66

N-(3-Chloro-2-methylphenyl)-2-[(2S)-tetrahydrofuran-2-yl]-6-({[2-(trifluoromethyl)phenyl] carbonyl}amino)-1H-benzimidazole-4-carboxamide hydrochloride The titled compound was obtained as white powder according to the procedure as described in Example 11, using (2S)-tetrahydro-2-furancarbonyl chloride (prepared as described in WO2006/79642) instead of methoxyacetyl chloride.
MS (ESI+) m/z 543 (M+H)$^+$, Rt=2.56 minutes (method A)

Example 67

2-[(2S)-Tetrahydrofuran-2-yl]-N-[2-(trifluoromethyl) benzyl]-6-({[2-(trifluoromethyl)phenyl] carbonyl}amino)-1H-benzimidazole-4-carboxamide hydrochloride The titled compound was obtained as white powder according to the procedure as described in Example 11, using (2S)-tetrahydro-2-furancarbonyl chloride (prepared as described in WO2006/79642) instead of methoxyacetyl chloride, and 2-(trifluoromethyl)benzylamine instead of 3-chloro-2-methylaniline.
MS (ESI+) m/z 577 (M+H)$^+$, Rt=2.25 minutes (method A)

Example 68

2-(1-Acetylazetidin-3-yl)-N-(3-chloro-2-methylphenyl)-6-({[2-(trifluoromethyl)phenyl] carbonyl}amino)-1H-benzimidazole-4-carboxamide hydrochloride To a solution of tert-butyl 3-{4-[(3-chloro-2-methylphenyl)carbamoyl]-6-({[2-(trifluoro methyl)phenyl] carbonyl}amino)-1H-benzimidazole-2-anyl}azetidine-1-carboxylate (Example 61) (50 mg) in methylene chloride (2 mL), was added thioanisole (50 µL). To the mixture was added TFA (1 mL) under ice-cooling, and the mixture was stirred at room temperature for 2 hours. The reaction mixture was poured into saturated aqueous sodium bicarbonate and extracted with ethyl acetate. The organic layer was washed with brine, dried over anhydrous magnesium sulfate, and the solvent was removed under reduced pressure. The residue was triturated in n-hexane/ethyl acetate, and the precipitate was collected by filtration and dried to obtain 2-(azetidin-3-yl)-N-(3-chloro-2-methylphenyl)-6-({[2-(trifluoromethyl) phenyl]carbonyl}amino)-1H-benzimidazole-4-carboxamide (38 mg). This was dissolved in THF (1 mL), pyridine (23 µL) was added, and the mixture was stirred under ice-cooling. To the mixture was added dropwise acetyl chloride (7.7 µL), and it was stirred at room temperature for 2 hours. The reaction mixture was poured into ice water, and extracted with ethyl acetate. The organic layer was washed with brine, dried over anhydrous magnesium sulfate, and the solvent was removed under reduced pressure. The residue was purified on column chromatography to obtain 2-(1-acetylazetidin-3-yl)-N-(3-chloro-2-methylphenyl)-6-({[2-(trifluoromethyl)phenyl] carbonyl}amino)-1H-benzimidazole-4-carboxamide (7.5 mg). This was dissolved in MeOH (0.5 mL), treated with 1M hydrogen chloride/MeOH, and concentrated to obtain the titled compound (5.5 mg) as slightly gray powder.
MS (ESI+) m/z 570 (M+H)$^+$, Rt=1.98 minutes (method A)

Example 69 tert-Butyl (2S)-2-{4-[(3-chloro-2-methylphenyl)
carbamoyl]-6-({[2-(trifluoromethyl)phenyl]
carbonyl}amino)-1H-benzimidazol-2-yl}pyrrolidine
1-carboxylate The titled compound was obtained as white powder according to the procedures as described in Steps 1 to 7 of Example 11, using tert-butyl (2S)-2-(chlorocarbonyl)pyrrolidine-1-carboxylate (prepared as described in Tetrahedron Asymmetry, 2007, 18, 2011) instead of methoxyacetyl chloride.
MS (ESI+) m/z 642 (M+H)$^+$, Rt=2.77 minutes (method A)

Example 70 tert-Butyl (2R)-2-{4-[(3-chloro-2-methylphenyl)
carbamoyl]-6-({[2-(trifluoromethyl)phenyl]
carbonyl}amino)-1H-benzimidazol-2-yl}pyrrolidine-
1-carboxylate The titled compound was obtained as white powder according to the procedures as described in Steps 1 to 7 of Example 11, using tert-butyl (2R)-2-(chlorocarbonyl)pyrrolidine-1-carboxylate (prepared as described in Tetrahedron Asymmetry, 2007, 18, 2011) instead of methoxyacetyl chloride.
MS (ESI+) m/z 642 (M+H)$^+$, Rt=2.77 minutes (method A)

Example 71

N-(3-Chloro-2-methylphenyl)-2-[(2S)-pyrrolidin-2-
yl]-6-({[2-(trifluoromethyl)phenyl]carbonyl}amino)-
1H-benzimidazole-4-carboxamide dihydrochloride To a solution of tert-butyl (2S)-2-{4-[(3-chloro-2-methylphenyl)carbamoyl]-6-({[2-(trifluoromethyl)phenyl]carbonyl}amino)-1H-benzimidazole-2-yl}pyrrolidine-1-carboxylate (26 mg) (Example 69) in ethyl acetate (2 mL), was added 4N hydrogen chloride/ethyl acetate solution (2 mL), and the mixture was stirred at room temperature for 2 hours. N-hexane was added to the reaction mixture, the precipitate was collected, and dried to obtain the titled compound (20 mg) as pale yellow powder.
MS (ESI+) m/z 542 (M+H)$^+$, Rt=1.65 minutes (method A)

Example 72

N-(3-Chloro-2-methylphenyl)-2-[(2S)-1-methylpyr-
rolidin-2-yl]-6-({[2-(trifluoromethyl)phenyl]
carbonyl}amino)-1H-benzimidazole-4-carboxamide To a solution of N-(3-chloro-2-methylphenyl)-2-[(2S)-pyrrolidin-2-yl]-6-({[2-(trifluoromethyl)phenyl]carbonyl}amino)-1H-benzimidazole-4-carboxamide (Example 71) (25 mg) in MeOH (0.4 mL), was added 38% aqueous formaldehyde solution (7.2 µL), and the mixture was stirred at room temperature overnight. To the mixture was added 2-picoline borane (10 mg), it was stirred for 3 hours, and the solvent was removed under reduced pressure. The residue was purified on column chromatography to obtain the titled compound (11 mg) as white powder.
MS (ESI+) m/z 556 (M+H)$^+$, Rt=1.67 minutes (method A)

Example 73

2-[(2S)-1-Acetylpyrrolidin-2-yl]-N-(3-chloro-2-me-
thylphenyl)-6-({[2-(trifluoromethyl)phenyl]
carbonyl}amino)-1H-benzimidazole-4-carboxamide To a solution of N-(3-chloro-2-methylphenyl)-2-[(2S)-pyrrolidin-2-yl]-6-({[2-(trifluoromethyl)phenyl]carbonyl}amino)-1H-benzimidazole-4-carboxamide (Example 71) (26 mg) in THF solution (0.5 mL), was added pyridine (12 µL), and the mixture was stirred under ice-cooling. To the mixture was added acetyl chloride (5.1 µL), and it was stirred at room temperature for 1 hour. To the reaction mixture was added ice water, and the mixture was extracted with ethyl acetate. The organic layer was washed with brine, dried over anhydrous magnesium sulfate, and the solvent was removed under reduced pressure. The residue was purified on column chromatography to obtain the titled compound (15 mg) as white powder.
MS (ESI+) m/z 584 (M+H)$^+$, Rt=2.26 minutes (method A)

Example 74

N-(3-Chloro-2-methylphenyl)-2-[(2-methoxyethoxy)
methyl]-6-({[2-(trifluoromethyl)phenyl]
carbonyl}amino)-1H-benzimidazole-4-carboxamide
hydrochloride The titled compound was obtained as white powder according to the procedure as described in Example 11, using 2-(methoxyethoxy)acetyl chloride instead of methoxyacetyl chloride.
MS (ESI+) m/z 561 (M+H)$^+$, Rt=2.43 minutes (method A)

Example 75

N-(3-Chloro-2-methylphenyl)-2-(1-methoxy-2-meth-
ylpropan-2-yl)-6-({[2-(trifluoromethyl)phenyl]
carbonyl}amino)-1H-benzimidazole-4-carboxamide
hydrochloride The titled compound was obtained as white powder according to the procedure as described in Example 11, using 3-methoxy-2,2-dimethylpropanoyl chloride (prepared as described in Bull. Chem. Soc. Jpn., 2001, 74, 1695) instead of methoxyacetyl chloride.
MS (ESI+) m/z 559 (M+H)$^+$, Rt=2.82 minutes (method A)

Example 76

2-tert-Butyl-N-(3-chloro-2-methylphenyl)-6-({[2-
(trifluoromethyl)phenyl]carbonyl}amino)-1H-benz-
imidazole-4-carboxamide hydrochloride The titled compound was obtained as white powder according to the procedure as described in Example 11, using pivaloyl chloride instead of methoxyacetyl chloride.
MS (ESI+) m/z 529 (M+H)$^+$, Rt=3.03 minutes (method A)

Example 77

2-tert-Butyl-6-({[2-(trifluoromethyl)phenyl]
carbonyl}amino)-N-{[3-(trifluoromethyl)pyridin-2-
yl]methyl}-1H-benzimidazole-4-carboxamide dihy-
drochloride The titled compound was obtained as white powder according to the procedure as described in Example 11, using pivaloyl chloride instead of methoxyacetyl chloride, and 2-(aminomethyl)-3-(trifluoromethyl)pyridine instead of 3-chloro-2-methylaniline.

MS (ESI+) m/z 564 (M+H)$^+$, Rt=2.39 minutes (method A)

Example 78

N-(3-Chloro-2-methylphenyl)-2-(2-ethoxyethyl)-6-({[2-(trifluoromethyl)phenyl]carbonyl}amino)-1H-benzimidazole-4-carboxamide hydrochloride The titled compound was obtained as white powder according to the procedure as described in Example 11, using 3-ethoxy-propionylchloride (prepared as described in EP1803350) instead of methoxyacetyl chloride.

MS (ESI+) m/z 545 (M+H)$^+$, Rt=2.69 minutes (method A)

Example 79

N-(3-Chloro-2-methylphenyl)-2-(ethoxymethyl)-6-({[2-(trifluoromethyl)phenyl]carbonyl}amino)-1H-benzimidazole-4-carboxamide hydrochloride The titled compound was obtained as white powder according to the procedure as described in Example 11, using ethoxyacetyl chloride (prepared as described in US2004/39038) instead of methoxyacetyl chloride.

MS (ESI+) m/z 531 (M+H)$^+$, Rt=2.77 minutes (method A)

Example 80

2-(Ethoxymethyl)-6-({[2-(trifluoromethyl)phenyl]carbonyl}amino)-N-{[3-(trifluoromethyl)pyridin-2-yl]methyl}-1H-benzimidazole-4-carboxamide dihydrochloride The titled compound was obtained as white powder according to the procedure as described in Example 11, using ethoxyacetyl chloride (prepared as described in US2004/39038) instead of methoxyacetyl chloride, and 2-(aminomethyl)-3-(trifluoromethyl)pyridine instead of 3-chloro-2-methylaniline.

MS (ESI+) m/z 566 (M+H)$^+$, Rt=2.18 minutes (method A)

Example 81

N-(3-Chloro-2-methylphenyl)-2-(2-methoxyethyl)-6-({[2-(trifluoromethyl)phenyl]carbonyl}amino)-1H-benzimidazole-4-carboxamide hydrochloride The titled compound was obtained as white powder according to the procedure as described in Example 11, using methoxypropionyl chloride instead of methoxyacetyl chloride.

MS (ESI+) m/z 531 (M+H)$^+$, Rt=2.58 minutes (method A)

Example 82

N-(3-Chloro-2-methylphenyl)-2-(2,2-dimethylpropyl)-6-({[2-(trifluoromethyl)phenyl]carbonyl}amino)-1H-benzimidazole-4-carboxamide hydrochloride The titled compound was obtained as white powder according to the procedure as described in Example 11, using tert-butylacetyl chloride instead of methoxyacetyl chloride.

MS (ESI+) m/z 543 (M+H)$^+$, Rt=3.25 minutes (method A)

Example 83

N-(3-Chloro-2-methylphenyl)-2-cyclopropyl-6-({[2-(trifluoromethyl)phenyl]carbonyl}amino)-1H-benzimidazole-4-carboxamide hydrochloride The titled compound was obtained as white powder according to the procedure as described in Example 11, using cyclopropanecarbonyl chloride instead of methoxyacetyl chloride.

MS (ESI+) m/z 513 (M+H)$^+$, Rt=2.91 minutes (method A)

Example 84

N-(3-Chloro-2-methylphenyl)-2-(2-methylpentan-2-yl)-6-({[2-(trifluoromethyl)phenyl]carbonyl}amino)-1H-benzimidazole-4-carboxamide hydrochloride The titled compound was obtained as white powder according to the procedure as described in Example 11, using 2,2-dimethylpentanoyl chloride (prepared as described in J. Am. Chem. Soc., 1974, 96, 1518) instead of methoxyacetyl chloride.

MS (ESI+) m/z 557 (M+H)$^+$, Rt=3.16 minutes (method B)

Example 85

N-(3-Chloro-2-methylphenyl)-2-(1-methylcyclopropyl)-6-({[2-(trifluoromethyl)phenyl]carbonyl}amino)-1H-benzimidazole-4-carboxamide hydrochloride The titled compound was obtained as white powder according to the procedure as described in Example 11, using 1-methyl-cyclopropanecarbonyl chloride (prepared as described in WO2009/68512) instead of methoxyacetyl chloride.

MS (ESI+) m/z 527 (M+H)$^+$, Rt=3.16 minutes (method A)

Elemental Analysis for $C_{27}H_{22}ClF_3N_4O_2 \cdot HCl + 1.0H_2O$

Calcd. (%) C, 55.78; H, 4.33; N, 9.64.

Found. (%) C, 55.48; H, 3.94; N, 9.63.

Example 86

2-tert-Butyl-N-(3-chloro-4-methylphenyl)-6-({[2-(trifluoromethyl)phenyl]carbonyl}amino)-1H-benzimidazole-4-carboxamide hydrochloride The titled compound was obtained as white powder according to the procedure as described in Example 11, using pivaloyl chloride instead of methoxyacetyl chloride, and 3-chloro-4-methylaniline instead of 3-chloro-2-methylaniline.

MS (ESI+) m/z 529 (M+H)$^+$, Rt=2.83 minutes (method B)

Example 87

2-tert-Butyl-N-(3-chloro-2-methylphenyl)-6-{[(2,5-dichlorophenyl)carbonyl]amino}-1H-benzimidazole-4-carboxamide hydrochloride

Step 1

Methyl 6-amino-2-tert-butyl-1H-benzimidazole-4-carboxylate

The title compound was obtained as white powder according to the procedures as described in Step 1 to Step 4 of Example 11, using pivaloyl chloride instead of methoxyacetyl chloride in Step 1.

Step 2

2-tert-Butyl-6-{[(2,5-dichlorophenyl)carbonyl]amino}-1H-benzimidazole-4-carboxylic acid The title compound was obtained according to the procedures as described in Step 4 and Step 5 of Example 1, using methyl 6-amino-2-tert-butyl-1H-benzimidazole-4-carboxylate instead of methyl 6-amino-1H-benzimidazole-4-carboxylate, and 2,5-dichlorobenzoyl chloride instead of 2-(trifluoromethyl)benzoyl chloride.

Step 3

2-tert-Butyl-N-(3-chloro-2-methylphenyl)-6-{[(2,5-dichlorophenyl)carbonyl]amino}-1H-benzimidazole-4-carboxamide hydrochloride The title compound was obtained according to the procedures as described in Step 7 and Step 8 of Example 11, using 2-tert-butyl-6-{[(2,5-dichlorophenyl)carbonyl]amino}-1H-benzimidazole-4-carboxylic acid instead of 2-(methoxymethyl)-6-({[2-(trifluoromethyl)phenyl]carbonyl}amino)-1H-benzimidazole-4-carboxylic acid.
MS (ESI+) m/z 529 (M+H)$^+$, Rt=2.97 minutes (method B)

Example 88

2-tert-Butyl-N-(3-chloro-4-methylphenyl)-6-{[(2,5-dichlorophenyl)carbonyl]amino}-1H-benzimidazole-4-carboxamide hydrochloride The titled compound was obtained as white powder according to the procedures as described in Step 7 and Step 8 of Example 11, using 2-tert-butyl-6-{[(2,5-dichlorophenyl)carbonyl]amino}-1H-benzimidazole-4-carboxylic acid instead of 2-(methoxymethyl)-6-({[2-(trifluoromethyl)phenyl]carbonyl}amino)-1H-benzimidazole-4-carboxylic acid, and 3-chloro-4-methylaniline instead of 3-chloro-2-methylaniline.
MS (ESI+) m/z 529 (M+H)$^+$, Rt=3.05 minutes (method B)

Example 89

N-(3-Chloro-2-methylphenyl)-2-[1-(trifluoromethyl)cyclopropyl]-6-({[2-(trifluoromethyl)phenyl]carbonyl}amino)-1H-benzimidazole-4-carboxamide The titled compound was obtained as white powder according to the procedures as described in Steps 1 to 7 of Example 11, using 1-(trifluoromethyl)cyclopropanecarbonyl chloride (prepared as described in WO2005/23773) instead of methoxyacetyl chloride.
MS (ESI+) m/z 581 (M+H)$^+$, Rt=3.15 minutes (method A)

Example 90

N-(3-Chloro-2-methylphenyl)-2-(methoxymethyl)-1-methyl-6-({[2-(trifluoromethyl)phenyl]carbonyl}amino)-1H-benzimidazole-4-carboxamide

Step 1

2-(Methoxymethyl)-1-methyl-6-({[2-(trifluoromethyl)phenyl]carbonyl}amino)-1H-benzimidazole-4-carboxylic acid The titled compound was obtained according to the procedure as described in Example 46, using methyl 2-(methoxymethyl)-6-({[2-(trifluoromethyl)phenyl]carbonyl}amino)-1H-benzimidazole-4-carboxylate instead of methyl 6-({[2-(trifluoromethyl)phenyl]carbonyl}amino)-1H-benzimidazole-4-carboxylate.

Step 2

N-(3-Chloro-2-methylphenyl)-2-(methoxymethyl)-1-methyl-6-({[2-(trifluoromethyl)phenyl]carbonyl}amino)-1H-benzimidazole-4-carboxamide The titled compound was obtained as colorless powder according to the procedure as described in Step 7 of Example 11, using 2-(methoxymethyl)-1-methyl-6-({[2-(trifluoromethyl)phenyl]carbonyl}amino)-1H-benzimidazole-4-carboxylic acid instead of 2-(methoxymethyl)-6-({[2-(trifluoromethyl)phenyl]carbonyl}amino)-1H-benzimidazole-4-carboxylic acid.
MS (ESI+) m/z 531 (M+H)$^+$, Rt=2.58 minutes (method A)

Example 91

N-(2-Chlorobenzyl)-2-(methoxymethyl)-1-methyl-6-({[2-(trifluoromethyl)phenyl]carbonyl}amino)-1H-benzimidazole-4-carboxamide The titled compound was obtained as colorless powder according to the procedure as described in Step 7 of Example 11, using 2-(methoxymethyl)-1-methyl-6-({[2-(trifluoromethyl)phenyl]carbonyl}amino)-1H-benzimidazole-4-carboxylic acid instead of 2-(methoxymethyl)-6-({[2-(trifluoromethyl)phenyl]carbonyl}amino)-1H-benzimidazole-4-carboxylic acid, and 2-chloro benzylamine instead of 3-chloro-2-methylaniline.
MS (ESI+) m/z 531 (M+H)$^+$, Rt=2.25 minutes (method A)

Example 92

6-{[(2-Chloro-6-fluorophenyl)carbonyl]amino}-N-(3-chloro-2-methylphenyl)-2-(methoxymethyl)-1H-benzimidazole-4-carboxamide hydrochloride

Step 1

6-Amino-N-(3-chloro-2-methylphenyl)-2-(methoxymethyl)-1H-benzimidazole-4-carboxamide To a suspension of methyl 2-(methoxymethyl)-6-nitro-1H-benzimidazole-4-carboxylate (Example 11, Step 3) (4.8 g) in MeOH (120 mL), were added lithium hydroxide hydrate (4.56 g) and water (54 mL). The mixture was stirred at room temperature for 16 hours. Under ice-cooling, 1N hydrochloric acid was added slowly to the reaction mixture to adjust the pH to about 2. The precipitate was collected by filtration and dried to obtain 2-(methoxymethyl)-6-nitro-1H-benzimidazole-4-carboxylic acid (4.6 g). To the solution of 2-(methoxymethyl)-6-nitro-1H-benzimidazole-4-carboxylic acid (4.6 g) in DMF (90 mL), HBTU (8.23 g), triethylamine (2.19 g) and 3-chloro-2-methylaniline (3.07 g) were added sequentially, and the solution was stirred for 18 hours. The reaction mixture was poured into saturated aqueous sodium bicarbonate and stirred for 1 hour. The precipitate was collected by filtration and washed sequentially with water and ethyl acetate to obtain N-(3-chloro-2-methylphenyl)-2-(methoxymethyl)-6-nitro-1H-benzimidazole-4-carboxamide (7.2 g) as pale yellow powder. To the solution of N-(3-chloro-2-methylphenyl)-2-(methoxymethyl)-6-nitro-1H-benzimidazole-4-carboxamide (7.2 g) in MeOH-THF (1:1, 120 mL), were added 1% platinum+0.1% copper-activated carbon (Degussa type CF105 R/W) (1.4 g). The mixture was stirred under hydrogen atmosphere (3 atm) for 4 hours. The catalyst was filtered off, and the mother liquid was concentrated. The residual solid was washed with ethyl acetate to obtain 6-amino-N-(3-chloro-2-methylphenyl)-2-(methoxymethyl)-1H-benzimidazole-4-carboxamide (5.1 g) as pale yellow powder.

Step 2

6-{[(2-Chloro-6-fluorophenyl)carbonyl]amino}-N-(3-chloro-2-methylphenyl)-2-(methoxymethyl)-1H-benzimidazole-4-carboxamide hydrochloride To a solution of 6-amino-N-(3-chloro-2-methylphenyl)-2-(methoxymethyl)-1H-benzimidazole-4-carboxamide (40 mg) in THF (1 mL), was added N,N-diisopropylethylamine (24 µL), and the mixture was stirred under ice-cooling. To the mixture was added 2-chloro-6-fluorobenzoyl chloride (24 mg), and it was stirred for 3 hours. To the reaction mixture was added saturated aqueous sodium bicarbonate, and it was extracted with ethyl acetate. The ethyl acetate layer was washed with brine, dried over anhydrous magnesium sulfate, and concentrated under reduced pressure.
The residue was purified on column chromatography to obtain 6-{[(2-chloro-6-fluorophenyl)carbonyl]amino}-N-(3-chloro-2-methylphenyl)-2-(methoxymethyl)-1H-benzimidazole-4-carboxamide (50 mg). This was dissolved in ethyl acetate (2 mL), and treated with 4N hydrogen chloride/ethyl acetate (1.2 Eq). The precipitate was collected by filtration, and dried to obtain the titled compound (40 mg) as white powder.
MS (ESI+) m/z 501 (M+H)$^+$, Rt=2.39 minutes (method A)

Example 93

6-{[(2-Chloro-4-fluorophenyl)carbonyl]amino}-N-(3-chloro-2-methylphenyl)-2-methoxymethyl-1H-benzimidazole-4-carboxamide hydrochloride The titled compound was obtained as pale yellow powder according to the procedure as described in Step 2 of Example 92, using 2-chloro-4-fluorobenzoyl chloride instead of 2-chloro-6-fluorobenzoyl chloride.
MS (ESI+) m/z 501 (M+H)$^+$, Rt=2.40 minutes (method A)

Example 94

6-{[(2-Chloro-5-fluorophenyl)carbonyl]amino}-N-(3-chloro-2-methylphenyl)-2-(methoxymethyl)-1H-benzimidazole-4-carboxamide hydrochloride The titled compound was obtained as white powder according to the procedure as described in Step 2 of Example 92, using 2-chloro-5-fluorobenzoyl chloride instead of 2-chloro-6-fluorobenzoyl chloride.
MS (ESI+) m/z 501 (M+H)$^+$, Rt=2.41 minutes (method A)

Example 95

N-(3-Chloro-2-methylphenyl)-6-{[(2-chlorophenyl)carbonyl]amino}-2-(methoxymethyl)-1H-benzimidazole-4-carboxamide hydrochloride The titled compound was obtained as white powder according to the procedure as described in Step 2 of Example 92, using 2-chlorobenzoyl chloride instead of 2-chloro-6-fluorobenzoyl chloride.
MS (ESI+) m/z 483 (M+H)$^+$, Rt=2.36 minutes (method A)

Example 96

N-(3-Chloro-2-methylphenyl)-6-{[(2-chloropyridin-3-yl)carbonyl]amino}-2-(methoxymethyl)-1H-benzimidazole-4-carboxamide hydrochloride The titled compound was obtained as white powder according to the procedure as described in Step 2 of Example 92, using 2-chloronicotinoyl chloride instead of 2-chloro-6-fluorobenzoyl chloride.
MS (ESI+) m/z 484 (M+H)$^+$, Rt=2.16 minutes (method A)

Example 97

6-{[(2-Bromophenyl)carbonyl]amino}-N-(3-chloro-2-methylphen yl)-2-(methoxymethyl)-1H-benzimidazole-4-carboxamide hydrochloride The titled compound was obtained as white powder according to the procedure as described in Step 2 of Example 92, using 2-bromobenzoyl chloride instead of 2-chloro-6-fluorobenzoyl chloride.
MS (ESI+) m/z 527 (M+H)$^+$, Rt=2.39 minutes (method A)

Example 98

N-(3-Chloro-2-methylphenyl)-6-{[(2,6-dichlorophenyl)carbonyl]amino}-2-(methoxymethyl)-1H-benzimidazole-4-carboxamide hydrochloride The titled compound was obtained as white powder according to the procedure as described in Step 2 of Example 92, using 2,6-dichlorobenzoyl chloride instead of 2-chloro-6-fluorobenzoyl chloride.
MS (ESI+) m/z 517 (M+H)$^+$, Rt=2.46 minutes (method A)

Example 99

N-(3-Chloro-2-methylphenyl)-6-{[(2,5-dichlorophenyl)carbonyl]amino}-2-(methoxymethyl)-1H-benzimidazole-4-carboxamide hydrochloride The titled compound was obtained as white powder according to the procedure as described in Step 2 of Example 92, using 2,5-dichlorobenzoyl chloride instead of 2-chloro-6-fluorobenzoyl chloride.
MS (ESI+) m/z 517 (M+H)$^+$, Rt=2.54 minutes (method A)

Example 100

6-{[(2-Chloro-3-fluorophenyl)carbonyl]amino}-N-(3-chloro-2-methylphenyl)-2-(methoxymethyl)-1H-benzimidazole-4-carboxamide hydrochloride The titled compound was obtained as white powder according to the procedure as described in Step 2 of Example 92, using 2-chloro-3-fluorobenzoyl chloride instead of 2-chloro-6-fluorobenzoyl chloride.

MS (ESI+) m/z 501 (M+H)$^+$, Rt=2.43 minutes (method A)

Example 101

6-{[(2-Chloro-3,6-difluorophenyl)carbonyl]amino}-N-(3-chloro-2-methylphenyl)-2-(methoxymethyl)-1H-benzimidazole-4-carboxamide hydrochloride The titled compound was obtained as white powder according to the procedure as described in Step 2 of Example 92, using 2-chloro-3,6-difluorobenzoyl chloride instead of 2-chloro-6-fluorobenzoyl chloride.

MS (ESI+) m/z 519 (M+H)$^+$, Rt=2.46 minutes (method A)

Example 102

6-{[(2-Bromo-6-chlorophenyl)carbonyl]amino}-N-(3-chloro-2-m ethylphenyl)-2-(methoxymethyl)-1H-benzimidazole-4-carboxamide hydrochloride The titled compound was obtained as white powder according to the procedure as described in Step 2 of Example 92, using 2-chloro-6-bromobenzoyl chloride (prepared as described in WO2008/124575) instead of 2-chloro-6-fluorobenzoyl chloride.

MS (ESI+) m/z 561 (M+H)$^+$, Rt=2.50 minutes (method A)

Example 103

6-{[(2-Bromo-6-fluorophenyl)carbonyl]amino}-N-(3-chloro-2-m ethylphenyl)-2-(methoxymethyl)-1H-benzimidazole-4-carboxamide hydrochloride To a solution of 6-amino-N-(3-chloro-2-methylphenyl)-2-(methoxymethyl)-1H-benzimidazole-4-carboxamide (50 mg) in DMF (1.5 mL), were added HBTU (66 mg), N,N-diisopropylethylamine (30 μL) and 2-bromo-6-fluorobenzoic acid (38 mg) in turn, and the mixture was stirred at room temperature for 24 hours. The reaction mixture was poured into saturated aqueous sodium bicarbonate, and extracted with ethyl acetate. The organic layer was separated, washed sequentially with water and brine, dried over anhydrous magnesium sulfate, and concentrated under reduced pressure. The residue was purified on column chromatography to obtain 6-{[(2-bromo-6-fluorophenyl) carbonyl]amino}-N-(3-chloro-2-m ethylphenyl)-2-(methoxymethyl)-1H-benzimidazole-4-carboxamide (46 mg). This was dissolved in ethyl acetate (2 mL), and treated with 4N hydrogen chloride/ethyl acetate (1.2 Eq). The precipitate was collected by filtration, and dried to obtain the titled compound (24 mg) as white powder.

MS (ESI+) m/z 545 (M+H)$^+$, Rt=2.44 minutes (method A)

Example 104

N-(3-Chloro-2-methylphenyl)-6-{[(2-chloro-6-methylphenyl)carbonyl]amino}-2-(methoxymethyl)-1H-benzimidazole-4-carboxamide hydrochloride The titled compound was obtained as white powder according to the procedure as described in Example 103, using 2-chloro-6-methylbenzoic acid instead of 2-bromo-6-fluorobenzoic acid.

MS (ESI+) m/z 497 (M+H)$^+$, Rt=2.44 minutes (method A)

Example 105

N-(3-Chloro-2-methylphenyl)-6-{[(2-chloro-4-methylphenyl)carbonyl]amino}-2-(methoxymethyl)-1H-benzimidazole-4-carboxamide hydrochloride The titled compound was obtained as white powder according to the procedure as described in Example 103, using 2-chloro-4-methylbenzoic acid instead of 2-bromo-6-fluorobenzoic acid.

MS (ESI+) m/z 497 (M+H)$^+$, Rt=2.47 minutes (method A)

Example 106

6-{[(5-Bromo-2-chlorophenyl)carbonyl]amino}-N-(3-chloro-2-m ethylphenyl)-2-(methoxymethyl)-1H-benzimidazole-4-carboxamide hydrochloride The titled compound was obtained as white powder according to the procedure as described in Example 103, using 5-bromo-2-chlorobenzoic acid instead of 2-bromo-6-fluorobenzoic acid.

MS (ESI+) m/z 561 (M+H)$^+$, Rt=2.62 minutes (method A)

Example 107

6-{[(2-Bromo-5-chlorophenyl)carbonyl]amino}-N-(3-chloro-2-m ethylphenyl)-2-(methoxymethyl)-1H-benzimidazole-4-carboxamide hydrochloride The titled compound was obtained as white powder according to the procedure as described in Example 103, using 2-bromo-5-chlorobenzoic acid instead of 2-bromo-6-fluorobenzoic acid.

MS (ESI+) m/z 561 (M+H)$^+$, Rt=2.63 minutes (method A)

Example 108

N-(3-Chloro-2-methylphenyl)-6-{[(2-chloro-5-methylphenyl)carbonyl]amino}-2-(methoxymethyl)-1H-benzimidazole-4-carboxamide hydrochloride The titled compound was obtained as white powder according to the procedure as described in Example 103, using 2-chloro-5-methylbenzoic acid instead of 2-bromo-6-fluorobenzoic acid.

MS (ESI+) m/z 497 (M+H)$^+$, Rt=2.54 minutes (method A)

Example 109

N-(3-Chloro-2-methylphenyl)-2-(methoxymethyl)-6-({[5-methyl-2-(trifluoromethyl)phenyl]carbonyl}amino)-1H-benzimidazole-4-carboxamide hydrochloride The titled compound was obtained as white powder according to the procedure as described in Example 103, using 5-methyl-2-(trifluoromethyl)benzoic acid instead of 2-bromo-6-fluorobenzoic acid.
MS (ESI+) m/z 531 (M+H)$^+$, Rt=2.59 minutes (method A)

Example 110

6-({[2,5-Bis(trifluoromethyl)phenyl]carbonyl}amino)-N-(3-chloro-2-methylphenyl)-2-(methoxymethyl)-1H-benzimidazole-4-carboxamide hydrochloride The titled compound was obtained as white powder according to the procedure as described in Example 103, using 2,5-bis(trifluoromethyl)benzoic acid instead of 2-bromo-6-fluorobenzoic acid.
MS (ESI+) m/z 585 (M+H)$^+$, Rt=2.76 minutes (method A)

Example 111

6-({[2,4-Bis(trifluoromethyl)phenyl]carbonyl}amino)-N-(3-chloro-2-methylphenyl)-2-(methoxymethyl)-1H-benzimidazole-4-carboxamide hydrochloride The titled compound was obtained as white powder according to the procedure as described in Example 103, using 2,4-bis(trifluoromethyl)benzoic acid instead of 2-bromo-6-fluorobenzoic acid.
MS (ESI+) m/z 585 (M+H)$^+$, Rt=2.80 minutes (method A)

Example 112

N-(3-Chloro-2-methylphenyl)-6-({[5-fluoro-2-(trifluoromethyl)phenyl]carbonyl}amino)-2-(methoxymethyl)-1H-benzimidazole-4-carboxamide hydrochloride The titled compound was obtained as white powder according to the procedure as described in Example 103, using 5-fluoro-2-(trifluoromethyl)benzoic acid instead of 2-bromo-6-fluorobenzoic acid.
MS (ESI+) m/z 535 (M+H)$^+$, Rt=2.68 minutes (method A)

Example 113

N-(3-Chloro-2-methylphenyl)-6-({[2-chloro-6-(trifluoromethyl)phenyl]carbonyl}amino)-2-(methoxymethyl)-1H-benzimidazole-4-carboxamide hydrochloride The titled compound was obtained as white powder according to the procedure as described in Example 103, using 2-chloro-6-(trifluoromethyl)benzoic acid instead of 2-bromo-6-fluorobenzoic acid.
MS (ESI+) m/z 551 (M+H)$^+$, Rt=2.76 minutes (method A)

Example 114

N-(3-Chloro-2-methylphenyl)-6-[({2-chloro-5-[2-(propan-2-yl oxy)ethoxy]phenyl}carbonyl)amino]-2-(methoxymethyl)-1H-benz imidazole-4-carboxamide hydrochloride Under argon atmosphere, potassium tert-butoxide (168 mg) was added to a solution of 2-isopropoxyethanol (172 µL) in NMP (1.5 mL). The mixture was stirred at room temperature for 10 minutes, 2-chloro-5-fluorobenzoic acid (87 mg) was added, and it was then stirred at 130° C. for 4 hours. The reaction mixture was cooled on ice bath, water was added, and it was then acidified with 1N hydrochloric acid and extracted with ethyl acetate. The organic layer was separated, washed with brine, and dried over anhydrous magnesium sulfate, and concentrated under reduced pressure to obtain crude 2-chloro-5-[2-(propan-2-yloxy)ethoxy]benzoic acid. This was dissolved in DMF (2 mL), HATU (61 mg), N,N-diisopropylethylamine (29 µL) and 6-amino-N-(3-chloro-2-methylphenyl)-2-(methoxymethyl)-1H-benzimidazole-4-carboxamide (50 mg) were added in this order, and it was stirred at room temperature for 12 hours. The reaction mixture was poured into saturated aqueous sodium bicarbonate, and extracted with ethyl acetate. The organic layer was separated, washed sequentially with water and brine, dried over anhydrous magnesium sulfate, and concentrated under reduced pressure. The residue was purified on column chromatography to obtain N-(3-chloro-2-methylphenyl)-6-[({2-chloro-5-[2-(propan-2-yl oxy)ethoxy]phenyl}carbonyl)amino]-2-(methoxymethyl)-1H-benz imidazole-4-carboxamide (41 mg) as white powder. This was dissolved in ethyl acetate (2 mL), and treated with 4N hydrogen chloride/ethyl acetate (1.2 Eq). The precipitate was collected by filtration, and dried to obtain the titled compound (28 mg) as white powder.
MS (ESI+) m/z 585 (M+H)$^+$, Rt=3.14 minutes (method A)

Example 115

6-({[2-Chloro-5-(2-ethoxyethoxy)phenyl]carbonyl}amino)-N-(3-chloro-2-methylphenyl)-2-(methoxymethyl)-1H-benzimidazole-4-carboxamide hydrochloride The titled compound was obtained as white powder according to the procedure as described in Example 114, using 2-ethoxyethanol instead of 2-isopropoxy ethanol.
MS (ESI+) m/z 571 (M+H)$^+$, Rt=2.71 minutes (method A)

Example 116

6-({[2-Chloro-5-(3-methoxypropyl)phenyl]carbonyl}amino)-N-(3-chloro-2-methylphenyl)-2-(methoxymethyl)-1H-benzimidazole-4-carboxamide hydrochloride The titled compound was obtained as pale yellow powder according to the procedure as described in Example 103, using 2-chloro-5-(3-methoxypropyl) benzoic acid (prepared as described in Bioorg. Med. Chem. Lett., 2010, 20, 2204) instead of 2-bromo-6-fluorobenzoic acid.
MS (ESI+) m/z 555 (M+H)$^+$, Rt=2.73 minutes (method A)

Example 117

6-({[5-(3-tert-Butoxy-1-propynyl)-2-chlorophenyl]carbonyl}amino)-N-(3-chloro-2-methylphenyl)-2-(methoxymethyl)-1H-benz imidazole-4-carboxamide hydrochloride The titled compound was obtained as pale yellow powder according to the procedure as described in Example 103, using 5-(3-tert-butoxy-1-propynyl)-2-chlorobenzoic acid (Reference Example 6) instead of 2-bromo-6-fluorobenzoic acid.

MS (ESI+) m/z 593 (M+H)$^+$, Rt=3.17 minutes (method A)

Example 118

6-({[5-(3-tert-Butoxypropyl)-2-chlorophenyl]carbonyl}amino)-N-(3-chloro-2-methylphenyl)-2-(methoxymethyl)-1H-benzimidazole-4-carboxamide hydrochloride The titled compound was obtained as white powder according to the procedure as described in Example 103, using 5-(3-tert-butoxypropyl)-2-chlorobenzoic acid (Reference Example 7) instead of 2-bromo-6-fluorobenzoic acid.

MS (ESI+) m/z 597 (M+H)$^+$, Rt=3.28 minutes (method A)

Example 119

6-({[2-Chloro-5-(3-hydroxy-3-methylbutyl)phenyl]carbonyl}amino)-N-(3-chloro-2-methylphenyl)-2-(methoxymethyl)-1H-benzimidazole-4-carboxamide hydrochloride The titled compound was obtained as pale yellow powder according to the procedure as described in Example 103, using 2-chloro-5-(3-hydroxy-3-methylbutyl)benzoic acid (Reference Example 8) instead of 2-bromo-6-fluorobenzoic acid.

MS (ESI+) m/z 569 (M+H)$^+$, Rt=2.64 minutes (method A)

Example 120

6-({[2-Chloro-5-(ethoxymethyl)phenyl]carbonyl}amino)-N-(3-chloro-2-methylphenyl)-2-(methoxymethyl)-1H-benzimidazole-4-carboxamide The titled compound was obtained as white powder according to the procedure as described in Example 103, using 2-chloro-5-(ethoxymethyl)benzoic acid (Reference Example 1) instead of 2-bromo-6-fluorobenzoic acid.

MS (ESI+) m/z 541 (M+H)$^+$, Rt=2.52 minutes (method A)

Example 121

6-[({2-Chloro-5-[(2-ethoxyethoxy)methyl]phenyl}carbonyl)amino]-N-(3-chloro-2-methylphenyl)-2-(methoxymethyl)-1H-benzimidazole-4-carboxamide hydrochloride The titled compound was obtained as white powder according to the procedure as described in Example 103, using 2-chloro-5-[(2-ethoxyethoxy)methyl]benzoic acid (Reference Example 2) instead of 2-bromo-6-fluorobenzoic acid.

MS (ESI+) m/z 585 (M+H)$^+$, Rt=2.51 minutes (method A)

Example 122

6-({[2-Chloro-5-(2-cyclopropylethyl)phenyl]carbonyl}amino)-N-(3-chloro-2-methylphenyl)-2-(methoxymethyl)-1H-benzimidazole-4-carboxamide The titled compound was obtained as white powder according to the procedure as described in Example 103, using 2-chloro-5-(2-cyclopropylethyl)benzoic acid (Reference Example 4) instead of 2-bromo-6-fluorobenzoic acid.

MS (ESI+) m/z 551 (M+H)$^+$, Rt=2.92 minutes (method A)

Example 123

N-(3-Chloro-2-methylphenyl)-6-({[2-chloro-5-(2-phenylethyl)phenyl]carbonyl}amino)-2-(methoxymethyl)-1H-benzimidazole-4-carboxamide hydrochloride The titled compound was obtained as white powder according to the procedure as described in Example 103, using 2-chloro-5-(2-phenylethyl)benzoic acid (Reference Example 5) instead of 2-bromo-6-fluorobenzoic acid.

MS (ESI+) m/z 587 (M+H)$^+$, Rt=2.98 minutes (method A)

Example 124

N-(3-Chloro-2-methylphenyl)-2-cyclopentyl-6-({[2-(trifluoro methyl)phenyl]carbonyl}amino)-1H-benzimidazole-4-carboxamide hydrochloride

Step 1

Methyl 2-cyclopentyl-6-nitro-1H-benzimidazole-4-carboxylate

The titled compound was obtained as pale yellow powder according to the procedure as described in Steps 1 to 3 of Example 11, using cyclopentanecarbonyl chloride instead of methoxyacetyl chloride.

Step 2

6-Amino-N-(3-chloro-2-methylphenyl)-2-cyclopentyl-1H-benzimidazole-4-carboxamide The titled compound was obtained as yellow powder according to the procedure as described in Step 1 of Example 92, using methyl 2-cyclopentyl-6-nitro-1H-benzimidazole-4-carboxylate instead of methyl 2-(methoxymethyl)-6-nitro-1H-benzimidazole-4-carboxylate.

Step 3

N-(3-Chloro-2-methylphenyl)-2-cyclopentyl-6-({[2-(trifluoro methyl)phenyl]carbonyl}amino)-1H-benzimidazole-4-carboxamide hydrochloride The titled compound was obtained as white powder according to the procedure as described in Step 2 of Example 92, using 6-amino-N-(3-chloro-2-methylphenyl)-2-cyclopentyl-1H-benzimidazole-4-carboxamide instead of 6-amino-N-(3-chloro-2-methylphenyl)-2-(methoxymethyl)-1H-benzimidazole-4-carboxamide, and 2-(trifluoromethyl)benzoyl chloride instead of 2-chloro-6-fluorobenzoyl chloride.

MS (ESI+) m/z 541 (M+H)$^+$, Rt=3.21 minutes (method A)

Example 125

N-(3-Chloro-2-methylphenyl)-2-cyclopentyl-6-{[(2,5-dichloro phenyl)carbonyl]amino}-1H-benzimidazole-4-carboxamide hydrochloride The titled compound was obtained as white powder according to the procedure as described in Step 2 of Example 92, using 6-amino-N-(3-chloro-2-methylphenyl)-2-cyclopentyl-1H-benzimidazole-4-carboxamide instead of 6-amino-N-(3-chloro-2-methylphenyl)-2-(methoxymethyl)-1H-benzimidazole-4-carboxamide, and 2,5-dichlorobenzoyl chloride instead of 2-chloro-6-fluorobenzoyl chloride.
MS (ESI+) m/z 543 (M+H)$^+$, Rt=3.32 minutes (method A)

Example 126

6-{[(2-Chloro-6-fluorophenyl)carbonyl]amino}-N-(3-chloro-2-methylphenyl)-2-cyclopentyl-1H-benzimidazole-4-carboxamide hydrochloride The titled compound was obtained as white powder according to the procedure as described in Step 2 of Example 92, using 6-amino-N-(3-chloro-2-methylphenyl)-2-cyclopentyl-1H-benzimidazole-4-carboxamide instead of 6-amino-N-(3-chloro-2-methylphenyl)-2-(methoxymethyl)-1H-benzimidazole-4-carboxamide.
MS (ESI+) m/z 525 (M+H)$^+$, Rt=3.24 minutes (method A)

Example 127

6-{[(2-Chloro-6-fluorophenyl)carbonyl]amino}-N-(3-chloro-2-methylphenyl)-2-[(2R)-tetrahydrofuran-2-yl]-1H-benzimidazole-4-carboxamide hydrochloride

Step 1

Methyl 6-nitro-2-[(2R)-tetrahydrofuran-2-yl]-1H-benzimidazole-4-carboxylate

The titled compound was obtained as pale yellow powder according to the procedure as described in Steps 1 to 3 of Example 11, using (2R)-tetrahydro-2-furancarbonyl chloride (prepared as described in WO2006/79642) instead of methoxyacetyl chloride.

Step 2

6-Amino-N-(3-chloro-2-methylphenyl)-2-[(2R)-tetrahydrofuran-2-yl]-1H-benzimidazole-4-carboxamide The titled compound was obtained as yellow powder according to the procedure as described in Step 1 of Example 92, using methyl 6-nitro-2-[(2R)-tetrahydrofuran-2-yl]-1H-benzimidazole-4-carboxylate instead of methyl 2-(methoxymethyl)-6-nitro-1H-benzimidazole-4-carboxylate.

Step 3

6-{[(2-Chloro-6-fluorophenyl)carbonyl]amino}-N-(3-chloro-2-methylphenyl)-2-[(2R)-tetrahydrofuran-2-yl]-1H-benzimidazole-4-carboxamide hydrochloride The titled compound was obtained as white powder according to the procedure as described in Step 2 of Example 92, using 6-amino-N-(3-chloro-2-methylphenyl)-2-[(2R)-tetrahydrofuran-2-yl]-1H-benzimidazole-4-carboxamide instead of 6-amino-N-(3-chloro-2-methylphenyl)-2-(methoxymethyl)-1H-benzimidazole-4-carboxamide.
MS (ESI+) m/z 527 (M+H)$^+$, Rt=2.75 minutes (method A)

Example 128

N-(3-Chloro-2-methylphenyl)-6-{[(2,6-dichlorophenyl)carbonyl]amino}-2-[(2R)-tetrahydrofuran-2-yl]-1H-benzimidazole-4-carboxamide hydrochloride The titled compound was obtained as pale yellow powder according to the procedure as described in Step 2 of Example 92, using 6-amino-N-(3-chloro-2-methylphenyl)-2-[(2R)-tetrahydrofuran-2-yl]-1H-benzimidazole-4-carboxamide instead of 6-amino-N-(3-chloro-2-methylphenyl)-2-(methoxymethyl)-1H-benzimidazole-4-carboxamide, and 2,6-dichlorobenzoyl chloride instead of 2-chloro-6-fluorobenzoyl chloride.
MS (ESI+) m/z 543 (M+H)$^+$, Rt=2.80 minutes (method A)

Example 129

N-(3-Chloro-2-methylphenyl)-6-{[(2,5-dichlorophenyl)carbonyl]amino}-2-[(2R)-tetrahydrofuran-2-yl]-1H-benzimidazole-4-carboxamide hydrochloride The titled compound was obtained as white powder according to the procedure as described in Step 2 of Example 92, using 6-amino-N-(3-chloro-2-methylphenyl)-2-[(2R)-tetrahydrofuran-2-yl]-1H-benzimidazole-4-carboxamide instead of 6-amino-N-(3-chloro-2-methylphenyl)-2-(methoxymethyl)-1H-benzimidazole-4-carboxamide, and 2,5-dichlorobenzoyl chloride instead of 2-chloro-6-fluorobenzoyl chloride.
MS (ESI+) m/z 543 (M+H)$^+$, Rt=2.86 minutes (method A)

Example 130

N-(3-Chloro-2-methylphenyl)-2-[(2S)-5-oxopyrrolidin-2-yl]-6-({[2-(trifluoromethyl)phenyl]carbonyl}amino)-1H-benzimidazole-4-carboxamide hydrochloride The titled compound was obtained as white powder according to the procedure as described in Example 11, using (S)-(−)-2-pyrrolidone 5-carbonyl chloride (prepared as described in Tetrahedron Lett., 1997, 38, 2259) instead of methoxyacetyl chloride.
MS (ESI+) m/z 556 (M+H)$^+$, Rt=2.03 minutes (method A)

Example 131

N-(3-Chloro-2-methylphenyl)-2-[(2R)-5-oxopyrrolidin-2-yl]-6-({[2-(trifluoromethyl)phenyl]carbonyl}amino)-1H-benzimidazole-4-carboxamide hydrochloride The titled compound was obtained as white powder according to the procedure as described in Example 11, using (R)-(+)-2-pyrrolidone-5-carbonyl chloride (prepared as described in Tetrahedron Lett., 1997, 38, 2259) instead of methoxyacetyl chloride.
MS (ESI+) m/z 556 (M+H)$^+$, Rt=2.03 minutes (method A)

Example 132

N-(3-Chloro-2-methylphenyl)-2-[2-oxo-2-(pyrrolidin-1-yl)ethyl]-6-({[2-(trifluoromethyl)phenyl]carbonyl}amino)-1H-benzimidazole-4-carboxamide hydrochloride

Step 1

Methyl 2-(2-ethoxy-2-oxoethyl)-1H-benzimidazole-4-carboxylate

A solution of methyl 2,3-diaminobenzoate (680 mg) and ethyl 3-amino-3-ethoxyacrylate hydrochloride (880 mg) in EtOH (12 mL) was stirred at 60° C. for 2 hours. EtOH was removed under reduced pressure, and the residue was purified on column chromatography to obtain the titled compound (1.14 g) as a pale yellow solid.

Step 2

Methyl 2-(2-ethoxy-2-oxoethyl)-6-({[2-(trifluoromethyl)phenyl]carbonyl}amino)-1H-benzimidazole-4-carboxylate The titled compound was obtained as pale yellow powder according to the procedures as described in Steps 3 to 5 of Example 11, using methyl 2-(2-ethoxy-2-oxoethyl)-1H-benzimidazole-4-carboxylate instead of methyl 1H-benzimidazole-4-carboxylate as a starting material.

Step 3

Methyl 2-[2-oxo-2-(pyrrolidin-1-yl)ethyl]-6-({[2-(trifluoromethyl)phenyl]carbonyl}amino)-1H-benzimidazole-4-carboxylate Pyrrolidine (1 mL) was added to methyl 2-(2-ethoxy-2-oxoethyl)-6-({[2-(trifluoromethyl)phenyl]carbonyl}amino)-1H-benzimidazole-4-carboxylate (80 mg), and the solution was stirred at 70° C. for 30 minutes. The reaction mixture was diluted with ethyl acetate, and washed with brine. The ethyl acetate layer was concentrated under reduced pressure. The residue was purified on column chromatography to obtain the titled compound (74 mg) as white powder.

Step 4

2-[2-Oxo-2-(pyrrolidin-1-yl)ethyl]-6-({[2-(trifluoromethyl)phenyl]carbonyl}amino)-1H-benzimidazole-4-carboxylic acid A solution of methyl 2-[2-oxo-2-(pyrrolidin-1-yl)ethyl]-6-({[2-(trifluoromethyl)phenyl]carbonyl}amino)-1H-benzimidazole-4-carboxylate (74 mg) and lithium hydroxide hydrate (66 mg) in MeOH-water (1:1, 2 mL) was stirred at 50° C. for 30 minutes. The solvent was removed under reduced pressure, water was added, and the residue was neutralized by 1N hydrochloric acid under ice-cooling. The precipitate was collected by filtration, washed with diethyl ether, and dried under reduced pressure to obtain the titled compound (60 mg) as pale yellow powder.

Step 5

N-(3-Chloro-2-methylphenyl)-2-[2-oxo-2-(pyrrolidin-1-yl)ethyl]-6-({[2-(trifluoromethyl)phenyl]carbonyl}amino)-1H-benzimidazole-4-carboxamide hydrochloride To a solution of 2-[2-oxo-2-(pyrrolidin-1-yl)ethyl]-6-({[2-(trifluoromethyl)phenyl]carbonyl}amino)-1H-benzimidazole-4-carboxylic acid (30 mg) and HATU (30 mg) in DMF (0.5 mL), were added N,N-diisopropylethylamine (28 μL) and 3-chloro-2-methylaniline (10 μL), and the mixture was stirred at room temperature for 15 minutes. The reaction mixture was diluted with ethyl acetate, washed with brine, and the organic layer was concentrated under reduced pressure. The residue was purified on column chromatography to obtain pale yellow powder (28 mg). This was suspended in MeOH (1 mL), and 2N hydrogen chloride/EtOH solution (1 Eq) was added to obtain a homogeneous solution, which was then concentrated under reduced pressure. The residue was triturated in diethyl ether and washed. The precipitate was collected by filtration and dried under reduced pressure to obtain the titled compound (20 mg) as white powder.

MS (ESI+) m/z 584 (M+H)$^+$, Rt=2.24 minutes (method A)

Example 133

N-(3-Chloro-2-methylphenyl)-2-[2-(dimethylamino)-2-oxoethyl]-6-({[2-(trifluoromethyl)phenyl]carbonyl}amino)-1H-benzimidazole-4-carboxamide hydrochloride

Step 1

Methyl 2-[2-(dimethylamino)-2-oxoethyl]-6-({[2-(trifluoromethyl)phenyl]carbonyl}amino)-1H-benzimidazole-4-carboxylate The titled compound was obtained as pale yellow powder according to the procedure as described in Step 3 of Example 132, using 40% aqueous dimethylamine solution and THF instead of pyrrolidine.

Step 2

2-[2-(Dimethylamino)-2-oxoethyl]-6-({[2-(trifluoromethyl)phenyl]carbonyl}amino)-1H-benzimidazole-4-carboxylic acid The titled compound was obtained as gray powder according to the procedure as described in Step 4 of Example 132, using methyl 2-[2-(dimethylamino)-2-oxoethyl]-6-({[2-(trifluoromethyl)phenyl]carbonyl}amino)-1H-benzimidazole-4-carboxylate instead of methyl 2-[2-oxo-2-(pyrrolidin-1-yl)ethyl]-6-({[2-(trifluoromethyl)phenyl]carbonyl}amino)-1H-benzimidazole-4-carboxylate.

Step 3

N-(3-Chloro-2-methylphenyl)-2-[2-(dimethylamino)-2-oxoethyl]-6-({[2-(trifluoromethyl)phenyl]carbonyl}amino)-1H-benzimidazole-4-carboxamide hydrochloride The titled compound was obtained as pale yellow powder according to the procedure as described in Step 5 of Example 132, using 2-[2-(dimethylamino)-2-oxoethyl]-6-({[2-(trifluoromethyl)phenyl]carbonyl}amino)-1H-benzimidazole-4-carboxylic acid instead of 2-[2-oxo-2-(pyrrolidin-1-yl)ethyl]-6-({[2-(trifluoromethyl)phenyl]carbonyl}amino)-1H-benzimidazole-4-carboxylic acid.

MS (ESI+) m/z 558 (M+H)+, Rt=2.12 minutes (method A)

Example 134

N-(3-Chloro-2-methylphenyl)-2-[2-(methylamino)-2-oxoethyl]-6-({[2-(trifluoromethyl)phenyl]carbonyl}amino)-1H-benzimidazole-4-carboxamide hydrochloride Step 1

Methyl 2-[2-(methylamino)-2-oxoethyl]-6-({[2-(trifluoromethyl)phenyl]carbonyl}amino)-1H-benzimidazole-4-carboxylate The titled compound was obtained as white powder according to the procedure as described in Step 3 of Example 132, using 40% aqueous methylamine solution and THF instead of pyrrolidine.

Step 2

2-[2-(Methylamino)-2-oxoethyl]-6-({[2-(trifluoromethyl)phen yl]carbonyl}amino)-1H-benzimidazole-4-carboxylic acid The titled compound was obtained as brown powder according to the procedure as described in Step 4 of Example 132, using methyl 2-[2-(methylamino)-2-oxoethyl]-6-({[2-(trifluoromethyl)phen yl]carbonyl}amino)-1H-benzimidazole-4-carboxylate instead of methyl 2-[2-oxo-2-(pyrrolidin-1-yl)ethyl]-6-({[2-(trifluoromethyl)phenyl]carbonyl}amino)-1H-benzimidazole-4-carboxylate.

Step 3

N-(3-Chloro-2-methylphenyl)-2-[2-(methylamino)-2-oxoethyl]-6-({[2-(trifluoromethyl)phenyl]carbonyl}amino)-1H-benzimidazole-4-carboxamide hydrochloride The titled compound was obtained as pale red powder according to the procedure as described in Step 5 of Example 132, using 2-[2-(methylamino)-2-oxoethyl]-6-({[2-(trifluoromethyl)phen yl]carbonyl}amino)-1H-benzimidazole-4-carboxylic acid instead of 2-[2-oxo-2-(pyrrolidin-1-yl)ethyl]-6-({[2-(trifluoromethyl)phenyl]carbonyl}amino)-1H-benzimidazole-4-carboxylic acid.

MS (ESI+) m/z 544 (M+H)+, Rt=1.98 minutes (method A)

Example 135

2-Chloro-N-(3-chloro-2-methylphenyl)-6-({[2-(trifluoromethyl)phenyl]carbonyl}amino)-1H-benzimidazole-4-carboxamide Step 1

Methyl 2-chloro-1H-benzimidazole-4-carboxylate

A solution of methyl 2-oxo-2,3-dihydro-1H-benzimidazole-4-carboxylate (prepared as described in US2009/186879) (2.0 g) in phosphoryl chloride (18 mL) was stirred at 120° C. for 2.5 hours. Excessive phosphoryl chloride was removed under reduced pressure. To the residue was added saturated aqueous sodium bicarbonate under ice-cooling, and it was extracted with ethyl acetate. The ethyl acetate layer was dried over anhydrous magnesium sulfate and concentrated. The residue was purified on column chromatography to obtain the titled compound (1.5 g) as white powder.

Step 2

Methyl 2-chloro-6-nitro-1H-benzimidazole-4-carboxylate

The titled compound (0.98 g) was obtained as pale yellow powder according to the procedure as described in Step 2 of Example 1, using methyl 2-chloro-1H-benzimidazole-4-carboxylate (1.46 g) instead of methyl-1H-benzimidazole-4-carboxylate.

Step 3

Methyl 6-amino-2-chloro-1H-benzimidazole-4-carboxylate

To a solution of methyl 2-chloro-6-nitro-1H-benzimidazole-4-carboxylate (0.87 g) in MeOH (100 mL), was added 1% platinum+0.1% copper-activated carbon (Degussa type CF105 R/W) (0.19 g), and the mixture was stirred under hydrogen atmosphere (0.2 MPa) for 4 hours. The reaction mixture was filtered off through celite and washed with MeOH. The mother liquid was concentrated to obtain the titled compound (0.78 g) as yellow powder.

Step 4

Methyl 2-chloro-6-({[2-(trifluoromethyl)phenyl]carbonyl}amino)-1H-benzimidazole-4-carboxylate The titled compound (0.69 g) was obtained as colorless powder according to the procedure as described in Step 4 of Example 1, using methyl 6-amino-2-chloro-1H-benzimidazole-4-carboxylate (0.78 g) instead of methyl 6-amino-1H-benzimidazole-4-carboxylate.

Step 5

2-Chloro-6-({[2-(trifluoromethyl)phenyl]carbonyl}amino)-1H-benzimidazole-4-carboxylic acid The titled compound (620 mg) was obtained as white powder according to the procedure as described in Step 5 of Example 1, using methyl 2-chloro-6-({[2-(trifluoromethyl)phenyl]carbonyl}amino)-1H-benzimidazole-4-carboxylate (688 mg) instead of methyl 6-({[2-(trifluoromethyl)phenyl]carbonyl}amino)-1H-benzimidazole-4-carboxylate.

Step 6

2-Chloro-N-(3-chloro-2-methylphenyl)-6-({[2-(trifluoromethyl)phenyl]carbonyl}amino)-1H-benzimidazole-4-carboxamide Oxalyl chloride (1.42 mL) was added dropwise to a stirring solution of 2-chloro-6-({[2-(trifluoromethyl)phenyl]carbonyl}amino)-1H-benzimidazole-4-carboxylic acid (1.27 g) in THF (13 mL) under ice-cooling. To the mixture was added DMF (five drops), and it was stirred at room temperature for 2 hours. From the reaction mixture was removed the solvent and excessive oxalyl chloride under reduced pressure. To the residue was added toluene, and it was concentrated under reduced pressure, dried, and then dissolved in THF (10 mL). The solution was dropped slowly to a solution of 3-chloro-2-methylaniline (0.42 mL) and N,N-diisopropylethylamine (2.3 mL) in THF (10 mL) under ice-cooling for 1 hour. The reaction mixture was diluted with ethyl acetate, washed with brine, dried over anhydrous magnesium sulfate, and concentrated under reduced pressure. The residue was purified on column chromatography to obtain the titled compound (0.58 g) as white powder.

MS (ESI+) m/z 507 (M+H)$^+$, Rt=2.56 minutes (method A)

Example 136

N-(3-Chloro-2-methylphenyl)-2-[(2-methoxyethyl)amino]-6-({[2-(trifluoromethyl)phenyl]carbonyl}amino)-1H-benzimidazole-4-carboxamide hydrochloride 2-Methoxyethylamine (2 mL) was added to 2-chloro-N-(3-chloro-2-methylphenyl)-6-({[2-(trifluoromethyl)phenyl]carbonyl}amino)-1H-benzimidazole-4-carboxamide (40 mg, Example 135). The mixture was stirred at 150° C. in a sealed pressure-proof stainless steel container for 17 hours. The reaction mixture was washed with brine and concentrated under reduced pressure. The residue was purified on column chromatography to obtain N-(3-chloro-2-methylphenyl)-2-[(2-methoxyethyl)amino]-6-({[2-(trifluoromethyl)phenyl]carbonyl}amino)-1H-benzimidazole-4-carboxamide (35 mg) as white powder. This was dissolved in MeOH (1 mL), 2N hydrogen chloride/EtOH solution (1 Eq) was added, and it was stirred and concentrated. The residue was triturated in diethyl ether, and the precipitate was collected by filtration and dried to obtain the titled compound (28 mg) as white powder.

MS (ESI+) m/z 546 (M+H)$^+$, Rt=1.80 minutes (method A)

Example 137

N-(3-Chloro-2-methylphenyl)-2-[(2-hydroxyethyl)amino]-6-({[2-(trifluoromethyl)phenyl]carbonyl}amino)-1H-benzimidazole-4-carboxamide hydrochloride The titled compound was obtained as brown powder according to the procedure as described in Example 136, using 2-aminoethanol instead of 2-methoxyethylamine.

MS (ESI+) m/z 532 (M+H)$^+$, Rt=1.58 minutes (method A)

Example 138

N-(3-Chloro-2-methylphenyl)-2-(methylamino)-6-({[2-(trifluoromethyl)phenyl]carbonyl}amino)-1H-benzimidazole-4-carboxamide hydrochloride The titled compound was obtained as white powder according to the procedure as described in Example 136, using 40% aqueous methylamine solution instead of 2-methoxyethylamine.

MS (ESI+) m/z 502 (M+H)$^+$, Rt=1.69 minutes (method A)

Example 139

N-(3-Chloro-2-methylphenyl)-2-(ethylamino)-6-({[2-(trifluoromethyl)phenyl]carbonyl}amino)-1H-benzimidazole-4-carboxamide hydrochloride The titled compound was obtained as white powder according to the procedure as described in Example 136, using 70% aqueous ethylamine solution instead of 2-methoxyethylamine.

MS (ESI+) m/z 516 (M+H)$^+$, Rt=1.80 minutes (method A)

Example 140

N-(3-Chloro-2-methylphenyl)-2-[(2,2-dimethylpropyl)amino]-6-({[2-(trifluoromethyl)phenyl]carbonyl}amino)-1H-benzimidazole-4-carboxamide hydrochloride The titled compound was obtained as white powder according to the procedure as described in Example 136, using neopentylamine instead of 2-methoxyethylamine.

MS (ESI+) m/z 558 (M+H)$^+$, Rt=2.22 minutes (method A)
Elemental Analysis for $C_{28}H_{27}Cl_3N_5O_2 \cdot HCl+0.5H_2O$
Calcd. (%) C, 55.73; H, 4.84; N, 11.61.
Found. (%) C, 55.99; H, 4.75; N, 11.69.

Example 141

N-(3-Chloro-2-methylphenyl)-2-(cyclopentylamino)-6-({[2-(trifluoromethyl)phenyl]carbonyl}amino)-1H-benzimidazole-4-carboxamide hydrochloride The titled compound was obtained as white powder according to the procedure as described in Example 136, using cyclopentylamine instead of 2-methoxyethylamine.

MS (ESI+) m/z 556 (M+H)$^+$, Rt=2.10 minutes (method A)

Example 142

N-(3-Chloro-2-methylphenyl)-2-(piperidin-1-yl)-6-({[2-(trifluoromethyl)phenyl]carbonyl}amino)-1H-benzimidazole-4-carboxamide hydrochloride The titled compound was obtained as white powder according to the procedure as described in Example 136, using piperidine instead of 2-methoxyethylamine.

MS (ESI+) m/z 556 (M+H)$^+$, Rt=2.54 minutes (method A)

Example 143

N-(3-Chloro-2-methylphenyl)-2-(4-methylpiperazin-1-yl)-6-({[2-(trifluoromethyl)phenyl]carbonyl}amino)-1H-benzimidazole-4-carboxamide dihydrochloride The titled compound was obtained as white powder according to the procedure as described in Example 136, using 1-methylpiperazine instead of 2-methoxyethylamine.

MS (ESI+) m/z 571 (M+H)$^+$, Rt=1.63 minutes (method A)

Example 144

2-[Bis(2-hydroxyethyl)amino]-N-(3-chloro-2-methylphenyl)-6-({[2-(trifluoromethyl)phenyl]carbonyl}amino)-1H-benzimidazole-4-carboxamide hydrochloride The titled compound was obtained as white powder according to the procedure as described in Example 136, using diethanolamine instead of 2-methoxyethylamine.
MS (ESI+) m/z 576 (M+H)$^+$, Rt=1.66 minutes (method A)

Example 145

N-(3-Chloro-2-methylphenyl)-2-(dimethylamino)-6-({[2-(trifluoromethyl)phenyl]carbonyl}amino)-1H-benzimidazole-4-carboxamide hydrochloride The titled compound was obtained as pale yellow powder according to the procedure as described in Example 136, using 50% aqueous dimethylamine solution instead of 2-methoxyethylamine.
MS (ESI+) m/z 516 (M+H)$^+$, Rt=2.13 minutes (method A)
Elemental Analysis for $C_{25}H_{21}ClF_3N_5O_2 \cdot HCl + 0.5H_2O$
Calcd. (%) C, 53.49; H, 4.13; N, 12.48.
Found. (%) C, 53.44; H, 4.17; N, 12.39.

Example 146

N-(3-Chloro-2-methylphenyl)-2-{[2-(morpholin-4-yl)ethyl]amino}-6-({[2-(trifluoromethyl)phenyl]carbonyl}amino)-1H-benzimidazole-4-carboxamide hydrochloride The titled compound was obtained as pink powder according to the procedure as described in Example 136, using 4-(2-aminoethyl)morpholine instead of 2-methoxyethylamine.
MS (ESI+) m/z 601 (M+H)$^+$, Rt=1.53 minutes (method A)

Example 147

N-(3-Chloro-2-methylphenyl)-2-{[2-(dimethylamino)ethyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using N,N-dimethylethylenediamine instead of 2-methoxyethylamine.
MS (ESI+) m/z 559 (M+H)$^+$, Rt=1.51 minutes (method A)

Example 148

N-(3-Chloro-2-methylphenyl)-2-(3-hydroxyazetidin-1-yl)-6-({[2-(trifluoromethyl)phenyl]carbonyl}amino)-1H-benzimidazole-4-carboxamide hydrochloride The titled compound was obtained as white powder according to the procedure as described in Example 136, using 3-hydroxyazetidine hydrochloride, N,N-diisopropylethylamine and EtOH instead of 2-methoxyethylamine.
MS (ESI+) m/z 544 (M+H)$^+$, Rt=1.77 minutes (method A)

Example 149

N-(3-Chloro-2-methylphenyl)-2-[(3S)-3-(dimethylamino)pyrrolidin-1-yl]-6-({[2-(trifluoromethyl)phenyl]carbonyl}amino)-1H-benzimidazole-4-carboxamide dihydrochloride The titled compound was obtained as brown powder according to the procedure as described in Example 136, using (S)-(−)-3-dimethylaminopyrrolidine, N,N-diisopropylethylamine and EtOH instead of 2-methoxyethylamine.
MS (ESI+) m/z 585 (M+H)$^+$, Rt=1.53 minutes (method A)

Example 150

N-(3-Chloro-2-methylphenyl)-2-[(3S)-3-hydroxypyrrolidin-1-yl]-6-({[2-(trifluoromethyl)phenyl]carbonyl}amino)-1H-benzimidazole-4-carboxamide hydrochloride The titled compound was obtained as pale yellow powder according to the procedure as described in Example 136, using (S)-3-hydroxypyrrolidine, N,N-diisopropylethylamine and EtOH instead of 2-methoxyethylamine.
MS (ESI+) m/z 558 (M+H)$^+$, Rt=1.75 minutes (method A)

Example 151

N-(3-Chloro-2-methylphenyl)-2-{[2-(diethylamino)ethyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using N,N-diethylethylenediamine instead of 2-methoxyethylamine.
MS (ESI+) m/z 587 (M+H)$^+$, Rt=1.57 minutes (method A)

Example 152

N-(3-Chloro-2-methylphenyl)-2-{[2-(pyrrolidin-1-yl)ethyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using 1-(2-aminoethyl)pyrrolidine instead of 2-methoxyethylamine.
MS (ESI+) m/z 585 (M+H)$^+$, Rt=1.59 minutes (method A)

Example 153

N-(3-Chloro-2-methylphenyl)-2-{[3-(dimethylamino)propyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using N,N-dimethyl-1,3-propanediamine instead of 2-methoxyethylamine.
MS (ESI+) m/z 573 (M+H)$^+$, Rt=1.43 minutes (method A)

Example 154

N-(3-Chloro-2-methylphenyl)-2-{[3-(dimethylamino)-2,2-dimethylpropyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using N,N,2,2-tetramethyl-1,3-propanediamine instead of 2-methoxyethylamine.
MS (ESI+) m/z 601 (M+H)$^+$, Rt=1.56 minutes (method A)

Example 155

N-(3-Chloro-2-methylphenyl)-2-{[2-(dipropan-2-ylamino)ethyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using N,N-diisopropylethylenediamine instead of 2-methoxyethylamine.
MS (ESI+) m/z 615 (M+H)$^+$, Rt=1.69 minutes (method A)

Example 156

N-(3-Chloro-2-methylphenyl)-2-(morpholin-4-yl)-6-({[2-(trifluoromethyl)phenyl]carbonyl}amino)-1H-benzimidazole-4-carboxamide The titled compound was obtained as pale yellow powder according to the procedure as described in Example 136 using morpholine instead of 2-methoxyethylamine.
MS (ESI+) m/z 558 (M+H)$^+$, Rt=2.25 minutes (method A)

Example 157

2-Amino-N-(3-chloro-2-methylphenyl)-6-({[2-(trifluoromethyl)phenyl]carbonyl}amino)-1H-benzimidazole-4-carboxamide hydrochloride According to the procedure as described in Example 136, N-(3-chloro-2-methylphenyl)-2-[(4-methoxybenzyl)amino]-6-({[2-(trifluoromethyl)phenyl]carbonyl}amino)-1H-benzimidazole-4-carboxamide (97 mg) was obtained as yellow powder, using 4-methoxybenzylamine instead of 2-methoxyethylamine. This was dissolved in TFA (2 mL), and the solution was stirred at 70° C. for 2 hours, and TFA was removed under reduced pressure. To the residue was added saturated aqueous sodium bicarbonate, and it was extracted with ethyl acetate. The ethyl acetate layer was washed with brine, dried over anhydrous magnesium sulfate, and concentrated under reduced pressure. The residue was purified on column chromatography to obtain 2-amino-N-(3-chloro-2-methylphenyl)-6-({[2-(trifluoromethyl)phenyl]carbonyl}amino)-1H-benzimidazole-4-carboxamide (35 mg). This was suspended in MeOH (3 mL), 2N hydrogen chloride/MeOH solution (0.3 mL) was added, and MeOH was removed under reduced pressure. The residue was triturated in 2-propanol/diethyl ether, and the precipitate was collected by filtration and dried to obtain the titled compound (21 mg) as yellow powder.
MS (ESI+) m/z 488 (M+H)$^+$, Rt=1.62 minutes (method A)

Example 158

N-(3-Chloro-2-methylphenyl)-2-[(3-hydroxy-2,2-dimethylpropyl)amino]-6-({[2-(trifluoromethyl)phenyl]carbonyl}amino)-1H-benzimidazole-4-carboxamide hydrochloride The titled compound was obtained as pale yellow powder according to the procedure as described in Example 136, using 3-amino-2,2-dimethyl-1-propanol instead of 2-methoxyethylamine.
MS (ESI+) m/z 574 (M+H)$^+$, Rt=1.81 minutes (method A)

Example 159

N-(3-Chloro-2-methylphenyl)-2-{[(3-methyloxetan-3-yl)methyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using 1-(3-methyloxetan-3-yl)methanamine (prepared as described in US2009/76062) instead of 2-methoxyethylamine.
MS (ESI+) m/z 572 (M+H)$^+$, Rt=1.66 minutes (method A)

Example 160 tert-Butyl N-{4-[(3-chloro-2-methylphenyl)carbamoyl]-6-({[2-(trifluoro methyl)phenyl]carbonyl}amino)-1H-benzimidazol-2-yl}glycinate hydrochloride The titled compound was obtained as pale yellow powder according to the procedure as described in Example 136, using glycine tert-butyl ester instead of 2-methoxyethylamine.
MS (ESI+) m/z 602 (M+H)$^+$, Rt=2.42 minutes (method A)

Example 161

N-{4-[(3-Chloro-2-methylphenyl)carbamoyl]-6-({[2-(trifluoro methyl)phenyl]carbonyl}amino)-1H-benzimidazol-2-yl}glycine hydrochloride TFA (1 mL) was added to a solution of tert-butyl N-{4-[(3-chloro-2-methylphenyl)carbamoyl]-6-({[2-(trifluoro methyl)phenyl]carbonyl}amino)-1H-benzimidazol-2-yl}glycinate (95 mg) in methylene chloride (2 mL), and the mixture was stirred for 1 hour at room temperature, and concentrated. The residue was neutralized with 1N aqueous NaOH under ice-cooling and extracted with EtOAc. The ethyl acetate layer was dried over anhydrous magnesium sulfate and concentrated. The residue was purified on column chromatography to obtain N-{4-[(3-chloro-2-methylphenyl)carbamoyl]-6-({[2-(trifluoro methyl)phenyl]carbonyl}amino)-1H-benzimidazol-2-yl}glycine (50 mg) as white powder. N-{4-[(3-chloro-2-methylphenyl)carbamoyl]-6-({[2-(trifluoro methyl)phenyl]carbonyl}amino)-1H-benzimidazol-2-yl}glycine (16 mg) was suspended in MeOH. To the suspension was added 2N hydrogen chloride/EtOH solution (1 Eq) to obtain a homogeneous solution. The solvent was removed under reduced pressure. The residue was triturated in diethyl ether, and the precipitate was collected by filtration and dried to obtain the titled compound (12 mg) as white powder.
MS (ESI+) m/z 546 (M+H)$^+$, Rt=1.74 minutes (method A)

Example 162

N-(3-Chloro-2-methylphenyl)-2-[(3-hydroxy-2,2-dimethylpropyl)amino]-1-methyl-6-({[2-(trifluoromethyl)phenyl]carbonyl}amino)-1H-benzimidazole-4-carboxamide hydrochloride Sodium hydroxide powder (6.2 mg) was added to a solution of N-(3-chloro-2-methylphenyl)-2-[(3-hydroxy-2,2-dimethylpropyl)amino]-6-({[2-(trifluoromethyl)phenyl]carbonyl}amino)-1H-benzimidazole-4-carboxamide (80 mg) in DMF (2 mL), the solution was stirred at room temperature for 30 minutes, methyl iodide (8.7 µL) was added, and it was stirred for 17 hours. The reaction mixture was diluted with ethyl acetate, washed with brine, and concentrated under reduced pressure. The residue was purified on column chromatography to obtain N-(3-chloro-2-methylphenyl)-2-[(3-hydroxy-2,2-dimethylpropyl)amino]-1-methyl-6-({[2-(trifluoromethyl)phenyl]carbonyl}amino)-1H-benzimidazole-4-carboxamide (20 mg) as white powder. This was suspended in MeOH, 2N hydrogen chloride/EtOH (1 Eq) was added, it was stirred to obtain a solution, and the solvent was removed under reduced pressure. The residue was washed with diethyl ether, and the precipitate was collected by filtration and dried to obtain the titled compound (15 mg) as white powder.

MS (ESI+) m/z 588 (M+H)$^+$, Rt=2.06 minutes (method A)

Example 163

N-(3-Chloro-2-methylphenyl)-2-[(3-methoxy-2,2-dimethylpropyl)amino]-6-({[2-(trifluoromethyl)phenyl]carbonyl}amino)-1H-benzimidazole-4-carboxamide hydrochloride The titled compound was obtained as white powder according to the procedure as described in Example 136, using 3-methoxy-2,2-dimethyl propylamine (prepared as described in WO2007/28051) instead of 2-methoxyethylamine.

MS (ESI+) m/z 588 (M+H)$^+$, Rt=2.11 minutes (method A)
Elemental Analysis for $C_{29}H_{29}ClF_3N_5O_3 \cdot HCl+0.5H_2O$
Calcd. (%) C, 54.98; H, 4.93; N, 11.06.
Found. (%) C, 54.94; H, 4.63; N, 11.09.

Example 164

N-(3-Chloro-2-methylphenyl)-2-(pyrrolidin-1-yl)-6-({[2-(trifluoromethyl)phenyl]carbonyl}amino)-1H-benzimidazole-4-carboxamide hydrochloride The titled compound was obtained as pale yellow powder according to the procedure as described in Example 136, using pyrrolidine instead of 2-methoxyethylamine.

MS (ESI+) m/z 542 (M+H)$^+$, Rt=2.15 minutes (method A)
Elemental Analysis for $C_{27}H_{23}ClF_3N_5O_2 \cdot HCl+1.0H_2O$
Calcd. (%) C, 54.37; H, 4.39; N, 11.74.
Found. (%) C, 54.34; H, 4.66; N, 12.26.

Example 165

2-(Azetidin-1-yl)-N-(3-chloro-2-methylphenyl)-6-({[2-(trifluoromethyl)phenyl]carbonyl}amino)-1H-benzimidazole-4-carboxamide hydrochloride A solution of 2-chloro-N-(3-chloro-2-methylphenyl)-6-({[2-(trifluoromethyl)phenyl]carbonyl}amino)-1H-benzimidazole-4-carboxamide (80 mg, Example 135), azetidine hydrochloride (60 mg) and N,N-diisopropylethylamine (208 µL) in EtOH (1.8 mL) was reacted at 120° C. for 20 minutes in a microwave reactor (Biotage, Initiator). The reaction mixture was concentrated under reduced pressure, and the residue was purified on column chromatography to obtain 2-(azetidin-1-yl)-N-(3-chloro-2-methylphenyl)-6-({[2-(trifluoromethyl)phenyl]carbonyl}amino)-1H-benzimidazole-4-carboxamide (27 mg). This was dissolved in MeOH (1 mL), 2N hydrogen chloride/MeOH solution (1 Eq) was added, and it was stirred and concentrated. The residue was triturated in diethyl ether, and the precipitate was collected by filtration and dried to obtain the titled compound (21 mg) as white powder.

MS (ESI+) m/z 528 (M+H)$^+$, Rt=2.09 minutes (method A)

Example 166

N-(3-Chloro-2-methylphenyl)-2-(3-methoxyazetidin-1-yl)-6-({[2-(trifluoromethyl)phenyl]carbonyl}amino)-1H-benzimidazole-4-carboxamide hydrochloride The titled compound was obtained as white powder according to the procedure as described in Example 136, using 3-methoxy azetidine hydrochloride, N,N-diisopropylethylamine and EtOH instead of 2-methoxyethylamine.

MS (ESI+) m/z 558 (M+H)$^+$, Rt=2.20 minutes (method A)

Example 167

N-(3-Chloro-2-methylphenyl)-2-[(2-hydroxy-2-methylpropyl)amino]-6-({[2-(trifluoromethyl)phenyl]carbonyl}amino)-1H-benz imidazole-4-carboxamide hydrochloride The titled compound was obtained as pale yellow powder according to the procedure as described in Example 136, using 1-amino-2-methyl-2-propanol (prepared as described in WO2009/57827) and THF instead of 2-methoxyethylamine.

MS (ESI+) m/z 560 (M+H)$^+$, Rt=1.87 minutes (method A)

Example 168

N-(3-Chloro-2-methylphenyl)-2-{[(2S)-tetrahydrofuran-2-ylmethyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using (S)-(+)-tetrahydrofurfurylamine and THF instead of 2-methoxyethylamine.

MS (ESI+) m/z 572 (M+H)$^+$, Rt=2.04 minutes (method A)

Example 169

N-(3-Chloro-2-methylphenyl)-2-{[(2R)-tetrahydrofuran-2-ylmethyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using (R)-(−)-tetrahydrofurfurylamine and THF instead of 2-methoxyethylamine.

MS (ESI+) m/z 572 (M+H)$^+$, Rt=2.04 minutes (method A)
Elemental Analysis for C$_{28}$H$_{25}$Cl$_3$N$_5$O$_3$.HCl+0.7H$_2$O.
Calcd. (%) C, 54.15; H, 4.45; N, 11.28.
Found. (%) C, 54.16; H, 4.57; N, 11.19.

Example 170

N-(3-Chloro-2-methylphenyl)-2-{[(2S)-1-hydroxy-3-methylbutan-2-yl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using (S)-(+)-2-amino-3-methyl-1-butanol and THF instead of 2-methoxyethylamine.
MS (ESI+) m/z 574 (M+H)$^+$, Rt=1.98 minutes (method A)

Example 171

N-(3-Chloro-2-methylphenyl)-2-{[(2R)-1-hydroxy-3-methylbutan-2-yl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using (R)-(−)-2-amino-3-methyl-1-butanol and THF instead of 2-methoxyethylamine.
MS (ESI+) m/z 574 (M+H)$^+$, Rt=1.98 minutes (method A)

Example 172

N-(3-Chloro-2-methylphenyl)-2-{[(2S)-1-hydroxy-3,3-dimethyl butan-2-yl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using (S)-tert-leucinol and THF instead of 2-methoxyethylamine. MS (ESI+) m/z 588 (M+H)$^+$, Rt=2.20 minutes (method A)

Example 173

N-(3-Chloro-2-methylphenyl)-2-[(3-methoxy-2,2-dimethylpropyl)(methyl)amino]-6-({[2-(trifluoromethyl)phenyl]carbonyl}amino)-1H-benzimidazole-4-carboxamide hydrochloride The titled compound was obtained as pale yellow powder according to the procedure as described in Example 136, using 3-methoxy-N,2,2-trimethylpropan-1-amine (Reference Example 9) and THF instead of 2-methoxyethylamine.
MS (ESI+) m/z 602 (M+H)$^+$, Rt=2.71 minutes (method A)

Example 174

N-(3-Chloro-2-methylphenyl)-2-[(3-methoxypropyl)amino]-6-({[2-(trifluoromethyl)phenyl]carbonyl}amino)-1H-benzimidazole-4-carboxamide hydrochloride The titled compound was obtained as pale yellow powder according to the procedure as described in Example 136, using 3-methoxypropylamine and THF instead of 2-methoxyethylamine.
MS (ESI+) m/z 560 (M+H)$^+$, Rt=2.10 minutes (method A)

Example 175

N-(3-Chloro-2-methylphenyl)-2-{[2-(propan-2-yloxy)ethyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using 2-aminoethyl isopropyl ether and THF instead of 2-methoxyethylamine.
MS (ESI+) m/z 574 (M+H)$^+$, Rt=2.29 minutes (method A)

Example 176

2-[(2-tert-Butoxyethyl)amino]-N-(3-chloro-2-methylphenyl)-6-({[2-(trifluoromethyl)phenyl]carbonyl}amino)-1H-benzimidazole-4-carboxamide hydrochloride The titled compound was obtained as pale yellow powder according to the procedure as described in Example 136, using O-tert-butyl-2-aminoethanol and THF instead of 2-methoxyethylamine.
MS (ESI+) m/z 588 (M+H)$^+$, Rt=2.42 minutes (method A)

Example 177

N-(3-Chloro-2-methylphenyl)-2-[(2-methoxy-2-methylpropyl)amino]-6-({[2-(trifluoromethyl)phenyl]carbonyl}amino)-1H-benz imidazole-4-carboxamide hydrochloride The titled compound was obtained as pale yellow powder according to the procedure as described in Example 136, using 2-methoxy-2-methylpropylamine and THF instead of 2-methoxyethylamine.
MS (ESI+) m/z 574 (M+H)$^+$, Rt=2.30 minutes (method A)

Example 178

N-(3-Chloro-2-methylphenyl)-2-{[2-(methylsulfanyl)ethyl]amino}-6-({[2-(trifluoromethyl)phenyl]carbonyl}amino)-1H-benzimidazole-4-carboxamide hydrochloride The titled compound was obtained as pale yellow powder according to the procedure as described in Example 136, using 2-(methylthio)ethylamine and THF instead of 2-methoxyethylamine.
MS (ESI+) m/z 562 (M+H)$^+$, Rt=2.51 minutes (method A)

Example 179

N-(3-Chloro-2-methylphenyl)-2-(methylsulfanyl)-6-({[2-(trifluoromethyl)phenyl]carbonyl}amino)-1H-benzimidazole-4-carboxamide

Step 1

Methyl 2-(methylsulfanyl)-1H-benzimidazole-4-carboxylate

To a solution of methyl 2-sulfanyl-1H-benzimidazole-4-carboxylate (prepared as described in WO2003/106430) (1.0 g) in DMF (15 mL), were added potassium carbonate (700 mg) and methyl iodide (0.32 mL), and the mixture was stirred at room temperature for 3 days. The reaction mixture was diluted with ethyl acetate, washed with brine, dried over anhydrous magnesium sulfate, and concentrated under reduced pressure. The residue was purified on column chromatography to obtain the titled compound (860 mg) as white powder.

Step 2

Methyl 2-(methylsulfanyl)-6-nitro-1H-benzimidazole-4-carboxylate

The titled compound (840 mg) was obtained as pale yellow powder according to the procedure as described in Step 2 of Example 1, using methyl 2-(methylsulfanyl)-1H-benzimidazole-4-carboxylate (860 mg) instead of methyl-1H-benzimidazole-4-carboxylate.

Step 3

Methyl 6-amino-2-(methylsulfanyl)-1H-benzimidazole-4-carboxylate

The titled compound (380 mg) was obtained as pale yellow powder according to the procedure as described in Step 3 of Example 1, using methyl 2-(methylsulfanyl)-6-nitro-1H-benzimidazole-4-carboxylate (840 mg) instead of methyl 6-nitro-1H-benzimidazole-4-carboxylate.

Step 4

Methyl 2-(methylsulfanyl)-6-({[2-(trifluoromethyl)phenyl]carbonyl}amino)-1H-benzimidazole-4-carboxylate The titled compound (250 mg) was obtained as white powder according to the procedure as described in Step 4 of Example 1, using methyl 6-amino-2-(methylsulfanyl)-1H-benzimidazole-4-carboxylate (150 mg) instead of methyl 6-amino-1H-benzimidazole-4-carboxylate.

Step 5

2-(Methylsulfanyl)-6-({[2-(trifluoromethyl)phenyl]carbonyl}amino)-1H-benzimidazole-4-carboxylic acid The titled compound (240 mg) was obtained as pale yellow powder according to the procedure as described in Step 5 of Example 1, using methyl 2-(methylsulfanyl)-6-({[2-(trifluoromethyl)phenyl]carbonyl}amino)-1H-benzimidazole-4-carboxylate (250 mg) instead of methyl 6-({[2-(trifluoromethyl)phenyl]carbonyl}amino)-1H-benzimidazole-4-carboxylate.

Step 6

N-(3-Chloro-2-methylphenyl)-2-(methylsulfanyl)-6-({[2-(trifluoromethyl)phenyl]carbonyl}amino)-1H-benzimidazole-4-carboxamide The titled compound (35 mg) was obtained as white powder according to the procedure as described in Step 6 of Example 135, using 2-(methylsulfanyl)-6-({[2-(trifluoromethyl)phenyl]carbonyl}amino)-1H-benzimidazole-4-carboxylic acid (45 mg) instead of 2-chloro-6-({[2-(trifluoromethyl)phenyl]carbonyl}amino)-1H-benzimidazole-4-carboxylic acid.

MS (ESI+) m/z 519 (M+H)$^+$, Rt=2.79 minutes (method A)

Example 180

N-(3-Chloro-2-methylphenyl)-2-(methylsulfonyl)-6-({[2-(trifluoromethyl)phenyl]carbonyl}amino)-1H-benzimidazole-4-carboxamide To a solution of N-(3-chloro-2-methylphenyl)-2-(methylsulfanyl)-6-({[2-(trifluoromethyl)phenyl]carbonyl}amino)-1H-benzimidazole-4-carboxamide (33 mg) in MeOH (5 mL), was added an aqueous solution (0.5 mL) of Oxone monopersulfate compound (75 mg), and the mixture was stirred at room temperature for 17 hours. Additionally, to the mixture was added an aqueous solution (0.5 mL) of Oxone monopersulfate compound (50 mg), and it was stirred for 3 hours. The reaction mixture was diluted with ethyl acetate and washed with saturated aqueous sodium bicarbonate. The organic layer was separated, and concentrated under reduced pressure. The residue was purified on column chromatography to obtain the titled compound (11 mg) as white powder.

MS (ESI+) m/z 551 (M+H)$^+$, Rt=2.54 minutes (method A)

Example 181

N-(3-Chloro-2-methylphenyl)-2-(methylsulfinyl)-6-({[2-(trifluoromethyl)phenyl]carbonyl}amino)-1H-benzimidazole-4-carboxamide To a solution of N-(3-chloro-2-methylphenyl)-2-(methylsulfanyl)-6-({[2-(trifluoromethyl)phenyl]carbonyl}amino)-1H-benzimidazole-4-carboxamide (26 mg) in THF (3 mL), was added an aqueous solution of m-chloroperbenzoic acid (75%, 12 mg) (1 mL), and the mixture was stirred at room temperature for 3 hours. The reaction mixture was diluted with ethyl acetate, washed sequentially with saturated aqueous sodium bicarbonate and brine, dried over anhydrous magnesium sulfate, and concentrated under reduced pressure. The residue was purified on column chromatography to yield the titled compound (10 mg) as pale yellow powder.

MS (ESI+) m/z 535 (M+H)$^+$, Rt=2.42 minutes (method A)

Example 182

6-{[(2-Chloro-6-fluorophenyl)carbonyl]amino}-N-(3-chloro-2-methylphenyl)-2-(dimethylamino)-1H-benzimidazole-4-carboxamide hydrochloride Step 1

Methyl 2-(dimethylamino)-1H-benzimidazole-4-carboxylate (Dichloromethylene)dimethyliminium chloride (4.93 g) was added to a solution of methyl 2,3-diaminobenzoate (4.2 g) in methylene chloride (75 mL), and the solution was stirred on oil bath at 50° C. for 1 hour. To the reaction mixture was added saturated aqueous sodium bicarbonate, and it was extracted with ethyl acetate. The organic layer was separated, washed with brine and concentrated under reduced pressure. The residue was purified on column chromatography to obtain the titled compound (4.7 g) as a pale yellow solid.

Step 2

Methyl 2-(dimethylamino)-6-nitro-1H-benzimidazole-4-carboxylate

The titled compound (1.8 g) was obtained as orange powder according to the procedure as described in Step 2 of Example 1, using methyl 2-(dimethylamino)-1H-benzimidazole-4-carboxylate (4.57 g) instead of methyl 1H-benzimidazole-4-carboxylate.

Step 3

2-(Dimethylamino)-6-nitro-1H-benzimidazole-4-carboxylic acid

A solution of methyl 2-(dimethylamino)-6-nitro-1H-benzimidazole-4-carboxylate (1.5 g) and lithium hydroxide hydrate (2.4 g) in THF—$H_2O$ (1:1, 100 mL) was stirred at 50° C. for 2 hours. THF was removed under reduced pressure, and 1N hydrochloric acid was added to the residue with stirring under ice-cooling to adjust the pH to 5. The precipitate was collected by filtration and dried under reduced pressure to obtain the titled compound (1.38 g) as yellow solid.

Step 4

N-(3-Chloro-2-methylphenyl)-2-(dimethylamino)-6-nitro-1H-benzimidazole-4-carboxamide To a solution of 2-(dimethylamino)-6-nitro-1H-benzimidazole-4-carboxylic acid (520 mg) and HBTU (1.03 g) in DMF (6 mL), were added N,N-diisopropylethylamine (942 μL) and 3-chloro-2-methylaniline (323 μl), and the mixture was stirred at room temperature for 15 hours. The reaction mixture was diluted with ethyl acetate-THF (1:1), washed with brine, and the organic layer was dried over anhydrous magnesium sulfate and concentrated under reduced pressure. The residue was washed with MeOH to obtain the titled compound (650 mg) as a yellow solid.

Step 5

6-Amino-N-(3-chloro-2-methylphenyl)-2-(dimethylamino)-1H-benzimidazole-4-carboxamide To a suspension of N-(3-chloro-2-methylphenyl)-2-(dimethylamino)-6-nitro-1H-benzimidazole-4-carboxamide (580 mg) in MeOH-THF (1:1, 60 mL), was added 2N hydrogen chloride/EtOH (1 mL). To the mixture was added 1% platinum+0.1% copper-activated carbon (Degussa type CF105 R/W) (150 mg) and it was stirred vigorously under hydrogen atmosphere (0.2 MPa) for 3 hours. The reaction mixture was filtered off through celite, and the mother liquid was concentrated. To the residue was added saturated aqueous sodium bicarbonate, and it was extracted with ethyl acetate. The ethyl acetate layer was washed with brine, dried over anhydrous magnesium sulfate, and concentrated under reduced pressure. The residue was purified on column chromatography to obtain the titled compound (265 mg) as brown powder.

Step 6

6-{[(2-Chloro-6-fluorophenyl)carbonyl]amino}-N-(3-chloro-2-methylphenyl)-2-(dimethylamino)-1H-benzimidazole-4-carboxamide hydrochloride To a solution of 6-amino-N-(3-chloro-2-methylphenyl)-2-(dimethylamino)-1H-benzimidazole-4-carboxamide (30 mg) in THF (1 mL), was added N,N-diisopropylethylamine (22 μL). The mixture was stirred under ice-cooling, 2-chloro-6-fluorobenzoyl chloride (13 μL) was added slowly, and it was stirred for 2 hours. The reaction mixture was diluted with ethyl acetate, washed sequentially with saturated aqueous sodium bicarbonate and brine, dried over anhydrous magnesium sulfate and concentrated under reduced pressure. The residue was purified on column chromatography to obtain 6-{[(2-chloro-6-fluorophenyl)carbonyl]amino}-N-(3-chloro-2-methylphenyl)-2-(dimethylamino)-1H-benzimidazole-4-carboxamide (30 mg) as pale yellow powder. This was suspended in MeOH (1 mL), and 1N hydrogen chloride/MeOH (1 Eq) was added to obtain a homogeneous solution, and MeOH was removed under reduced pressure. The residue was triturated in n-hexane/ethyl acetate (1:1), and the precipitate was collected by filtration and dried under reduced pressure to obtain the titled compound (23 mg) as pale yellow powder.

MS (ESI+) m/z 500 (M+H)$^+$, Rt=2.13 minutes (method A)

Example 183

N-(3-Chloro-2-methylphenyl)-6-{[(2,6-dichlorophenyl)carbonyl]amino}-2-(dimethylamino)-1H-benzimidazole-4-carboxamide hydrochloride The titled compound was obtained as white powder according to the procedure as described in Step 6 of Example 182, using 2,6-dichlorobenzoyl chloride instead of 2-chloro-6-fluorobenzoyl chloride.

MS (ESI+) m/z 516 (M+H)$^+$, Rt=2.19 minutes (method A)

Example 184

N-(3-Chloro-2-methylphenyl)-6-{[(2,4-dichlorophenyl)carbonyl]amino}-2-(dimethylamino)-1H-benzimidazole-4-carboxamide hydrochloride The titled compound was obtained as white powder according to the procedure as described in Step 6 of Example 182, using 2,4-dichlorobenzoyl chloride instead of 2-chloro-6-fluorobenzoyl chloride.

MS (ESI+) m/z 516 (M+H)$^+$, Rt=2.31 minutes (method A)

Example 185

N-(3-Chloro-2-methylphenyl)-6-{[(2,5-dichlorophenyl)carbonyl]amino}-2-(dimethylamino)-1H-benzimidazole-4-carboxamide hydrochloride The titled compound was obtained as white powder according to the procedure as described in Step 6 of Example 182, using 2,5-dichlorobenzoyl chloride instead of 2-chloro-6-fluorobenzoyl chloride.

MS (ESI+) m/z 516 (M+H)$^+$, Rt=2.31 minutes (method A)
Elemental Analysis for $C_{24}H_{20}Cl_3N_5O_2 \cdot HCl + 0.5H_2O$
Calcd. (%) C, 51.27; H, 3.94; N, 12.46.
Found. (%) C, 51.10; H, 4.02; N, 12.45.

Example 186

6-{[(2-Bromo-6-fluorophenyl)carbonyl]amino}-N-(3-chloro-2-m ethylphenyl)-2-(dimethylamino)-1H-benzimidazole-4-carboxamide hydrochloride The titled compound was obtained as gray powder according to the procedure as described in Step 6 of Example 182, using 2-bromo-6-fluorobenzoyl chloride (prepared as described in WO2007/144327) instead of 2-chloro-6-fluorobenzoyl chloride.
MS (ESI+) m/z 544 (M+H)⁺, Rt=2.23 minutes (method A)

Example 187

6-{[(2-Bromo-6-chlorophenyl)carbonyl]amino}-N-(3-chloro-2-m ethylphenyl)-2-(dimethylamino)-1H-benzimidazole-4-carboxamide hydrochloride The titled compound was obtained as light brown powder according to the procedure as described in Step 6 of Example 182, using 2-bromo-6-chlorobenzoyl chloride instead of 2-chloro-6-fluorobenzoyl chloride.
MS (ESI+) m/z 560 (M+H)⁺, Rt=2.29 minutes (method A)

Example 188

6-({[2-Chloro-5-(cyclopropylethynyl)phenyl]carbonyl}amino)-N-(3-chloro-2-methylphenyl)-2-(dimethylamino)-1H-benzimidazole-4-carboxamide hydrochloride To a solution of 2-chloro-5-(cyclopropylethynyl)benzoic acid (33 mg, Reference Example 3), 6-amino-N-(3-chloro-2-methylphenyl)-2-(dimethylamino)-1H-benzimidazole-4-carboxamide (50 mg) and HATU (72 mg) in DMF (1 mL), was added N,N-diisopropylethylamine (66 µL), and the mixture was stirred at room temperature for 17 hours. The reaction mixture was diluted with ethyl acetate, and washed sequentially with saturated aqueous sodium bicarbonate and brine, dried over anhydrous magnesium sulfate, and concentrated under reduced pressure. The residue was purified on column chromatography to obtain 6-({[2-chloro-5-(cyclopropylethynyl)phenyl]carbonyl}amino)-N-(3-chloro-2-methylphenyl)-2-(dimethylamino)-1H-benzimidazole-4-carboxamide (74 mg). This was suspended in MeOH (1 mL), 2N hydrogen chloride/EtOH solution (1 Eq) was added to obtain a homogeneous solution, and the solvent was removed under reduced pressure. The residue was triturated in ethyl acetate, and the precipitate was collected by filtration and dried under reduced pressure to obtain the titled compound (58 mg) as pale yellow powder.
MS (ESI+) m/z 546 (M+H)⁺, Rt=2.60 minutes (method A)

Example 189

N-(3-Chloro-2-methylphenyl)-6-{[(2,5-dichlorophenyl)carbonyl]amino}-2-[(3-hydroxy-2,2-dimethylpropyl)amino]-1H-benzimidazole-4-carboxamide hydrochloride Step 1

Methyl 2-chloro-6-{[(2,5-dichlorophenyl) carbonyl]amino}-1H-benzimidazole-4-carboxylate The titled compound (1.68 g) was obtained as colorless amorphous according to the procedure as described in Step 4 of Example 1, using methyl 6-amino-2-chloro-1H-benzimidazole-4-carboxylate instead of methyl 6-amino-1H-benzimidazole-4-carboxylate, and 2,5-dichlorobenzoyl chloride instead of 2-(trifluoromethyl)benzoyl chloride.

Step 2

2-Chloro-6-{[(2,5-dichlorophenyl)carbonyl]amino}-1H-benzimidazole-4-carboxylic acid The titled compound (1.41 g) was obtained as white powder according to the procedure as described in Step 5 of Example 1, using methyl 2-chloro-6-{[(2,5-dichlorophenyl)carbonyl]amino}-1H-benzimidazole-4-carboxylate (1.68 g) instead of methyl 6-({[2-(trifluoromethyl)phenyl]carbonyl}amino)-1H-benzimidazole-4-carboxylate.

Step 3

2-Chloro-N-(3-chloro-2-methylphenyl)-6-{[(2,5-dichlorophenyl)carbonyl]amino}-1H-benzimidazole-4-carboxamide The titled compound was obtained as a white solid according to the procedure as described in Step 6 of Example 135, using 2-chloro-6-{[(2,5-dichlorophenyl)carbonyl]amino}-1H-benzimidazole-4-carboxylic acid instead of 2-chloro-6-({[2-(trifluoromethyl)phenyl]carbonyl}amino)-1H-benzimidazole-4-carboxylic acid.

Step 4

N-(3-Chloro-2-methylphenyl)-6-{[(2,5-dichlorophenyl)carbonyl]amino}-2-[(3-hydroxy-2,2-dimethylpropyl)amino]-1H-benzimidazole-4-carboxamide hydrochloride THF (1 mL) was added to 2-chloro-N-(3-chloro-2-methylphenyl)-6-{[(2,5-dichlorophenyl)carbonyl]amino}-1H-benzimidazole-4-carboxamide (50 mg) and 3-amino-2,2-dimethyl-1-propanol (400 mg). The mixture was stirred at 150° C. in a sealed pressure-proof stainless steel container for 8 hours. The reaction mixture was diluted with ethyl acetate, washed with brine and concentrated under reduced pressure. The residue was purified on column chromatography to obtain N-(3-chloro-2-methylphenyl)-6-{[(2,5-dichlorophenyl)carbonyl]amino}-2-[(3-hydroxy-2,2-dimethylpropyl)amino]-1H-benzimidazole-4-carboxamide (50 mg) as pale yellow powder. This was dissolved in MeOH (1 mL), and 2N Hydrogen chloride/EtOH solution (1 Eq) was added, and it was stirred and concentrated. The residue was triturated in diethyl ether, and the precipitate was collected by filtration and dried to obtain the titled compound (40 mg) as white powder.
MS (ESI+) m/z 574 (M+H)⁺, Rt=2.06 minutes (method A)

Example 190

N-(3-Chloro-2-methylphenyl)-6-{[(2,5-dichlorophenyl)carbonyl]amino}-2-[(3-methoxy-2,2-dimethylpropyl)amino]-1H-benzimidazole-4-carboxamide hydrochloride The titled compound was obtained as white powder according to the procedure as described in Example 189, using 3-methoxy-2,2-dimethylpropylamine instead of 3-amino-2,2-dimethyl-1-propanol.
MS (ESI+) m/z 588 (M+H)⁺, Rt=2.41 minutes (method A)

Example 191

N-(3-Chloro-2-methylphenyl)-6-{[(2,5-dichlorophenyl)carbonyl]amino}-2-[(2-hydroxy-2-methylpropyl)amino]-1H-benzimidazole-4-carboxamide hydrochloride The titled compound was obtained as white powder according to the procedure as described in Example 189, using 2-hydroxy-2-methylpropylamine instead of 3-amino-2,2-dimethyl-1-propanol.
MS (ESI+) m/z 560 (M+H)$^+$, Rt=2.12 minutes (method A)

Example 192

N-(3-Chloro-2-methylphenyl)-6-{[(2,5-dichlorophenyl)carbonyl]amino}-2-[(2-methoxy-2-methylpropyl)amino]-1H-benzimidazole-4-carboxamide hydrochloride The titled compound was obtained as pale yellow powder according to the procedure as described in Example 189, using 2-methoxy-2-methylpropylamine instead of 3-amino-2,2-dimethyl-1-propanol.
MS (ESI+) m/z 574 (M+H)$^+$, Rt=2.48 minutes (method A)

Example 193

N-(3-Chloro-2-methylphenyl)-6-{[(2,5-dichlorophenyl)carbonyl]amino}-2-{[2-(propan-2-yloxy)ethyl]amino}-1H-benzimidazole-4-carboxamide hydrochloride The titled compound was obtained as milky white powder according to the procedure as described in Example 189, using 2-aminoethyl isopropyl ether instead of 3-amino-2,2-dimethyl-1-propanol.
MS (ESI+) m/z 574 (M+H)$^+$, Rt=2.60 minutes (method A)
Elemental Analysis for $C_{27}H_{26}Cl_3N_5O_3 \cdot HCl+0.1H_2O$
Calcd. (%) C, 52.89; H, 4.47; N, 11.42.
Found. (%) C, 52.55; H, 4.10; N, 11.36.

Example 194

6-{[(2-Chloro-6-fluorophenyl)carbonyl]amino}-N-(3-chloro-2-methylphenyl)-2-{[2-(propan-2-yloxy)ethyl]amino}-1H-benzimidazole-4-carboxamide hydrochloride

Step 1

2-Chloro-6-{[(2-chloro-6-fluorophenyl)carbonyl]amino}-N-(3-chloro-2-methylphenyl)-1H-benzimidazole-4-carboxamide The titled compound was obtained as a white solid according to the procedures as described in Steps 1 to 3 of Example 189, using 2-chloro-6-fluorobenzoyl chloride instead of 2,5-dichlorobenzoyl chloride in Step 1.

Step 2

6-{[(2-Chloro-6-fluorophenyl)carbonyl]amino}-N-(3-chloro-2-methylphenyl)-2-{[2-(propan-2-yloxy)ethyl]amino}-1H-benzimidazole-4-carboxamide hydrochloride THF (1 mL) was added to 2-chloro-6-{[(2-chloro-6-fluorophenyl)carbonyl]amino}-N-(3-chloro-2-methylphenyl)-1H-benzimidazole-4-carboxamide (50 mg) and 2-aminoethyl isopropyl ether (32 mg). The mixture was stirred at 150° C. in a sealed pressure-proof stainless steel container for 17 hours. The reaction mixture was diluted with ethyl acetate and washed with brine and concentrated under reduced pressure. The residue was purified on column chromatography to obtain 6-{[(2-chloro-6-fluorophenyl)carbonyl]amino}-N-(3-chloro-2-methylphenyl)-2-{[2-(propan-2-yloxy)ethyl]amino}-1H-benzimidazole-4-carboxamide (41 mg) as pale yellow powder. This was dissolved in MeOH (1 mL), 2N hydrogen chloride/EtOH solution (1 Eq) was added, and it was stirred and concentrated. The residue was triturated in diethyl ether, and the precipitate was collected by filtration and dried to obtain the titled compound (35 mg) as white powder.
MS (ESI+) m/z 558 (M+H)$^+$, Rt=2.41 minutes (method A)

Example 195

2-[(2-tert-Butoxyethyl)amino]-6-{[(2-chloro-6-fluorophenyl) carbonyl]amino}-N-(3-chloro-2-methylphenyl)-1H-benzimidazole-4-carboxamide hydrochloride The titled compound was obtained as white powder according to the procedure as described in Step 2 of Example 194, using O-tert-butyl 2-aminoethanol instead of 2-aminoethyl isopropyl ether.
MS (ESI+) m/z 572 (M+H)$^+$, Rt=2.49 minutes (method A)

Example 196

6-{[(2-Chloro-6-fluorophenyl)carbonyl]amino}-N-(3-chloro-2-methylphenyl)-2-[(3-methoxy-2,2-dimethylpropyl)amino]-1H-benzimidazole-4-carboxamide hydrochloride The titled compound was obtained as white powder according to the procedure as described in Step 2 of Example 194, using 3-methoxy-2,2-dimethylpropylamine instead of 2-aminoethyl isopropyl ether.
MS (ESI+) m/z 572 (M+H)$^+$, Rt=2.51 minutes (method A)

Example 197

6-{[(2-Chloro-6-fluorophenyl)carbonyl]amino}-N-(3-chloro-2-methylphenyl)-2-[(2-methoxy-2-methylpropyl)amino]-1H-benzimidazole-4-carboxamide hydrochloride The titled compound was obtained as white powder according to the procedure as described in Step 2 of Example 194, using 2-methoxy-2-methylpropylamine instead of 2-aminoethyl isopropyl ether.
MS (ESI+) m/z 558 (M+H)$^+$, Rt=2.34 minutes (method A)

Example 198

6-{[(2-Chloro-6-fluorophenyl)-carbonyl]amino}-N-(3-chloro-2-methylphenyl)-2-{[(2S)-tetrahydrofuran-2-ylmethyl]amino}-1H-benzimidazole-4-carboxamide hydrochloride The titled compound was obtained as pale pink powder according to the procedure as described in Step 2 of Example 194, using (S)-(+)-tetrahydrofurfurylamine instead of 2-aminoethyl isopropyl ether.
MS (ESI+) m/z 556 (M+H)$^+$, Rt=2.28 minutes (method A)

Example 199

6-{[(2-Chloro-6-fluorophenyl)-carbonyl]amino}-N-(3-chloro-2-methylphenyl)-2-{[(2R)-tetrahydrofuran-2-ylmethyl]amino}-1H-benzimidazole-4-carboxamide hydrochloride The titled compound was obtained as pale pink powder according to the procedure as described in Step 2 of Example 194, using (R)-(−)-tetrahydrofurfurylamine instead of 2-aminoethyl isopropyl ether.
MS (ESI+) m/z 556 (M+H)$^+$, Rt=2.28 minutes (method A)

Example 200

6-{[(2-Chloro-6-fluorophenyl)carbonyl]amino}-N-(3-chloro-2-methylphenyl)-2-[(3-hydroxy-2,2-dimethylpropyl)amino]-1H-benzimidazole-4-carboxamide hydrochloride The titled compound was obtained as pale yellow powder according to the procedure as described in Step 2 of Example 194, using 3-amino-2,2-dimethyl-1-propanol instead of 2-aminoethyl isopropyl ether.
MS (ESI+) m/z 558 (M+H)$^+$, Rt=2.22 minutes (method A)

Example 201

6-{[(2-Chloro-6-fluorophenyl)-carbonyl]amino}-N-(3-chloro-2-methylphenyl)-2-{[(2S)-1-hydroxy-3-methylbutan-2-yl]amino}-1H-benzimidazole-4-carboxamide hydrochloride The titled compound was obtained as pale yellow powder according to the procedure as described in Step 2 of Example 194, using (S)-(+)-2-amino-3-methyl-1-butanol instead of 2-aminoethyl isopropyl ether.
MS (ESI+) m/z 558 (M+H)$^+$, Rt=2.31 minutes (method A)

Example 202

N-(3-Chloro-4-methylphenyl)-2-(dimethylamino)-6-({[2-(trifluoromethyl)phenyl]carbonyl}amino)-1H-benzimidazole-4-carboxamide hydrochloride

Step 1

2-(Dimethylamino)-6-({[2-(trifluoromethyl)phenyl]carbonyl}amino)-1H-benzimidazole-4-carboxylic acid To a stirring solution of methyl 6-amino-2-chloro-1H-benzimidazole-4-carboxylate (400 mg, Example 135, Step 3) and triethylamine (209 µL) in THF (18 mL), 2-(trifluoromethyl) benzoyl chloride (316 µL) was dropped slowly under ice-cooling. After 1 hour, the reaction mixture was diluted with ethyl acetate, washed sequentially with water and brine, dried over anhydrous magnesium sulfate, and concentrated under reduced pressure to obtain crude methyl 2-chloro-6-({[2-(trifluoromethyl)phenyl]carbonyl}amino)-1H-benzimidazole-4-carboxylate. This was dissolved in THF (15 mL) and MeOH (7 mL), 1N aqueous lithium hydroxide solution (9 mL) was added, and it was stirred at room temperature overnight. THF and MeOH were removed under reduced pressure. To the residue was added water, and it was neutralized with 1N hydrochloric acid under ice-cooling. The precipitation was collected by filtration to obtain crude 2-chloro-6-({[2-(trifluoromethyl)phenyl]carbonyl}amino)-1H-benzimidazole-4-carboxylic acid. This was dissolved in THF (10 mL), 40% aqueous dimethylamine solution (7 mL) was added, and it was stirred at 120° C. for 14 hours. The reaction mixture was cooled to room temperature, and THF was removed under reduced pressure. To the residue was added water, and the pH was adjusted to 3-4 with 1N hydrochloric acid under ice-cooling. The precipitate was collected by filtration, washed with diethyl ether, and dried under reduced pressure to obtain the titled compound (589 mg) as slightly yellow solid.

Step 2

N-(3-Chloro-4-methylphenyl)-2-(dimethylamino)-6-({[2-(trifluoromethyl)phenyl]carbonyl}amino)-1H-benzimidazole-4-carboxamide hydrochloride To a solution of 2-(dimethylamino)-6-({[2-(trifluoromethyl)phenyl]carbonyl}amino)-1H-benzimidazole-4-carboxylic acid (50 mg) and HATU (82 mg) in DMF (1 mL), were added N,N-diisopropylethylamine (88 µL) and 3-chloro-4-methylaniline (26 µL), and the mixture was stirred at room temperature for 1 hour. The reaction mixture was diluted with ethyl acetate, washed sequentially with saturated aqueous sodium bicarbonate and brine, dried over anhydrous magnesium sulfate, and concentrated under reduced pressure. The residue was purified on column chromatography to obtain N-(3-chloro-4-methylphenyl)-2-(dimethylamino)-6-({[2-(trifluoromethyl)phenyl]carbonyl}amino)-1H-benzimidazole-4-carboxamide (65 mg) as white powder. This was suspended in MeOH (1.5 mL), 2N hydrogen chloride/MeOH (1 Eq) was added, and it was stirred and concentrated. The residue was triturated in diethyl ether, and the precipitate was collected by filtration and dried to obtain the titled compound (40 mg) as white powder.
MS (ESI+) m/z 516 (M+H)$^+$, Rt=2.20 minutes (method A)

Example 203

N-(4-tert-Butylphenyl)-2-(dimethylamino)-6-({[2-(trifluoromethyl)phenyl]carbonyl}amino)-1H-benzimidazole-4-carboxamide hydrochloride The titled compound was obtained as pale yellow powder according to the procedure as described in Step 2 of Example 202, using 4-tert-butylaniline instead of 3-chloro-4-methylaniline.
MS (ESI+) m/z 524 (M+H)$^+$, Rt=2.30 minutes (method A)

Example 204

N-(2,3-Dihydro-1H-inden-5-yl)-2-(dimethylamino)-6-({[2-(trifluoromethyl)phenyl]carbonyl}amino)-1H-benzimidazole-4-carboxamide hydrochloride The titled compound was obtained as gray powder according to the procedure as described in Step 2 of Example 202, using 5-aminoindan instead of 3-chloro-4-methylaniline.
MS (ESI+) m/z 508 (M+H)$^+$, Rt=2.11 minutes (method A)

Example 205

6-{[(2-Chloro-6-fluorophenyl)carbonyl]amino}-N-(3-chloro-4-methylphenyl)-2-(dimethylamino)-1H-benzimidazole-4-carboxamide hydrochloride

Step 1

6-Amino-N-(3-chloro-4-methylphenyl)-2-(dimethylamino)-1H-benzimidazole-4-carboxamide N-(3-Chloro-4-methylphenyl)-2-(dimethylamino)-6-nitro-1H-benzimidazole-4-carboxamide (520 mg) was obtained as yellow powder according to the procedure as described in Step 4 of Example 182, using 3-chloro-4-methylaniline instead of 3-chloro-2-methylaniline. This was then reacted according to the procedure as described in Step 5 of Example 182, to obtain the titled compound (358 mg) as yellow powder.

Step 2

6-{[(2-Chloro-6-fluorophenyl)carbonyl]amino}-N-(3-chloro-4-methylphenyl)-2-(dimethylamino)-1H-benzimidazole-4-carboxamide hydrochloride To a solution of 6-amino-N-(3-chloro-4-methylphenyl)-2-(dimethylamino)-1H-benzimidazole-4-carboxamide (50 mg) in THF (1.5 mL), was added N,N-diisopropylethylamine (37 μL) and the mixture was stirred under ice-cooling. To the mixture was added slowly 2-chloro-6-fluorobenzoyl chloride (24 μL), and it was stirred for 2 hours. The reaction mixture was diluted with ethyl acetate, washed sequentially with saturated aqueous sodium bicarbonate and brine, dried over anhydrous magnesium sulfate, and concentrated under reduced pressure. The residue was purified on column chromatography to obtain 6-{[(2-chloro-6-fluorophenyl)carbonyl]amino}-N-(3-chloro-4-methylphenyl)-2-(dimethylamino)-1H-benzimidazole-4-carboxamide (30 mg) as pale yellow powder. This was then suspended in MeOH (1 mL), 2N hydrogen chloride/MeOH (1 Eq) was added to obtain a homogeneous solution, and MeOH was removed under reduced pressure. The residue was triturated in n-hexane/ethyl acetate (1:1), and the precipitate was collected by filtration and dried to obtain the titled compound (24 mg) as pale purple powder.

MS (ESI+) m/z 500 (M+H)$^+$, Rt=2.20 minutes (method A)

Example 206

N-(3-Chloro-4-methylphenyl)-6-{[(2,6-dichlorophenyl)carbonyl]amino}-2-(dimethylamino)-1H-benzimidazole-4-carboxamide hydrochloride The titled compound was obtained as pale purple powder according to the procedure as described in Step 2 of Example 205, using 2,6-dichlorobenzoyl chloride instead of 2-chloro-6-fluorobenzoyl chloride.

MS (ESI+) m/z 516 (M+H)$^+$, Rt=2.26 minutes (method A)

Example 207

N-(3-Chloro-4-methylphenyl)-6-{[(2,5-dichlorophenyl)carbonyl]amino}-2-(dimethylamino)-1H-benzimidazole-4-carboxamide hydrochloride The titled compound was obtained as white powder according to the procedure as described in Step 2 of Example 205, using 2,5-dichlorobenzoyl chloride instead of 2-chloro-6-fluorobenzoyl chloride.

MS (ESI+) m/z 516 (M+H)$^+$, Rt=2.39 minutes (method A)

Elemental Analysis for $C_{24}H_{20}Cl_3N_5O_2 \cdot HCl$

Calcd. (%) C, 52.10; H, 3.83; N, 12.66.

Found. (%) C, 51.96; H, 3.61; N, 12.76.

Example 208

N-(3-Chloro-2-methylphenyl)-2-cyclopropyl-6-{[(2,5-dichloro phenyl)carbonyl]amino}-1H-benzimidazole-4-carboxamide hydrochloride

Step 1

Methyl 6-amino-2-cyclopropyl-1H-benzimidazole-4-carboxylate

The title compound was obtained as white powder according to the procedures as described in Step 1 to Step 4 of Example 11, using cyclopropanecarbonyl chloride instead of methoxyacetyl chloride in Step 1.

Step 2

2-Cyclopropyl-6-{[(2,5-dichlorophenyl)carbonyl]amino}-1H-benzimidazole-4-carboxylic acid The title compound was obtained according to the procedures as described in Step 4 and Step 5 of Example 1, using methyl 6-amino-2-cyclopropyl-1H-benzimidazole-4-carboxylate instead of methyl 6-amino-1H-benzimidazole-4-carboxylate, and 2,5-dichlorobenzoyl chloride instead of 2-(trifluoromethyl)benzoyl chloride.

Step 3

N-(3-Chloro-2-methylphenyl)-2-cyclopropyl-6-{[(2,5-dichloro phenyl)carbonyl]amino}-1H-benzimidazole-4-carboxamide hydrochloride The title compound was obtained according to the procedures as described in Step 7 and Step 8 of Example 11, using 2-cyclopropyl-6-{[(2,5-dichlorophenyl)carbonyl]amino}-1H-benzimidazole-4-carboxylic acid instead of 2-(methoxymethyl)-6-({[2-(trifluoromethyl)phenyl]carbonyl}amino)-1H-benzimidazole-4-carboxylic acid.

MS (ESI+) m/z 513 (M+H)$^+$, Rt=1.88 minutes (method A)

Example 209

N-(3-Chloro-4-methylphenyl)-2-cyclopropyl-6-{[(2,5-dichloro phenyl)carbonyl]amino}-1H-benzimidazole-4-carboxamide hydrochloride The titled compound was obtained as white powder according to the procedures as described in Step 7 and Step 8 of Example 11, using 2-cyclopropyl-6-{[(2,5-dichlorophenyl)carbonyl]amino}-1H-benzimidazole-4-carboxylic acid instead of 2-(methoxymethyl)-6-({[2-(trifluoromethyl)phenyl]carbonyl}amino)-1H-benzimidazole-4-carboxylic acid, and 3-chloro-4-methylaniline instead of 3-chloro-2-methylaniline.

MS (ESI+) m/z 513 (M+H)$^+$, Rt=1.85 minutes (method A)

Example 210

N-(3-Chloro-2-methylphenyl)-6-{[(2,5-dichlorophenyl)carbonyl]amino}-2-(1-methylcyclopropyl)-1H-benzimidazole-4-carboxamide hydrochloride

Step 1

Methyl 6-amino-2-(1-methylcyclopropyl)-1H-benzimidazole-4-carboxylate

The title compound was obtained as white powder according to the procedures as described in Step 1 to Step 4 of Example 11, using 1-methyl-cyclopropanecarbonyl chloride (prepared as described in WO2009/68512) instead of methoxyacetyl chloride in Step 1.

Step 2

2-(1-Methylcyclopropyl)-6-{[(2,5-dichlorophenyl)carbonyl]amino}-1H-benzimidazole-4-carboxylic acid The title compound was obtained according to the procedures as described in Step 4 and Step 5 of Example 1, using methyl 6-amino-2-(1-methylcyclopropyl)-1H-benzimidazole-4-carboxylate instead of methyl 6-amino-1H-benzimidazole-4-carboxylate, and 2,5-dichlorobenzoyl chloride instead of 2-(trifluoromethyl)benzoyl chloride.

Step 3

N-(3-Chloro-2-methylphenyl)-6-{[(2,5-dichlorophenyl)carbonyl]amino}-2-(1-methylcyclopropyl)-1H-benzimidazole-4-carboxamide hydrochloride The title compound was obtained according to the procedures as described in Step 7 and Step 8 of Example 11, using 2-(1-methylcyclopropyl)-6-{[(2,5-dichlorophenyl)carbonyl]amino}-1H-benzimidazole-4-carboxylic acid instead of 2-(methoxymethyl)-6-({[2-(trifluoromethyl)phenyl]carbonyl}amino)-1H-benzimidazole-4-carboxylic acid.
MS (ESI+) m/z 527 (M+H)$^+$, Rt=2.12 minutes (method A)

Example 211

N-(3-Chloro-4-methylphenyl)-6-{[(2,5-dichlorophenyl)carbonyl]amino}-2-(1-methylcyclopropyl)-1H-benzimidazole-4-carboxamide hydrochloride The titled compound was obtained as white powder according to the procedures as described in Step 7 and Step 8 of Example 11, using 2-(1-methylcyclopropyl)-6-{[(2,5-dichlorophenyl)carbonyl]amino}-1H-benzimidazole-4-carboxylic acid instead of 2-(methoxymethyl)-6-({[2-(trifluoromethyl)phenyl]carbonyl}amino)-1H-benzimidazole-4-carboxylic acid, and 3-chloro-4-methylaniline instead of 3-chloro-2-methylaniline.
MS (ESI+) m/z 527 (M+H)$^+$, Rt=2.18 minutes (method A)

Example 212

N-(3-Chloro-2-methylphenyl)-2-(methoxymethyl)-6-({[2-(methylsulfonyl)phenyl]carbonyl}amino)-1H-benzimidazole-4-carboxamide The titled compound was obtained as pale yellow powder according to the procedure as described in Example 103, using 2-(methylsulfonyl)benzoic acid instead of 2-bromo-6-fluorobenzoic acid.
MS (ESI+) m/z 527 (M+H)$^+$, Rt=2.08 minutes (method A)

Example 213

N-(3-Chloro-4-methylphenyl)-6-{[(2,5-dichlorophenyl)carbonyl]amino}-2-(2-methoxyethyl)-1H-benzimidazole-4-carboxamide hydrochloride

Step 1

Methyl 6-amino-2-(2-methoxyethyl)-1H-benzimidazole-4-carboxylate

The title compound was obtained as white powder according to the procedures as described in Step 1 to Step 4 of Example 11, using methoxypropionyl chloride instead of methoxyacetyl chloride in Step 1.

Step 2

2-(2-Methoxyethyl)-6-{[(2,5-dichlorophenyl)carbonyl]amino}-1H-benzimidazole-4-carboxylic acid The title compound was obtained according to the procedures as described in Step 4 and Step 5 of Example 1, using methyl 6-amino-2-(2-methoxyethyl)-1H-benzimidazole-4-carboxylate instead of methyl 6-amino-1H-benzimidazole-4-carboxylate, and 2,5-dichlorobenzoyl chloride instead of 2-(trifluoromethyl)benzoyl chloride.

Step 3

N-(3-Chloro-4-methylphenyl)-6-{[(2,5-dichlorophenyl)carbonyl]amino}-2-(2-methoxyethyl)-1H-benzimidazole-4-carboxamide hydrochloride The title compound was obtained according to the procedures as described in Step 7 and Step 8 of Example 11, using 2-(2-methoxyethyl)-6-{[(2,5-dichlorophenyl)carbonyl]amino}-1H-benzimidazole-4-carboxylic acid instead of 2-(methoxymethyl)-6-({[2-(trifluoromethyl)phenyl]carbonyl}amino)-1H-benzimidazole-4-carboxylic acid.
MS (ESI+) m/z 531 (M+H)$^+$, Rt=2.43 minutes (method A)

Example 214

2-(Methoxymethyl)-N-phenyl-6-({[2-(trifluoromethyl)phenyl]carbonyl}amino)-1H-benzimidazole-4-carboxamide hydrochloride The titled compound was obtained as colorless powder according to the procedure as described in Example 11, using aniline instead of 3-chloro-2-methylaniline.
MS (ESI+) m/z 469 (M+H)$^+$, Rt=2.01 minutes (method A)

Example 215

2-(Methoxymethyl)-N-propyl-6-({[2-(trifluoromethyl)phenyl]carbonyl}amino)-1H-benzimidazole-4-carboxamide hydrochloride The titled compound was obtained as colorless powder according to the procedure as described in Example 11, using n-propylamine instead of 3-chloro-2-methylaniline.
MS (ESI+) m/z 435 (M+H)$^+$, Rt=1.61 minutes (method A)

Example 216

2-(Methoxymethyl)-N-(pyridin-3-yl)-6-({[2-(trifluoromethyl)phenyl]carbonyl}amino)-1H-benzimidazole-4-carboxamide hydrochloride The titled compound was obtained as colorless powder according to the procedure as described in Example 11, using 3-aminopyridine instead of 3-chloro-2-methylaniline.
MS (ESI+) m/z 470 (M+H)$^+$, Rt=1.25 minutes (method A)

Example 217

N-Benzyl-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using benzylamine instead of 3-chloro-2-methylaniline.
MS (ESI+) m/z 483 (M+H)$^+$, Rt=1.83 minutes (method A)

Example 218

N-(Cyclohexylmethyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using cyclohexanemethylamine instead of 3-chloro-2-methylaniline.
MS (ESI+) m/z 489 (M+H)$^+$, Rt=2.11 minutes (method A)

Example 219

2-(Methoxymethyl)-N-(naphthalen-1-yl)-6-({[2-(trifluoromethyl)phenyl]carbonyl}amino)-1H-benzimidazole-4-carboxamide hydrochloride The titled compound was obtained as colorless powder according to the procedure as described in Example 11, using 1-naphthylamine instead of 3-chloro-2-methylaniline.
MS (ESI+) m/z 519 (M+H)$^+$, Rt=2.29 minutes (method A)

Example 220

2-(Methoxymethyl)-N-(thiophen-3-yl)-6-({[2-(trifluoromethyl)phenyl]carbonyl}amino)-1H-benzimidazole-4-carboxamide hydrochloride The titled compound was obtained as colorless powder according to the procedure as described in Example 11, using 3-aminothiophene instead of 3-chloro-2-methylaniline.
MS (ESI+) m/z 475 (M+H)$^+$, Rt=1.92 minutes (method A)

Example 221

N-(2,1,3-Benzothiadiazol-4-yl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 4-amino-2,1,3-benzothiadiazole instead of 3-chloro-2-methylaniline.
MS (ESI+) m/z 527 (M+H)$^+$, Rt=2.16 minutes (method A)

Example 222

N-(1,1-Dioxide-1-benzothiophen-6-yl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 6-aminobenzo[b]thiophene 1,1-dioxide instead of 3-chloro-2-methylaniline.
MS (ESI+) m/z 557 (M+H)$^+$, Rt=1.82 minutes (method A)

Example 223

2-(Methoxymethyl)-N-(thiophen-2-ylmethyl)-6-({[2-(trifluoro methyl)phenyl]carbonyl}amino)-1H-benzimidazole-4-carboxamide hydrochloride The titled compound was obtained as colorless powder according to the procedure as described in Example 11, using 2-thiophene methylamine instead of 3-chloro-2-methylaniline.
MS (ESI+) m/z 489 (M+H)$^+$, Rt=1.77 minutes (method A)

Example 224

N-(1H-Indol-5-yl)-2-(methoxymethyl)-6-({[2-(trifluoromethyl)phenyl]carbonyl}amino)-1H-benzimidazole-4-carboxamide The titled compound was obtained as colorless powder according to the procedure as described in Example 11, using 5-aminoindole instead of 3-chloro-2-methylaniline.
MS (ESI+) m/z 508 (M+H)$^+$, Rt=1.75 minutes (method A)

Example 225

N-(1,3-Benzothiazol-2-yl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 2-aminobenzothiazole instead of 3-chloro-2-methylaniline.
MS (ESI+) m/z 526 (M+H)$^+$, Rt=2.20 minutes (method A)

Example 226

N-(2,2-Dimethylpropyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using neopentyl amine instead of 3-chloro-2-methylaniline.
MS (ESI+) m/z 463 (M+H)$^+$, Rt=1.95 minutes (method A)

Example 227

2-(Methoxymethyl)-N-(thiophen-2-yl)-6-({[2-(trifluoromethyl)phenyl]carbonyl}amino)-1H-benzimidazole-4-carboxamide hydrochloride The titled compound was obtained as colorless powder according to the procedure as described in Example 11, using 2-aminothiophene instead of 3-chloro-2-methylaniline.
MS (ESI+) m/z 475 (M+H)$^+$, Rt=1.94 minutes (method A)

Example 228

N-(5-Chloro-1,3-benzoxazol-2-yl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 2-amino-5-chlorobenzoxazole instead of 3-chloro-2-methylaniline.
MS (ESI+) m/z 544 (M+H)$^+$, Rt=2.09 minutes (method A)

Example 229

N-(2-Benzylphenyl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 2-benzylaniline instead of 3-chloro-2-methylaniline.
MS (ESI+) m/z 559 (M+H)$^+$, Rt=2.34 minutes (method A)

Example 230

2-(Methoxymethyl)-N-(quinolin-8-yl)-6-({[2-(trifluoromethyl)phenyl]carbonyl}amino)-1H-benzimidazole-4-carboxamide hydrochloride The titled compound was obtained as pale yellow powder according to the procedure as described in Example 11, using 8-aminoquinoline instead of 3-chloro-2-methylaniline.
MS (ESI+) m/z 520 (M+H)$^+$, Rt=2.03 minutes (method A)

Example 231

N-(Cycloheptylmethyl)-2-(methoxymethyl)-6-({[2-(trifluoromethyl)phenyl]carbonyl}amino)-1H-benzimidazole-4-carboxamide hydrochloride The titled compound was obtained as pale yellow powder according to the procedure as described in Example 11, using cycloheptanemethyleneamine instead of 3-chloro-2-methylaniline.
MS (ESI+) m/z 503 (M+H)$^+$, Rt=2.23 minutes (method A)

Example 232

N-(1,3-Benzoxazol-2-yl)-2-(methoxymethyl)-6-({[2-(trifluoro methyl)phenyl]carbonyl}amino)-1H-benzimidazole-4-carboxamide hydrochloride The titled compound was obtained as colorless powder according to the procedure as described in Example 11, using 2-aminobenzoxazole instead of 3-chloro-2-methylaniline.
MS (ESI+) m/z 510 (M+H)$^+$, Rt=1.80 minutes (method A)

Example 233

N-(6-Chloro-1,3-benzoxazol-2-yl)-2-(methoxymethyl)-6-({[2-(trifluoromethyl)phenyl]carbonyl}amino)-1H-benzimidazole-4-carboxamide hydrochloride The titled compound was obtained as colorless powder according to the procedure as described in Example 11, using 2-amino-6-chlorobenzoxazole instead of 3-chloro-2-methylaniline.
MS (ESI+) m/z 544 (M+H)$^+$, Rt=2.09 minutes (method A)

Example 234

N-[3-Chloro-2-(hydroxymethyl)phenyl]-2-(methoxymethyl)-6-({[2-(trifluoromethyl)phenyl]carbonyl}amino)-1H-benzimidazole-4-carboxamide The titled compound was obtained as colorless powder according to the procedure as described in Example 11, using (2-amino-6-chlorophenyl)methanol (prepared as described in J. Med. Chem., 2005, 48, 2080) instead of 3-chloro-2-methylaniline.
MS (ESI+) m/z 533 (M+H)$^+$, Rt=2.08 minutes (method A)

Example 235

N-(3-Chloro-4-methylphenyl)-6-{[(2,5-dichlorophenyl)carbonyl]amino}-2-(dimethylamino)-1H-benzimidazole-4-carboxamide methanesulfonate To a suspension of N-(3-chloro-4-methylphenyl)-6-{[(2,5-dichlorophenyl)carbonyl]amino}-2-(dimethylamino)-1H-benzimidazole-4-carboxamide (200 mg) (obtained in Example 207) in MeOH (2 ml), was added methanesulfonic acid (1 Eq). The mixture was stirred at room temperature for 30 minutes, and filtered off through glass filter to collect crystals, which were dried under reduced pressure to obtain the titled compound (180 mg) as white powder.
Elemental Analysis for $C_{24}H_{20}Cl_3N_5O_2 \cdot CH_3SO_3H+1.5H_2O$
Calcd. (%) C, 46.92; H, 4.25; N, 10.94.
Found. (%) C, 46.85; H, 4.04; N, 10.89.

Example 236

N-(3-Chloro-4-methylphenyl)-6-{[(2,5-dichlorophenyl)carbonyl]amino}-2-(dimethylamino)-1H-benzimidazole-4-carboxamide 4-methylbenzenesulfonate The titled compound was obtained as white powder according to the procedure as described in Example 235, using p-toluenesulfonic acid monohydrate (1 Eq) instead of methanesulfonic acid.
Elemental Analysis for $C_{24}H_{20}Cl_3N_5O_2 \cdot C_7H_8O_3S+1.2H_2O$
Calcd. (%) C, 52.40; H, 4.31; N, 9.86.
Found. (%) C, 52.24; H, 4.28; N, 9.95.

Example 237

N-(3-Chloro-4-methylphenyl)-6-{[(2,5-dichlorophenyl)carbonyl]amino}-2-(dimethylamino)-1H-benzimidazole-4-carboxamide sulfate The titled compound was obtained as white powder according to the procedure as described in Example 235, using sulfuric acid (1 Eq) instead of methanesulfonic acid.
Elemental Analysis for $C_{24}H_{20}Cl_3N_5O_2—H_2SO_4+1.5H_2O$
Calcd. (%) C, 44.91; H, 3.93; N, 10.91.
Found. (%) C, 44.71; H, 3.81; N, 10.85.

Example 238

N-(3-Chloro-2-methylphenyl)-2-(methoxymethyl)-6-({[2-(trifluoromethyl)phenyl]carbonyl}amino)-1H-benzimidazole-4-carboxamide methanesulfonate Methanesulfonic acid (1 Eq) was added to a suspension of N-(3-chloro-2-methylphenyl)-2-(methoxymethyl)-6-({[2-(trifluoromethyl)phenyl]carbonyl}amino)-1H-benzimidazole-4-carboxamide (250 mg) (obtained in Example 11) in MeOH (2 ml). After stirring for 30 minutes at room temperature, MeOH was removed under reduced pressure to obtain the titled compound as white powder.
Elemental Analysis for $C_{25}H_{20}ClF_3N_4O_3 \cdot CH_3SO_3H + 1.0H_2O$
Calcd. (%) C, 49.49; H, 4.15; N, 8.88.
Found. (%) C, 49.20; H, 4.14; N, 8.78.

Example 239

N-(3-Chloro-2-methylphenyl)-2-(methoxymethyl)-6-({[2-(trifluoromethyl)phenyl]carbonyl}amino)-1H-benzimidazole-4-carboxamide 4-methylbenzenesulfonate The titled compound was obtained as white powder according to the procedure as described in Example 238, using p-toluenesulfonic acid monohydrate (1 Eq) instead of methanesulfonic acid.
Elemental Analysis for $C_{25}H_{20}ClF_3N_4O_3 \cdot C_7H_8O_3S$
Calcd. (%) C, 55.78; H, 4.10; N, 8.13.
Found. (%) C, 55.62; H, 4.12; N, 8.16.

Example 240

N-(3-Chloro-2-methylphenyl)-2-(methoxymethyl)-6-({[2-(trifluoromethyl)phenyl]carbonyl}amino)-1H-benzimidazole-4-carboxamide sulfate The titled compound was obtained as white powder according to the procedure as described in Example 238, using sulfuric acid (1 Eq) instead of methanesulfonic acid.
Elemental Analysis for $C_{25}H_{20}ClF_3N_4O_3 \cdot H_2SO_4 + 0.5H_2O$
Calcd. (%) C, 48.12; H, 3.72; N, 8.98.
Found. (%) C, 48.34; H, 3.57; N, 8.99.

Example 241

N-(3-Chloro-2-methylphenyl)-2-(1-methylcyclopropyl)-6-({[2-(trifluoromethyl)phenyl]carbonyl}amino)-1H-benzimidazole-4-carboxamide methanesulfonate Methanesulfonic acid (1 Eq) was added to a suspension of N-(3-chloro-2-methylphenyl)-2-(1-methylcyclopropyl)-6-({[2-(trifluoromethyl)phenyl]carbonyl}amino)-1H-benzimidazole-4-carboxamide (250 mg) (obtained in Example 85) in MeOH (2 ml). After stirring at room temperature for 30 minutes, MeOH was removed under reduced pressure to obtain the titled compound as white powder.
Elemental Analysis for $C_{27}H_{22}ClF_3N_4O_2 \cdot CH_3SO_3H + 0.5H_2O$
Calcd. (%) C, 53.21; H, 4.31; N, 8.86.
Found. (%) C, 52.97; H, 4.14; N, 8.90.

Example 242

N-(3-Chloro-2-methylphenyl)-2-(1-methylcyclopropyl)-6-({[2-(trifluoromethyl)phenyl]carbonyl}amino)-1H-benzimidazole-4-carboxamide 4-methylbenzenesulfonate The titled compound was obtained as white powder according to the procedure as described in Example 241, using p-toluenesulfonic acid monohydrate (1 Eq) instead of methanesulfonic acid.
Elemental Analysis for $C_{27}H_{22}ClF_3N_4O_2 \cdot C_7H_8O_3S$
Calcd. (%) C, 58.41; H, 4.32; N, 8.01.
Found. (%) C, 58.13; H, 4.50; N, 8.00.

Example 243

N-(3-Chloro-2-methylphenyl)-2-(1-methylcyclopropyl)-6-({[2-(trifluoromethyl)phenyl]carbonyl}amino)-1H-benzimidazole-4-carboxamide sulfate The titled compound was obtained as white powder according to the procedure as described in Example 241, using sulfuric acid (1 Eq) instead of methanesulfonic acid.
Elemental Analysis for $C_{27}H_{22}ClF_3N_4O_2 \cdot H_2SO_4 + 0.6H_2O$
Calcd. (%) C, 51.00; H, 3.99; N, 8.81.
Found. (%) C, 51.35; H, 4.39; N, 8.85.

Example 244

N-(3-Chloro-2-methylphenyl)-6-{[(3-fluoropyridin-2-yl)carbonyl]amino}-2-(methoxymethyl)-1H-benzimidazole-4-carboxamide hydrochloride The titled compound was obtained as white powder according to the procedure as described in Example 103, using 3-fluoropyridine-2-carboxylic acid instead of 2-bromo-6-fluorobenzoic acid.
MS (ESI+) m/z 468 (M+H)$^+$, Rt=2.17 minutes (method A)

Example 245

N-(3-Chloro-2-methylphenyl)-6-{[(3-chloropyridin-4-yl)carbonyl]amino}-2-(methoxymethyl)-1H-benzimidazole-4-carboxamide hydrochloride The titled compound was obtained as pale yellow powder according to the procedure as described in Example 103, using 3-chloropicolinic acid instead of 2-bromo-6-fluorobenzoic acid.
MS (ESI+) m/z 484 (M+H)$^+$, Rt=2.08 minutes (method A)

Example 246

N-(3-Chloro-2-methylphenyl)-6-{[(3,5-dichloropyridin-4-yl)carbonyl]amino}-2-(methoxymethyl)-1H-benzimidazole-4-carboxamide hydrochloride The titled compound was obtained as white powder according to the procedure as described in Example 103, using 3,5-dichloroisonicotinic acid instead of 2-bromo-6-fluorobenzoic acid.
MS (ESI+) m/z 518 (M+H)$^+$, Rt=2.24 minutes (method A)

Example 247

6-{[(5-Butoxy-2-chlorophenyl)carbonyl]amino}-N-(3-chloro-2-methylphenyl)-2-(methoxymethyl)-1H-benzimidazole-4-carboxamide hydrochloride The titled compound was obtained as white powder according to the procedure as described in Example 103, using 5-butoxy-2-chlorobenzoic acid (prepared in Reference Example 10) instead of 2-bromo-6-fluorobenzoic acid.

MS (ESI+) m/z 555 (M+H)$^+$, Rt=2.67 minutes (method A)

Example 248

6-({[2-Chloro-5-(2,2-difluoroethoxy)phenyl]carbonyl}amino)-N-(3-chloro-2-methylphenyl)-2-(methoxymethyl)-1H-benzimidazole-4-carboxamide hydrochloride The titled compound was obtained as white powder according to the procedure as described in Example 103, using 2-chloro-5-(2,2-difluoroethoxy)benzoic acid (prepared in Reference Example 11) instead of 2-bromo-6-fluorobenzoic acid.

MS (ESI+) m/z 563 (M+H)$^+$, Rt=1.66 minutes (method A)

Example 249

N-(3-Chloro-2-methylphenyl)-6-({[2-chloro-5-(4,4,4-trifluorobutoxy)phenyl]carbonyl}amino)-2-(methoxymethyl)-1H-benzimidazole-4-carboxamide hydrochloride The titled compound was obtained as white powder according to the procedure as described in Example 103, using 2-chloro-5-(4,4,4-trifluorobutoxy)benzoic acid (prepared in Reference Example 12) instead of 2-bromo-6-fluorobenzoic acid.

MS (ESI+) m/z 609 (M+H)$^+$, Rt=1.99 minutes (method A)

The chemical structures of the compounds of Examples 1 to 249 are shown in the following Tables 1 to 14.

TABLE 1

| Example | Structure |
|---|---|
| 1 | 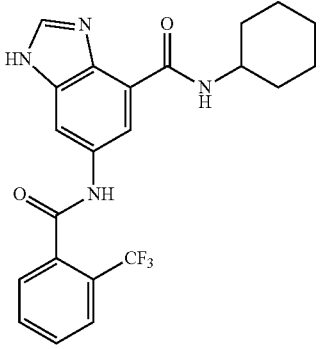 [SMILES: O=C(Nc1cc(C(=O)NC2CCCCC2)c2nc[nH]c2c1)c1ccccc1C(F)(F)F] |
| 2 | 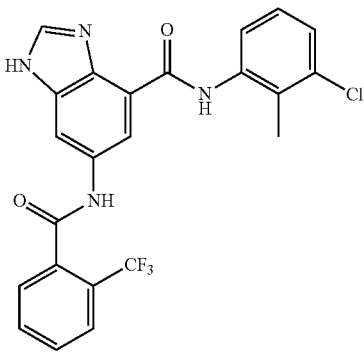 [SMILES: Cc1c(Cl)cccc1NC(=O)c1cc(NC(=O)c2ccccc2C(F)(F)F)cc2[nH]cnc12] |
| 3 | 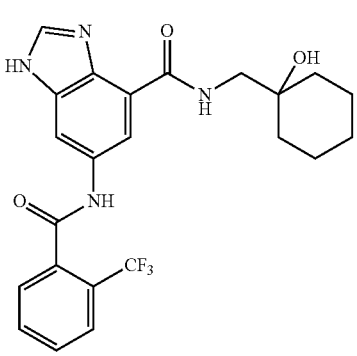 [SMILES: O=C(Nc1cc(C(=O)NCC2(O)CCCCC2)c2nc[nH]c2c1)c1ccccc1C(F)(F)F] |
| 5 | 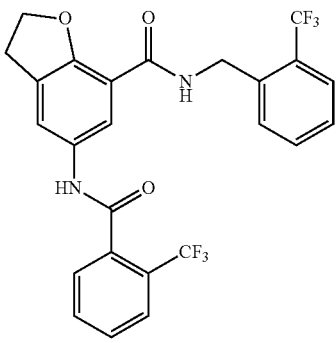 [SMILES: O=C(Nc1cc2c(c(C(=O)NCc3ccccc3C(F)(F)F)c1)OCC2)c1ccccc1C(F)(F)F] |
| 6 | 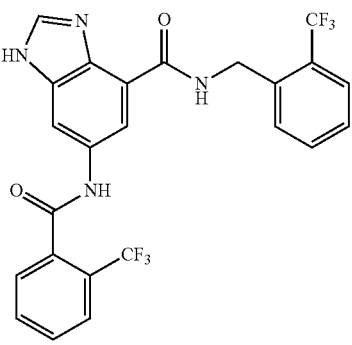 |

TABLE 1-continued

| Example | Structure |
|---|---|
| 7 | (2,3-dihydrobenzofuran-7-yl)-N-cyclohexyl carboxamide with 5-[2-(trifluoromethyl)benzamido] substituent |
| 8 | (2,3-dihydrobenzofuran-7-yl)-N-(3-chloro-2-methylphenyl) carboxamide with 5-[2-(trifluoromethyl)benzamido] substituent |
| 9 | (1H-indazol-7-yl)-N-cyclohexyl carboxamide with 5-[2-(trifluoromethyl)benzamido] substituent |
| 10 | (1H-indazol-7-yl)-N-[2-(trifluoromethyl)benzyl] carboxamide with 5-[2-(trifluoromethyl)benzamido] substituent |
| 11 | 2-(methoxymethyl)-1H-benzimidazol-4-yl)-N-(3-chloro-2-methylphenyl) carboxamide with 6-[2-(trifluoromethyl)benzamido] substituent, HCl |
| 12 | (2-methyl-1H-benzimidazol-4-yl)-N-[2-(trifluoromethyl)benzyl] carboxamide with 6-[2-(trifluoromethyl)benzamido] substituent, HCl |
| 13 | (2-methyl-1H-benzimidazol-4-yl)-N-cyclohexyl carboxamide with 6-[2-(trifluoromethyl)benzamido] substituent, HCl |
| 14 | (2-methyl-1H-benzimidazol-4-yl)-N-(3-chloro-2-methylphenyl) carboxamide with 6-[2-(trifluoromethyl)benzamido] substituent, HCl |

TABLE 1-continued

| Example | Structure |
|---|---|
| 15 | 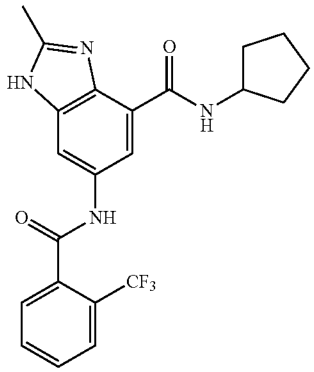 [SMILES: Cc1nc2c(C(=O)NC3CCCC3)cc(NC(=O)c3ccccc3C(F)(F)F)cc2[nH]1] |
| 16 | 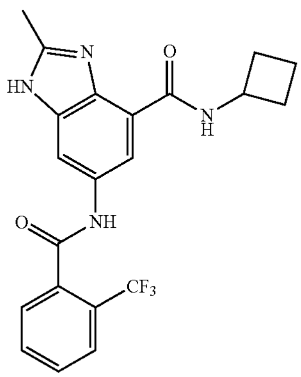 [SMILES: Cc1nc2c(C(=O)NC3CCC3)cc(NC(=O)c3ccccc3C(F)(F)F)cc2[nH]1] |
| 17 | 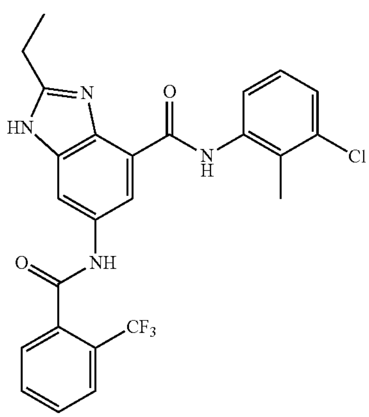 [SMILES: CCc1nc2c(C(=O)Nc3cccc(Cl)c3C)cc(NC(=O)c3ccccc3C(F)(F)F)cc2[nH]1] |
| 18 | 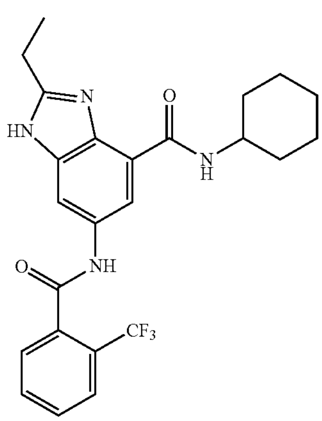 [SMILES: CCc1nc2c(C(=O)NC3CCCCC3)cc(NC(=O)c3ccccc3C(F)(F)F)cc2[nH]1] |

TABLE 2

| Example | Structure |
|---|---|
| 19 | 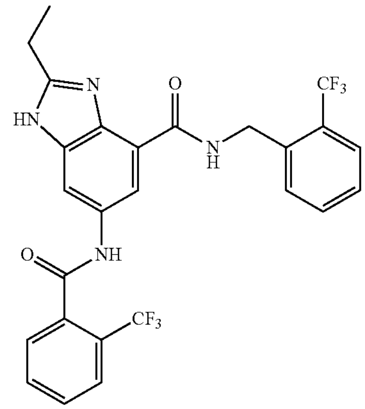 [SMILES: CCc1nc2c(C(=O)NCc3ccccc3C(F)(F)F)cc(NC(=O)c3ccccc3C(F)(F)F)cc2[nH]1] |
| 20 | 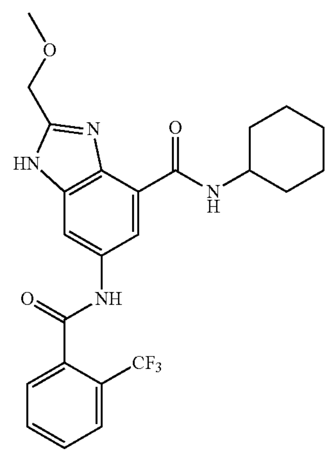 [SMILES: COCc1nc2c(C(=O)NC3CCCCC3)cc(NC(=O)c3ccccc3C(F)(F)F)cc2[nH]1] |
| 21 | 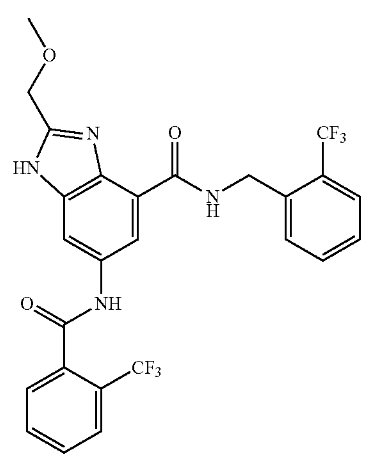 [SMILES: COCc1nc2c(C(=O)NCc3ccccc3C(F)(F)F)cc(NC(=O)c3ccccc3C(F)(F)F)cc2[nH]1] |

TABLE 2-continued
| Example | Structure |
|---|---|
| 22 | 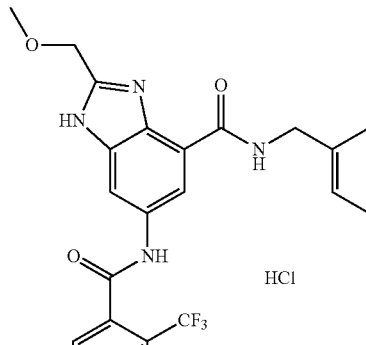 |
| 23 | 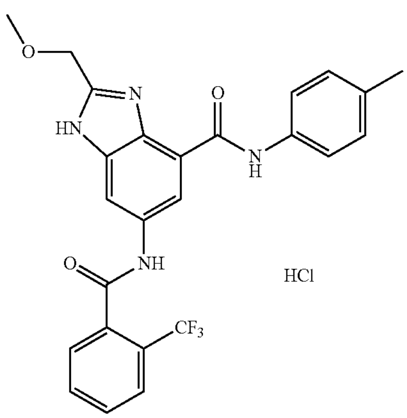 |
| 24 | 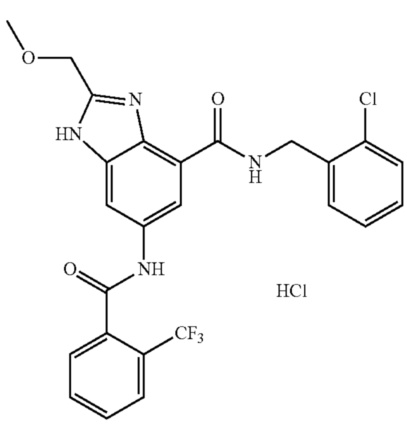 [SMILES: COCc1nc2c(C(=O)NCc3ccccc3Cl)cc(NC(=O)c3ccccc3C(F)(F)F)cc2[nH]1 ; Cl] |
| 25 | 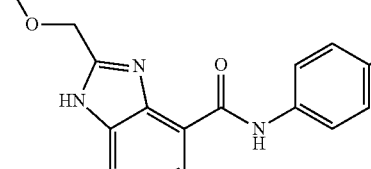 |
| 26 | 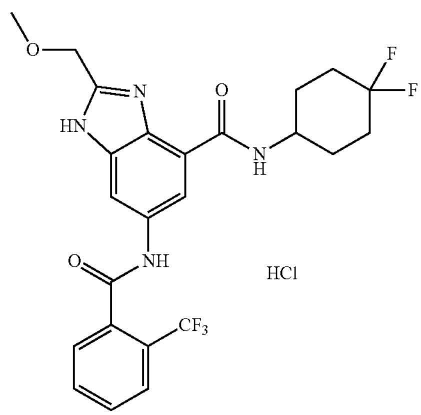 [SMILES: COCc1nc2c(C(=O)NC3CCC(F)(F)CC3)cc(NC(=O)c3ccccc3C(F)(F)F)cc2[nH]1 ; Cl] |
| 27 | 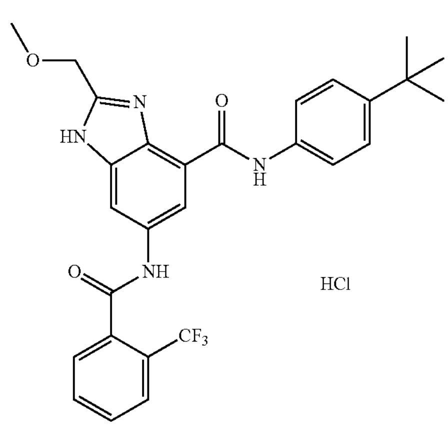 [SMILES: COCc1nc2c(C(=O)Nc3ccc(C(C)(C)C)cc3)cc(NC(=O)c3ccccc3C(F)(F)F)cc2[nH]1 ; Cl] |

TABLE 2-continued
| Example | Structure |
|---|---|
| 28 | 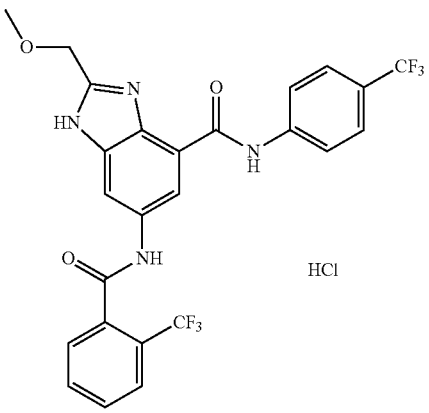 [SMILES: COCc1nc2c(C(=O)Nc3ccc(C(F)(F)F)cc3)cc(NC(=O)c3ccccc3C(F)(F)F)cc2[nH]1 ; Cl] HCl |
| 29 | 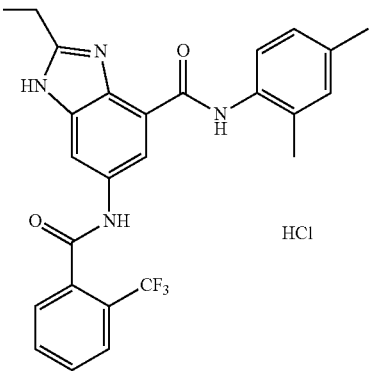 HCl |
| 30 | 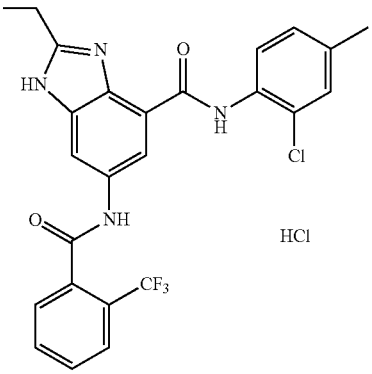 HCl |
| 31 | 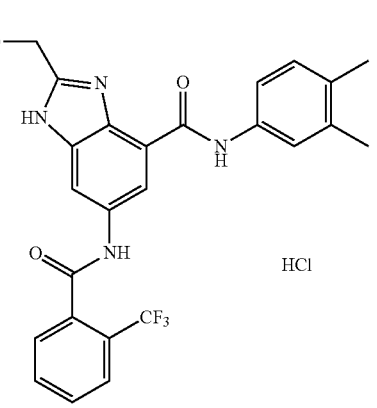 HCl |
| 32 | 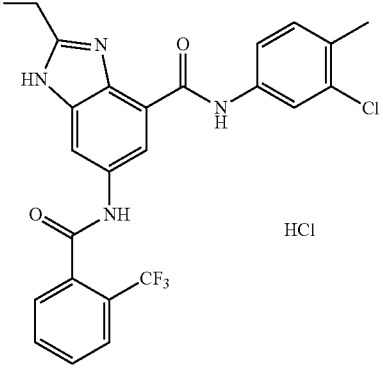 HCl |
| 33 | 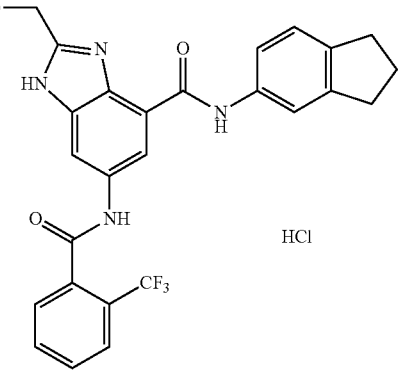 HCl |

TABLE 2-continued
| Example | Structure |
|---|---|
| 34 | 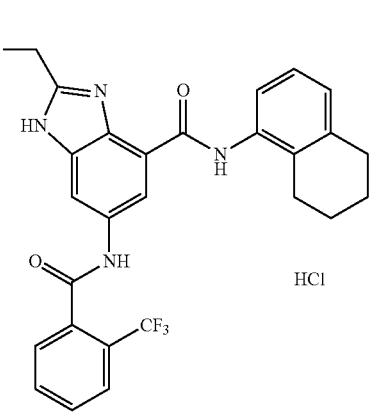 HCl |
| 35 | 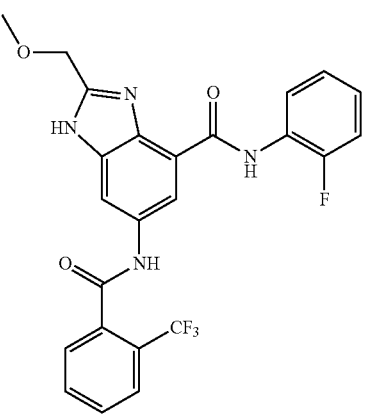 [SMILES: COCc1nc2c(C(=O)Nc3ccccc3F)cc(NC(=O)c3ccccc3C(F)(F)F)cc2[nH]1] |
| 36 | 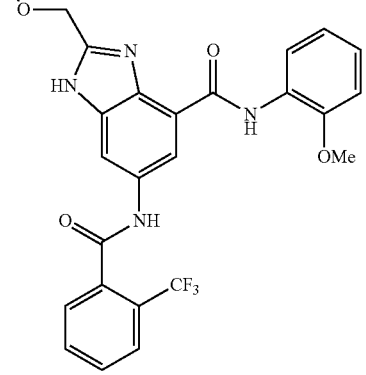 |
TABLE 3
| Example | Structure |
|---|---|
| 37 | 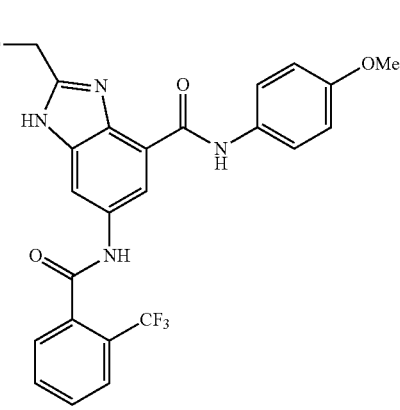 |
| 38 | 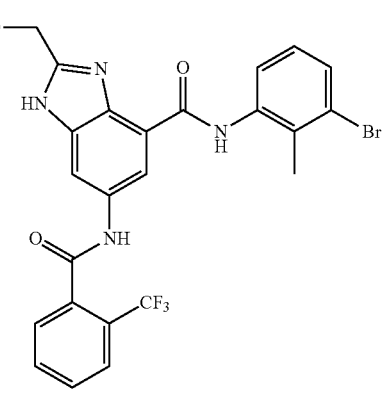 |
| 39 | 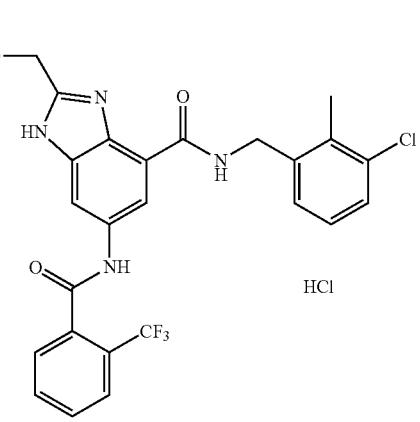 HCl |

TABLE 3-continued
| Example | Structure |
|---|---|
| 40 | 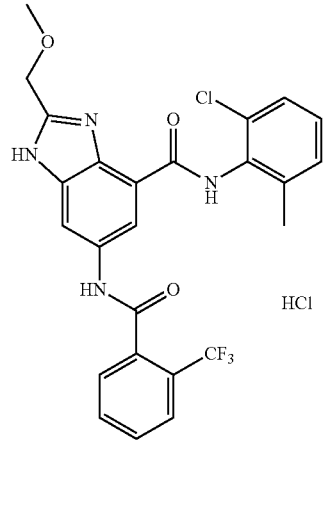 |
| 41 | 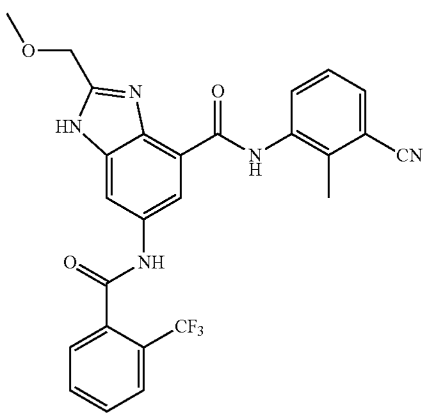 [SMILES: COCc1nc2c(C(=O)Nc3cccc(C#N)c3C)cc(NC(=O)c3ccccc3C(F)(F)F)cc2[nH]1] |
| 42 | 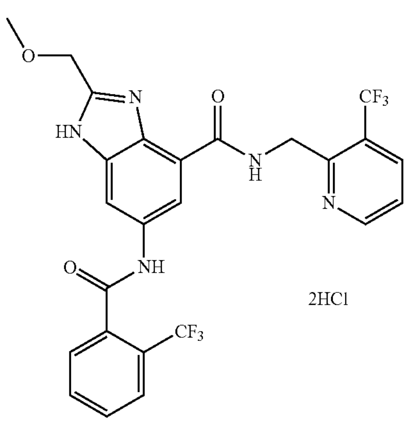 [SMILES: COCc1nc2c(C(=O)NCc3ncccc3C(F)(F)F)cc(NC(=O)c3ccccc3C(F)(F)F)cc2[nH]1] |
| 43 | 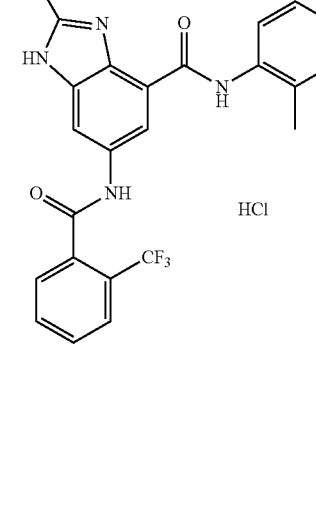 HCl |
| 44 | HCl |
| 45 | HCl |
(Structures for examples 41, 42, 44, 45 continue in the table; example 42 is labeled 2HCl.)

TABLE 3-continued
| Example | Structure |
|---|---|
| 46 | 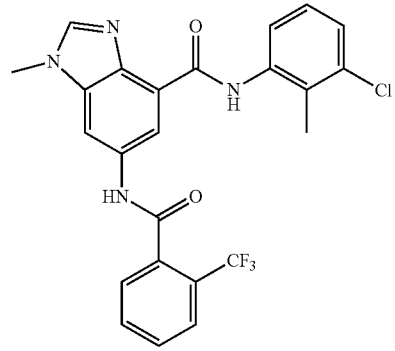 [SMILES: Cc1c(Cl)cccc1NC(=O)c1cc(NC(=O)c2ccccc2C(F)(F)F)cc2c1ncn2C] |
| 47 | 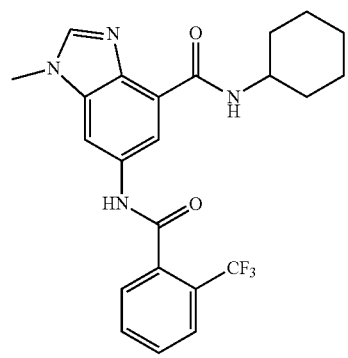 [SMILES: Cn1cnc2c(C(=O)NC3CCCCC3)cc(NC(=O)c3ccccc3C(F)(F)F)cc21] |
| 48 | 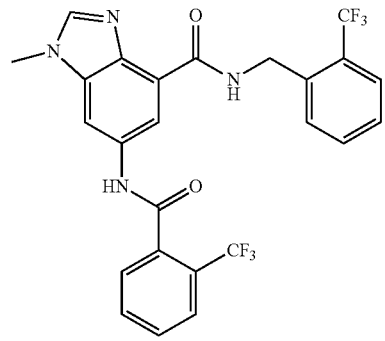 [SMILES: Cn1cnc2c(C(=O)NCc3ccccc3C(F)(F)F)cc(NC(=O)c3ccccc3C(F)(F)F)cc21] |
| 49 | 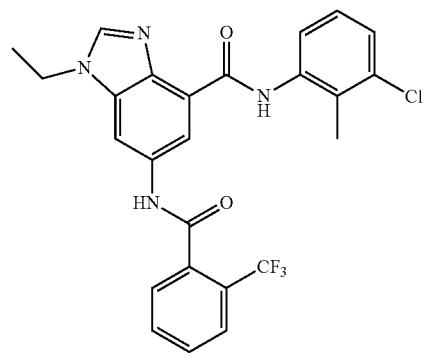 [SMILES: CCn1cnc2c(C(=O)Nc3cccc(Cl)c3C)cc(NC(=O)c3ccccc3C(F)(F)F)cc21] |
| 50 | 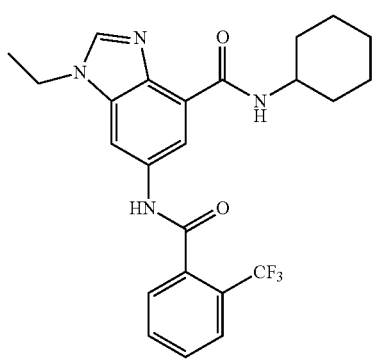 [SMILES: CCn1cnc2c(C(=O)NC3CCCCC3)cc(NC(=O)c3ccccc3C(F)(F)F)cc21] |
| 51 | 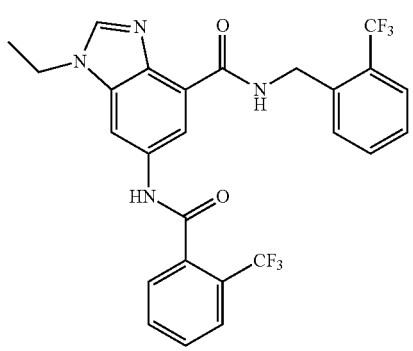 [SMILES: CCn1cnc2c(C(=O)NCc3ccccc3C(F)(F)F)cc(NC(=O)c3ccccc3C(F)(F)F)cc21] |
| 52 | 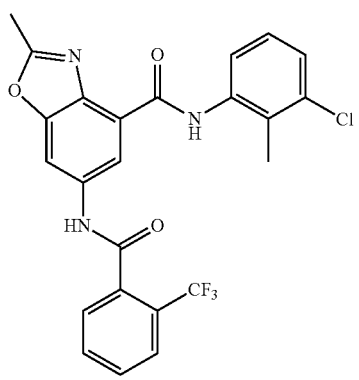 [SMILES: Cc1nc2c(C(=O)Nc3cccc(Cl)c3C)cc(NC(=O)c3ccccc3C(F)(F)F)cc2o1] |
| 53 | 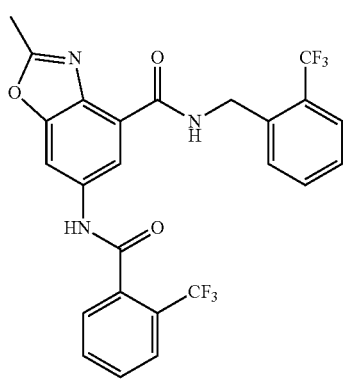 [SMILES: Cc1nc2c(C(=O)NCc3ccccc3C(F)(F)F)cc(NC(=O)c3ccccc3C(F)(F)F)cc2o1] |

TABLE 3-continued
| Example | Structure |
|---------|-----------|
| 54 | 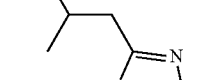 |
TABLE 4
| Example | Structure |
|---------|-----------|
| 55 | |
| 56 | |
| 57 | 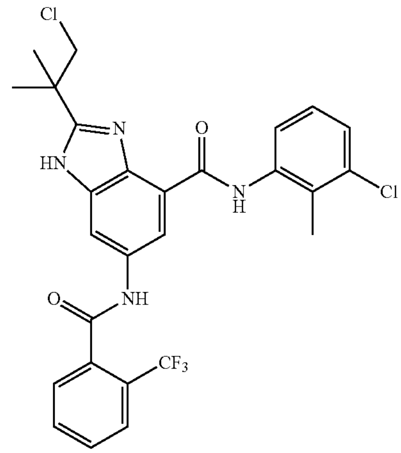 [SMILES: Cc1c(Cl)cccc1NC(=O)c1cc(NC(=O)c2ccccc2C(F)(F)F)cc2[nH]c(C(C)(C)CCl)nc12] |
| 58 | (HCl) |
| 59 | (HCl) |

TABLE 4-continued
| Example | Structure |
|---|---|
| 60 | 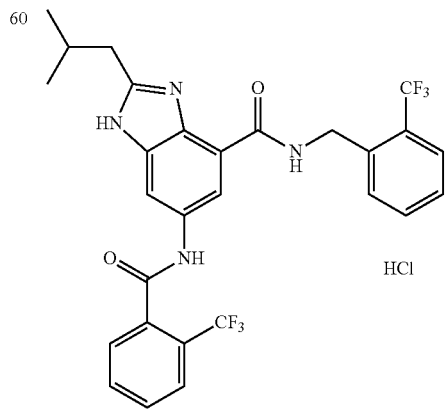 HCl |
| 61 | 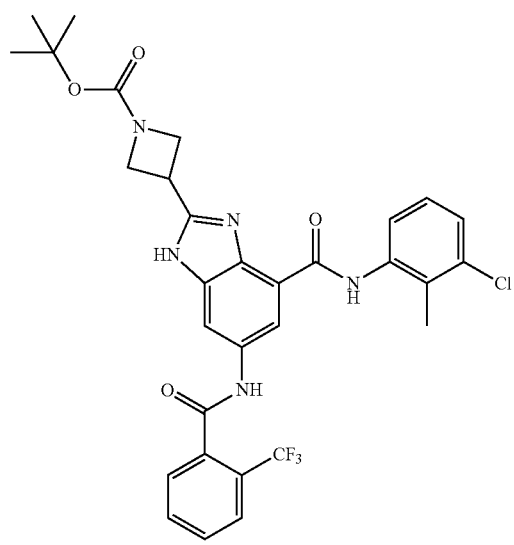 [SMILES: Cc1c(Cl)cccc1NC(=O)c1cc(NC(=O)c2ccccc2C(F)(F)F)cc2[nH]c(C3CN(C(=O)OC(C)(C)C)C3)nc12] |
| 62 | 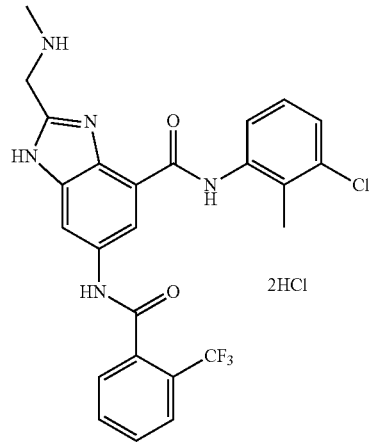 [SMILES: CNCc1nc2c(C(=O)Nc3cccc(Cl)c3C)cc(NC(=O)c3ccccc3C(F)(F)F)cc2[nH]1] 2HCl |
| 63 | 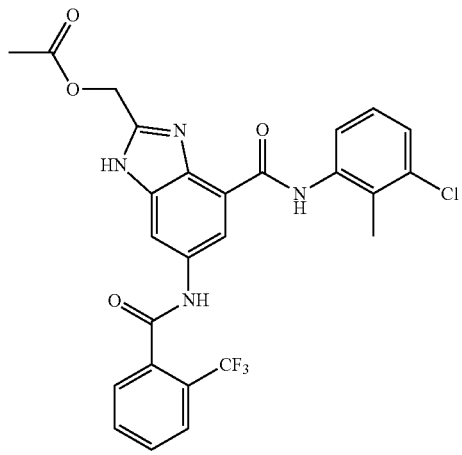 [SMILES: CC(=O)OCc1nc2c(C(=O)Nc3cccc(Cl)c3C)cc(NC(=O)c3ccccc3C(F)(F)F)cc2[nH]1] |
| 64 | 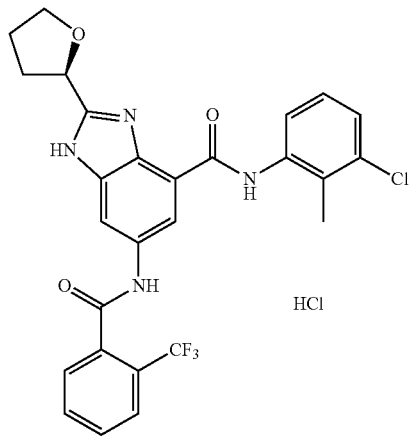 [SMILES: Cc1c(Cl)cccc1NC(=O)c1cc(NC(=O)c2ccccc2C(F)(F)F)cc2[nH]c([C@H]3CCCO3)nc12 ; Cl] HCl |
| 65 | 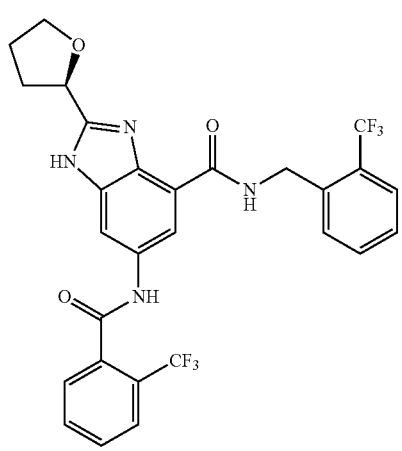 [SMILES: O=C(Nc1cc(C(=O)NCc2ccccc2C(F)(F)F)c2nc([C@H]3CCCO3)[nH]c2c1)c1ccccc1C(F)(F)F] |

TABLE 4-continued
| Example | Structure |
|---|---|
| 66 | 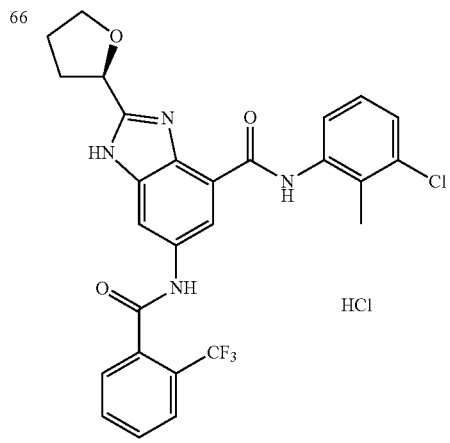 HCl |
| 67 | 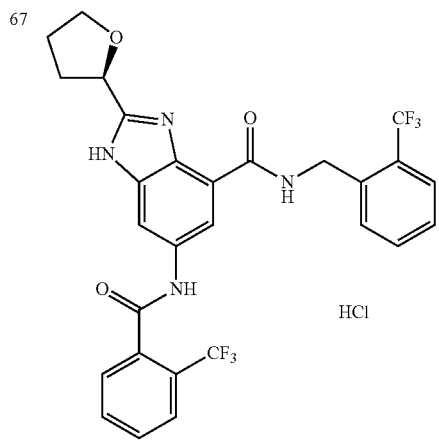 HCl |
| 68 | 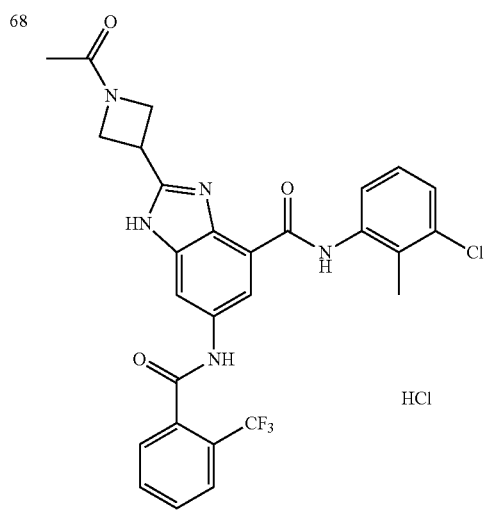 HCl |
| 69 | 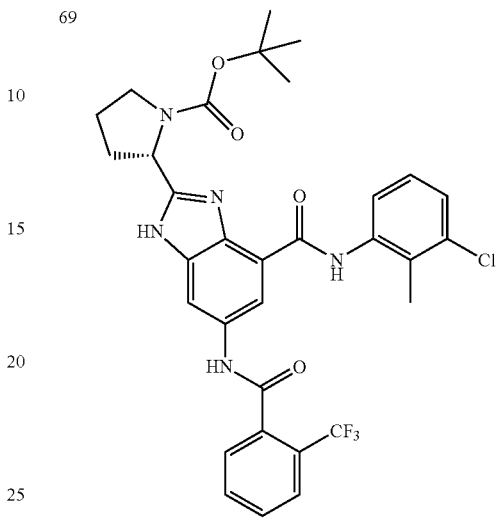 |
| 70 | 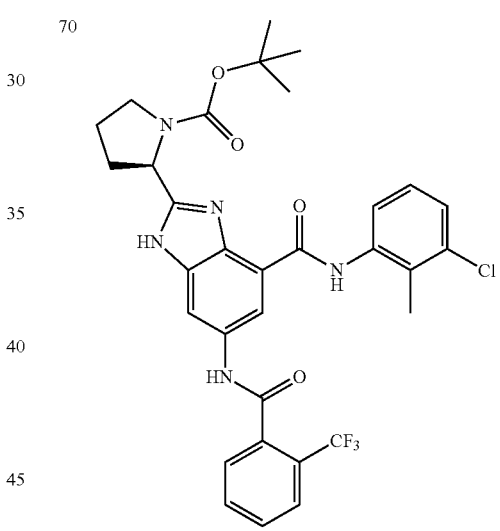 |
| 71 | 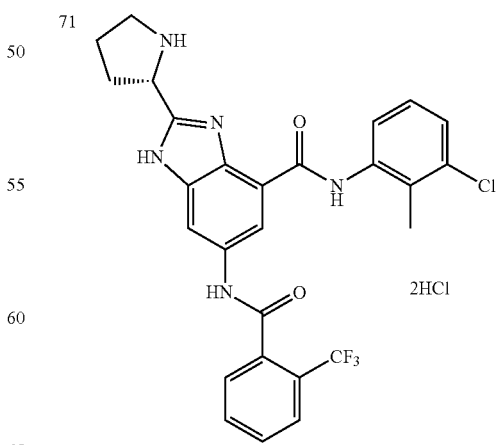 2HCl |

TABLE 4-continued
| Example | Structure |
|---|---|
| 72 | 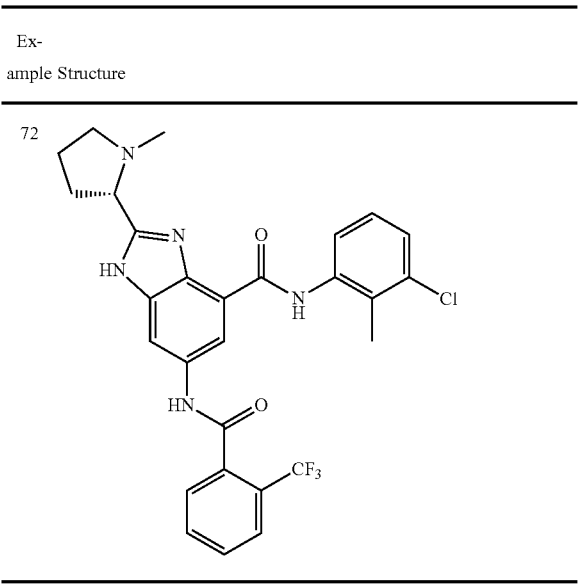 |
TABLE 5
| Example | Structure |
|---|---|
| 73 | 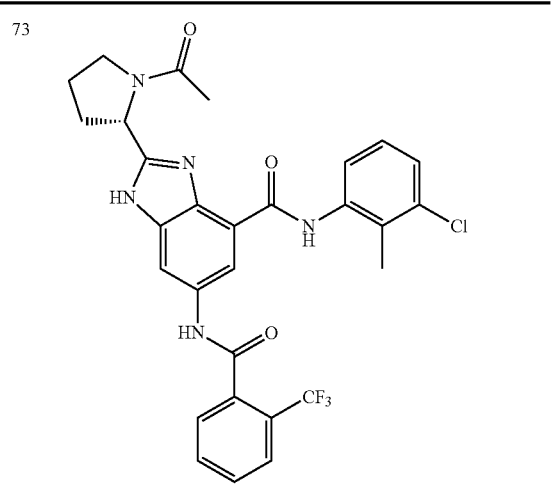 |
| 74 | 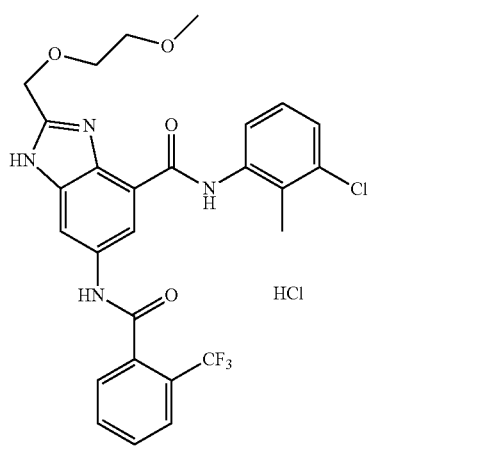 [SMILES: COCCOCc1nc2c(C(=O)Nc3cccc(Cl)c3C)cc(NC(=O)c3ccccc3C(F)(F)F)cc2[nH]1 ; Cl] |
| 75 | 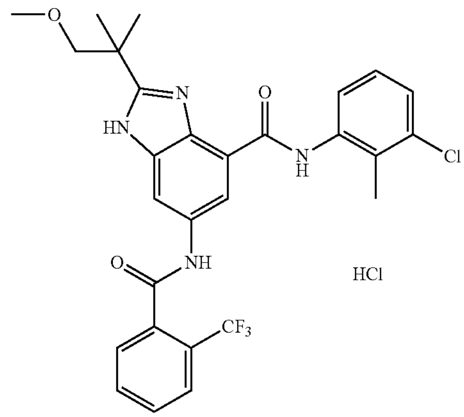 [SMILES: COCC(C)(C)c1nc2c(C(=O)Nc3cccc(Cl)c3C)cc(NC(=O)c3ccccc3C(F)(F)F)cc2[nH]1 ; Cl] |
| 76 | 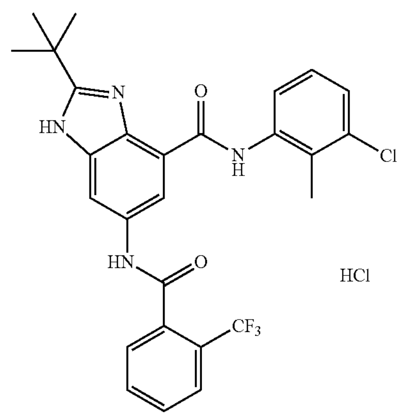 [SMILES: Cc1c(Cl)cccc1NC(=O)c1cc(NC(=O)c2ccccc2C(F)(F)F)cc2[nH]c(C(C)(C)C)nc12 ; Cl] |
| 77 | 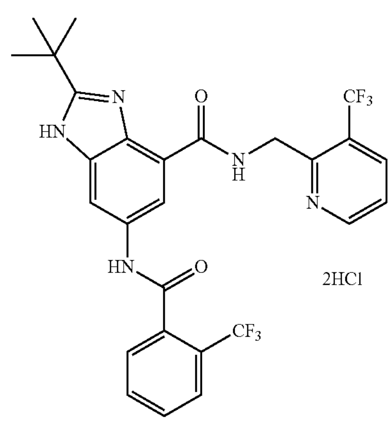 [SMILES: CC(C)(C)c1nc2c(C(=O)NCc3ncccc3C(F)(F)F)cc(NC(=O)c3ccccc3C(F)(F)F)cc2[nH]1 ; "2HCl"] |

TABLE 5-continued
| Example | Structure |
|---|---|
| 78 | 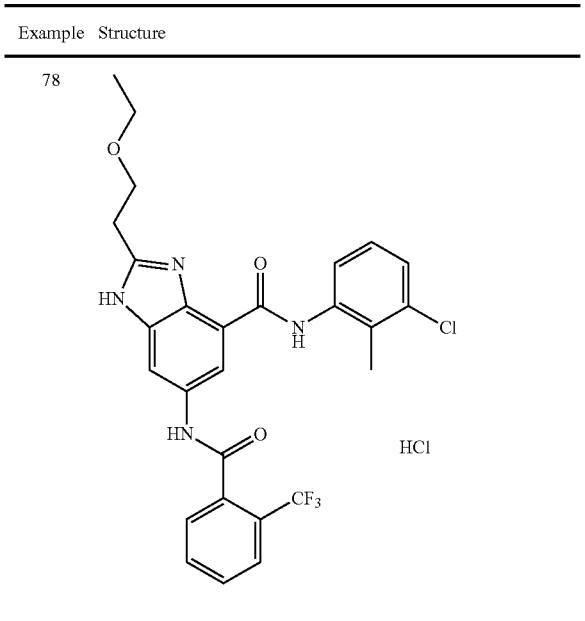 |
| 79 | 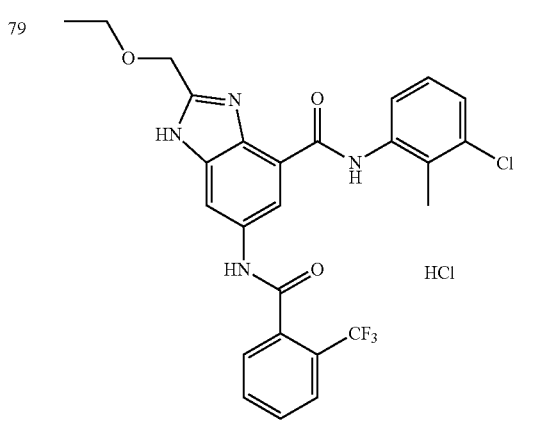 |
| 80 | 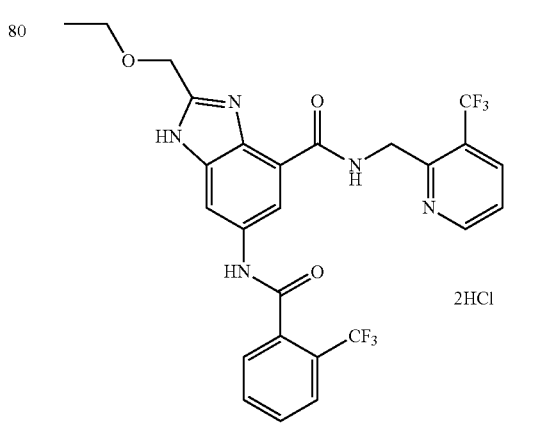 |
| 81 | 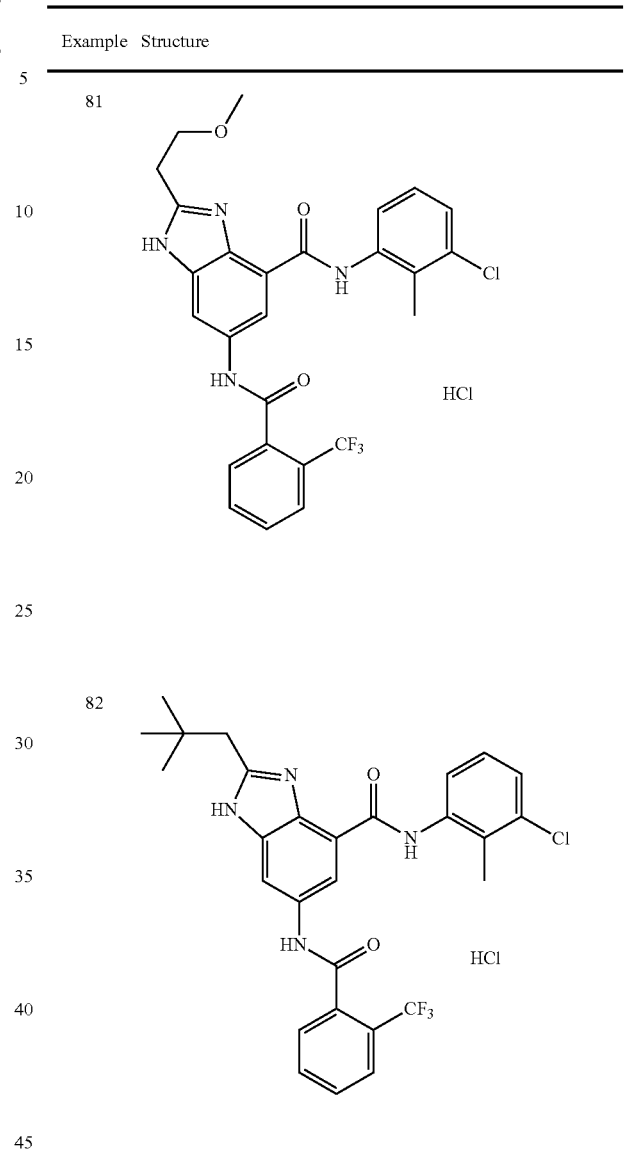 |
| 82 | 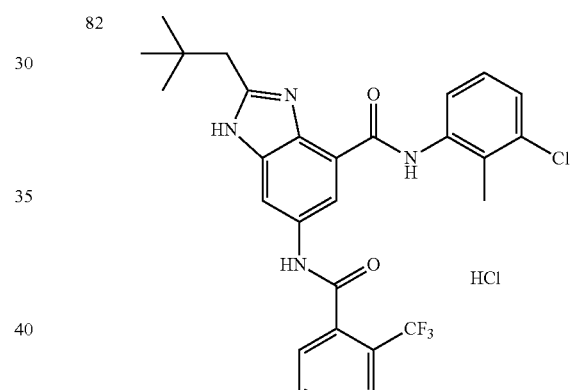 |
| 83 | 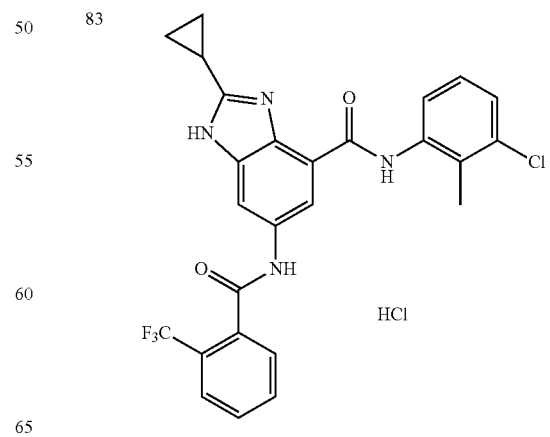 |

TABLE 5-continued
| Example | Structure |
|---|---|
| 84 | 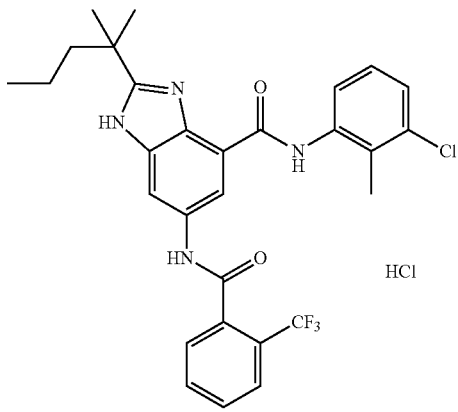 [SMILES: CCCC(C)(C)c1nc2c(C(=O)Nc3cccc(Cl)c3C)cc(NC(=O)c3ccccc3C(F)(F)F)cc2[nH]1 ; Cl] HCl |
| 85 | 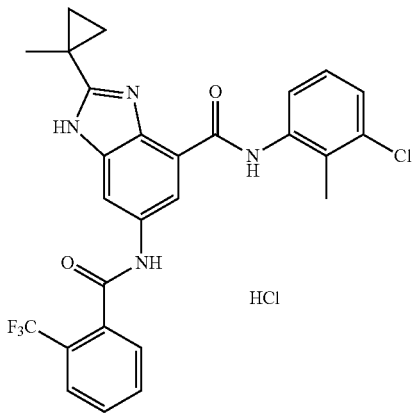 [SMILES: Cc1c(Cl)cccc1NC(=O)c1cc(NC(=O)c2ccccc2C(F)(F)F)cc2[nH]c(C3(C)CC3)nc12 ; Cl] HCl |
| 86 | 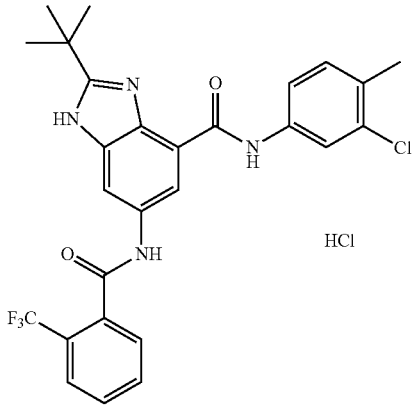 [SMILES: Cc1ccc(NC(=O)c2cc(NC(=O)c3ccccc3C(F)(F)F)cc3[nH]c(C(C)(C)C)nc23)cc1Cl ; Cl] HCl |
| 87 | 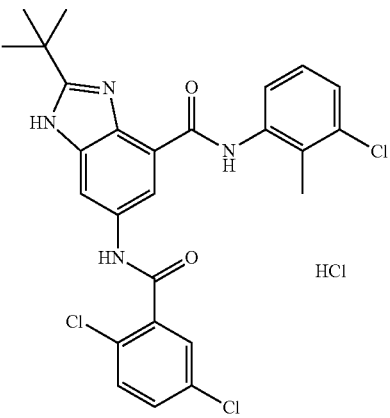 [SMILES: Cc1c(Cl)cccc1NC(=O)c1cc(NC(=O)c2cc(Cl)ccc2Cl)cc2[nH]c(C(C)(C)C)nc12 ; Cl] HCl |
| 88 | HCl |
| 89 | 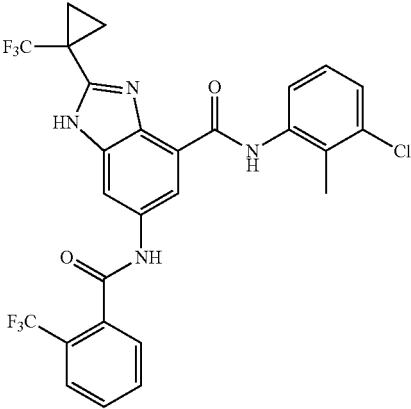 [SMILES: Cc1c(Cl)cccc1NC(=O)c1cc(NC(=O)c2ccccc2C(F)(F)F)cc2[nH]c(C3(C(F)(F)F)CC3)nc12] |

TABLE 5-continued
| Example | Structure |
|---|---|
| 90 | 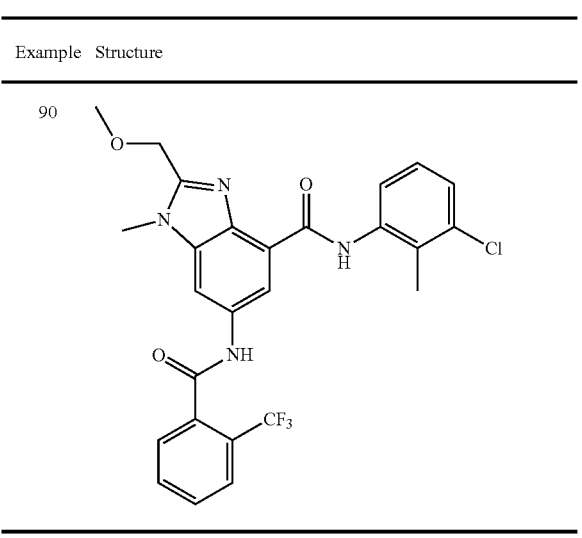 |
TABLE 6
| Example | Structure |
|---|---|
| 91 | 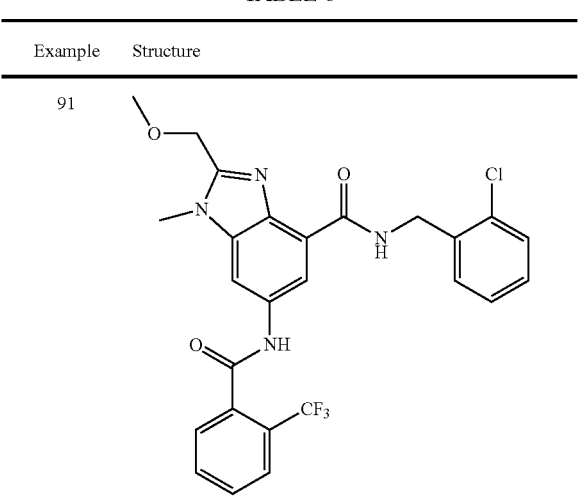 |
| 92 | (see below) |
TABLE 6-continued
| Example | Structure |
|---|---|
| 93 | 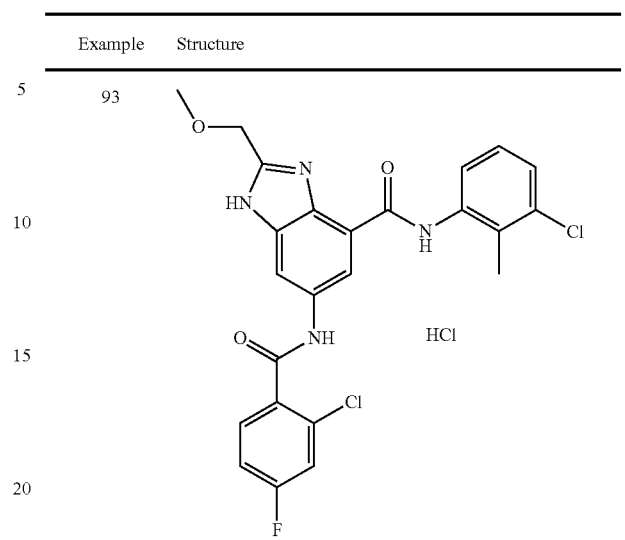 |
| 94 | 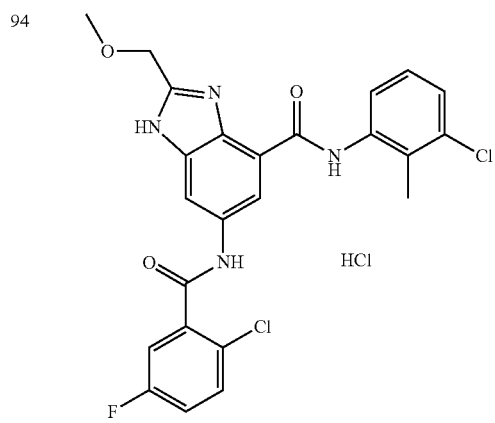 |
| 95 | 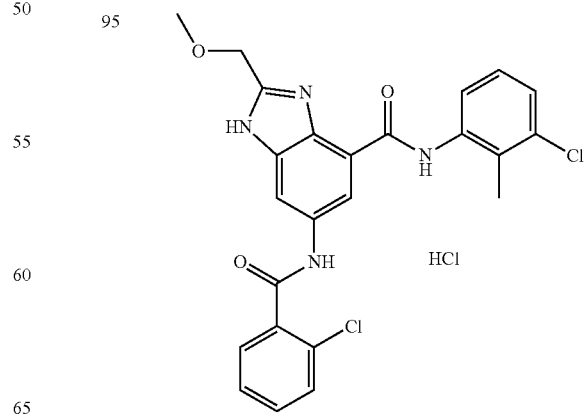 |

TABLE 6-continued
| Example | Structure |
|---|---|
| 96 | 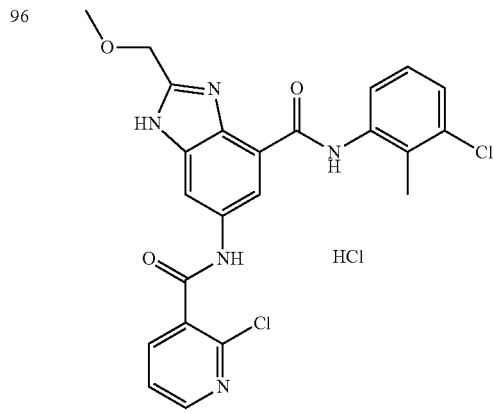 |
| 97 | 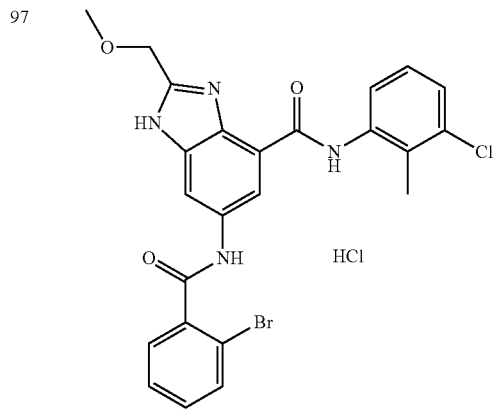 |
| 98 | 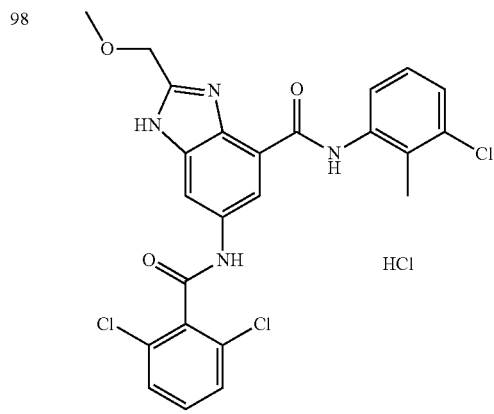 |
| 99 | 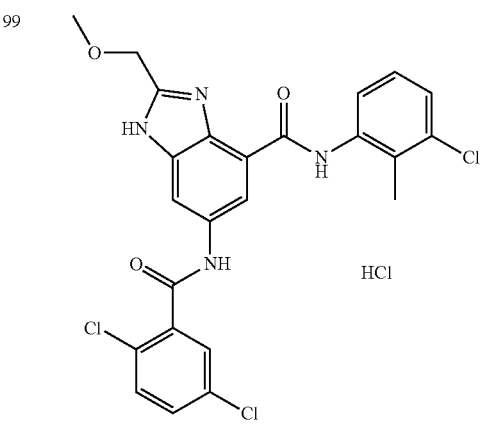 |
| 100 | 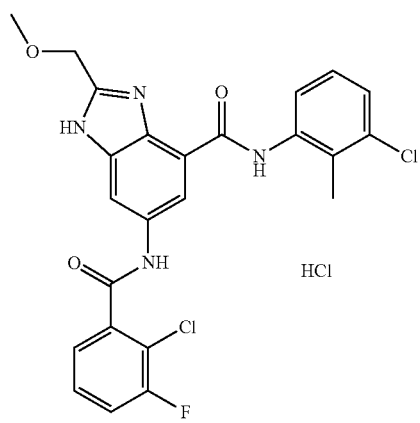 [SMILES: COCc1nc2c(C(=O)Nc3cccc(Cl)c3C)cc(NC(=O)c3cccc(F)c3Cl)cc2[nH]1 ; Cl] |
| 101 | 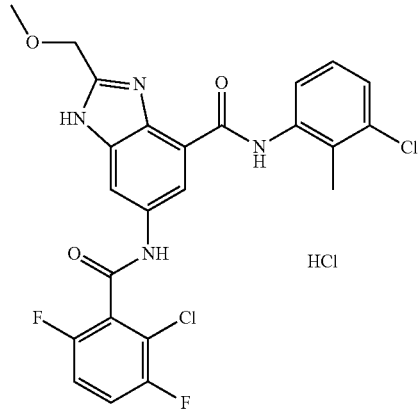 [SMILES: COCc1nc2c(C(=O)Nc3cccc(Cl)c3C)cc(NC(=O)c3c(F)ccc(F)c3Cl)cc2[nH]1 ; Cl] |

TABLE 6-continued
| Example | Structure |
|---------|-----------|
| 102 | 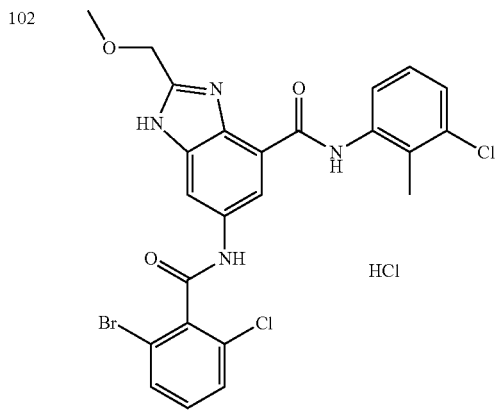 |
| 103 | 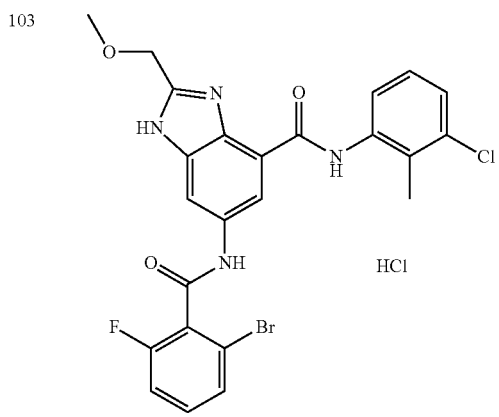 |
| 104 | 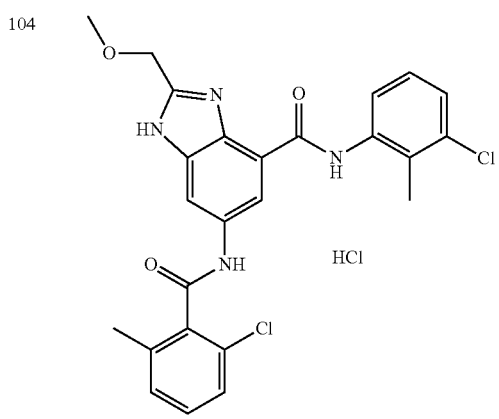 |
| 105 | 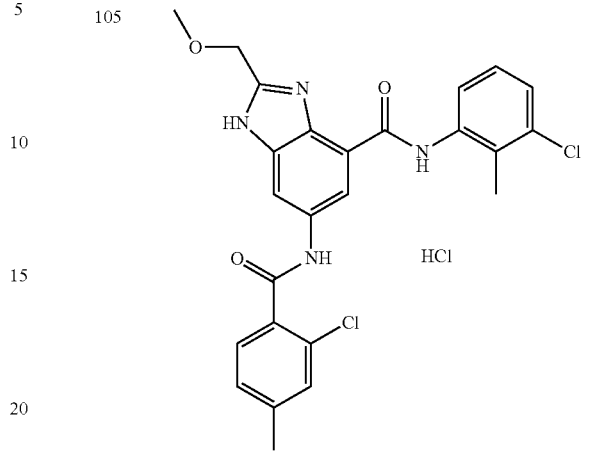 |
| 106 | 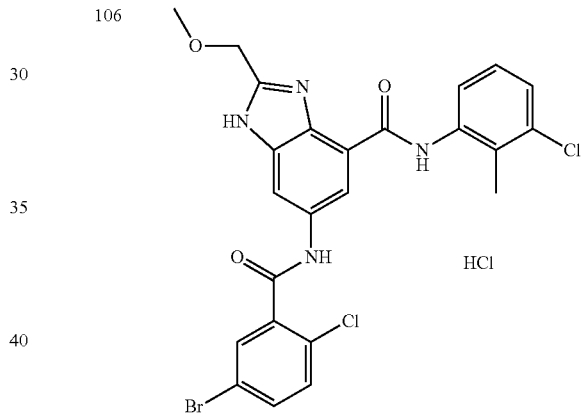 |
| 107 | 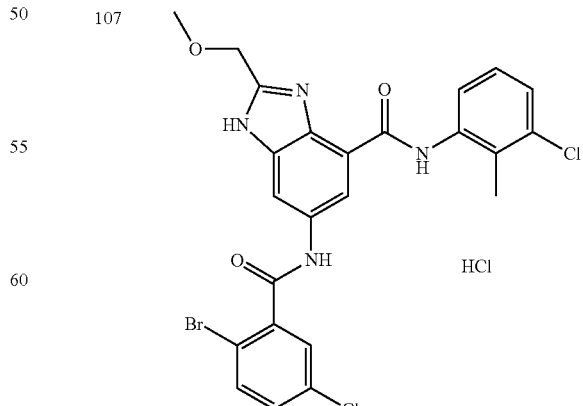 |

TABLE 6-continued
| Example | Structure |
|---|---|
| 108 | 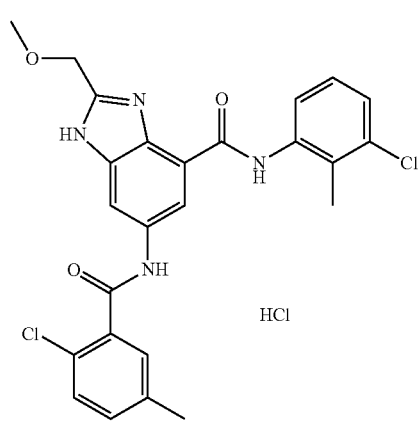 [SMILES: COCc1nc2c(C(=O)Nc3cccc(Cl)c3C)cc(NC(=O)c3cc(C)ccc3Cl)cc2[nH]1 ; Cl] |
TABLE 7
| Example | Structure |
|---|---|
| 109 | 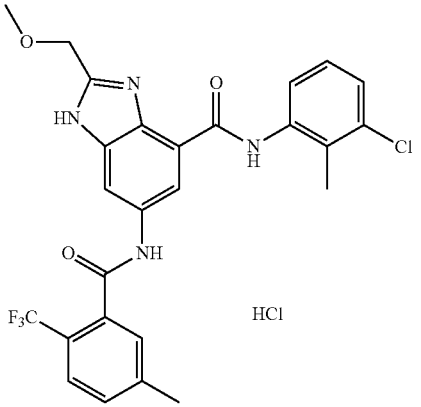 [SMILES: COCc1nc2c(C(=O)Nc3cccc(Cl)c3C)cc(NC(=O)c3cc(C)ccc3C(F)(F)F)cc2[nH]1 ; Cl] |
| 110 | 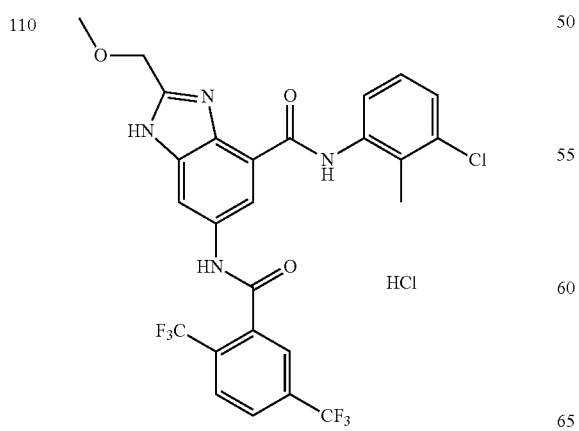 |
TABLE 7-continued
| Example | Structure |
|---|---|
| 111 | 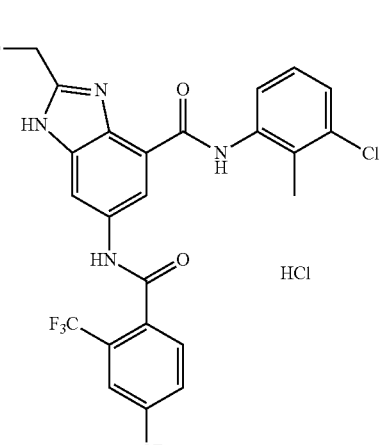 |
| 112 | 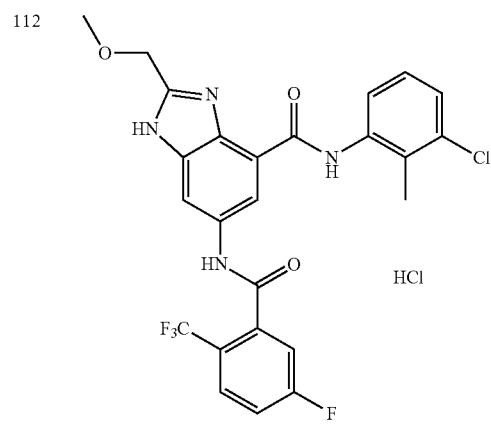 |
| 113 | 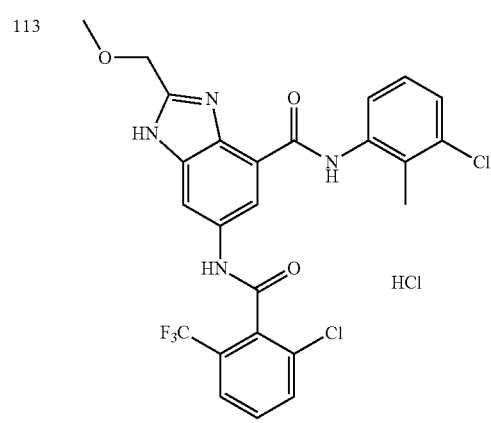 |

TABLE 7-continued
| Example | Structure |
|---------|-----------|
| 114 | 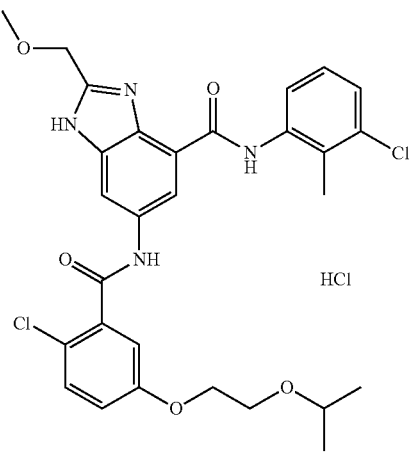 [SMILES: COCc1nc2c(C(=O)Nc3cccc(Cl)c3C)cc(NC(=O)c3cc(OCCOC(C)C)ccc3Cl)cc2[nH]1 ; Cl] |
| 115 | 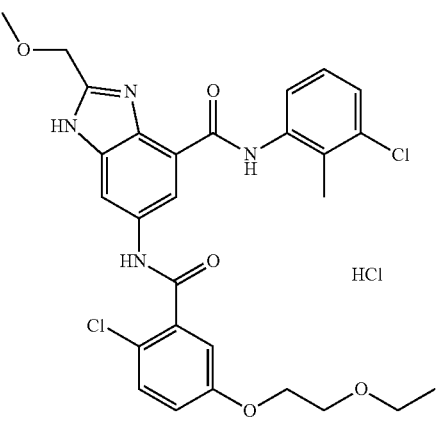 [SMILES: CCOCCOc1ccc(Cl)c(C(=O)Nc2cc(C(=O)Nc3cccc(Cl)c3C)c3nc(COC)[nH]c3c2)c1 ; Cl] |
| 116 | 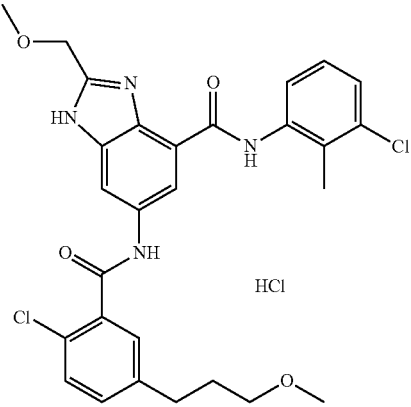 [SMILES: COCCCc1ccc(Cl)c(C(=O)Nc2cc(C(=O)Nc3cccc(Cl)c3C)c3nc(COC)[nH]c3c2)c1 ; Cl] |
| 117 | 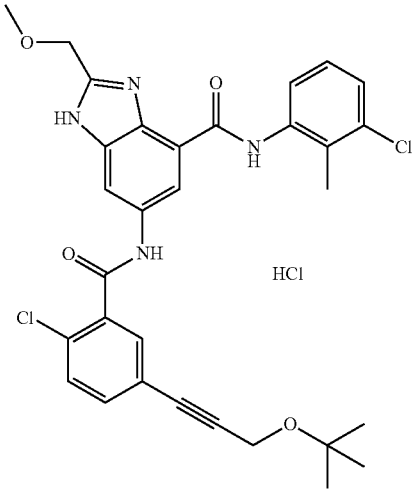 [SMILES: COCc1nc2c(C(=O)Nc3cccc(Cl)c3C)cc(NC(=O)c3cc(C#CCOC(C)(C)C)ccc3Cl)cc2[nH]1 ; Cl] |
| 118 | 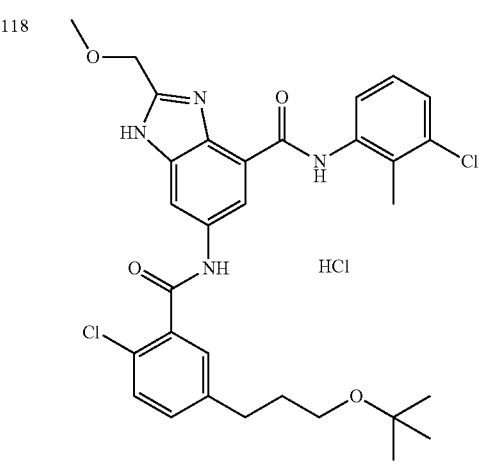 |
| 119 | 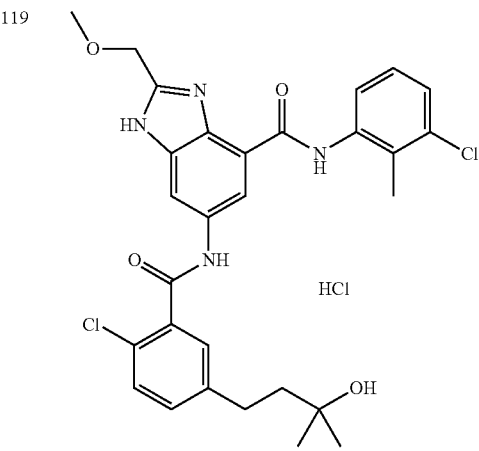 |

TABLE 7-continued
| Example | Structure |
|---|---|
| 120 | 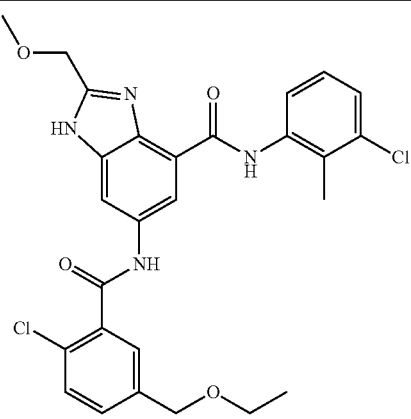 |
| 121 | 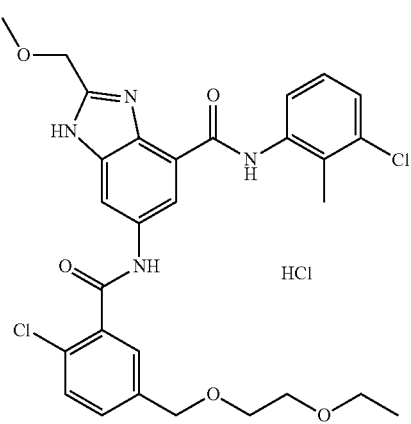 [SMILES: CCOCCOCc1ccc(Cl)c(C(=O)Nc2cc(C(=O)Nc3cccc(Cl)c3C)c3nc(COC)[nH]c3c2)c1 ; Cl] |
| 122 | 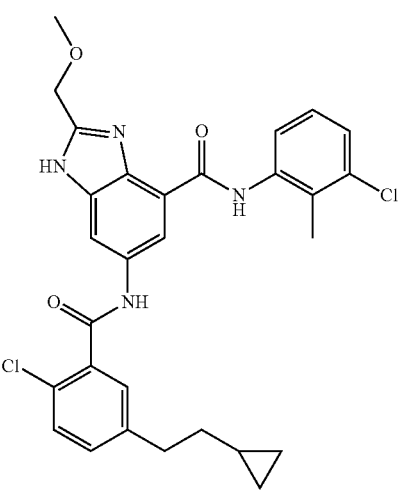 [SMILES: COCc1nc2c(C(=O)Nc3cccc(Cl)c3C)cc(NC(=O)c3cc(CCC4CC4)ccc3Cl)cc2[nH]1] |
| 123 | 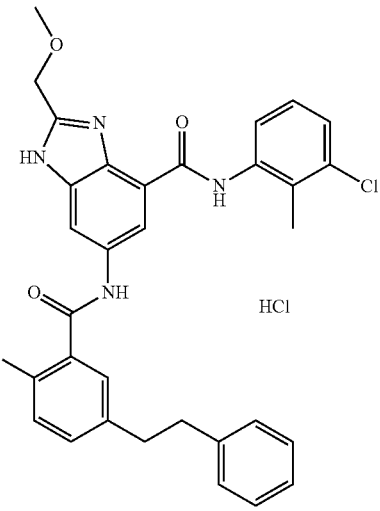 |
| 124 | 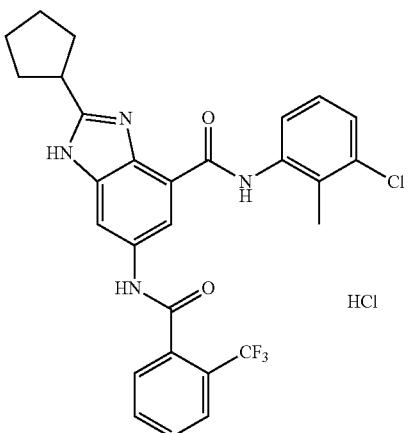 |
| 125 | 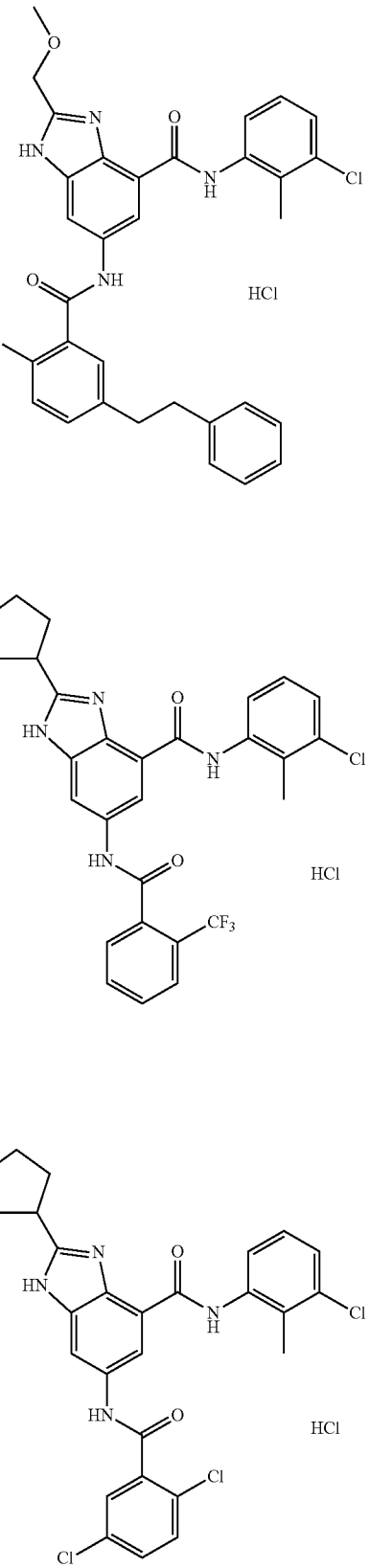 |

TABLE 7-continued
| Example | Structure |
|---|---|
| 126 | 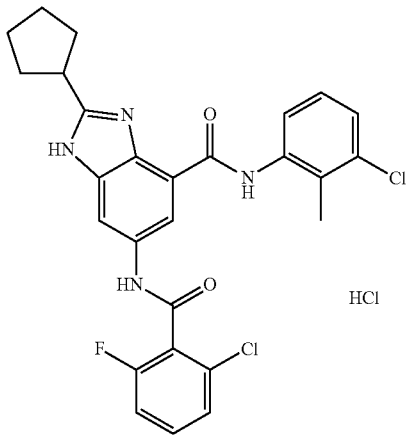 [SMILES: Cc1c(Cl)cccc1NC(=O)c1cc(NC(=O)c2c(F)cccc2Cl)cc2[nH]c(C3CCCC3)nc12 ; Cl] HCl |
TABLE 8
| Example | Structure |
|---|---|
| 127 | 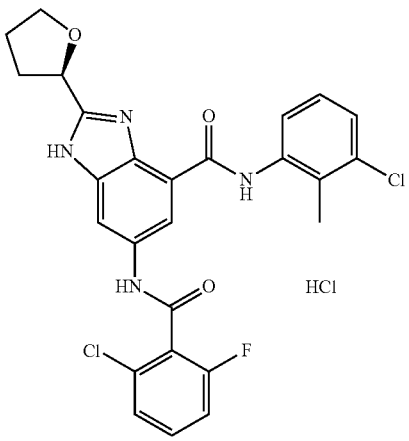 [SMILES: Cc1c(Cl)cccc1NC(=O)c1cc(NC(=O)c2c(Cl)cccc2Cl)cc2[nH]c([C@H]3CCCO3)nc12 ; Cl] HCl |
| 128 | 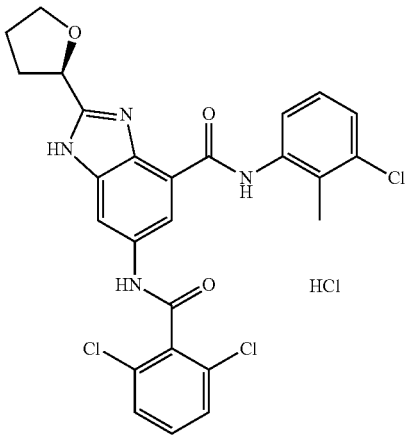 HCl |
TABLE 8-continued
| Example | Structure |
|---|---|
| 129 | 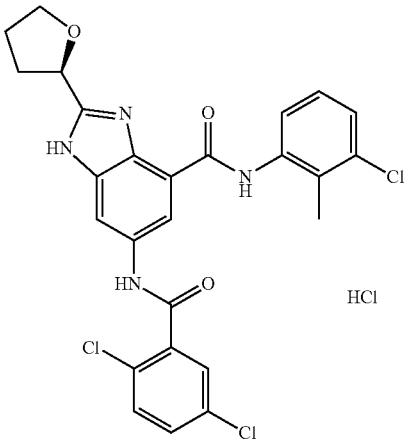 [SMILES: Cc1c(Cl)cccc1NC(=O)c1cc(NC(=O)c2cc(Cl)ccc2Cl)cc2[nH]c([C@H]3CCCO3)nc12 ; Cl] HCl |
| 130 | 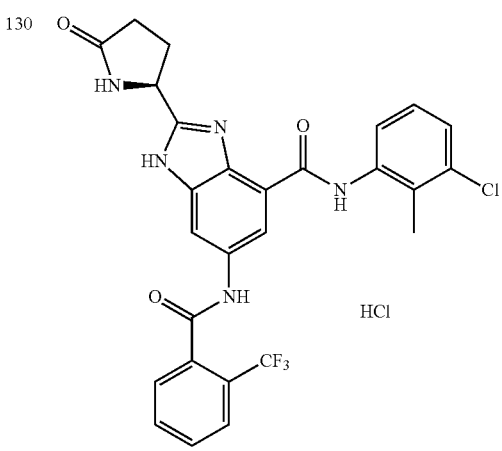 HCl |
| 131 | 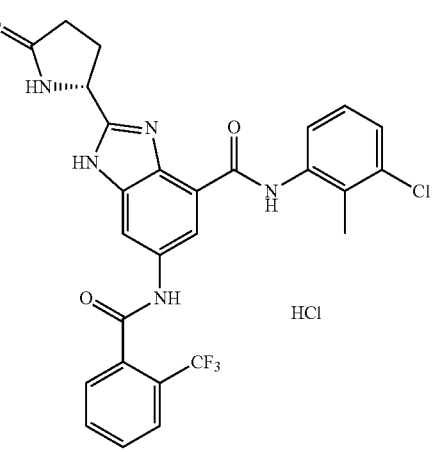 HCl |

TABLE 8-continued

| Example | Structure |
|---|---|
| 132 | (pyrrolidine-CH2-C(=O)- at 2-position of benzimidazole; benzimidazole-4-carboxamide to 3-chloro-2-methylphenyl; 6-NH-C(=O)-(2-trifluoromethylphenyl); HCl salt) |
| 133 | (Me2N-C(=O)-CH2- at 2-position of benzimidazole; benzimidazole-4-carboxamide to 3-chloro-2-methylphenyl; 6-NH-C(=O)-(2-trifluoromethylphenyl); HCl salt) |
| 134 | (MeNH-C(=O)-CH2- at 2-position of benzimidazole; benzimidazole-4-carboxamide to 3-chloro-2-methylphenyl; 6-NH-C(=O)-(2-trifluoromethylphenyl); HCl salt) |
| 135 | (2-Cl-benzimidazole; 4-carboxamide to 3-chloro-2-methylphenyl; 6-NH-C(=O)-(2-trifluoromethylphenyl)) |
| 136 | (2-(2-methoxyethylamino)-benzimidazole; 4-carboxamide to 3-chloro-2-methylphenyl; 6-NH-C(=O)-(2-trifluoromethylphenyl); HCl salt) |
| 137 | (2-(2-hydroxyethylamino)-benzimidazole; 4-carboxamide to 3-chloro-2-methylphenyl; 6-NH-C(=O)-(2-trifluoromethylphenyl); HCl salt) |
| 138 | (2-(methylamino)-benzimidazole; 4-carboxamide to 3-chloro-2-methylphenyl; 6-NH-C(=O)-(2-trifluoromethylphenyl); HCl salt) |

TABLE 8-continued
| Example | Structure |
|---|---|
| 139 | 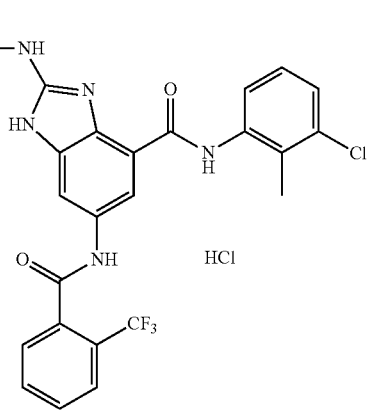 |
| 140 | 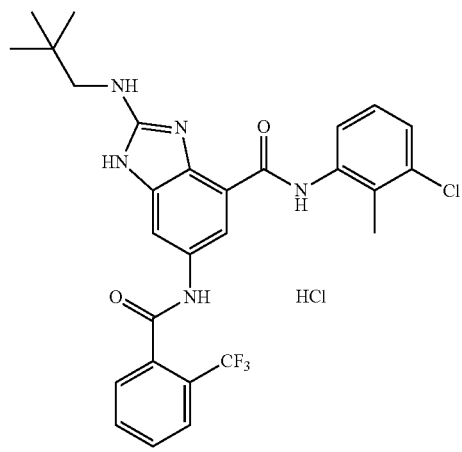 [SMILES: Cc1c(Cl)cccc1NC(=O)c1cc(NC(=O)c2ccccc2C(F)(F)F)cc2[nH]c(NCC(C)(C)C)nc12 ; Cl] |
| 141 | 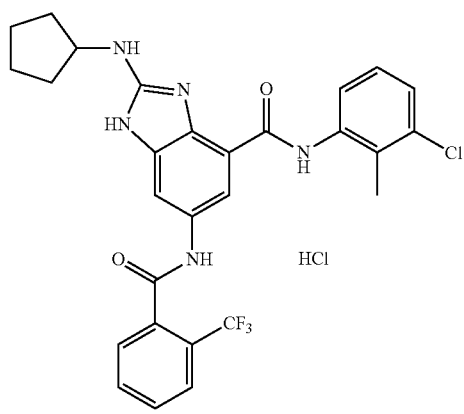 [SMILES: Cc1c(Cl)cccc1NC(=O)c1cc(NC(=O)c2ccccc2C(F)(F)F)cc2[nH]c(NC3CCCC3)nc12 ; Cl] |оз
| 142 | 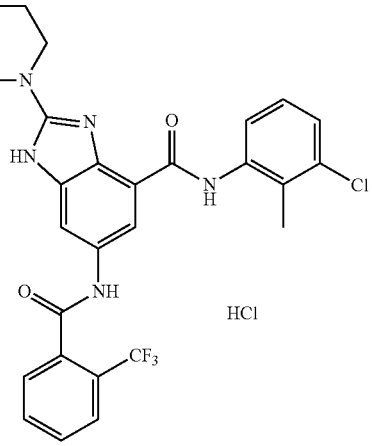 |
| 143 | 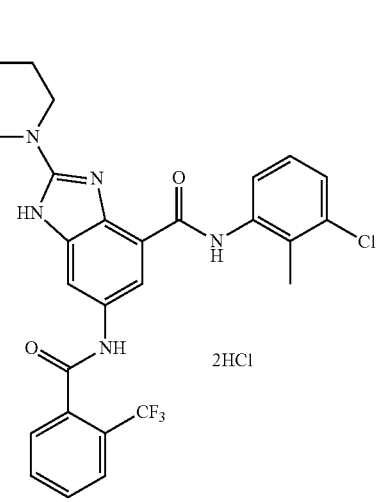 |
| 144 | 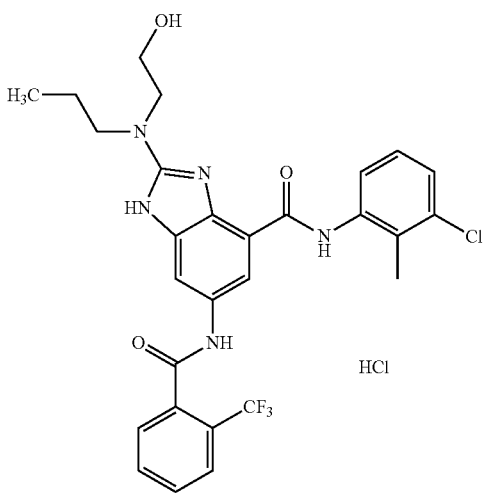 [SMILES: CCCN(CCO)c1nc2c(C(=O)Nc3cccc(Cl)c3C)cc(NC(=O)c3ccccc3C(F)(F)F)cc2[nH]1 ; Cl] |

TABLE 9
| Example | Structure |
|---------|-----------|
| 145 | 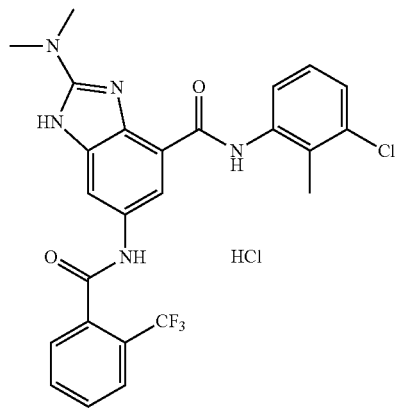 [SMILES: Cc1c(Cl)cccc1NC(=O)c1cc(NC(=O)c2ccccc2C(F)(F)F)cc2[nH]c(N(C)C)nc12 ; Cl] |
| 146 | 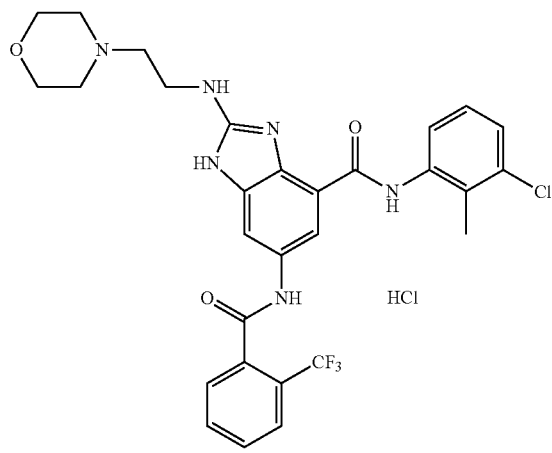 [SMILES: Cc1c(Cl)cccc1NC(=O)c1cc(NC(=O)c2ccccc2C(F)(F)F)cc2[nH]c(NCCN3CCOCC3)nc12 ; Cl] |
| 147 | 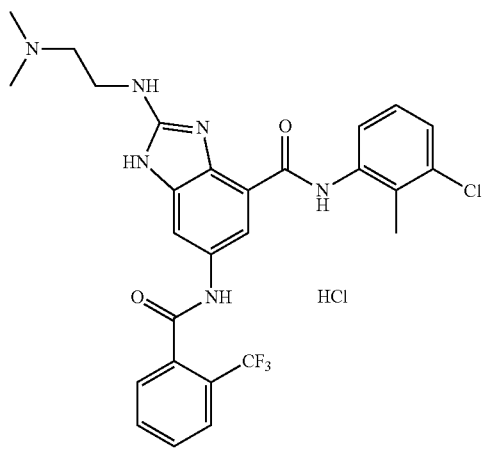 [SMILES: Cc1c(Cl)cccc1NC(=O)c1cc(NC(=O)c2ccccc2C(F)(F)F)cc2[nH]c(NCCN(C)C)nc12 ; Cl] |

TABLE 9-continued
| Example | Structure |
|---|---|
| 148 | 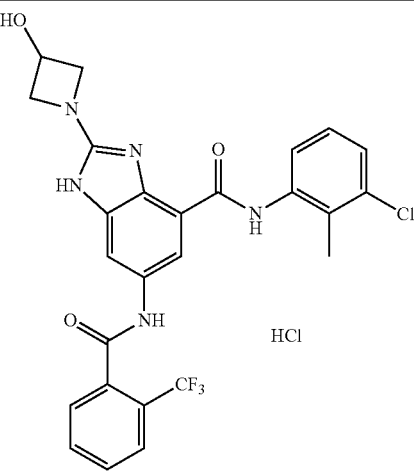 |
| 149 | 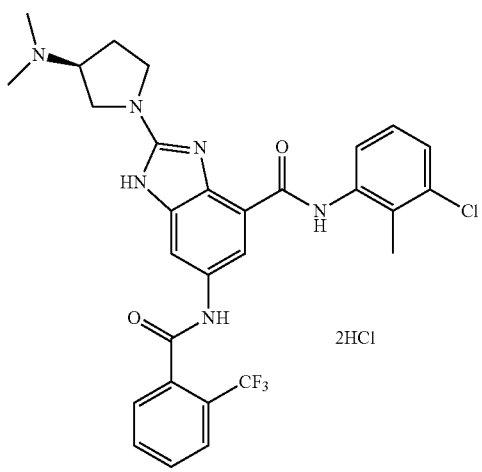 [SMILES: Cc1c(Cl)cccc1NC(=O)c1cc(NC(=O)c2ccccc2C(F)(F)F)cc2[nH]c(N3CC[C@H](N(C)C)C3)nc12 ; "2HCl"] |
| 150 | 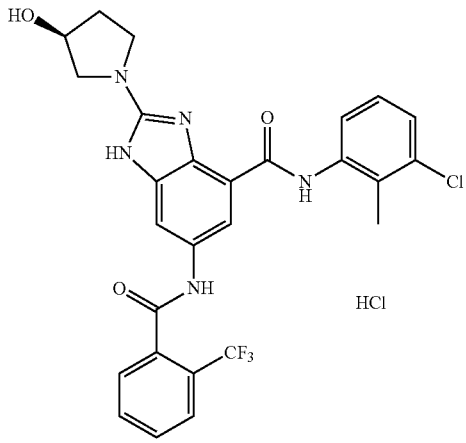 [SMILES: Cc1c(Cl)cccc1NC(=O)c1cc(NC(=O)c2ccccc2C(F)(F)F)cc2[nH]c(N3CC[C@H](O)C3)nc12 ; Cl] |

TABLE 9-continued
| Example | Structure |
|---|---|
| 151 | 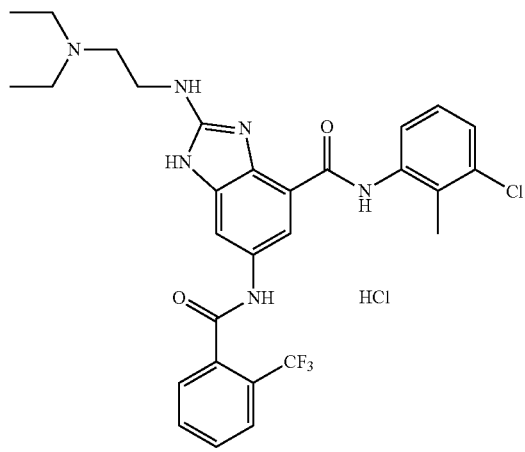 [SMILES: CCN(CC)CCNc1nc2c(C(=O)Nc3cccc(Cl)c3C)cc(NC(=O)c3ccccc3C(F)(F)F)cc2[nH]1 ; Cl] |
| 152 | 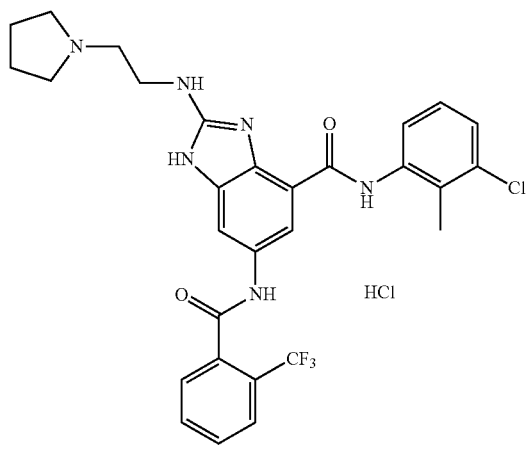 [SMILES: Cc1c(Cl)cccc1NC(=O)c1cc(NC(=O)c2ccccc2C(F)(F)F)cc2[nH]c(NCCN3CCCC3)nc12 ; Cl] |
| 153 | 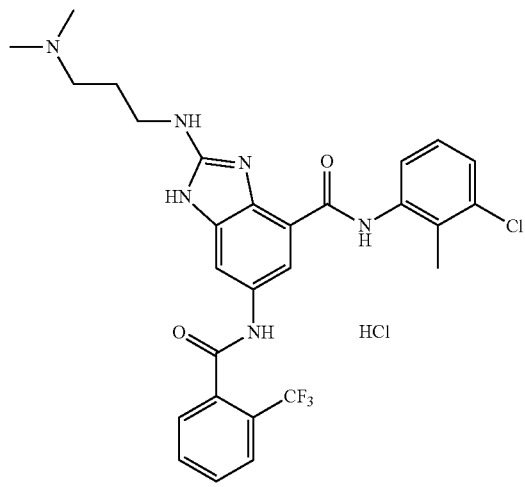 [SMILES: Cc1c(Cl)cccc1NC(=O)c1cc(NC(=O)c2ccccc2C(F)(F)F)cc2[nH]c(NCCCN(C)C)nc12 ; Cl] |

TABLE 9-continued
| Example | Structure |
|---|---|
| 154 | 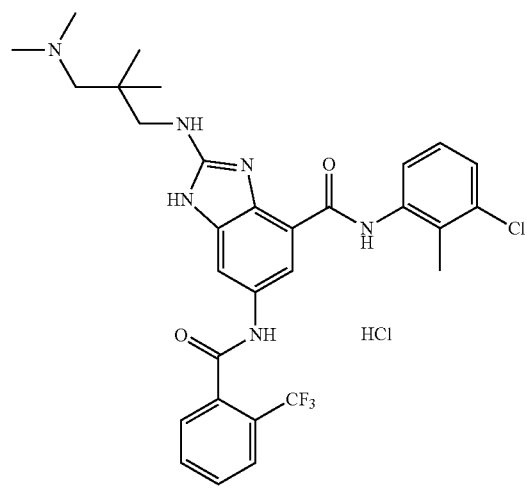 [SMILES: Cc1c(Cl)cccc1NC(=O)c1cc(NC(=O)c2ccccc2C(F)(F)F)cc2[nH]c(NCC(C)(C)CN(C)C)nc12 ; Cl] |
| 155 | 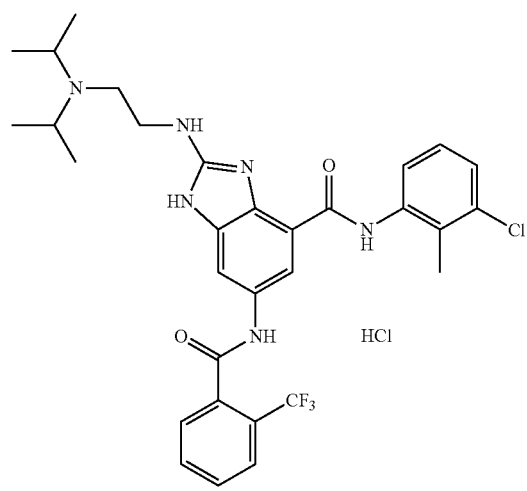 [SMILES: Cc1c(Cl)cccc1NC(=O)c1cc(NC(=O)c2ccccc2C(F)(F)F)cc2[nH]c(NCCN(C(C)C)C(C)C)nc12 ; Cl] |
| 156 | 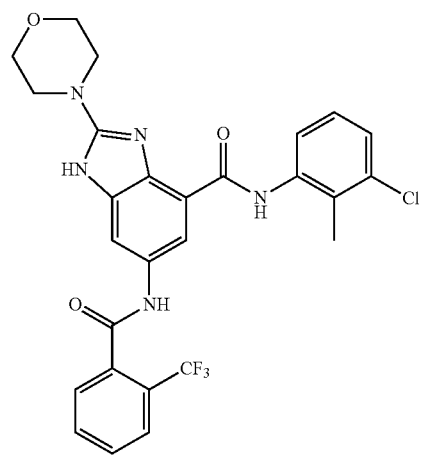 [SMILES: Cc1c(Cl)cccc1NC(=O)c1cc(NC(=O)c2ccccc2C(F)(F)F)cc2[nH]c(N3CCOCC3)nc12] |

TABLE 9-continued
| Example | Structure |
|---------|-----------|
| 157 | 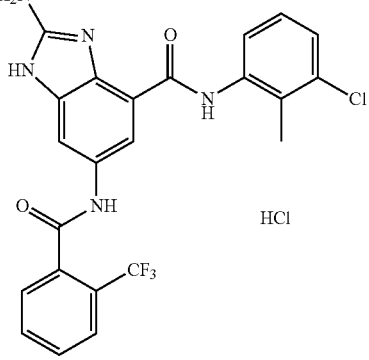 |
| 158 | 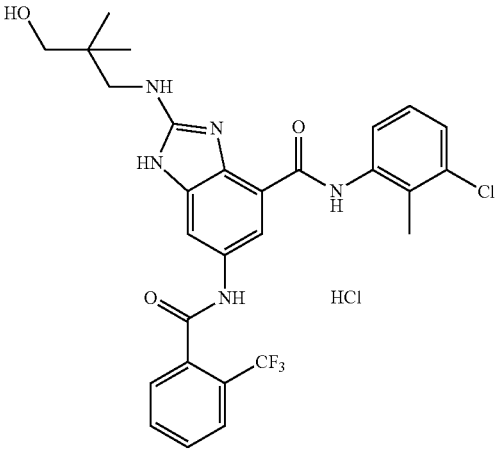 [SMILES: Cc1c(Cl)cccc1NC(=O)c1cc(NC(=O)c2ccccc2C(F)(F)F)cc2[nH]c(NCC(C)(C)CO)nc12 ; Cl] |
| 159 | 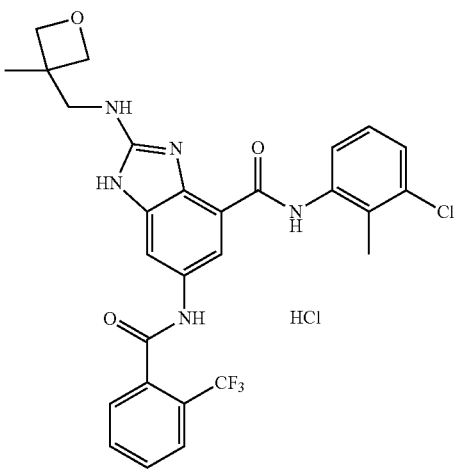 [SMILES: Cc1c(Cl)cccc1NC(=O)c1cc(NC(=O)c2ccccc2C(F)(F)F)cc2[nH]c(NCC3(C)COC3)nc12 ; Cl] |

TABLE 9-continued
| Example | Structure |
| --- | --- |
| 160 | 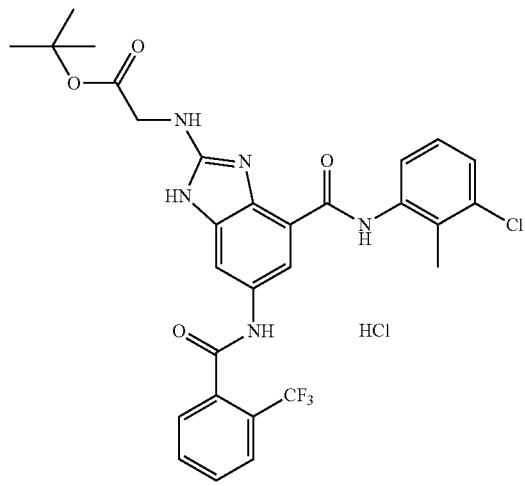 [SMILES: Cc1c(Cl)cccc1NC(=O)c1cc(NC(=O)c2ccccc2C(F)(F)F)cc2[nH]c(NCC(=O)OC(C)(C)C)nc12 ; Cl] |
| 161 | 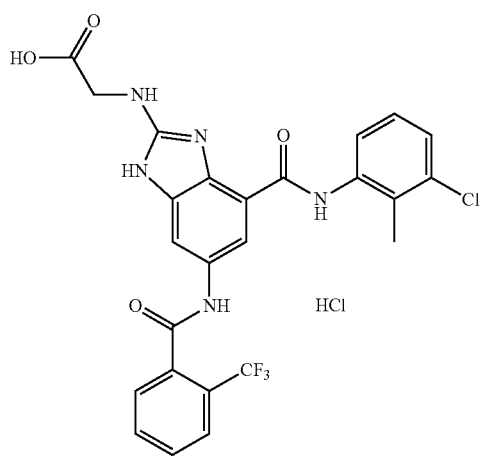 [SMILES: Cc1c(Cl)cccc1NC(=O)c1cc(NC(=O)c2ccccc2C(F)(F)F)cc2[nH]c(NCC(=O)O)nc12 ; Cl] |
| 162 | 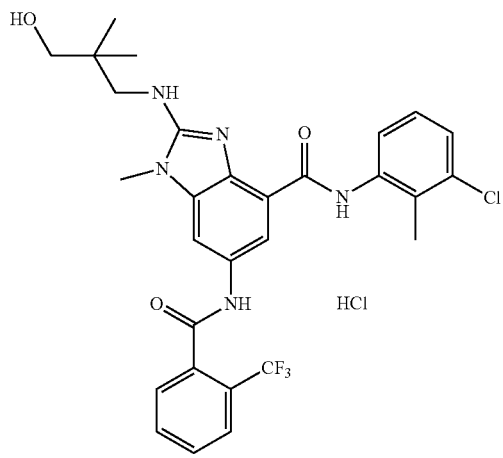 [SMILES: Cc1c(Cl)cccc1NC(=O)c1cc(NC(=O)c2ccccc2C(F)(F)F)cc2c1nc(NCC(C)(C)CO)n2C ; Cl] |

TABLE 10
| Example | Structure |
|---|---|
| 163 | 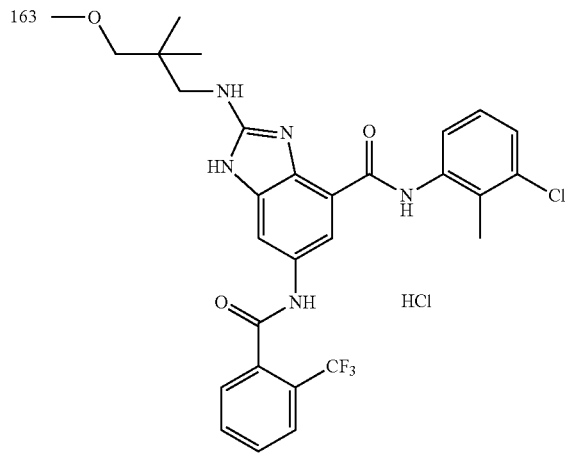 HCl |
| 164 | 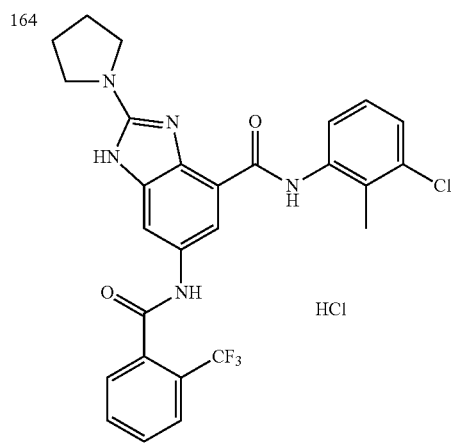 HCl |
| 165 | 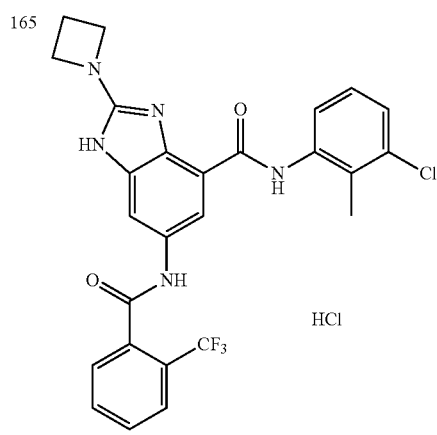 HCl |
TABLE 10-continued
| Example | Structure |
|---|---|
| 166 | 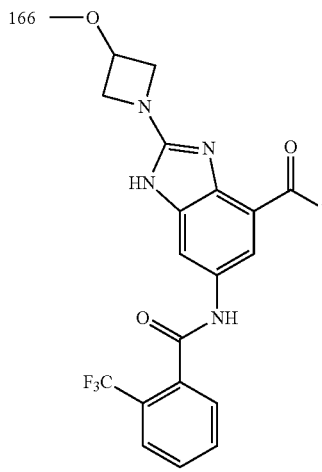 HCl |
| 167 | HCl |
| 168 | 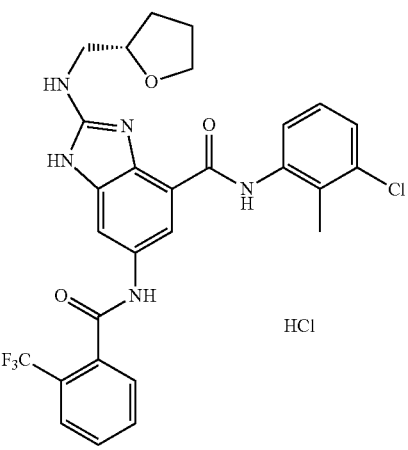 [SMILES: Cc1c(Cl)cccc1NC(=O)c1cc(NC(=O)c2ccccc2C(F)(F)F)cc2[nH]c(NC[C@@H]3CCCO3)nc12 ; Cl] HCl |

TABLE 10-continued
| Example | Structure |
|---|---|
| 169 | 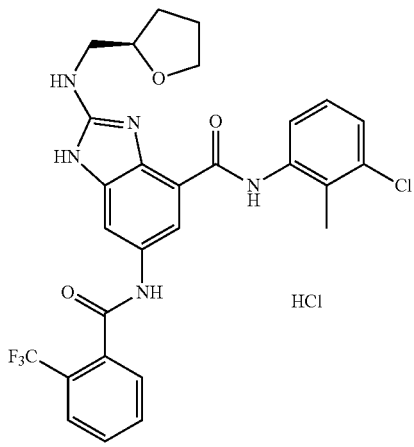 [SMILES: Cc1c(Cl)cccc1NC(=O)c1cc(NC(=O)c2ccccc2C(F)(F)F)cc2[nH]c(NC[C@H]3CCCO3)nc12 ; Cl] HCl |
| 170 | 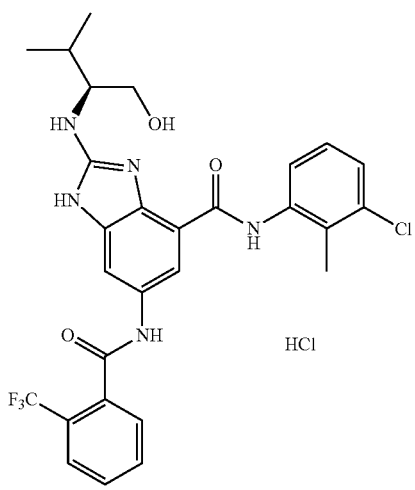 [SMILES: Cc1c(Cl)cccc1NC(=O)c1cc(NC(=O)c2ccccc2C(F)(F)F)cc2[nH]c(N[C@H](CO)C(C)C)nc12 ; Cl] HCl |
| 171 | 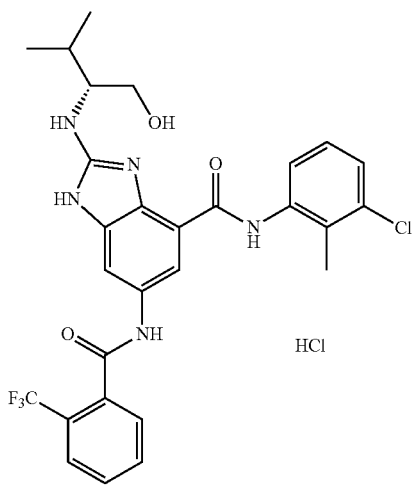 [SMILES: Cc1c(Cl)cccc1NC(=O)c1cc(NC(=O)c2ccccc2C(F)(F)F)cc2[nH]c(N[C@@H](CO)C(C)C)nc12 ; Cl] HCl |
| 172 | 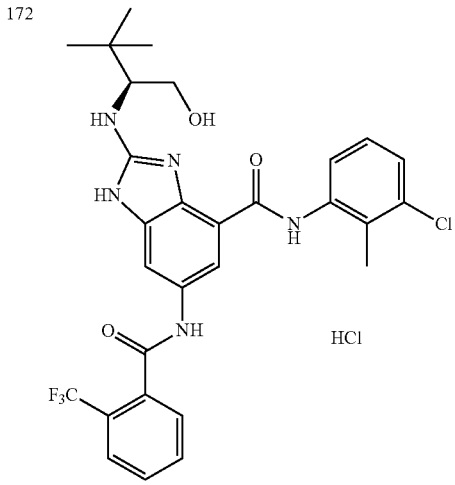 HCl |
| 173 | 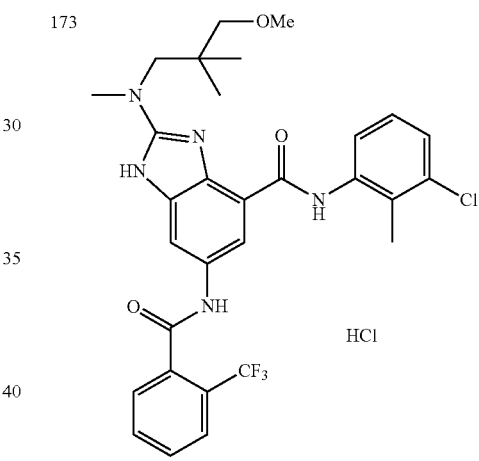 HCl |
| 174 | 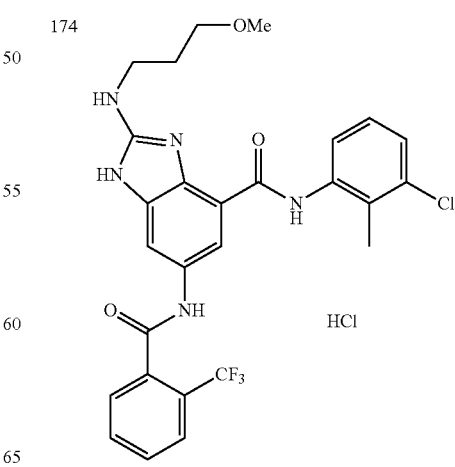 HCl |

TABLE 10-continued
| Example | Structure |
|---|---|
| 175 | 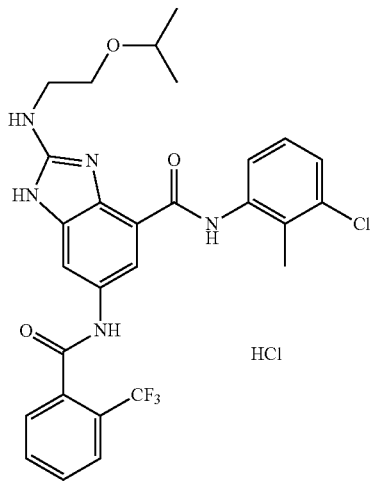 [SMILES: Cc1c(Cl)cccc1NC(=O)c1cc(NC(=O)c2ccccc2C(F)(F)F)cc2[nH]c(NCCOC(C)C)nc12 ; Cl] HCl |
| 176 | 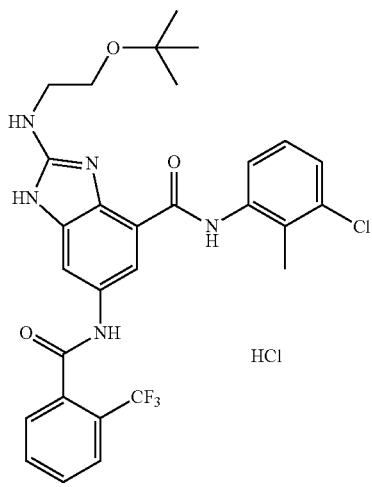 [SMILES: Cc1c(Cl)cccc1NC(=O)c1cc(NC(=O)c2ccccc2C(F)(F)F)cc2[nH]c(NCCOC(C)(C)C)nc12 ; Cl] HCl |
| 177 | 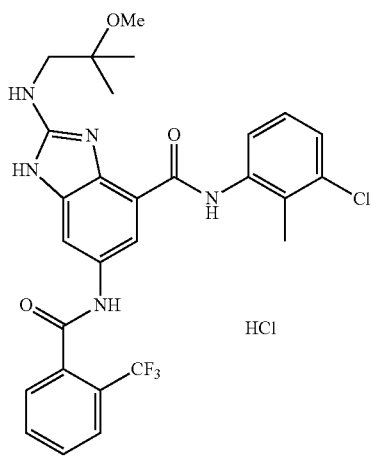 [SMILES: COC(C)(C)CNc1nc2c(C(=O)Nc3cccc(Cl)c3C)cc(NC(=O)c3ccccc3C(F)(F)F)cc2[nH]1 ; Cl] HCl |
| 178 | 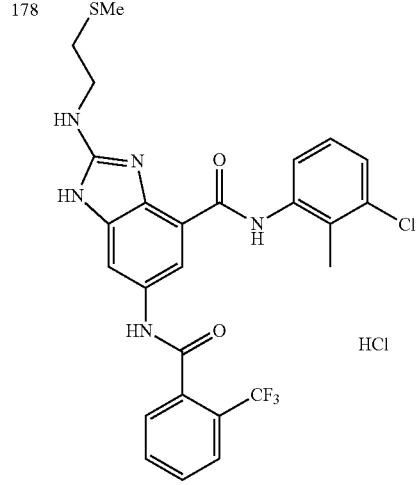 HCl |
| 179 | 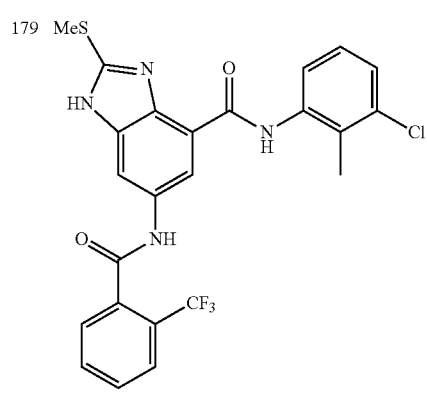 |
| 180 | 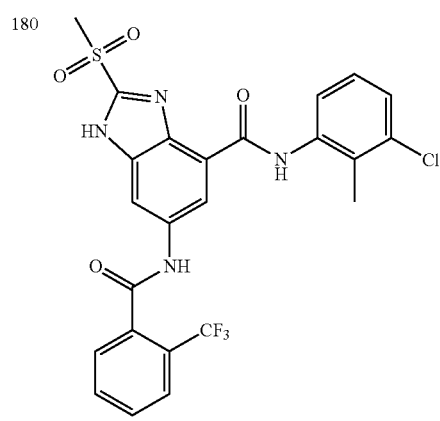 |

TABLE 11

| Example | Structure |
|---|---|
| 181 | (structure) |
| 182 | (structure) HCl |
| 183 | (structure) HCl |

TABLE 11-continued

| Example | Structure |
|---|---|
| 184 | (structure) HCl |
| 185 | (structure) HCl |
| 186 | (structure) HCl |

TABLE 11-continued
| Example | Structure |
|---|---|
| 187 | 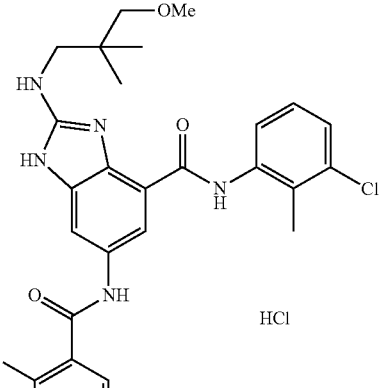 HCl |
| 188 | 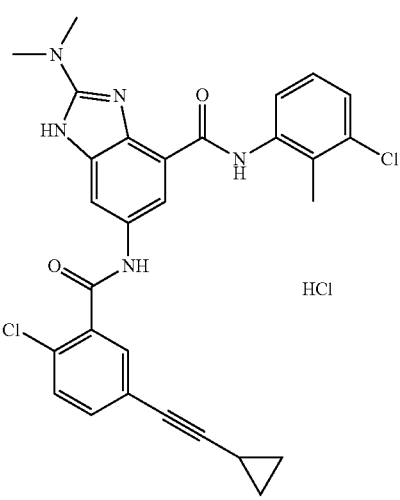 [SMILES: Cc1c(Cl)cccc1NC(=O)c1cc(NC(=O)c2cc(C#CC3CC3)ccc2Cl)cc2[nH]c(N(C)C)nc12 ; Cl] HCl |
| 189 | 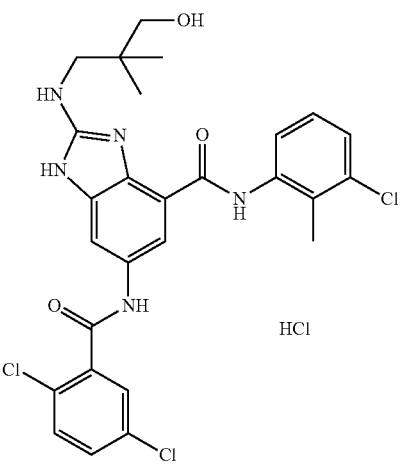 [SMILES: Cc1c(Cl)cccc1NC(=O)c1cc(NC(=O)c2cc(Cl)ccc2Cl)cc2[nH]c(NCC(C)(C)CO)nc12 ; Cl] HCl |
| 190 | HCl |
| 191 | 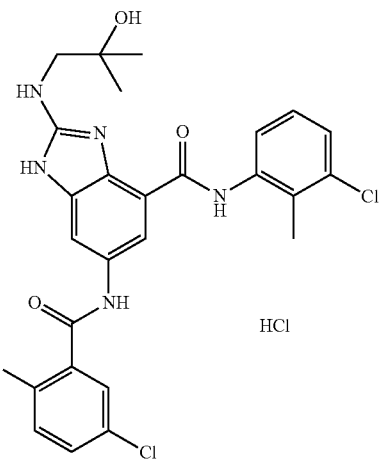 HCl |
| 192 | 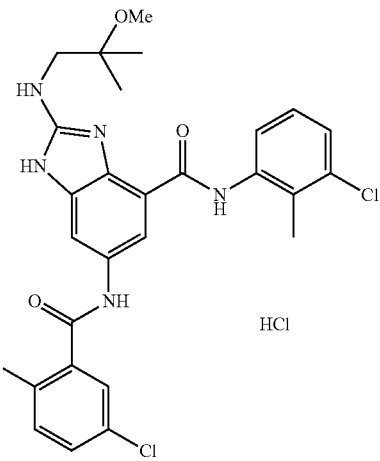 HCl |

TABLE 11-continued
| Example | Structure |
|---------|-----------|
| 193 | 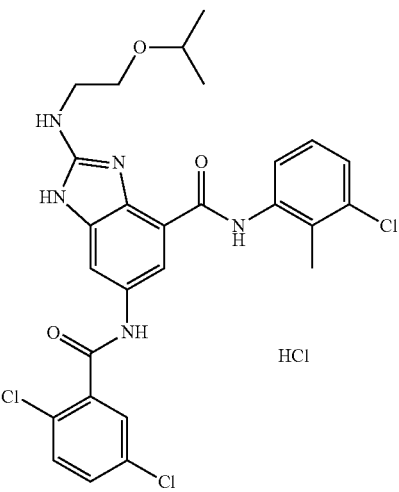 [SMILES: Cc1c(Cl)cccc1NC(=O)c1cc(NC(=O)c2cc(Cl)ccc2Cl)cc2[nH]c(NCCOC(C)C)nc12 ; Cl] HCl |
| 194 | 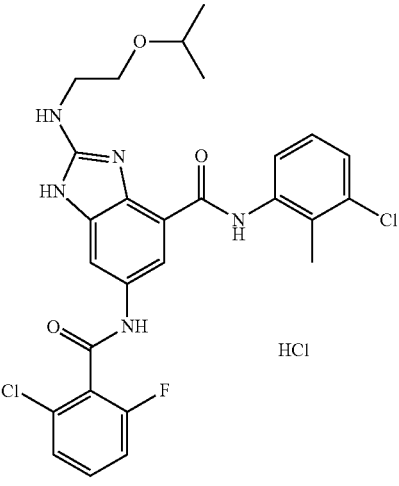 [SMILES: Cc1c(Cl)cccc1NC(=O)c1cc(NC(=O)c2c(F)cccc2Cl)cc2[nH]c(NCCOC(C)C)nc12 ; Cl] HCl |
| 195 | 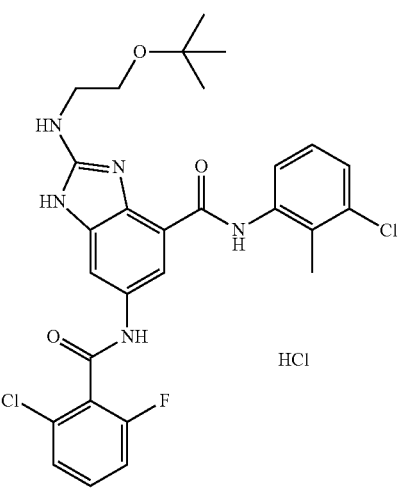 [SMILES: Cc1c(Cl)cccc1NC(=O)c1cc(NC(=O)c2c(F)cccc2Cl)cc2[nH]c(NCCOC(C)(C)C)nc12 ; Cl] HCl |
| 196 | 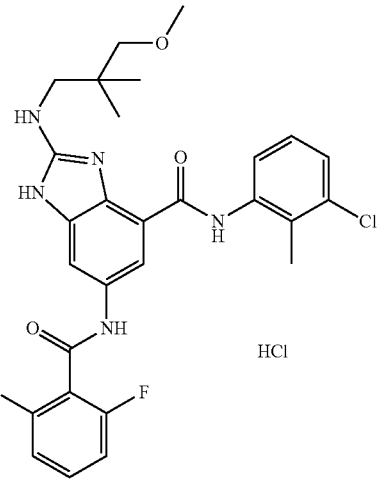 HCl |
| 197 | 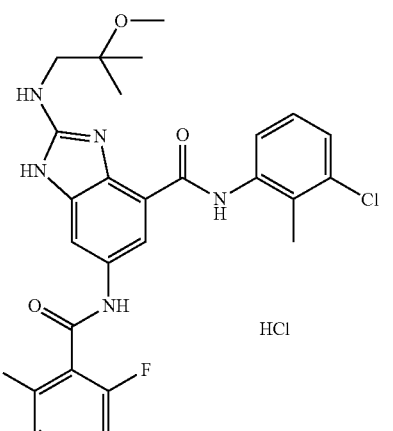 HCl |
| 198 | 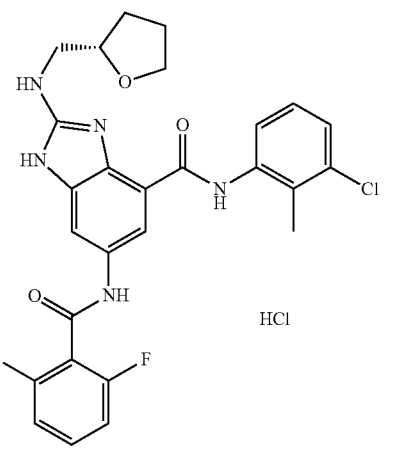 HCl |

TABLE 12
| Example | Structure |
|---|---|
| 199 | 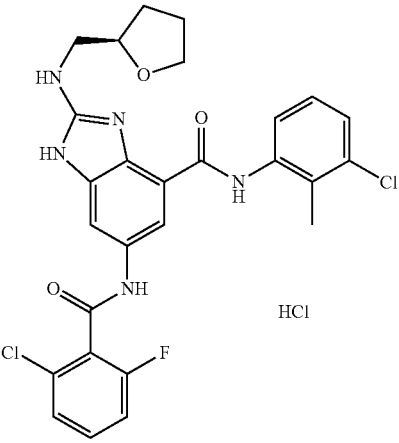 [SMILES: Cc1c(Cl)cccc1NC(=O)c1cc(NC(=O)c2c(F)cccc2Cl)cc2[nH]c(NC[C@H]3CCCO3)nc12 ; Cl] HCl |
| 200 | 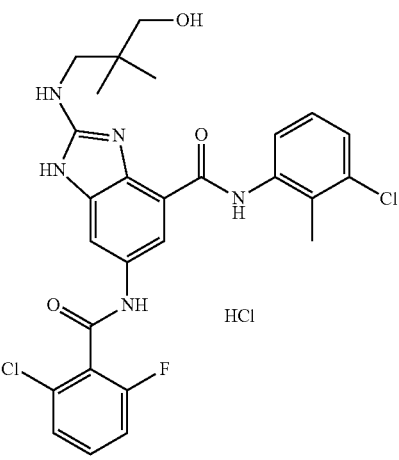 [SMILES: Cc1c(Cl)cccc1NC(=O)c1cc(NC(=O)c2c(F)cccc2Cl)cc2[nH]c(NCC(C)(C)CO)nc12 ; Cl] HCl |
| 201 | 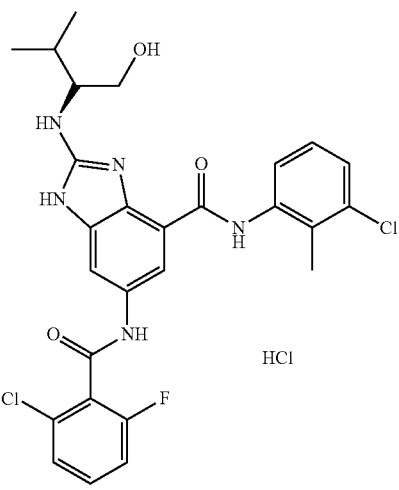 HCl |“
TABLE 12-continued
| Example | Structure |
|---|---|
| 202 | 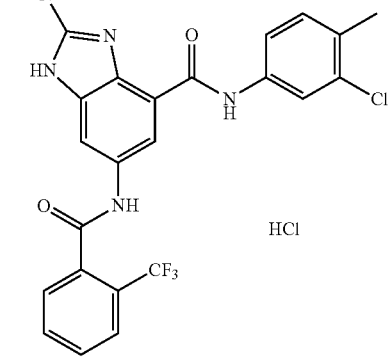 HCl |
| 203 | 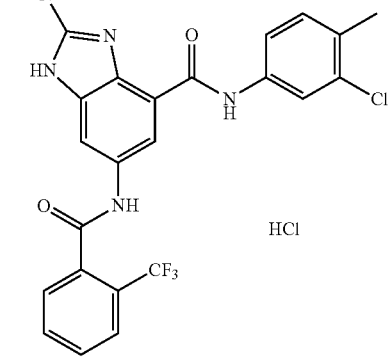 HCl |
| 204 | 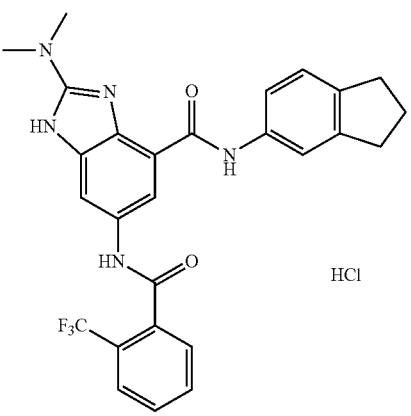 [SMILES: CN(C)c1nc2c(C(=O)Nc3ccc4c(c3)CCC4)cc(NC(=O)c3ccccc3C(F)(F)F)cc2[nH]1 ; Cl] HCl |

TABLE 12-continued
| Example | Structure |
|---|---|
| 205 | 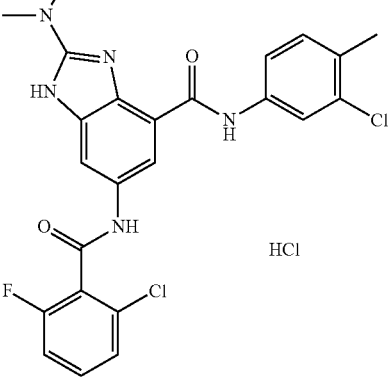 |
| 206 | 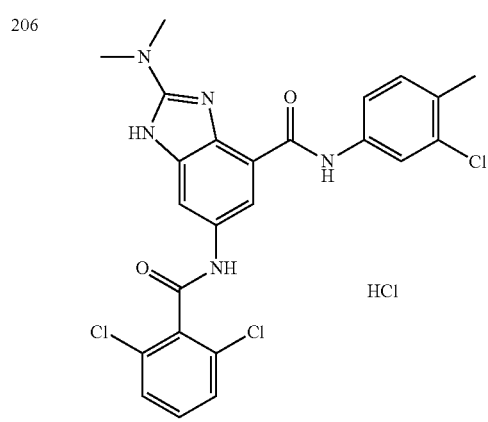 |
| 207 | 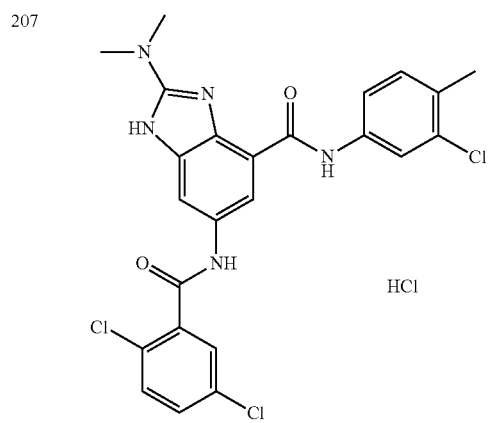 |
| 208 | 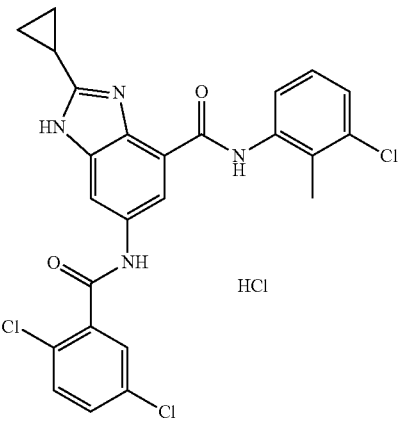 [SMILES: Cc1c(Cl)cccc1NC(=O)c1cc(NC(=O)c2cc(Cl)ccc2Cl)cc2[nH]c(C3CC3)nc12 ; Cl] |
| 209 | 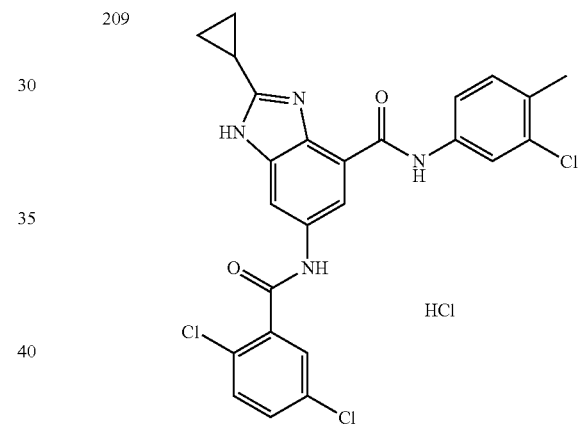 |
| 210 | 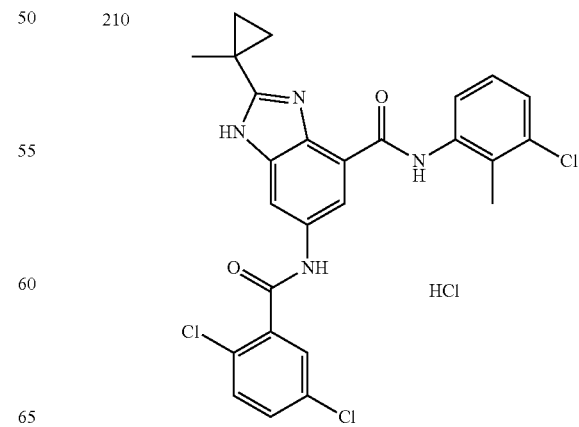 |

TABLE 12-continued
| Example | Structure |
|---|---|
| 211 | 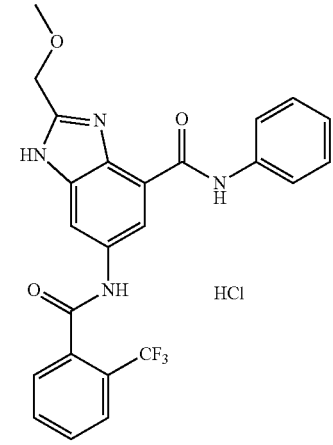 HCl |
| 212 | 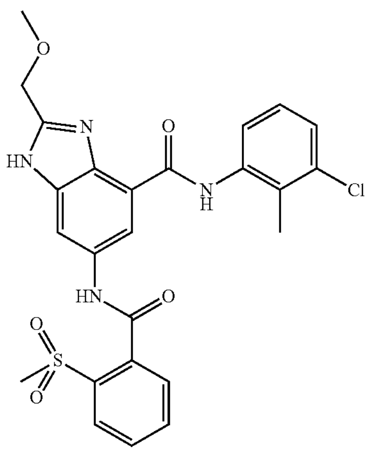 [SMILES: COCc1nc2c(C(=O)Nc3cccc(Cl)c3C)cc(NC(=O)c3ccccc3S(C)(=O)=O)cc2[nH]1] |
| 213 | 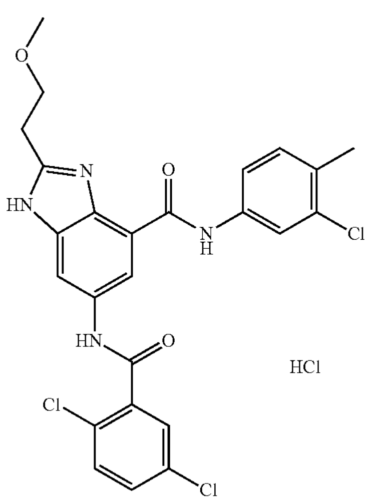 [SMILES: COCCc1nc2c(C(=O)Nc3ccc(C)c(Cl)c3)cc(NC(=O)c3cc(Cl)ccc3Cl)cc2[nH]1 ; Cl] |
TABLE 12-continued
| Example | Structure |
|---|---|
| 214 | 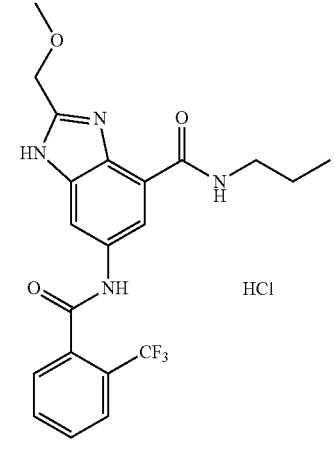 HCl |
| 215 | 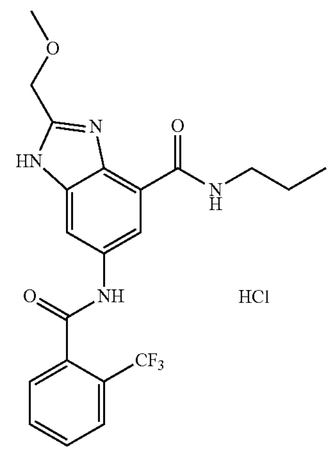 [SMILES: CCCNC(=O)c1cc(NC(=O)c2ccccc2C(F)(F)F)cc2[nH]c(COC)nc12 ; Cl] |
| 216 | 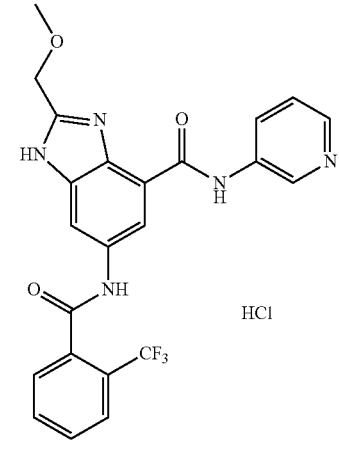 [SMILES: COCc1nc2c(C(=O)Nc3cccnc3)cc(NC(=O)c3ccccc3C(F)(F)F)cc2[nH]1 ; Cl] HCl |

TABLE 13
| Example | Structure |
|---|---|
| 217 | 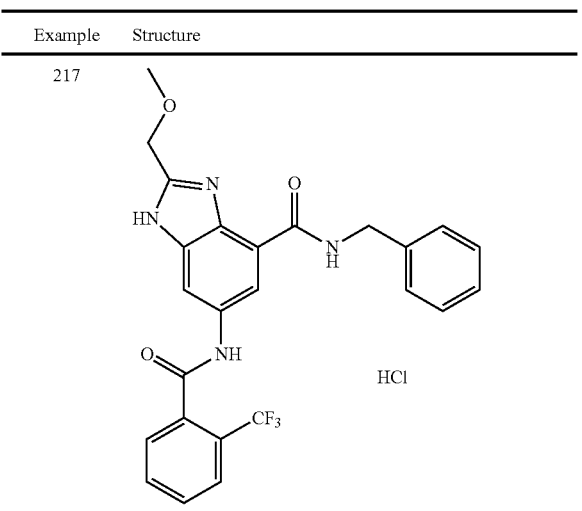 |
| 218 | 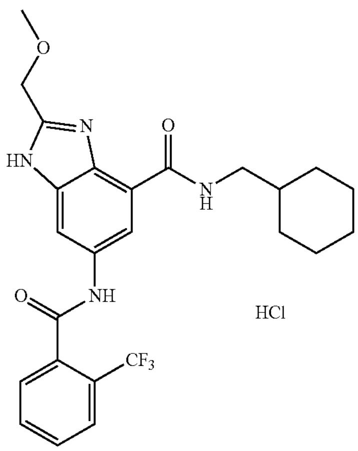 [SMILES: COCc1nc2c(C(=O)NCC3CCCCC3)cc(NC(=O)c3ccccc3C(F)(F)F)cc2[nH]1 ; Cl] |
| 219 | 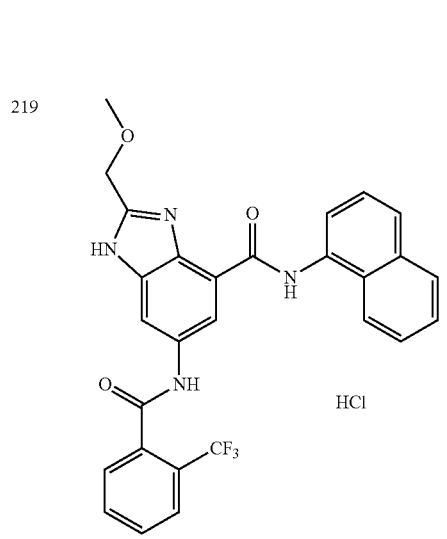 |
TABLE 13-continued
| Example | Structure |
|---|---|
| 220 | 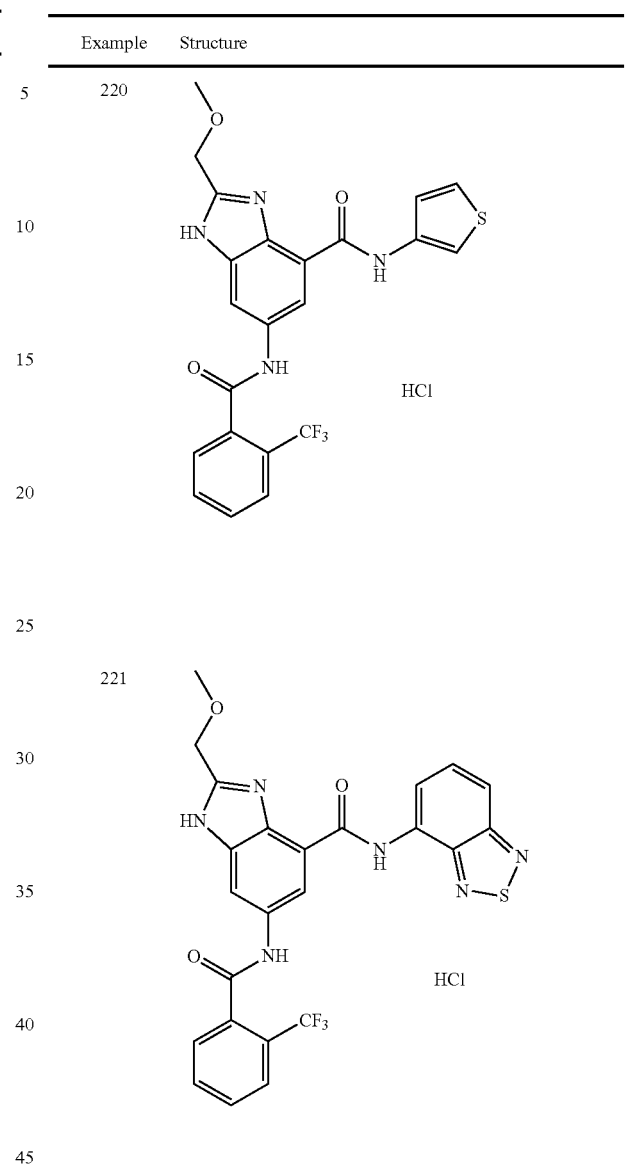 |
| 221 | 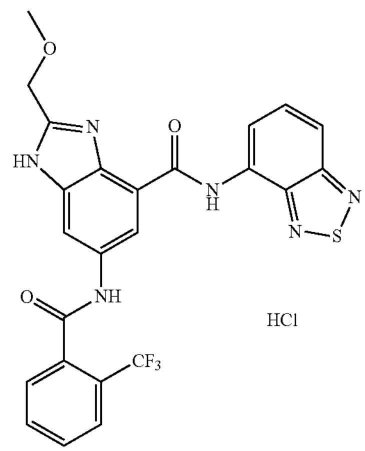 [SMILES: COCc1nc2c(C(=O)Nc3cccc4nsnc34)cc(NC(=O)c3ccccc3C(F)(F)F)cc2[nH]1 ; Cl] |
| 222 | 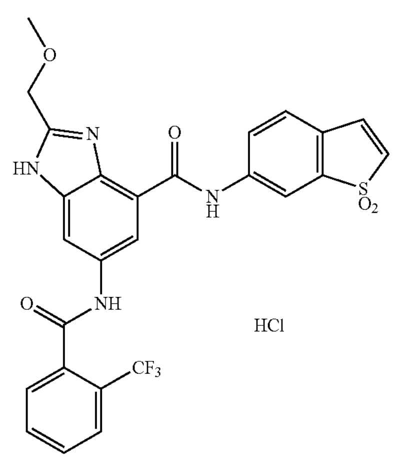 [SMILES: COCc1nc2c(C(=O)Nc3ccc4c(c3)S(=O)(=O)C=C4)cc(NC(=O)c3ccccc3C(F)(F)F)cc2[nH]1 ; Cl] |

TABLE 13-continued
| Example | Structure |
|---|---|
| 223 | 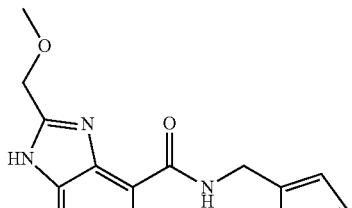 |
| 224 | 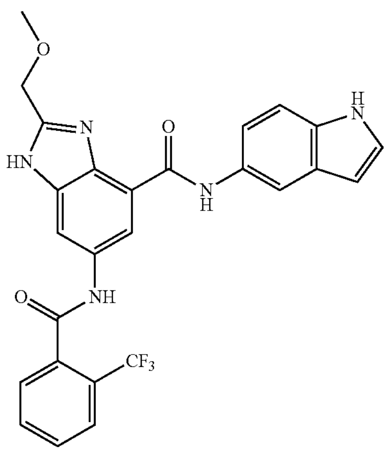 [SMILES: COCc1nc2c(C(=O)Nc3ccc4[nH]ccc4c3)cc(NC(=O)c3ccccc3C(F)(F)F)cc2[nH]1] |
| 225 | 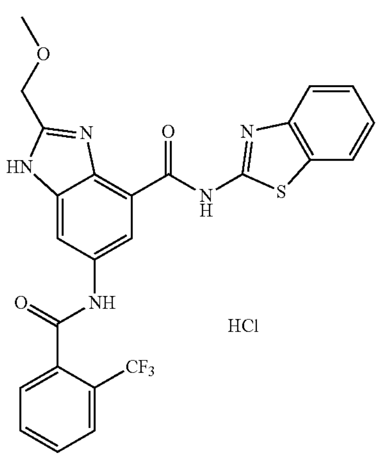 [SMILES: COCc1nc2c(C(=O)Nc3nc4ccccc4s3)cc(NC(=O)c3ccccc3C(F)(F)F)cc2[nH]1 ; Cl] |
| 226 | |
| 227 | |
| 228 | |

TABLE 13-continued
| Example | Structure |
|---|---|
| 229 | 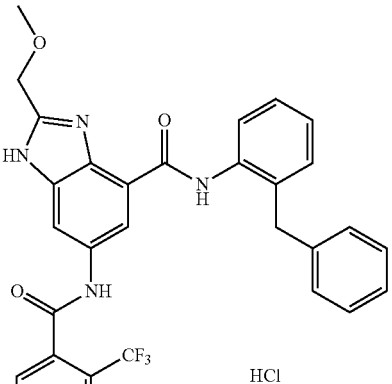 HCl |
| 230 | HCl |
| 231 | HCl |
| 232 | HCl |
| 233 | HCl |
| 234 | 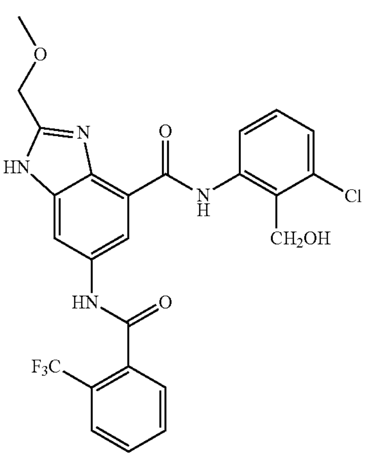 [SMILES: COCc1nc2c(C(=O)Nc3cccc(Cl)c3CO)cc(NC(=O)c3ccccc3C(F)(F)F)cc2[nH]1] |

TABLE 14
| Example | Structure |
|---------|-----------|
| 235 | 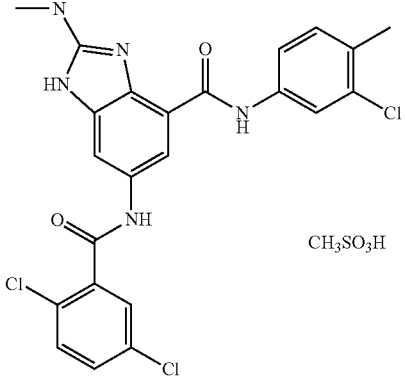 CH₃SO₃H |
| 236 | 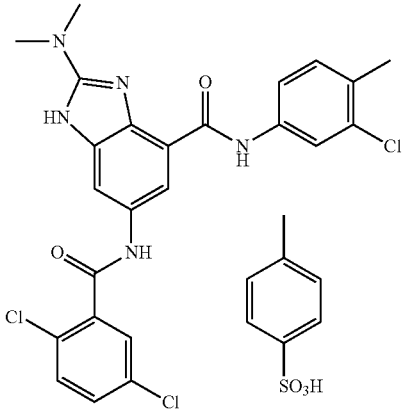 |
| 237 | 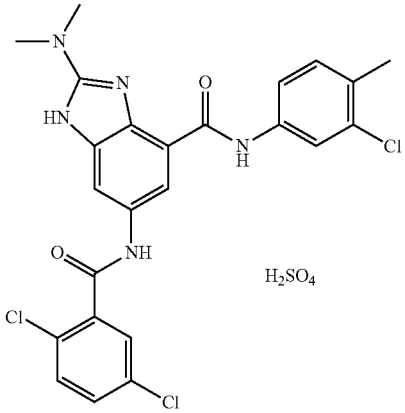 H₂SO₄ |
TABLE 14-continued
| Example | Structure |
|---------|-----------|
| 238 | 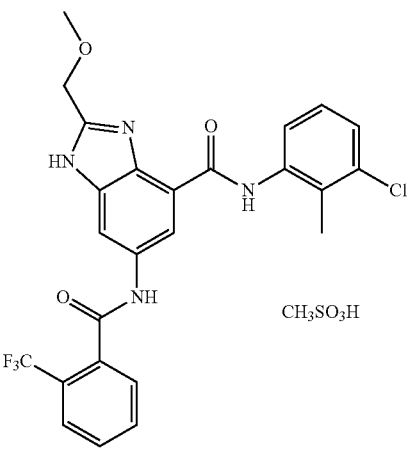 [SMILES: COCc1nc2c(C(=O)Nc3cccc(Cl)c3C)cc(NC(=O)c3ccccc3C(F)(F)F)cc2[nH]1 ; "CH3SO3H"] CH₃SO₃H |
| 239 | 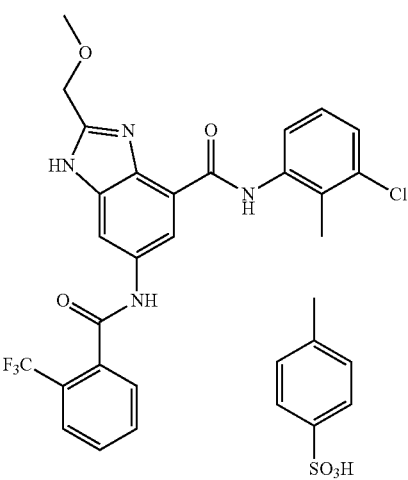 [SMILES: COCc1nc2c(C(=O)Nc3cccc(Cl)c3C)cc(NC(=O)c3ccccc3C(F)(F)F)cc2[nH]1 ; Cc1ccc(S(=O)(=O)O)cc1] |
| 240 | 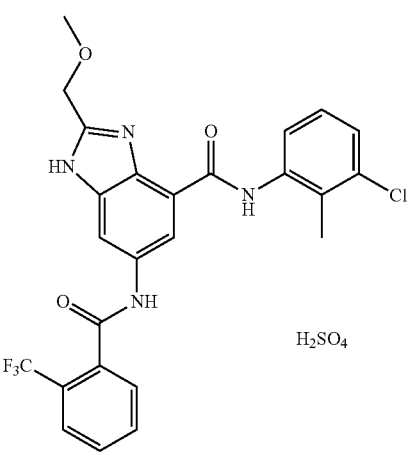 [SMILES: COCc1nc2c(C(=O)Nc3cccc(Cl)c3C)cc(NC(=O)c3ccccc3C(F)(F)F)cc2[nH]1 ; "H2SO4"] H₂SO₄ |

TABLE 14-continued

| Example | Structure |
|---------|-----------|
| 241 | (structure with 2-(1-methylcyclopropyl)benzimidazole carboxamide to 3-chloro-2-methylphenyl, with 2-(trifluoromethyl)benzamido substituent) CH₃SO₃H |
| 242 | (same core structure as 241) p-toluenesulfonic acid (4-methylbenzenesulfonic acid) |
| 243 | (same core structure as 241) H₂SO₄ |
| 244 | (2-(methoxymethyl)benzimidazole carboxamide to 3-chloro-2-methylphenyl, with 3-fluoropyridine-2-carboxamido substituent) HCl |
| 245 | (2-(methoxymethyl)benzimidazole carboxamide to 3-chloro-2-methylphenyl, with 3-chloropyridine-4-carboxamido substituent) HCl |
| 246 | (2-(methoxymethyl)benzimidazole carboxamide to 3-chloro-2-methylphenyl, with 3,5-dichloropyridine-4-carboxamido substituent) HCl |

TABLE 14-continued

| Example | Structure |
|---|---|
| 247 | 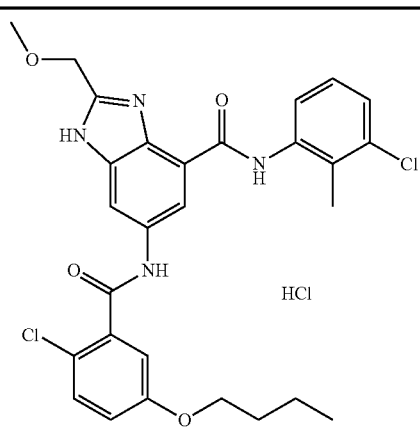 |
| 248 | 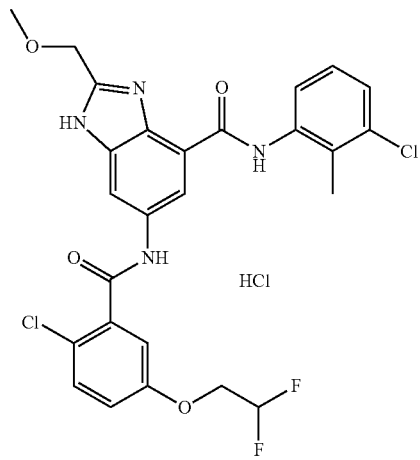 [SMILES: COCc1nc2c(C(=O)Nc3cccc(Cl)c3C)cc(NC(=O)c3cc(OCC(F)F)ccc3Cl)cc2[nH]1 ; Cl] |
| 249 | 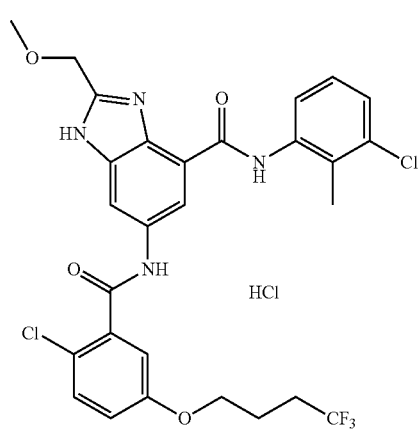 [SMILES: COCc1nc2c(C(=O)Nc3cccc(Cl)c3C)cc(NC(=O)c3cc(OCCCC(F)(F)F)ccc3Cl)cc2[nH]1 ; Cl] |

Test Example 1 mPGES-1 Inhibiting Activity mPGES-1 microsome fractions were prepared from CHO-K1 cells transiently transfected with plasmid encoding the human mPGES-1cDNA. Microsomes were diluted with potassium phosphate buffer containing reduced glutathione (pH7.4), and DMSO containing test compound or DMSO alone was added (such that DMSO final concentration would be 1% in each) and incubated at 4° C. for 20 minutes. Then, the enzymatic reactions were initiated by the addition of PGH2 substrate (final concentration 1 μM) and incubated at 4° C. for 60 seconds. The reaction was terminated by the addition of a citrate solution (final citrate concentration 50 mM) containing ferric chloride (final concentration 1 mg/mL). PGE2 production in the enzyme reaction aliquot was measured using HTRF kit (Cisbio International, catalogue #62P2APEC). The solution free of test compound was used as positive control, and the solution free of test compound and microsome sample was used as negative control. 100% activity was defined as PGE2 production in the positive control minus PGE2 production in negative control. IC50 value was calculated by standard method.

Test Example 2

Inhibition of PGE2 and PGF2α Production in A549 Cell

Human A549 cells were seeded onto a 96-well plate at $2 \times 10^4$ cells/100 μL per well and allowed to incubate overnight. After removing the culture medium and washing with phosphate buffered saline, the culture medium was replaced by RPMI culture medium with 3% FBS containing a DMSO solution containing test compound or DMSO alone (such that DMSO final concentration would be 0.10 in each). After incubation for 60 minutes, IL-1β (5 ng/well) was added and incubated at 37° C. for 24 hours. Then, PGE2 in the culture medium was measured using HTRF kit (Cisbio International, catalogue #62P2APEC), and PGF2α in the culture medium was measured using EIA kit (Cayman Chemical Company, catalogue #516011). The solution free of test compound was used as positive control, and the solution free of test compound and IL-1β was used as negative control. 100% activity was defined as PGE2 and PGF2α production in the positive control minus PGE2 and PGF2α production in the negative control. IC50 value was calculated by standard method.

The results of Test Example 1 and Test Example 2 are shown in Tables 15-18 ("-" means unadministered test).

TABLE 15

| Example | mPGES-1 Inhibition IC50 (nM) | A549 Cell PGE2 Production Inhibition IC50 (nM) | Example | mPGES-1 Inhibition IC50 (nM) | A549 Cell PGE2 Production Inhibition IC50 (nM) |
|---|---|---|---|---|---|
| 1 | 12.7 | 88.9 | 39 | 10.4 | 236.9 |
| 2 | 7.6 | 240.5 | 40 | 194.5 | 300.2 |
| 3 | 1.5 | 24.6 | 41 | 52.5 | 145.0 |
|  |  |  | 42 | 28.5 | 1857.9 |
| 5 | 453.4 | — | 43 | 70.7 | 438.3 |
| 6 | 27.4 | — | 44 | 4.1 | 1101.2 |
| 7 | 105.1 | 341.6 | 45 | 4.9 | 2084.5 |
| 8 | 160.3 | 105.8 | 46 | 26.0 | 230.8 |
| 9 | 452.2 | — | 47 | 269.6 | — |
| 10 | 332.8 | — | 48 | 49.9 | 146.3 |
| 11 | 6.6 | 12.9 | 49 | 100.3 | 375.3 |
| 12 | 7.1 | 41 | 50 | 140.3 | 810.2 |
| 13 | 35.1 | 75.6 | 51 | 120.2 | 330.4 |
| 14 | 3.8 | 15.2 | 52 | 40.2 | 280.7 |
| 15 | 37.4 | 465.0 | 53 | 179.3 | 279.9 |
| 16 | 63.9 | 1303.5 | 54 | 23.2 | 225.3 |
| 17 | 9.8 | 21.6 | 55 | 2.7 | 64.3 |
| 18 | 21.6 | 110.1 | 56 | 7.5 | 85.0 |
| 19 | 9.4 | 47.8 | 57 | 0.5 | 16.8 |
| 20 | 5.6 | 98 | 58 | 5.4 | 157.0 |
| 21 | 8.3 | 69.4 | 59 | 2.1 | 12.9 |
| 22 | 4.8 | 104.2 | 60 | 19.8 | 8.0 |
| 23 | 7.2 | 115.7 | 61 | 3.2 | 66.7 |
| 24 | 10.5 | 750.6 | 62 | 11.0 | 51.6 |

TABLE 15-continued

| Example | mPGES-1 Inhibition IC50 (nM) | A549 Cell PGE2 Production Inhibition IC50 (nM) | Example | mPGES-1 Inhibition IC50 (nM) | A549 Cell PGE2 Production Inhibition IC50 (nM) |
|---|---|---|---|---|---|
| 25 | 89.0 | 849.6 | 63 | 5.6 | 54.8 |
| 26 | 171.5 | 871.5 | 64 | 2.3 | 20.1 |
| 27 | 2.4 | 16.0 | 65 | 9.6 | 72.2 |
| 28 | 3.3 | 114.4 | 66 | 9.9 | 57.3 |
| 29 | 3.5 | 85.5 | 67 | 11.0 | 56.4 |
| 30 | 1.8 | 210.1 | 68 | 63.4 | 10000< |
| 31 | 4.1 | 69.0 | 69 | 10.0 | 21.6 |
| 32 | 5.2 | 71.7 | 70 | 4.6 | 146.9 |
| 33 | 3.0 | 33.6 | 71 | 33.1 | 227.2 |
| 34 | 4.9 | 27.6 | 72 | 9.8 | 60.0 |
| 35 | 20.3 | 204.6 | 73 | 18.6 | 76.4 |
| 36 | 147.2 | 234.2 | 74 | 71.3 | 10.4 |
| 37 | 23.3 | 265.1 | 75 | 31.7 | 19.7 |
| 38 | 6.6 | 17.4 | 76 | 0.2 | 5.5 |

TABLE 16

| Example | mPGES-1 Inhibition IC50 (nM) | A549 Cell PGE2 Production Inhibition IC50 (nM) | Example | mPGES-1 Inhibition IC50 (nM) | A549 Cell PGE2 Production Inhibition IC50 (nM) |
|---|---|---|---|---|---|
| 77 | 1.7 | 32.9 | 115 | 11.5 | 37.0 |
| 78 | 96.8 | 176.8 | 116 | 9.7 | 251.5 |
| 79 | 15.0 | 284.6 | 117 | 583.8 | — |
| 80 | 29.4 | 1251.4 | 118 | 7.3 | 5.3 |
| 81 | 5.0 | 404.5 | 119 | 207.6 | — |
| 82 | 0.4 | 6.3 | 120 | 57.5 | 513.2 |
| 83 | 9.8 | 16.5 | 121 | 6.3 | 432.4 |
| 84 | 0.8 | 6.5 | 122 | 9.7 | 1000< |
| 85 | 0.5 | 3.7 | 123 | 8.7 | 99.8 |
| 86 | 1.0 | 5.1 | 124 | 2.2 | 3.2 |
| 87 | 5.7 | 6.9 | 125 | 25.6 | 56.9 |
| 88 | 15.1 | 9.2 | 126 | 5.6 | 13.1 |
| 89 | 1.2 | 2.1 | 127 | 6.3 | 144.1 |
| 90 | 117.7 | 348.4 | 128 | 1 | 253.3 |
| 91 | 327.3 | — | 129 | 59.4 | 177.6 |
| 92 | 6.7 | 32.2 | 130 | 3.9 | 10000< |
| 93 | 4.2 | 153.5 | 131 | 32.8 | 10000< |
| 94 | 9.1 | 182.1 | 132 | 2.2 | 590.4 |
| 95 | 5.1 | 105.3 | 133 | 7.0 | 487.5 |
| 96 | 34.0 | 125.7 | 134 | 10.3 | 921.3 |
| 97 | 6.1 | 43.1 | 135 | 0.3 | 87.3 |
| 98 | 6.0 | 11.9 | 136 | 2.4 | 61.9 |
| 99 | 3.7 | 18.9 | 137 | 3.3 | 1106.7 |
| 100 | 33.3 | 122.2 | 138 | 2.2 | 87.4 |
| 101 | 77.8 | 117.9 | 139 | 1.9 | 72.8 |
| 102 | 1.6 | 49.1 | 140 | 0.2 | 33.0 |
| 103 | 2.8 | 59.6 | 141 | 0.4 | 36.5 |
| 104 | 2.9 | 71.1 | 142 | 0.4 | 82.7 |
| 105 | 8.9 | 324.6 | 143 | 5.3 | 87.5 |
| 106 | 4.5 | 63.8 | 144 | 9.7 | 2992.1 |
| 107 | 1.5 | 42.0 | 145 | 1.6 | 13.0 |
| 108 | 11.5 | 87.9 | 146 | 3.1 | 128.9 |
| 109 | 7.8 | 8.7 | 147 | 15.8 | 185.9 |
| 110 | 2.6 | 35.5 | 148 | 1.9 | 324.4 |
| 111 | 764.8 | — | 149 | 1.0 | 43.3 |
| 112 | 2.6 | 186.7 | 150 | 2.1 | 375.8 |
| 113 | 約 0.1 | 1.2 | 151 | 11.6 | 327.5 |
| 114 | 3.5 | 8.8 | 152 | 31.6 | 854.4 |

TABLE 17

| Example | mPGES-1 Inhibition IC50 (nM) | A549 Cell PGE2 Production Inhibition IC50 (nM) | Example | mPGES-1 Inhibition IC50 (nM) | A549 Cell PGE2 Production Inhibition IC50 (nM) |
|---|---|---|---|---|---|
| 153 | 22.3 | 617.8 | 191 | 3.9 | 49.5 |
| 154 | 20.0 | 64.4 | 192 | 9.9 | 18.1 |
| 155 | 100.6 | 208.7 | 193 | 0.4 | 18.9 |
| 156 | 1.6 | 24.6 | 194 | 0.4 | 33.8 |
| 157 | 3.9 | 10856.6 | 195 | 2.3 | 17.2 |
| 158 | 8.5 | 82.2 | 196 | 6.5 | 35.9 |
| 159 | 403.3 | — | 197 | 5.2 | 34.4 |
| 160 | 7.6 | 71.6 | 198 | 6.0 | 34.1 |
| 161 | 3.8 | 10000< | 199 | 9.7 | 43.2 |
| 162 | 23.8 | 52.2 | 200 | 4.6 | 107.6 |
| 163 | 5.9 | 23.2 | 201 | 0.5 | 253.0 |
| 164 | 0.3 | 13.3 | 202 | 4.9 | 5.9 |
| 165 | 1.3 | 7.4 | 203 | 1.4 | 5.2 |
| 166 | 3.2 | 29.0 | 204 | 1.0 | 12.2 |
| 167 | 1.0 | 217.3 | 205 | 3.7 | 25.6 |
| 168 | 3.2 | 23.9 | 206 | 3.2 | 74.5 |
| 169 | 2.4 | 88.6 | 207 | 3.6 | 6.2 |
| 170 | 3.2 | 17.8 | 208 | 0.7 | 13.0 |
| 171 | 4.7 | 97.8 | 209 | 1.0 | 10.3 |
| 172 | 4.5 | 134.4 | 210 | 4.7 | 13.8 |
| 173 | 1.1 | 60.8 | 211 | 2.5 | 8.5 |
| 174 | 2.0 | 117.2 | 212 | 42.3 | 305.4 |
| 175 | 3.6 | 143.9 | 213 | 0.9 | 141.6 |
| 176 | 0.3 | 138.4 | 214 | 5.2 | 60.7 |
| 177 | 8.3 | 45.2 | 215 | 140.4 | 772.5 |
| 178 | 1.2 | 12.8 | 216 | 203.6 | — |
| 179 | 3.6 | 20.2 | 217 | 26.9 | 316.7 |
| 180 | 1.1 | 773.6 | 218 | 5.3 | 42.8 |
| 181 | 1.1 | 705.0 | 219 | 2.0 | 26.0 |
| 182 | 1.6 | 38.4 | 220 | 8.6 | — |
| 183 | 1.9 | 6.1 | 221 | 2.2 | — |
| 184 | 1.0 | 138.2 | 222 | 661.1 | — |
| 185 | 4.5 | 5.6 | 223 | 68.2 | — |
| 186 | 6.1 | 13.9 | 224 | 26.5 | — |
| 187 | 3.6 | 12.7 | 225 | 15.6 | — |
| 188 | 456.9 | 1019.5 | 226 | 26.9 | — |
| 189 | 1.4 | 24.5 | 227 | 0.1 | — |
| 190 | 0.1 | 7.0 | 228 | 1.7 | — |

TABLE 18

| Example | mPGES-1 Inhibition IC50 (nM) | A549 Cell PGE2 Production Inhibition IC50 (nM) | Example | mPGES-1 Inhibition IC50 (nM) | A549 Cell PGE2 Production Inhibition IC50 (nM) |
|---|---|---|---|---|---|
| 229 | 2.3 | 39 | 244 | 56.2 | 104 |
| 230 | 1.9 | 100 | 245 | 25.7 | 166 |
| 231 | 1.9 | 150 | 246 | 35.9 | 132 |
| 232 | 7.7 | 125 | 247 | 68.4 | 55 |
| 233 | 2.5 | 195 | 248 | 201 | — |
| 234 | 97.4 | 198 | 249 | 404 | — |

Test Example 3

Inhibition of PGE2 Production in Human Whole Blood

Human whole blood assay was carried out according to Brideau et al. (Inflamm. Res., vol. 45, p. 68, 1996). Venous bloods from volunteers were collected into each tube (containing heparin). These volunteers did not have clinical appearance of inflammation and had not taken NSAID at least seven days before the blood collection. DMSO solution containing test compound or DMSO alone was added to the blood (such that DMSO final concentration would be 0.25% in each), and it was incubated at 37° C. for 20 minutes. LPS from

*E. coli* (*E. coli* serotype 0111:B4 diluted with phosphate-buffered saline) was added at the final concentration of 100 μg/mL and incubated at 37° C. for 24 hours. After the incubation, the blood was centrifuged at 2000 rpm for 5 minutes at 4° C., and PGE2 in the supernatant was measured using HTRF kit (Cisbio International, catalogue #62P2APEC). The solution free of test compound was used as positive control, and the solution free of test compound and LPS was used as negative control. 100% activity was defined as PGE2 production in the positive control minus PGE2 production in the negative control. IC50 value was calculated by standard method.

Test Example 4

Inhibition of PGE2 Production in Mouse Air Pouch Model

Air pouch was established in BALB/c mouse by the subcutaneous injection (twice at intervals of 3 days) of sterilized air into the back. 3 days after the second air injection, 0.5% zymosan was injected into the air pouch. 5 hours later, 1 mL of phosphate-buffered saline containing 10 μM indomethacin was injected into the air pouch to wash the interior thereof, and the white blood cells and PGE2 in the pouch fluid were measured. PGE2 was quantified using HTRF kit (Cisbio International, catalogue #62P2APEC). The test compound was suspended in 0.5% methylcellulose solution and administered orally 1 hour before the zymosan injection. The group which was administered only methylcellulose solution was used as control for comparison.

Test Example 5

Pharmacokinetic Assay in Rat

A 10 mg/5 mL liquid of a test compound was prepared by suspending the compound in 0.5% methylcellulose solution. The liquid was administered orally to female SD rats at fasting state at a dose of 10 mg/kg, and bloods were collected from the jugular vein 1, 2, 4 and 6 hours after the administration. The blood samples were centrifuged to separate plasma. After deproteinization of the plasma, the concentration of the test compound in plasma was measured by HPLC.

Test Example 6

Evaluation of Analgesic Effect Using Mouse Writhing Test

Analgesic effect was evaluated from pain-related behavior induced by the intraperitoneal injection of 0.6% acetic acid solution (10 mL/kg) into ddY mouse. The number of times of writhing in 20 minutes after the acetic acid injection was counted as pain-related behavior. The test compound was suspended in 0.5% methylcellulose solution and administered orally 1 hour before the acetic acid injection. The group which was administered only methylcellulose solution was used as control for comparison.

Test Example 7

Evaluation of Analgesic Effect Using Mouse Formalin Test

Analgesic effect was evaluated from pain-related behavior induced by the injection of 5% formalin solution (0.02 mL/mouse) into the right hind-foot pad of ICR mouse. The sum of the duration of licking in 30 minutes after the formalin injection was measured as pain-related behavior. The test compound was suspended in 0.5% methylcellulose solution and administered orally 1 hour before the formalin injection. The group which was administered only methylcellulose solution was used as control for comparison.

Test Example 8

Evaluation of Antiinflammatory Effect in Rat Carrageenan Edema Model

Antiinflammatory effect was evaluated from paw edema induced by the injection of 0.5% carrageenan solution (0.1 mL/rat) into the right hind-foot pad of SD rat. The volume of the paw was measured before and 3 hours after the carrageenan injection using a plethysmometer (Unicom Inc., catalogue #TK-105). Swelling volume was determined from the increase in the volume from the volume before the injection. The inhibiting rate was determined as the ratio of the average swelling volume in the group given the test compound to the average swelling in the control group. The test compound was suspended in 0.5% methylcellulose solution and administered orally 1 hour before the carrageenan injection. The group which was administered only methylcellulose solution was used as control for comparison.

The compound of the invention or a pharmaceutically acceptable salt thereof showed potent mPGES-1 inhibiting activity and inhibited PGE2 production, as shown in Test Example 1 and Test Example 2. Thus, it is particularly useful as an agent for the treatment or prevention of inflammatory bowel disease, irritable bowel syndrome, migraine, headache, low back pain, spinal stenosis, herniated disk, temporomandibular joint disorder, cervical syndrome, cervical spondylosis, endometriosis, adenomyosis, preterm labour and delivery, threatened premature delivery, dysmenorrhea, overactive bladder, nocturia, interstitial cystitis, neurodegenerative disease, psoriasis, rheumatoid arthritis, rheumatic fever, fibromyalgia, neuralgia, complex regional pain syndrome, fascial dysfunction, viral infections, bacterial infection, mycosis, burn, inflammation and pain after operation, injury and dental extraction, malignant tumors, atherosclerosis, stroke, gout, arthritis, osteoarthritis, juvenile arthritis, ankylosing spondylitis, tenosynovitis, ligament ossification, systemic lupus erythematosus, vasculitis, pancreatitis, nephritis, conjunctivitis, iritis, scleritis, uveitis, wound therapy, dermatitis, eczema, osteoporosis, asthma, chronic obstructive pulmonary disease, pulmonary fibrosis, allergic disease, familial adenomatous polyposis, scleroderma, bursitis, leiomyoma of uterus, prostatitis, and pain from cancer.

Formulation 1: 80 mg Tablets for oral administration

| Ingredient | Quantity (mg/tablet) |
| --- | --- |
| Compound of Example 1 | 5.0 |
| Corn starch | 46.6 |
| Cellulose, crystalline | 24.0 |
| Methylcellulose | 4.0 |
| Magnesium stearate | 0.4 |

The components are blended and compressed to form tablets.

The compound of the invention or a pharmaceutically acceptable salt thereof has mPGES-1 inhibiting activity and is particularly useful as an agent for the treatment or prevention of inflammatory bowel disease, irritable bowel syndrome, migraine, headache, low back pain, spinal stenosis, herniated disk, temporomandibular joint disorder, cervical syndrome, cervical spondylosis, endometriosis, adenomyosis, preterm labour and delivery, threatened premature delivery, dysmenorrhea, overactive bladder, nocturia, interstitial cystitis, neurodegenerative disease, psoriasis, rheumatoid arthritis, rheumatic fever, fibromyalgia, neuralgia, complex regional pain syndrome, fascial dysfunction, viral infections, bacterial infection, mycosis, burn, inflammation and pain after operation, injury and dental extraction, malignant tumors, atherosclerosis, stroke, gout, arthritis, osteoarthritis, juvenile arthritis, ankylosing spondylitis, tenosynovitis, ligament ossification, systemic lupus erythematosus, vasculitis, pancreatitis, nephritis, conjunctivitis, iritis, scleritis, uveitis, wound therapy, dermatitis, eczema, osteoporosis, asthma, chronic obstructive pulmonary disease, pulmonary fibrosis, allergic disease, familial adenomatous polyposis, scleroderma, bursitis, leiomyoma of uterus, prostatitis, and pain from cancer.

What is claimed is:

1. A compound selected from the group consisting of: N-(3-chloro-2-methylphenyl)-2-(methoxymethyl)-6-({[2-(trifluoromethyl)phenyl]carbonyl}amino)-1H-benzimidazole-4-carboxamide, pharmaceutically acceptable salts thereof, tautomers thereof, and pharmaceutically acceptable salts of tautomers thereof.

2. The compound according to claim 1, wherein the pharmaceutically acceptable salts and the pharmaceutically acceptable salts of tautomers are selected from the group consisting of hydrochloride, mesylate, tosylate, and sulfate.

3. A pharmaceutical composition comprising:
the compound according to claim 1; and
a pharmaceutically acceptable, non-toxic and inactive carrier.

4. A pharmaceutical composition comprising:
the compound according to claim 2; and
a pharmaceutically acceptable, non-toxic and inactive carrier.

5. A method of inhibiting mPGES-1 in a mammal, comprising the step of administering to the mammal the compound according to claim 1.

6. A method of inhibiting mPGES-1 in a mammal, comprising the step of administering to the mammal the compound according to claim 2.

7. A method of treating endometriosis, multiple sclerosis, rheumatoid arthritis, neuralgia, colon cancer, lung cancer, prostatic cancer, atherosclerosis, stroke, osteoarthritis, nephritis, asthma, familial adenomatous polyposis, or scleroderma, the method comprising the step of administering the compound according to claim 1 as an active ingredient.

8. A method of treating endometriosis, multiple sclerosis, rheumatoid arthritis, neuralgia, colon cancer, lung cancer, prostatic cancer, atherosclerosis, stroke, osteoarthritis, nephritis, asthma, familial adenomatous polyposis, or scleroderma, the method comprising the step of administering the compound according to claim 2 as an active ingredient.

9. A compound selected from the group consisting of: N-(3-chloro-2-methylphenyl)-2-(1-methylcyclopropyl)-6-({[2-(trifluoromethyl)phenyl]carbonyl}amino)-1H-benzimidazole-4-carboxamide, pharmaceutically acceptable salts thereof, tautomers thereof, and pharmaceutically acceptable salts of tautomers thereof.

10. The compound according to claim 9, wherein the pharmaceutically acceptable salts and the pharmaceutically acceptable salts of tautomers are selected from the group consisting of hydrochloride, mesylate, tosylate, and sulfate.

11. A pharmaceutical composition comprising:
the compound according to claim 9; and
a pharmaceutically acceptable, non-toxic and inactive carrier.

12. A pharmaceutical composition comprising:
the compound according to claim 10; and
a pharmaceutically acceptable, non-toxic and inactive carrier.

13. A method of inhibiting mPGES-1 in a mammal, comprising the step of administering to the mammal the compound according to claim 9.

14. A method of inhibiting mPGES-1 in a mammal, comprising the step of administering to the mammal the compound according to claim 10.

15. A method of treating endometriosis, multiple sclerosis, rheumatoid arthritis, neuralgia, colon cancer, lung cancer, prostatic cancer, atherosclerosis, stroke, osteoarthritis, nephritis, asthma, familial adenomatous polyposis, or scleroderma, the method comprising the step of administering the compound according to claim 9 as an active ingredient.

16. A method of treating endometriosis, multiple sclerosis, rheumatoid arthritis, neuralgia, colon cancer, lung cancer, prostatic cancer, atherosclerosis, stroke, osteoarthritis, nephritis, asthma, familial adenomatous polyposis, or scleroderma, the method comprising the step of administering the compound according to claim 10 as an active ingredient.

17. A compound selected from the group consisting of: N-(3-chloro-4-methylphenyl)-6-{[(2,5-dichlorophenyl)carbonyl]amino}-2-(dimethylamino)-1H-benzimidazole-4-carboxamide, pharmaceutically acceptable salts thereof, tautomers thereof, and pharmaceutically acceptable salts of tautomers thereof.

18. The compound according to claim 17, wherein the pharmaceutically acceptable salts and the pharmaceutically acceptable salts of tautomers are selected from the group consisting of hydrochloride, mesylate, tosylate, and sulfate.

19. A pharmaceutical composition comprising:
the compound according to claim 17; and
a pharmaceutically acceptable, non-toxic and inactive carrier.

20. A pharmaceutical composition comprising:
the compound according to claim 18; and
a pharmaceutically acceptable, non-toxic and inactive carrier.

21. A method of inhibiting mPGES-1 in a mammal, comprising the step of administering to the mammal the compound according to claim 17.

22. A method of inhibiting mPGES-1 in a mammal, comprising the step of administering to the mammal the compound according to claim 18.

23. A method of treating endometriosis, multiple sclerosis, rheumatoid arthritis, neuralgia, colon cancer, lung cancer, prostatic cancer, atherosclerosis, stroke, osteoarthritis, nephritis, asthma, familial adenomatous polyposis, or scleroderma, the method comprising the step of administering the compound according to claim 17 as an active ingredient.

24. A method of treating endometriosis, multiple sclerosis, rheumatoid arthritis, neuralgia, colon cancer, lung cancer, prostatic cancer, atherosclerosis, stroke, osteoarthritis, nephritis, asthma, familial adenomatous polyposis, or scleroderma, the method comprising the step of administering the compound according to claim 18 as an active ingredient.

* * * * *